US012649724B2

(12) United States Patent
Sakamoto

(10) Patent No.: US 12,649,724 B2
(45) Date of Patent: Jun. 9, 2026

(54) LIGHT EMITTING DEVICE AND AMINE COMPOUND FOR THE SAME

(71) Applicant: Samsung Display Co., Ltd., Yongin-si (KR)

(72) Inventor: Naoya Sakamoto, Yokohama (JP)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 1031 days.

(21) Appl. No.: 17/740,509

(22) Filed: May 10, 2022

(65) Prior Publication Data

US 2023/0012692 A1 Jan. 19, 2023

(30) Foreign Application Priority Data

Jun. 11, 2021 (KR) ........................ 10-2021-0076002

(51) Int. Cl.

| | |
|---|---|
| ***H10K 85/60*** | (2023.01) |
| ***C07C 211/54*** | (2006.01) |
| ***C07C 211/57*** | (2006.01) |
| ***C07C 211/61*** | (2006.01) |
| ***C07D 209/86*** | (2006.01) |
| ***C07D 213/38*** | (2006.01) |
| ***C07D 307/91*** | (2006.01) |
| ***C07D 333/76*** | (2006.01) |
| ***C07D 409/12*** | (2006.01) |
| *H10K 50/15* | (2023.01) |
| *H10K 50/16* | (2023.01) |

(52) U.S. Cl.

CPC .......... *C07D 307/91* (2013.01); *C07C 211/54* (2013.01); *C07C 211/57* (2013.01); *C07C 211/61* (2013.01); *C07D 209/86* (2013.01); *C07D 213/38* (2013.01); *C07D 333/76* (2013.01); *C07D 409/12* (2013.01); *H10K 85/615* (2023.02); *H10K 85/622* (2023.02); *H10K 85/631* (2023.02); *H10K 85/633* (2023.02); *H10K 85/636* (2023.02); *H10K 85/657* (2023.02); *H10K 85/6572* (2023.02); *H10K 85/6574* (2023.02); *H10K 85/6576* (2023.02); *C07B 2200/05* (2013.01); *H10K 50/15* (2023.02); *H10K 50/16* (2023.02)

(58) Field of Classification Search

None

See application file for complete search history.

(56) References Cited

U.S. PATENT DOCUMENTS

| | | | | |
|---|---|---|---|---|
| 10,205,102 | B2 | 2/2019 | Takada | |
| 10,879,471 | B2 | 12/2020 | Miyake et al. | |
| 2019/0237676 | A1* | 8/2019 | Miyake .............. | H10K 85/6576 |
| 2019/0378981 | A1 | 12/2019 | Yoo et al. | |
| 2020/0235297 | A1 | 7/2020 | Miyake et al. | |
| 2022/0158095 | A1* | 5/2022 | Huang ................. | C07D 333/76 |

FOREIGN PATENT DOCUMENTS

| | | | | |
|---|---|---|---|---|
| CN | 108084091 A | 5/2018 | | |
| CN | 110511151 | 11/2019 | | |
| CN | 113861041 A * | 12/2021 | ........... | C07C 211/58 |
| KR | 10-2016-0120609 | 10/2016 | | |
| KR | 10-1854886 | 5/2018 | | |
| KR | 10-2019-0091409 | 8/2019 | | |
| KR | 1020190124620 A | 11/2019 | | |
| KR | 10-2078171 | 2/2020 | | |
| KR | 1020200131929 A | 11/2020 | | |
| WO | 2020/220942 | 11/2020 | | |

OTHER PUBLICATIONS

Machine translation of CN-113861041-A, translation generated Jan. 2025, 19 pages. (Year: 2025).*

Machine translation of KR-20160120609-A, translation generated Jan. 2025, 25 pages. (Year: 2025).*

Machine translation of CN-108084091-A, translation generated Sep. 2025, 18 pages. (Year: 2025).*

* cited by examiner

*Primary Examiner* — Robert S Loewe

(74) *Attorney, Agent, or Firm* — CANTOR COLBURN LLP

(57) ABSTRACT

A light emitting device includes a first electrode, a second electrode disposed on the first electrode, and at least one functional layer disposed between the first electrode and the second electrode. The at least one functional layer includes an amine compound represented by Formula 1. A light emitting device including the amine compound may show improved efficiency and life characteristics.

[Formula 1]

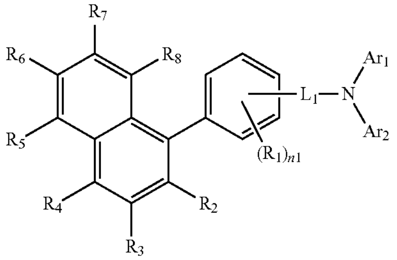

17 Claims, 6 Drawing Sheets

LIGHT EMITTING DEVICE AND AMINE COMPOUND FOR THE SAME

CROSS-REFERENCE TO RELATED APPLICATION(S)

This application claims priority to and benefits of Korean Patent Application No. 10-2021-0076002 under 35 U.S.C. § 119, filed on Jun. 11, 2021 in the Korean Intellectual Property Office, the entire contents of which are incorporated herein by reference.

BACKGROUND

1. Technical Field

The disclosure herein relates to an amine compound used as a hole transport material and a light emitting device including the same.

2. Description of the Related Art

Ongoing development continues for an organic electroluminescence display device as an image display device. The organic electroluminescence display device is a display device including a so-called self-luminescent light emitting device in which holes and electrons respectively injected from a first electrode and a second electrode recombine in an emission layer so that a light emitting material in an emission layer emits light to achieve display.

In the application of a light emitting device to an image display device, there is a demand for improving emission efficiency and device life, and continuous development is required on materials for a light emitting device which is capable of stably achieving such characteristics.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

The disclosure provides a light emitting device showing excellent emission efficiency and long-life characteristics.

The disclosure also provides an amine compound that is a material for a light emitting device having high efficiency and long-life characteristics.

An embodiment provides a light emitting device which may include a first electrode, a second electrode disposed on the first electrode, and at least one functional layer disposed between the first electrode and the second electrode, the at least one functional layer including an amine compound represented by Formula 1.

[Formula 1]

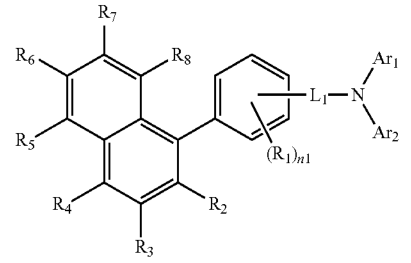

In Formula 1, $L_1$ may be direct linkage, a substituted or unsubstituted arylene group of 6 to 15 ring-forming carbon atoms, or a substituted or unsubstituted heteroarylene group of 2 to 15 ring-forming carbon atoms, $Ar_1$ may be a substituted or unsubstituted aryl group of 6 to 30 ring-forming carbon atoms, or a substituted or unsubstituted heteroaryl group of 2 to 30 ring-forming carbon atoms, wherein $Ar_1$ may not include an adamantyl group, $Ar_2$ may be a group represented by Formula 2, n1 may be an integer from 0 to 4, $R_1$ may be a hydrogen atom, a deuterium atom, a halogen atom, a substituted or unsubstituted oxy group, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring, at least one of $R_2$ to $R_8$ may be a substituted or unsubstituted aryl group of 6 to 30 ring-forming carbon atoms, or a substituted or unsubstituted heteroaryl group of 2 to 30 ring-forming carbon atoms, and the remainder of $R_2$ to $R_8$ may each independently be a hydrogen atom, a deuterium atom, a halogen atom, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms.

[Formula 2]

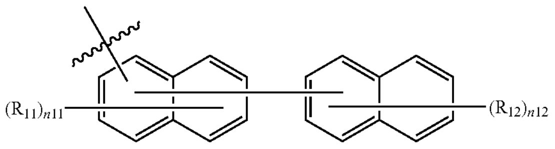

In Formula 2, n11 may be an integer from 0 to 6, n12 may be an integer from 0 to 7, and $R_{11}$ and $R_{12}$ may each independently be a hydrogen atom, a deuterium atom, a halogen atom, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms.

In an embodiment, the amine compound represented by Formula 1 may be represented by Formula 1-A or Formula 1-B.

[Formula 1-A]

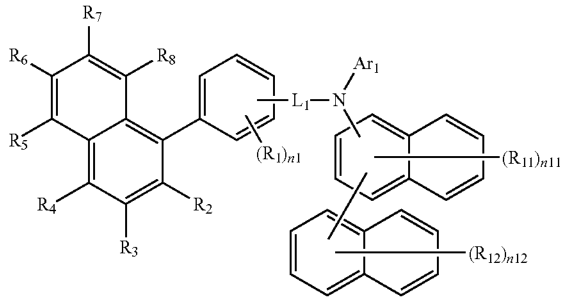

[Formula 1-B]

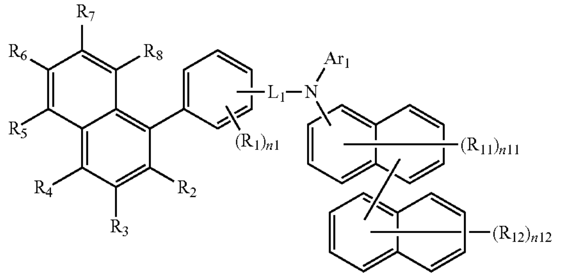

In Formula 1-A and Formula 1-B, $Ar_1$, $L_1$, n1, n11, n12, $R_1$ to $R_8$, $R_{11}$, and $R_{12}$ may be the same as defined in Formula 1 and Formula 2.

In an embodiment, the amine compound represented by Formula 1-A may be represented by Formula 1-A1 or Formula 1-A2.

[Formula 1-A1]

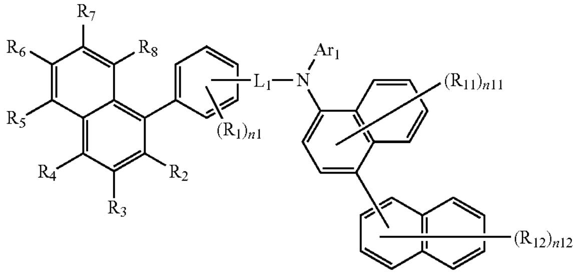

[Formula 1-A2]

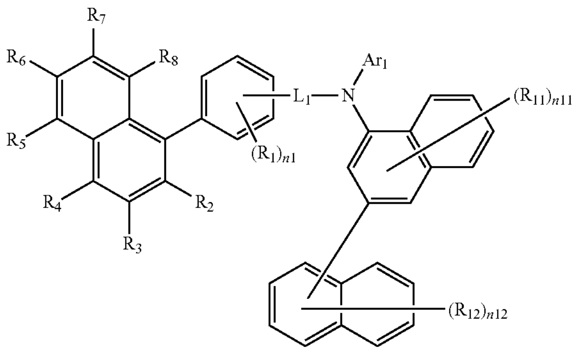

In Formula 1-A1 and Formula 1-A2, $Ar_1$, $L_1$, n1, n11, n12, $R_1$ to $R_8$, $R_{11}$, and $R_{12}$ may be the same as defined in Formula 1 and Formula 2.

In an embodiment, the amine compound represented by Formula 1-B may be represented by Formula 1-B1 or Formula 1-B2.

[Formula 1-B1]

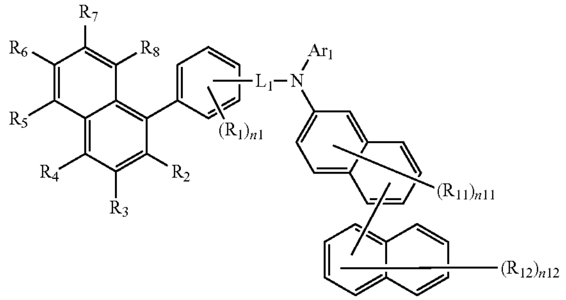

[Formula 1-B2]

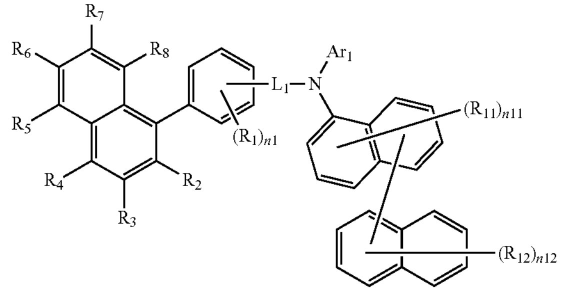

In Formula 1-B1 and Formula 1-B2, $Ar_1$, $L_1$, n1, n11, n12, $R_1$ to $R_8$, $R_{11}$, and $R_{12}$ may be the same as defined in Formula 1 and Formula 2.

In an embodiment, the amine compound represented by Formula 1 may be represented by Formula 1-C1 or Formula 1-C2.

[Formula 1-C1]

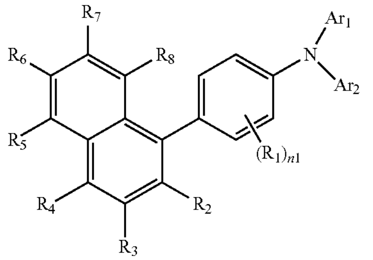

[Formula 1-C2]

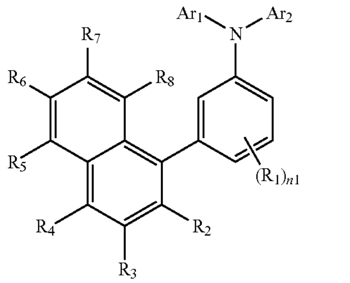

In Formula 1-C1 and Formula 1-C2, $Ar_1$, Are, n1, and $R_1$ to $R_8$ may be the same as defined in Formula 1.

In an embodiment, $Ar_1$ may be a group represented by any one of Ar1-1 to Ar1-6.

Ar1-1

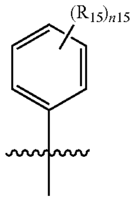

Ar1-2

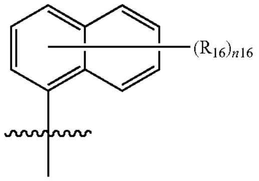

Ar1-3

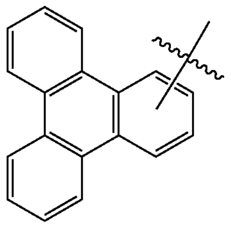

Ar1-4

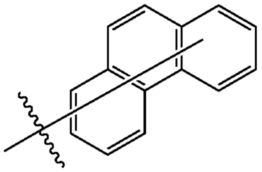

Ar1-5

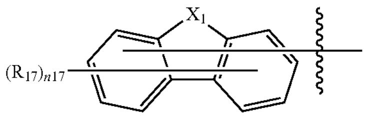

Ar1-6

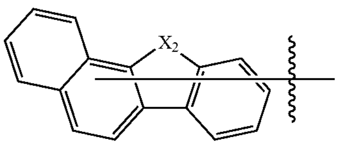

In Ar1-1, n15 may be an integer from 0 to 5, and $R_{15}$ may be a hydrogen atom, a substituted or unsubstituted alkyl group of 1 to 10 carbon atoms, or a substituted or unsubstituted aryl group of 6 to 30 ring-forming carbon atoms. In Ar1-2, n16 may be an integer from 0 to 7, and $R_{16}$ may be a hydrogen atom, a halogen atom, or a substituted or unsubstituted aryl group of 6 to 30 ring-forming carbon atoms. In Ar1-5, $X_1$ may be $N(R_{18})$, O, or S, n17 may be an integer from 0 to 7, and $R_{17}$ and $R_{18}$ may each independently be a hydrogen atom, or a substituted or unsubstituted aryl group of 6 to 30 ring-forming carbon atoms. In Ar1-6, $X_2$ may be O or S.

In an embodiment, in Formula 1, at least one of $R_1$ to $R_8$ may include a deuterium atom as a substituent, or at least one of $R_{11}$ and $R_{12}$ may be a deuterium atom.

In an embodiment, in Formula 1, at least one of $R_4$ and $R_8$ may be a substituted or unsubstituted phenyl group, a substituted or unsubstituted naphthyl group, a substituted or unsubstituted pyridine group, a substituted or unsubstituted carbazole group, a substituted or unsubstituted dibenzofuran group, or a substituted or unsubstituted dibenzothiophene group.

In an embodiment, the at least one functional layer may include an emission layer, a hole transport region disposed between the first electrode and the emission layer, and an electron transport region disposed between the emission layer and the second electrode, and the hole transport region may include the amine compound.

In an embodiment, the hole transport region may include a hole injection layer disposed on the first electrode, a hole transport layer disposed on the hole injection layer, and an electron blocking layer disposed on the hole transport layer, and at least one of the hole injection layer, the hole transport layer, and the electron blocking layer may include the amine compound.

In an embodiment, the amine compound may be one selected from Compound Group 1, which is explained below.

An embodiment provides an amine compound represented by Formula 1.

In an embodiment, in Formula 1, $Ar_1$ may be a substituted or unsubstituted phenyl group, a substituted or unsubstituted naphthyl group, a substituted or unsubstituted terphenyl group, a substituted or unsubstituted phenanthrene group, a substituted or unsubstituted triphenylene group, a substituted or unsubstituted carbazole group, a substituted or unsubstituted dibenzofuran group, a substituted or unsubstituted dibenzothiophene group, a substituted or unsubstituted naphthobenzofuran group, or a substituted or unsubstituted benzonaphthothiophene group.

BRIEF DESCRIPTION OF THE DRAWINGS

The accompanying drawings are included to provide a further understanding of the embodiments, and are incorporated in and constitute a part of this specification. The drawings illustrate embodiments of the disclosure and principles thereof. The above and other aspects and features of the disclosure will become more apparent by describing in detail embodiments thereof with reference to the attached drawings, in which.

DETAILED DESCRIPTION OF THE EMBODIMENTS

Figure 1:
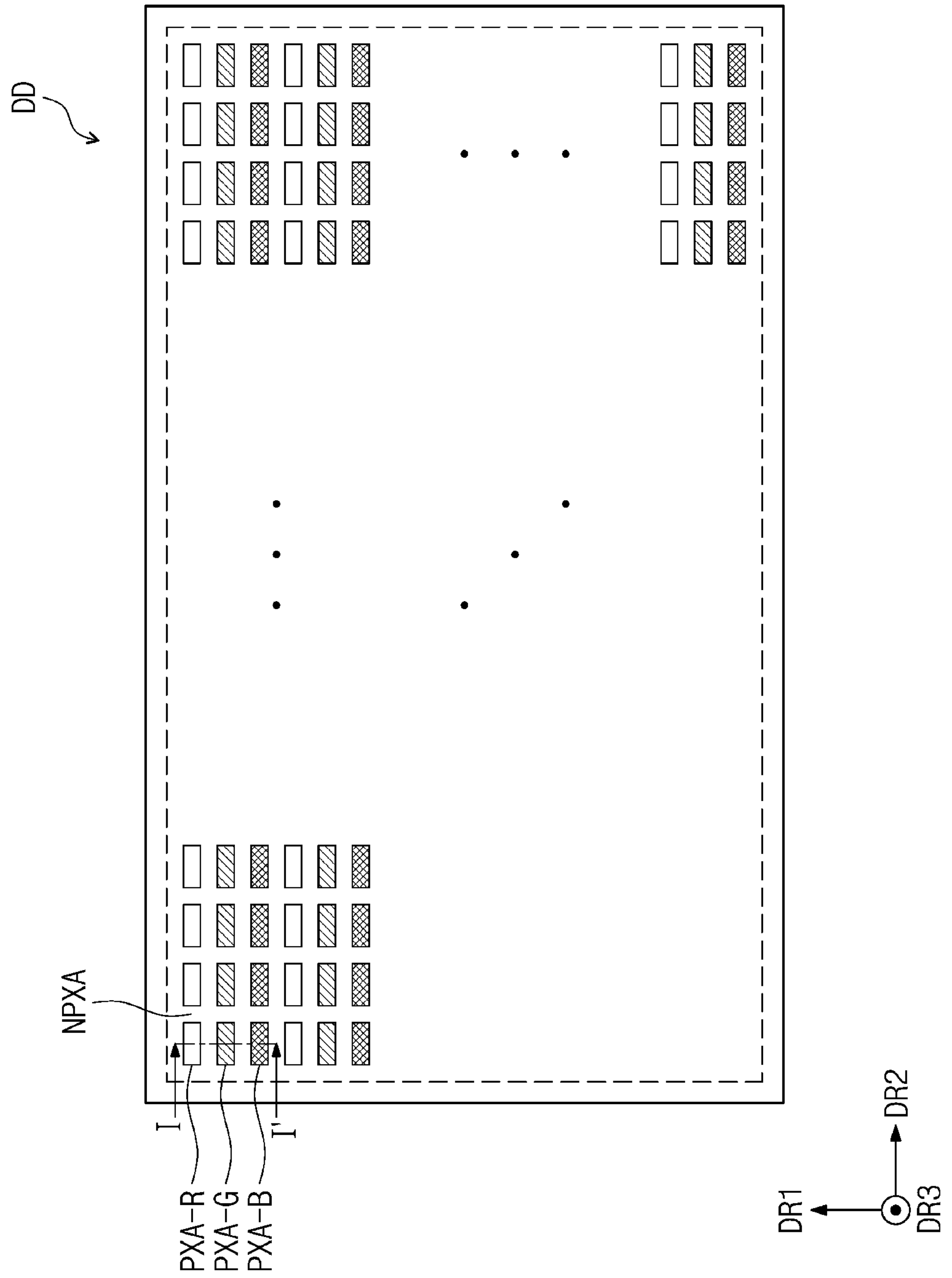
FIG. 1 is a plan view showing a display apparatus according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the specification, it will be understood that when an element (or region, layer, part, etc.) is referred to as being "on", "connected to", or "coupled to" another element, it can be directly on, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the specification, when an element is "directly on," "directly connected to," or "directly coupled to" another element, there are no intervening elements present. For example, "directly on" may mean that two layers or two elements are disposed without an additional element such as an adhesion element therebetween.

As used herein, the expressions used in the singular such as "a," "an," and "the," are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, ±10%, or ±5% of the stated value.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

Figure 2:
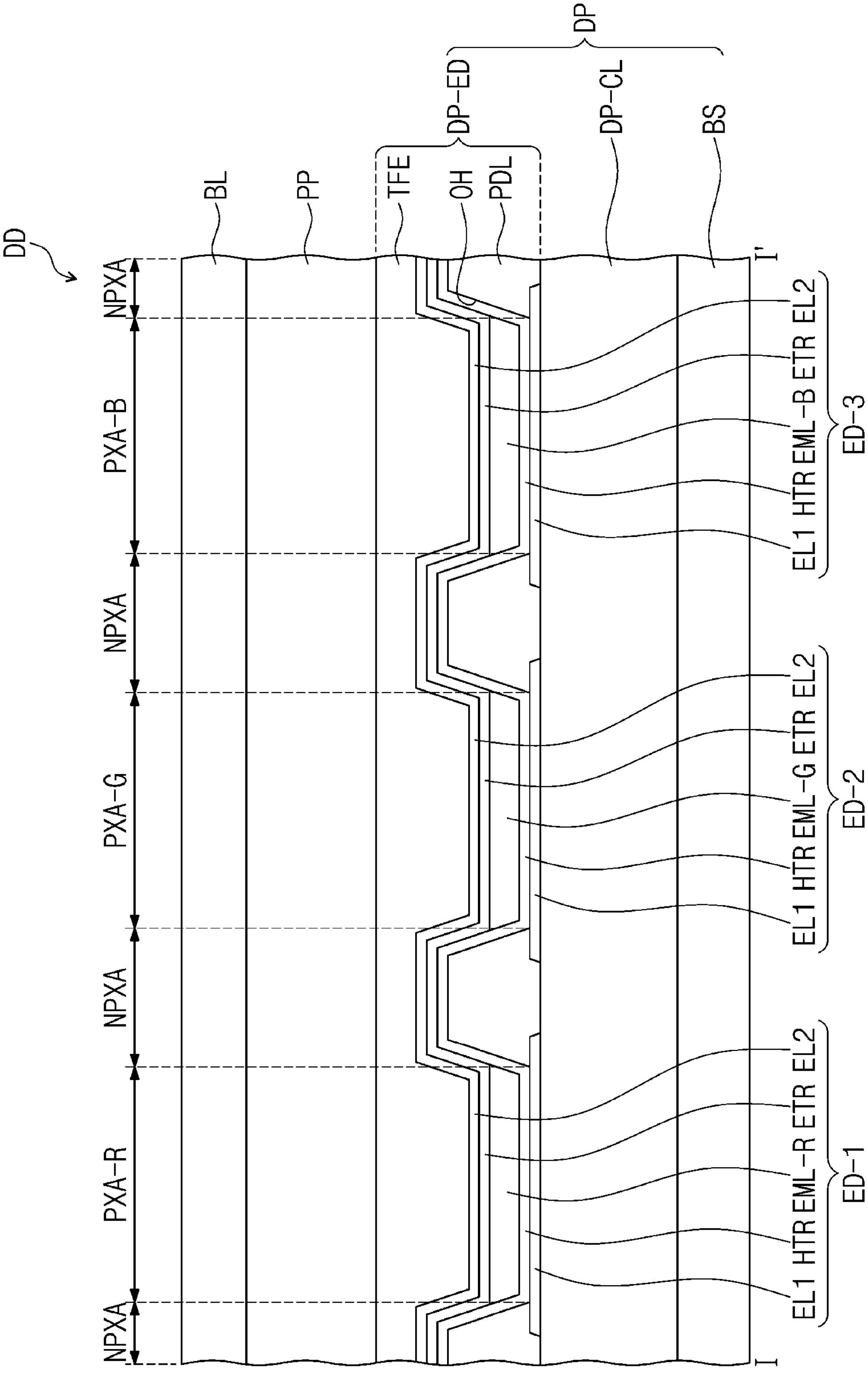
FIG. 2 is a schematic cross-sectional view showing a display apparatus according to an embodiment.

Hereinafter, embodiments will be explained referring to the drawings. FIG. 1 is a plan view showing an embodiment of a display apparatus DD. FIG. 2 is a schematic cross-sectional view of a display apparatus DD of an embodiment. FIG. 2 is a schematic cross-sectional view showing a part corresponding to line I-I' in FIG. 1.

The display apparatus DD may include a display panel DP and an optical layer PP disposed on the display panel DP. The display panel DP includes light emitting devices ED-1, ED-2, and ED-3. The display apparatus DD may include multiples of each of the light emitting devices ED-1, ED-2, and ED-3. The optical layer PP may be disposed on the display panel DP and may control light reflected at the display panel DP from an external light. The optical layer PP may include, for example, a polarization layer or a color filter layer. Although not shown in the drawings, in an embodiment, the optical layer PP may be omitted from the display apparatus DD.

A base substrate BL may be disposed on the optical layer PP. The base substrate BL may provide a base surface where the optical layer PP is disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawings, in an embodiment, the base substrate BL may be omitted.

The display apparatus DD according to an embodiment may further include a filling layer (not shown). The filling layer (not shown) may be disposed between a display device layer DP-ED and a base substrate BL. The filling layer (not shown) may be an organic layer. The filling layer (not shown) may include at least one of an acrylic resin, a silicon-based resin, and an epoxy-based resin.

The display panel DP may include a base layer BS, a circuit layer DP-CL provided on the base layer BS, and a display device layer DP-ED. The display device layer DP-ED may include a pixel definition layer PDL, light emitting devices ED-1, ED-2, and ED-3 disposed in the pixel definition layer PDL, and an encapsulation layer TFE disposed on the light emitting devices ED-1, ED-2, and ED-3.

The base layer BS may provide a base surface where the display device layer DP-ED is disposed. The base layer BS may be a glass substrate, a metal substrate, a plastic substrate, etc. However, embodiments are not limited thereto, and the base layer BS may include an inorganic layer, an organic layer, or a composite material layer.

In an embodiment, the circuit layer DP-CL is disposed on the base layer BS, and the circuit layer DP-CL may include multiple transistors (not shown). Each of the transistors (not shown) may include a control electrode, an input electrode, and an output electrode. For example, the circuit layer DP-CL may include switching transistors and driving transistors for driving the light emitting devices ED-1, ED-2, and ED-3 of the display device layer DP-ED.

Each of the light emitting devices ED-1, ED-2, and ED-3 may have a structure of a light emitting device ED of an embodiment according to FIG. 3 to FIG. 6, which will be explained later. Each of the light emitting devices ED-1, ED-2, and ED-3 may include a first electrode EL1, a hole transport region HTR, emission layers EML-R, EML-G, and EML-B, an electron transport region ETR, and a second electrode EL2.

FIG. 2 illustrates an embodiment where the emission layers EML-R, EML-G, and EML-B of light emitting devices ED-1, ED-2, and ED-3, are disposed in openings OH defined in a pixel definition layer PDL, and a hole transport region HTR, an electron transport region ETR, and a second electrode EL2 are each provided as common layers for all light emitting devices ED-1, ED-2, and ED-3. However, embodiments are not limited thereto. Although not illustrated in FIG. 2, in an embodiment, the hole transport region HTR and the electron transport region ETR may each be patterned and provided in the openings OH defined in the pixel definition layer PDL. For example, in an embodiment, the hole transport region HTR, the emission layers EML-R, EML-G, and EML-B, and the electron transport region ETR of the light emitting devices ED-1, ED-2, and ED-3 may each be provided by patterning with an ink jet printing method.

An encapsulation layer TFE may cover the light emitting devices ED-1, ED-2, and ED-3. The encapsulation layer TFE may encapsulate the display device layer DP-ED. The encapsulation layer TFE may be a thin film encapsulation layer. The encapsulation layer TFE may be one layer or a stack of multiple layers. The encapsulation layer TFE may include at least one insulating layer. The encapsulation layer TFE according to an embodiment may include at least one inorganic layer (hereinafter, an encapsulating inorganic layer). The encapsulation layer TFE according to an embodiment may include at least one organic layer (hereinafter, an encapsulating organic layer) and at least one encapsulating inorganic layer.

The encapsulating inorganic layer may protect the display device layer DP-ED from moisture and/or oxygen, and the encapsulating organic layer may protect the display device layer DP-ED from foreign materials such as dust particles. The encapsulating inorganic layer may include silicon nitride, silicon oxy nitride, silicon oxide, titanium oxide, or aluminum oxide, without limitation. The encapsulating organic layer may include an acrylic compound, an epoxy-based compound, etc. The encapsulating organic layer may include a photopolymerizable organic material, without limitation.

The encapsulation layer TFE may be disposed on the second electrode EL2 and may be disposed to fill the openings OH.

Referring to FIG. 1 and FIG. 2, the display apparatus DD may include non-luminous areas NPXA and luminous areas PXA-R, PXA-G, and PXA-B. The luminous areas PXA-R, PXA-G, and PXA-B may each be an area emitting light produced from the light emitting devices ED-1, ED-2, and ED-3, respectively. The luminous areas PXA-R, PXA-G, and PXA-B may be separated from each other on a plane.

The luminous areas PXA-R, PXA-G, and PXA-B may be areas separated from each other by the pixel definition layer PDL. The non-luminous areas NPXA may be areas between neighboring luminous areas PXA-R, PXA-G, and PXA-B and may be areas corresponding to the pixel definition layer PDL. In the disclosure, each of the luminous areas PXA-R, PXA-G, and PXA-B may correspond to a pixel. The pixel definition layer PDL may separate the light emitting devices ED-1, ED-2, and ED-3. The emission layers EML-R, EML-G, and EML-B of the light emitting devices ED-1, ED-2, and ED-3 may be disposed in the openings OH defined in the pixel definition layer PDL and separated from each other.

The luminous areas PXA-R, PXA-G, and PXA-B may be divided into multiple groups according to the color of light produced from each of the light emitting devices ED-1, ED-2, and ED-3. In the display apparatus DD of an embodiment, shown in FIG. 1 and FIG. 2, three luminous areas PXA-R, PXA-G, and PXA-B respectively emitting red light, green light, and blue light are illustrated as an embodiment. For example, the display apparatus DD of an embodiment may include a red luminous area PXA-R, a green luminous area PXA-G, and a blue luminous area PXA-B, which are separated from each other.

In the display apparatus DD according to an embodiment, multiple light emitting devices ED-1, ED-2, and ED-3 may each emit light having different wavelength regions. For example, in an embodiment, the display apparatus DD may include a first light emitting device ED-1 emitting red light, a second light emitting device ED-2 emitting green light, and a third light emitting device ED-3 emitting blue light. For example, each of the red luminous area PXA-R, the green luminous area PXA-G, and the blue luminous area PXA-B of the display apparatus DD may respectively correspond to the first light emitting device ED-1, the second light emitting device ED-2, and the third light emitting device ED-3.

However, embodiments are not limited thereto, and the first to third light emitting devices ED-1, ED-2, and ED-3 may emit light in a same wavelength region, or at least one thereof may emit light in a different wavelength region. For example, the first to third light emitting devices ED-1, ED-2, and ED-3 may all emit blue light.

The luminous areas PXA-R, PXA-G, and PXA-B in the display apparatus DD according to an embodiment may be arranged in a stripe shape. Referring to FIG. 1, multiple red luminous areas PXA-R, multiple green luminous areas PXA-G, and multiple blue luminous areas PXA-B may be arranged along a second directional axis DR2. The red luminous area PXA-R, the green luminous area PXA-G, and the blue luminous area PXA-B may be arranged by turns along a first directional axis DR1.

In FIG. 1 and FIG. 2, the areas of the luminous areas PXA-R, PXA-G, and PXA-B are shown as having a similar size, but embodiments are not limited thereto. The areas of the luminous areas PXA-R, PXA-G, and PXA-B may be different from each other according to a wavelength region of light emitted. The areas of the luminous areas PXA-R, PXA-G, and PXA-B may be areas in a plan view that are defined by the first directional axis DR1 and the second directional axis DR2.

The arrangement type of the luminous areas PXA-R, PXA-G, and PXA-B is not limited to the configuration shown in FIG. 1, and the arrangement order of the red luminous areas PXA-R, the green luminous areas PXA-G, and the blue luminous areas PXA-B may be provided in various combinations according to display quality characteristics which are required for the display apparatus DD. For example, the arrangement type of the luminous areas PXA-R, PXA-G, and PXA-B may be a PENTILE™ arrangement type, or a diamond arrangement type.

In an embodiment, the areas of the luminous areas PXA-R, PXA-G and PXA-B may be different from each other. For example, in an embodiment, an area of the green luminous area PXA-G may be smaller than an area of the blue luminous area PXA-B, but embodiments are not limited thereto.

Hereinafter, FIG. 3 to FIG. 6 are each a schematic cross-sectional view showing a light emitting device according to embodiments. The light emitting device ED according to an embodiment may each include a first electrode EL1, a hole transport region HTR, an emission layer EML, an electron transport region ETR, and a second electrode EL2 stacked in that order.

Figure 3:
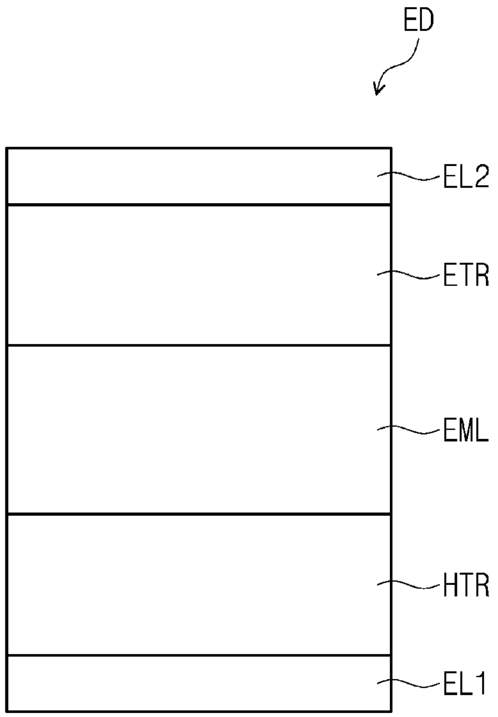
FIG. 3 is a schematic cross-sectional view showing a light emitting device according to an embodiment.
Figure 4:
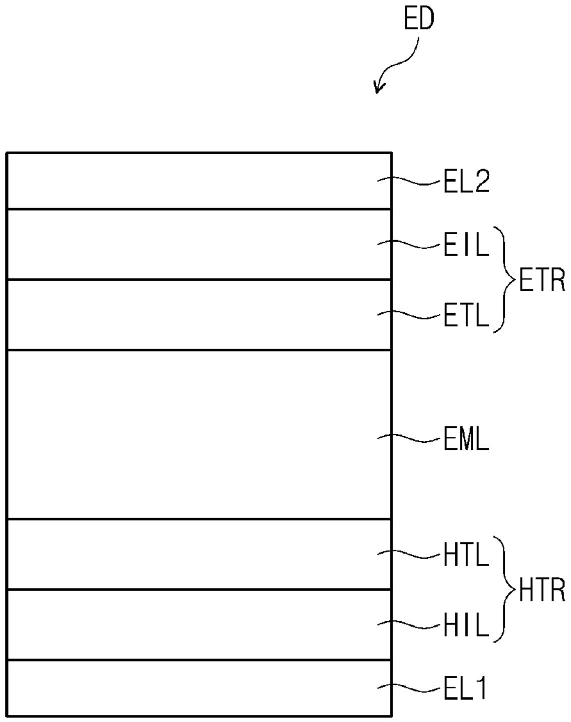
FIG. 4 is a schematic cross-sectional view showing a light emitting device according to an embodiment.
Figure 5:
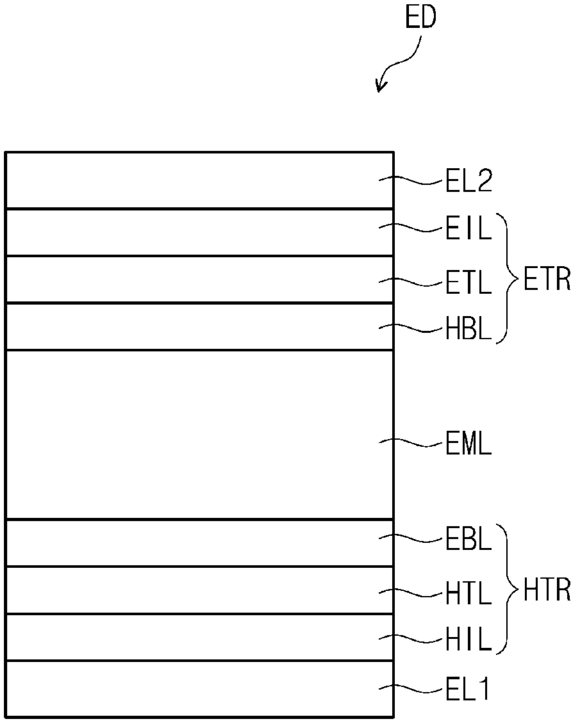
FIG. 5 is a schematic cross-sectional view showing a light emitting device according to an embodiment.
Figure 6:
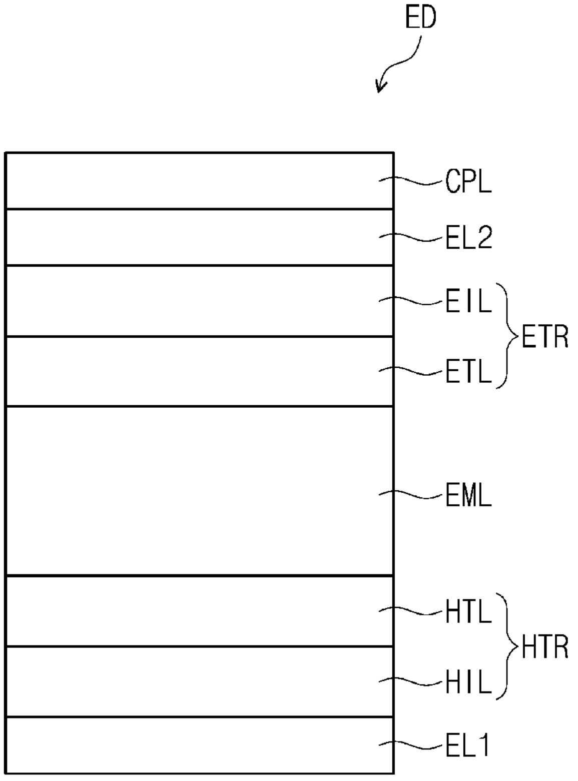
FIG. 6 is a schematic cross-sectional view showing a light emitting device according to an embodiment.

In comparison to FIG. 3, FIG. 4 shows a schematic cross-sectional view of a light emitting device ED of an embodiment, wherein a hole transport region HTR includes a hole injection layer HIL and a hole transport layer HTL, and an electron transport region ETR includes an electron injection layer EIL and an electron transport layer ETL. In comparison to FIG. 3, FIG. 5 shows a schematic cross-sectional view of a light emitting device ED of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. In comparison to FIG. 4, FIG. 6 shows a schematic cross-sectional view of a light emitting device ED of an embodiment, including a capping layer CPL disposed on the second electrode EL2.

The first electrode EL1 has conductivity. The first electrode EL1 may be formed using a metal material, a metal alloy, or a conductive compound. The first electrode EL1 may be an anode or a cathode. However, embodiments are not limited thereto. For example, the first electrode EL1 may be a pixel electrode. The first electrode EL1 may be a transmissive electrode, a transflective electrode, or a reflective electrode. If the first electrode EL1 is a transmissive electrode, the first electrode EL1 may include a transparent metal oxide such as indium tin oxide (ITO), indium zinc oxide (IZO), zinc oxide (ZnO), or indium tin zinc oxide (ITZO). If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, W, compounds thereof, or mixtures thereof (for example, a mixture of Ag and Mg). In another embodiment, the first electrode EL1 may have a structure including multiple layers including a reflective layer or a transflective layer formed using the above materials, and a transmissive conductive layer formed using ITO, IZO, ZnO, or ITZO. For example, the first electrode EL1 may include a three-layer structure of ITO/Ag/ITO. However, embodiments are not limited thereto. The first electrode EL1 may include the above-described metal materials, combinations of two or more metal materials selected from the above-described metal materials, or oxides of the above-described metal materials. A thickness of the first electrode EL1 may be in a range of about 700 Å to about 10,000 Å. For example, the thickness of the first electrode EL1 may be in a range of about 1,000 Å to about 3,000 Å.

The hole transport region HTR is provided on the first electrode EL1. In the light emitting device ED of an embodiment, the hole transport region HTR may include the amine compound of an embodiment.

In the description, the term "substituted or unsubstituted" may mean a group that is substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. Each of the substituents recited above may itself be substituted or unsubstituted. For example, a biphenyl group may be interpreted as an aryl group or as a phenyl group substituted with a phenyl group.

In the description, the term "combined with an adjacent group to form a ring" may mean a group that is bonded to an adjacent group to form a substituted or unsubstituted hydrocarbon ring, or to form a substituted or unsubstituted heterocycle. The hydrocarbon ring may include an aliphatic hydrocarbon ring and an aromatic hydrocarbon ring. The heterocycle may include an aliphatic heterocycle and an aromatic heterocycle. The hydrocarbon ring and the heterocycle may be monocyclic or polycyclic. A ring that is formed by combination of adjacent groups may be combined with another ring to form a spiro structure.

In the description, the term "adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other. For example, in 4,5-dimethylphenanthrene, two methyl groups may be interpreted as "adjacent groups" to each other.

In the description, examples of a halogen atom may include a fluorine atom, a chlorine atom, a bromine atom, or an iodine atom.

In the description, an alkyl group may be a linear, branched, or cyclic type. The number of carbon atoms in the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, an alkenyl group may be a hydrocarbon group including one or more carbon double bonds in the middle or at a terminal end of an alkyl group having two or more carbon atoms. The alkenyl group may be a linear chain or a branched chain. The number of carbon atoms is not specifically limited but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the description, a hydrocarbon ring group may be an optional functional group or a substituent derived from an aliphatic hydrocarbon ring. The hydrocarbon ring group may be a saturated hydrocarbon ring group of 5 to 20 ring-forming carbon atoms.

In the description, a heterocyclic group may include one or more of B, O, N, P, Si, or S as heteroatoms. If a heterocyclic group includes two or more heteroatoms, the two or more heteroatoms may be the same or different. The heterocyclic group may be a monocyclic heterocyclic group or polycyclic heterocyclic group, and the heterocyclic group may be a heteroaryl group. The number of ring-forming carbon atoms in the heterocyclic group may be 2 to 30, 2 to 20, or 2 to 10.

In the description, an aryl group may be an optional functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., without limitation.

In the description, a heteroaryl group may include one or more of B, O, N, P, Si, or S as heteroatoms. If the heteroaryl group includes two or more heteroatoms, the two or more heteroatoms may be the same or different. The heteroaryl group may be a monocyclic heterocyclic group or polycyclic heterocyclic group. The number of ring-forming carbon atoms in the heteroaryl group may be 2 to 30, 2 to 20, or 2 to 10. Examples of the heteroaryl group may include thiophene, furan, pyrrole, imidazole, triazole, pyridine, bipyridine, pyrimidine, triazine, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofurane, phenanthroline, thiazole, isooxazole, oxazole, oxadiazole, thiadiazole, phenothiazine, dibenzosilole, dibenzofuran, etc., without limitation.

In the description, the above description of the aryl group may be applied to an arylene group except that the arylene group is a divalent group. The above description of the heteroaryl group may be applied to a heteroarylene group except that the heteroarylene group is a divalent group.

In the description, a silyl group may include an alkyl silyl group or an aryl silyl group. Examples of the silyl group may include a trimethylsilyl group, a triethylsilyl group, a t-butyldimethylsilyl group, a propyldimethylsilyl group, a triphenylsilyl group, a diphenylsilyl group, a phenylsilyl group, etc., without limitation.

In the description, a thio group may include an alkyl thio group or an aryl thio group. The thio group may be an alkyl group or an aryl group combined with a sulfur atom. Examples of the thio group may include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., without limitation.

In the description, an oxy group may be an alkyl group or an aryl group combined with an oxygen atom. The oxy group may include an alkoxy group or an aryl oxy group. The alkoxy group may be a linear, branched, or cyclic chain. The number of carbon atoms in the alkoxy group is not specifically limited but may be, for example, 1 to 20 or 1 to 10. Examples of the oxy group may include a methoxy group, an ethoxy group, an n-propoxy group, an isopropoxy group, a butoxy group, a pentyloxy group, a hexyloxy group, an octyloxy group, a nonyloxy group, a decyloxy group, a benzyloxy group, etc. However, embodiments are not limited thereto.

In the description, the alkyl group in an alkylthio group, an alkyl sulfoxy group, an alkyl oxy group, an alkyl amino group, an alkyl boron group, an alkyl silyl group, or an alkyl amine group may be the same as the examples of the above-described alkyl group.

In the description, the aryl group in an aryl oxy group, an aryl thio group, an aryl sulfoxy group, an aryl amino group, an aryl boron group, an aryl silyl group, and an aryl amine group may be the same as the examples of the above-described aryl group.

In the description, a direct linkage may be a single bond.

In the description, -∤- and —* each indicate a binding site to a neighboring atom.

In a light emitting device ED of an embodiment, a hole transport region HTR may include an amine compound represented by Formula 1 below. The amine compound may include a substituted or unsubstituted binaphthyl group and a substituted or unsubstituted phenylnaphthyl group, combined with a nitrogen atom. The binaphthyl group may correspond to two naphthyl groups directly bonded. The phenylnaphthyl group may correspond to a phenyl group and a naphthyl group directly bonded.

[Formula 1]

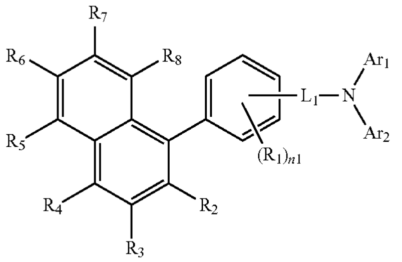

In Formula 1, $L_1$ may be a direct linkage, a substituted or unsubstituted arylene group of 6 to 15 ring-forming carbon atoms, or a substituted or unsubstituted heteroarylene group of 2 to 15 ring-forming carbon atoms. For example, $L_1$ may be a substituted or unsubstituted phenylene group.

In Formula 1, $Ar_1$ may be a substituted or unsubstituted aryl group of 6 to 30 ring-forming carbon atoms, or a substituted or unsubstituted heteroaryl group of 2 to 30 ring-forming carbon atoms, wherein $Ar_1$ may not include an adamantyl group. For example, $Ar_1$ may not be a substituted or unsubstituted adamantyl group, and $Ar_1$ may not include a substituted or unsubstituted adamantyl group as a substituent. If $Ar_1$ is an aryl group, the aryl group may not be a substituted or unsubstituted adamantyl group, and if $Ar_1$ is a substituted aryl group, a substituent of the aryl group may not include a substituted or unsubstituted adamantyl group. If $Ar_1$ is a substituted heteroaryl group, a substituent of the heteroaryl group may not include a substituted or unsubstituted adamantyl group.

In an embodiment, $Ar_1$ may be a substituted or unsubstituted phenyl group, a substituted or unsubstituted naphthyl group, a substituted or unsubstituted terphenyl group, a substituted or unsubstituted phenanthrene group, a substituted or unsubstituted triphenylene group, a substituted or unsubstituted carbazole group, a substituted or unsubstituted dibenzofuran group, a substituted or unsubstituted dibenzothiophene group, a substituted or unsubstituted naphthobenzofuran group, or a substituted or unsubstituted benzonaphthothiophene group. However, these are only examples, and embodiments are not limited thereto.

In Formula 1, n1 may be an integer from 0 to 4. When n1 is 2 or more, multiple $R_1$ groups may be the same, or at least one thereof may be different. In Formula 1, $R_1$ may be a hydrogen atom, a deuterium atom, a halogen atom, a substituted or unsubstituted oxy group, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

For example, n1 may be 2 or more, and any one of multiple $R_1$ groups may be an aryl oxy group and combined with an adjacent another $R_1$ to form a ring. Any one of $R_1$ represented by a phenoxy group may be combined with an adjacent another $R_1$ to form a substituted or unsubstituted dibenzofuran. However, these are only examples, and embodiments are not limited thereto.

In Formula 1, an least one of $R_2$ to $R_8$ may be a substituted or unsubstituted aryl group of 6 to 30 ring-forming carbon atoms, or a substituted or unsubstituted heteroaryl group of 2 to 30 ring-forming carbon atoms, and the remainder of $R_2$ to $R_8$ may each independently be a hydrogen atom, a deuterium atom, a halogen atom, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms. In an embodiment, at least one of $R_4$ and $R_8$ may be a substituted or unsubstituted phenyl group, a substituted or unsubstituted naphthyl group, a substituted or unsubstituted pyridine group, a substituted or unsubstituted carbazole group, a substituted or unsubstituted dibenzofuran group, or a substituted or unsubstituted dibenzothiophene group.

A phenyl group including $R_1$ and a naphthyl group including $R_2$ to $R_8$ may be substituted or unsubstituted phenylnaphthyl groups. In Formula 1, $Ar_2$ may be a substituted or unsubstituted binaphthyl group. In Formula 1, $Ar_2$ may be a group represented by Formula 2.

[Formula 2]

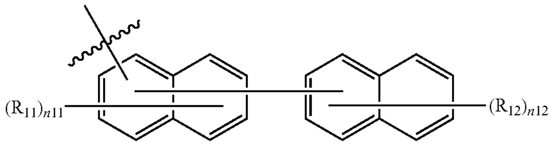

In Formula 2, n11 may be an integer from 0 to 6, and n12 may be an integer from 0 to 7. If n11 is 2 or more, multiple $R_{11}$ groups may be the same, or at least one thereof may be different. If n12 is 2 or more, multiple $R_{12}$ groups may be the same, or at least one thereof may be different.

In Formula 1, $R_{11}$ and $R_{12}$ may each independently be a hydrogen atom, a deuterium atom, a halogen atom, a substituted or unsubstituted alkyl group of 1 to 15 ring-forming carbon atoms, a substituted or unsubstituted aryl group of 6 to 30 ring-forming carbon atoms, or a substituted or unsubstituted heteroaryl group of 2 to 30 ring-forming carbon atoms. For example, $R_{11}$ and $R_{12}$ may each independently be a fluorine atom or a methyl group.

The amine compound represented by Formula 1 may include a deuterium atom. In an embodiment, at least one of $R_1$ to $R_8$ may include a deuterium atom as a substituent, or at least one of $R_{11}$ and $R_{12}$ may be a deuterium atom.

In Formula 1, the nitrogen atom to which $Ar_2$ is bonded and the naphthyl group including $R_{12}$ may be combined with the same benzene ring among two benzene rings of the naphthyl group including $R_{11}$. In another embodiment, the nitrogen atom to which $Ar_2$ is bonded and the naphthyl group including $R_{12}$ may be combined with different benzene rings among two benzene rings of the naphthyl group including $R_{11}$. For example, in an embodiment, the group represented by Formula 2 may be represented by any one of Formula 2-1 to Formula 2-9. In Table 1, Formula 2-1 to Formula 2-9 are shown.

TABLE 1

[Formula 2-1]

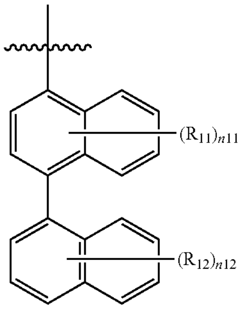

TABLE 1-continued
[Formula 2-2]
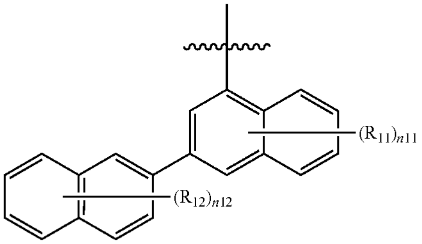
[Formula 2-3]
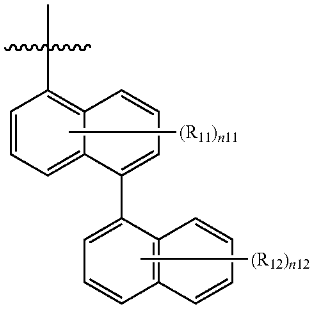
[Formula 2-4]
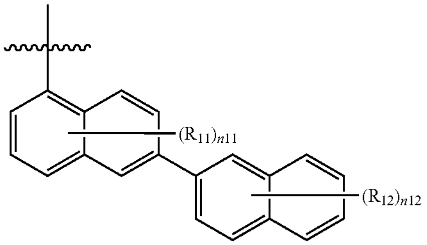
[Formula 2-5]
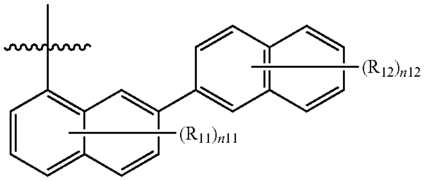
[Formula 2-6]
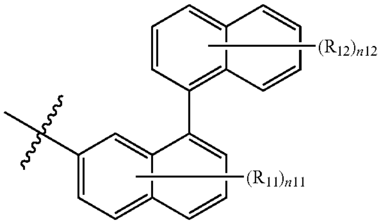
[Formula 2-7]
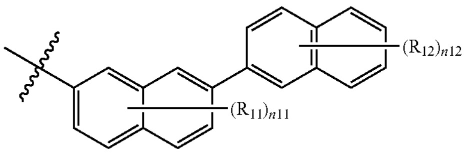
[Formula 2-8]
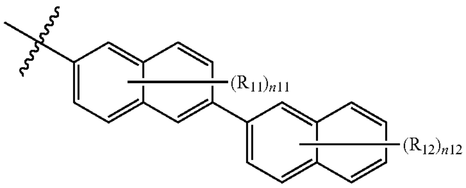

TABLE 1-continued

[Formula 2-9]

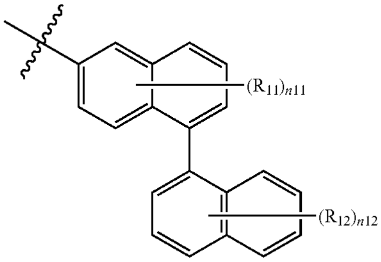

In Formula 2-1 to Formula 2-9, n11, n12, $R_{11}$, and $R_{12}$ may be the same as defined in Formula 2. Formula 2-1 and Formula 2-2 represent cases where the nitrogen atom to which $Ar_2$ is bonded and the naphthyl group including $R_{12}$ are combined with the same benzene ring among two benzene rings of the naphthyl group including $R_{11}$. Formula 2-3 to Formula 2-9 represent cases where the nitrogen atom to which $Ar_2$ is bonded and the naphthyl group including $R_{12}$ are combined with different benzene rings among two benzene rings of the naphthyl group including $R_{11}$.

According to an embodiment, $Ar_1$ may be a group represented by any one of Ar1-1 to Ar1-6 below. Ar1-1 represents a case where $Ar_1$ is a substituted or unsubstituted phenyl group, and Ar1-2 represents a case where $Ar_1$ is a substituted or unsubstituted naphthyl group. Ar1-3 represents a case where $Ar_1$ is an unsubstituted triphenylene group, and Ar1-4 represents a case where $Ar_1$ is an unsubstituted phenanthrene group. Ar1-5 represents a case where $Ar_1$ is a substituted or unsubstituted carbazole group, a substituted or unsubstituted dibenzofuran group, or a substituted or unsubstituted dibenzothiophene group. Ar1-6 represents a case where $Ar_1$ is an unsubstituted napthobenzofuran group or an unsubstituted benzonaphthothiophene group.

Ar1-1

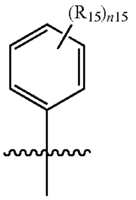

Ar1-2

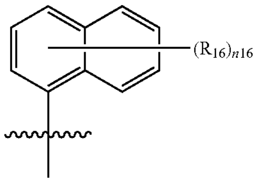

Ar1-3

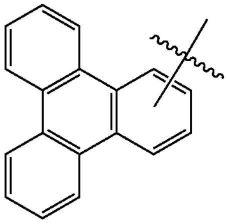

-continued

Ar1-4

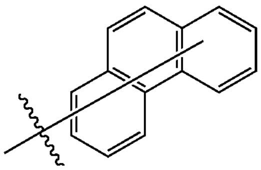

Ar1-5

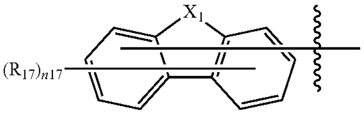

Ar1-6

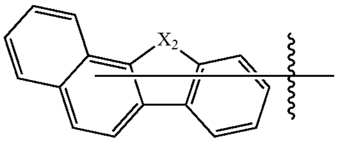

In Ar1-1, n15 may be an integer from 0 to 5. When n15 is 2 or more, multiple $R_{15}$ groups may be the same, or at least one thereof may be different. In Ar1-1, $R_{15}$ may be a hydrogen atom, a substituted or unsubstituted alkyl group of 1 to 10 carbon atoms, or a substituted or unsubstituted aryl group of 6 to 30 ring-forming carbon atoms. For example, $R_{15}$ may be a methyl group, a substituted or unsubstituted phenyl group, or a substituted or unsubstituted naphthyl group.

In Ar1-2, n16 may an integer from 0 to 7. When n16 is 2 or more, multiple $R_{16}$ groups may be the same, or at least one thereof may be different. In Ar1-2, $R_{16}$ may be a hydrogen atom, a halogen atom, or a substituted or unsubstituted aryl group of 6 to 30 ring-forming carbon atoms. For example, $R_{16}$ may be a fluorine atom or a substituted or unsubstituted biphenyl group.

In Ar1-5, $X_1$ may be $N(R_{18})$, O, or S. In Ar1-5, n17 may be an integer from 0 to 7, and $R_{17}$ and $R_{18}$ may each independently be a hydrogen atom, or a substituted or unsubstituted aryl group of 6 to 30 ring-forming carbon atoms. When n17 is 2 or more, multiple $R_{12}$ groups may be the same, or at least one thereof may be different. For example, $R_{17}$ and $R_{18}$ may each independently be a substituted or unsubstituted phenyl group. In Ar1-6, $X_2$ may be O or S.

In an embodiment, the amine compound represented by Formula 1 may be represented by Formula 1-A or Formula 1-B. Formula 1-A represents a case where the nitrogen atom to which $Ar_2$ is bonded and the naphthyl group including $R_{12}$ are combined with a same benzene ring of the naphthyl group including $R_{11}$. Formula 1-B represents a case where the nitrogen atom to which $Ar_2$ is bonded and the naphthyl group including $R_{12}$ are combined with different benzene rings of the naphthyl group including $R_{11}$. Formula 1-A corresponds to a case of Formula 1 where $Ar_2$ is a group represented by Formula 2-1 or Formula 2-2. Formula 1-B corresponds to a case of Formula 1 where $Ar_2$ is a group represented by any one of Formula 2-3 to Formula 2-9.

[Formula 1-A]

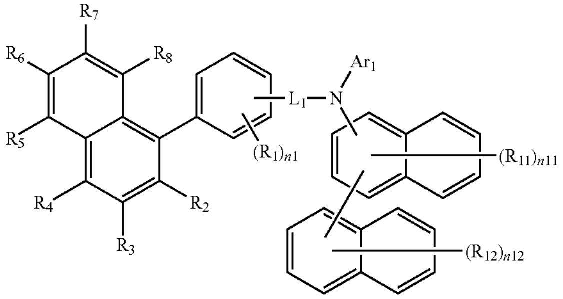

[Formula 1-B]

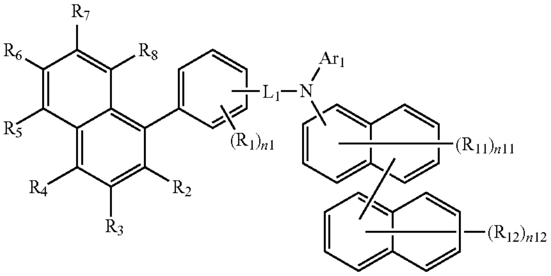

In Formula 1-A and Formula 1-B, $Ar_1$, $L_1$, n1, n11, n12, $R_1$ to $R_8$, $R_{11}$, and $R_{12}$ may be the same as defined in Formula 1 and Formula 2.

In an embodiment, the amine compound represented by Formula 1-A may be represented by Formula 1-A1 or Formula 1-A2. Formula 1-A1 represents a case of Formula 1-A where the nitrogen atom and the naphthyl group including $R_{12}$ are combined with two carbon atoms at para positions among the ring-forming carbon atoms of the naphthyl group including $R_{11}$. Formula 1-A2 represents a case of Formula 1-A where the nitrogen atom and the naphthyl group including $R_{12}$ are combined with two carbon atoms at meta positions among the ring-forming carbon atoms of the naphthyl group including $R_{11}$.

[Formula 1-A1]

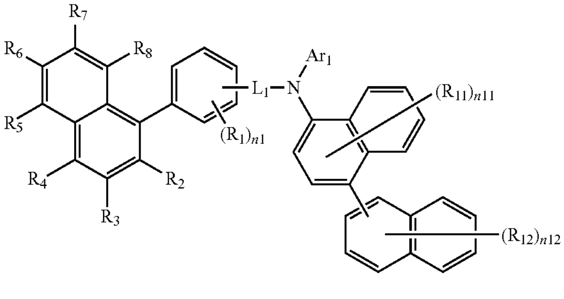

-continued

[Formula 1-A2]

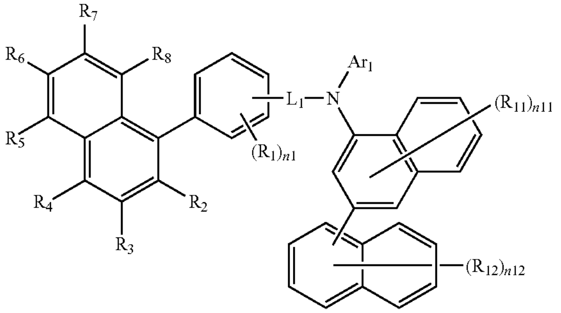

In Formula 1-A1 and Formula 1-A2, $Ar_1$, $L_1$, n1, n11, n12, $R_1$ to $R_8$, $R_{11}$, and $R_{12}$ may be the same as defined in Formula 1 and Formula 2.

In an embodiment, the amine compound represented by Formula 1-B may be represented by Formula 1-B1 or Formula 1-B2. Formula 1-B1 represents a case where $Ar_2$ is a group represented by any one of Formula 2-6 to Formula 2-9. Formula 1-B2 represents a case where $Ar_2$ is a group represented by any one of Formula 2-3 to Formula 2-5.

[Formula 1-B1]

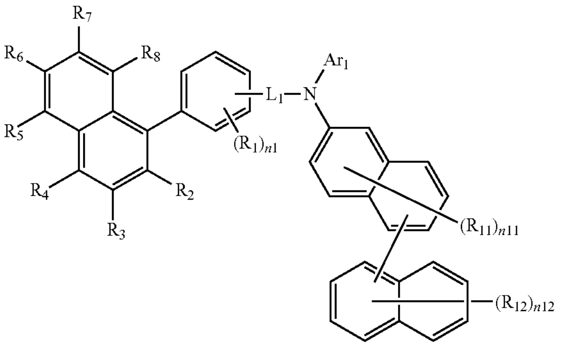

[Formula 1-B2]

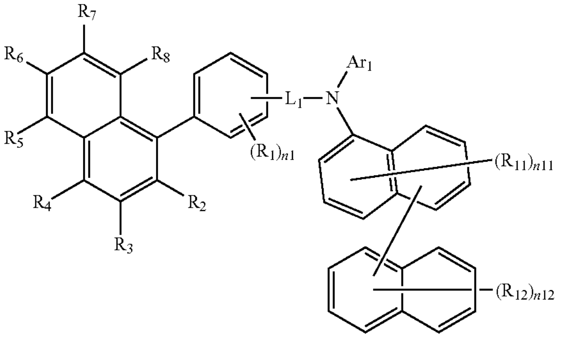

In Formula 1-B1 and Formula 1-B2, $Ar_1$, $L_1$, n1, n11, n12, $R_1$ to $R_8$, $R_{11}$, and $R_{12}$ may be the same as defined in Formula 1 and Formula 2.

In an embodiment, the amine compound represented by Formula 1 may be represented by Formula 1-C1 or Formula 1-C2. Formula 1-C1 and Formula 1-C2 each represent cases of Formula 1 where $L_1$ is a direct linkage. Formula 1-C1 represents a case of Formula 1 where the nitrogen atom and the naphthyl group including $R_2$ to $R_8$ are combined with two carbon atoms at para positions among the ring-forming carbon atoms of the phenyl group including $R_1$. The nitrogen atom is combined with any carbon atom among the two carbon atoms at para positions, and the naphthyl group including $R_2$ to $R_8$ is combined with the remaining carbon atom.

Formula 1-C2 represents a case of Formula 1 where the nitrogen atom and the naphthyl group including $R_2$ to $R_8$ are combined with two carbon atoms at meta positions among the ring-forming carbon atoms of the phenyl group including $R_1$. The nitrogen atom is combined with any carbon atom among the two carbon atoms at meta positions, and the naphthyl group including $R_2$ to $R_8$ is combined with the remaining carbon atom.

[Formula 1-C1]

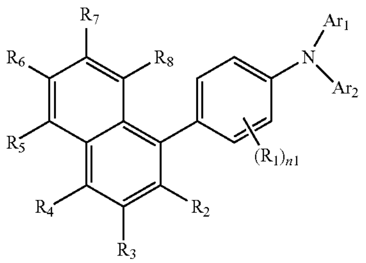

[Formula 1-C2]

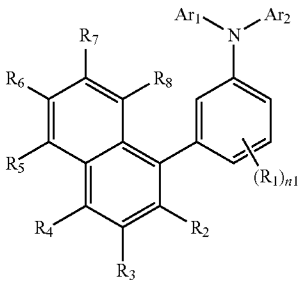

In Formula 1-C1 and Formula 1-C2, $Ar_1$, Are, n1, and $R_1$ to $R_8$ may be the same as defined in Formula 1.

The amine compound of an embodiment, represented by Formula 1, may be any one selected from Compound Group 1. The hole transport region HTR of the light emitting device ED of an embodiment may include at least one of the amine compounds in Compound Group 1.

[Compound Group 1]

1

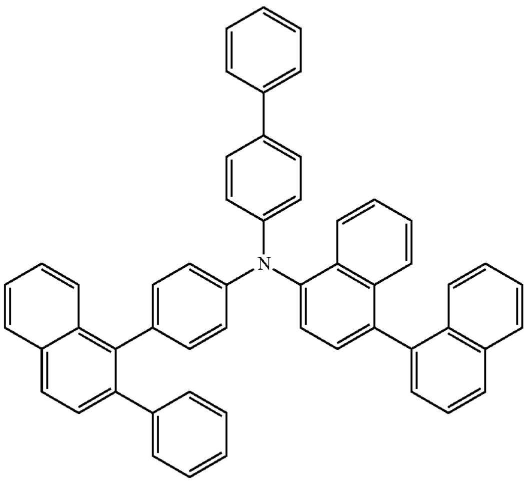

2

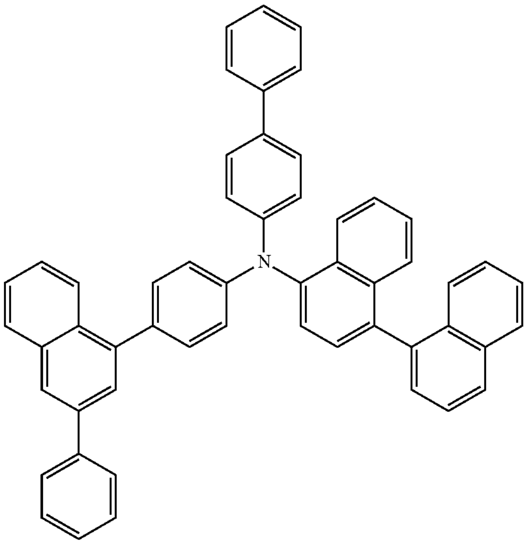

3

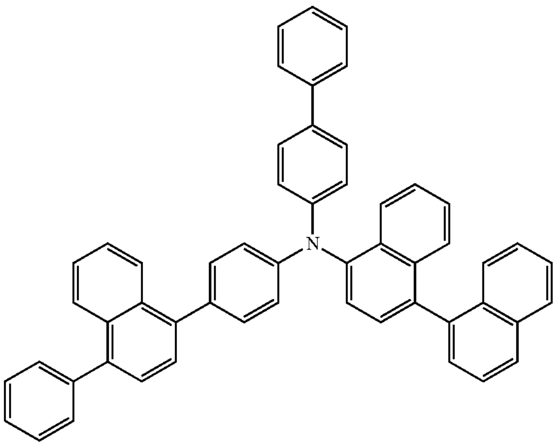

-continued
4
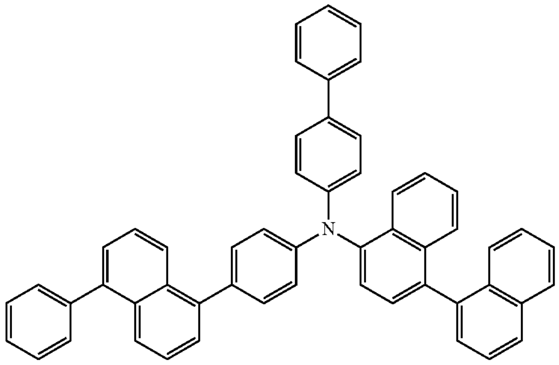
5
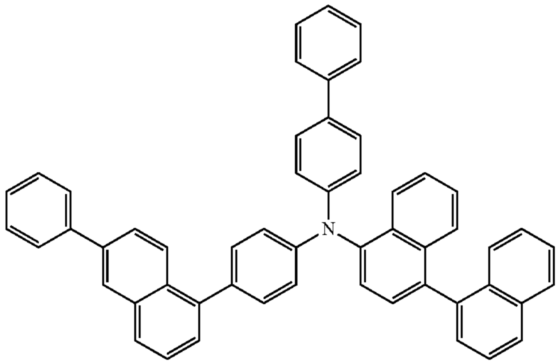
6
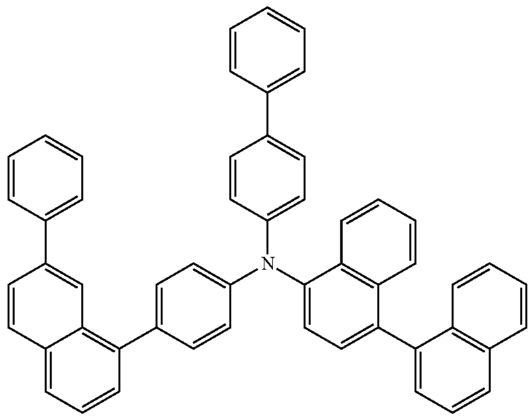
7
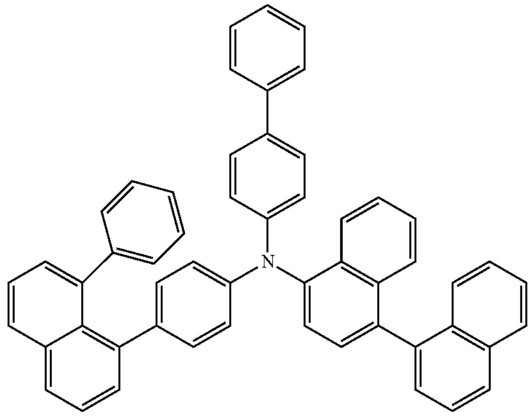
-continued
8
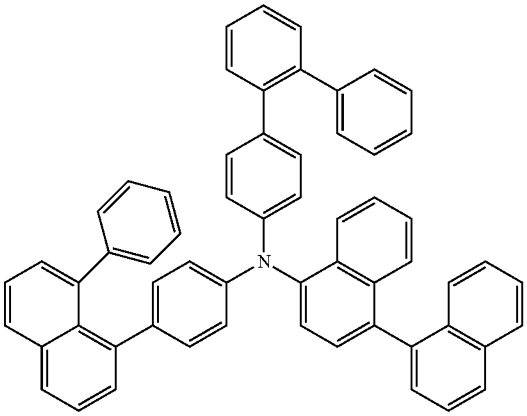
9
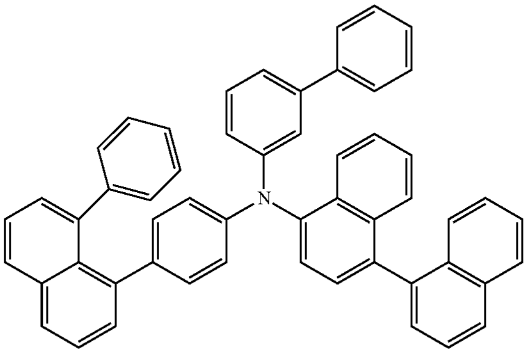
10
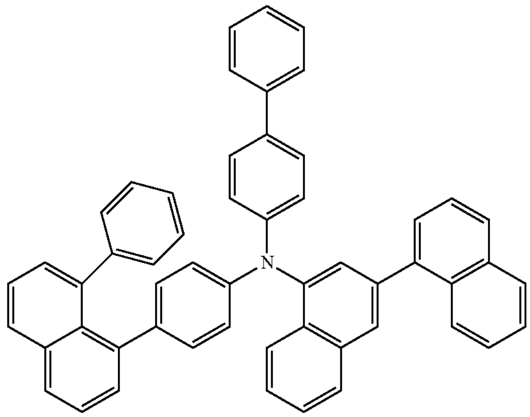
11
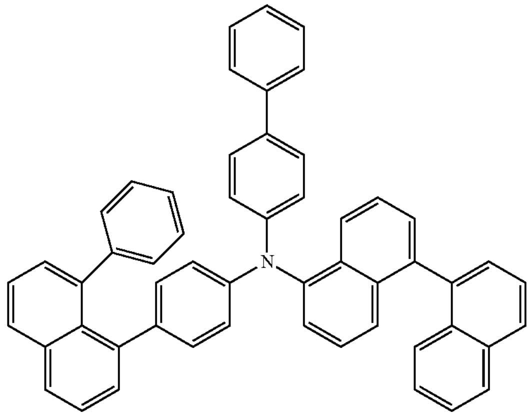

-continued
12
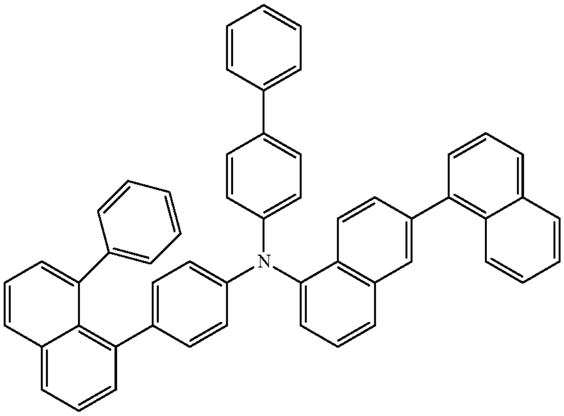
13
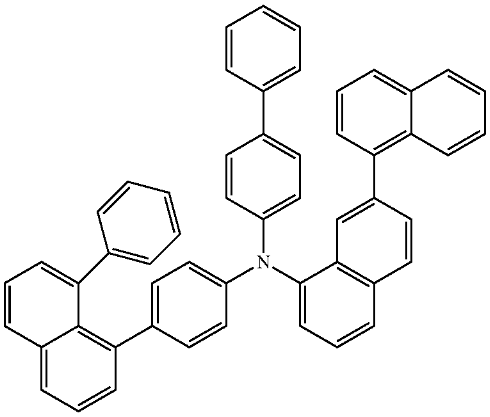
14
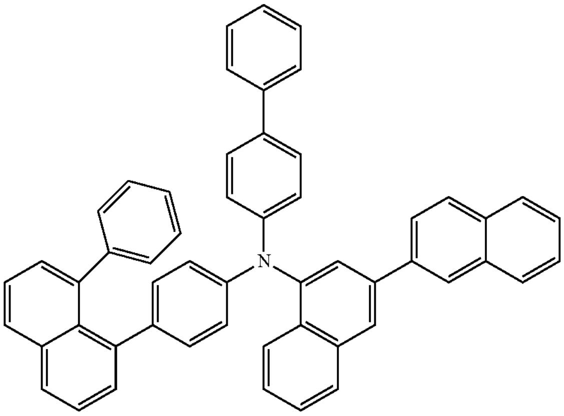
-continued
15
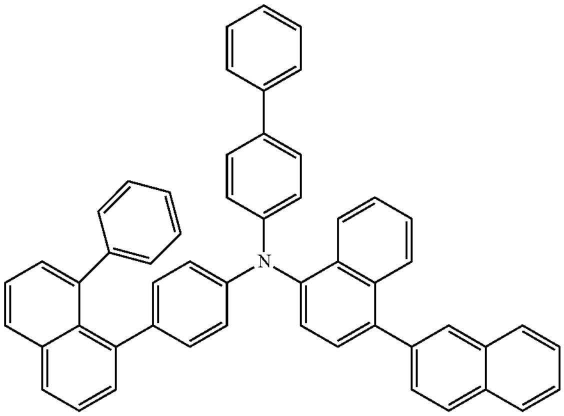
16
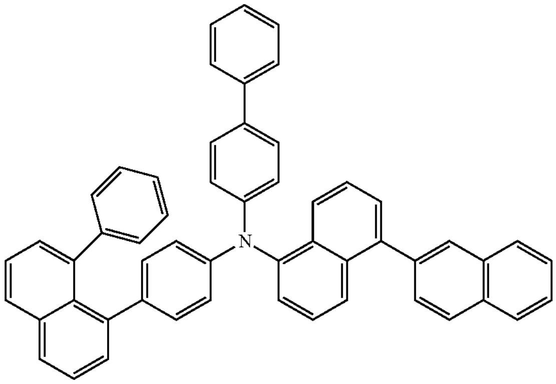
17
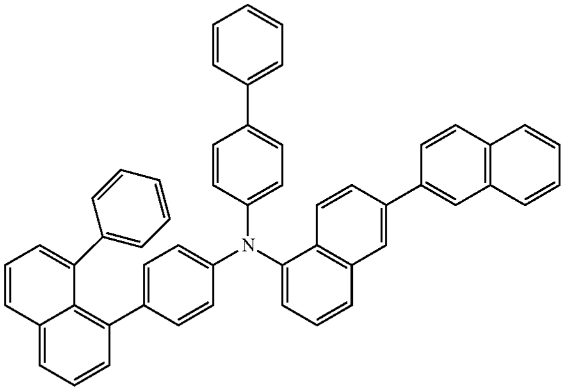

-continued
18
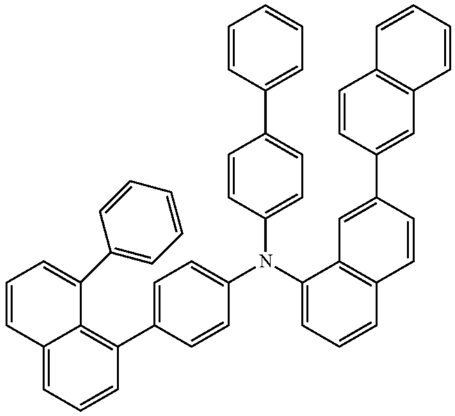
19
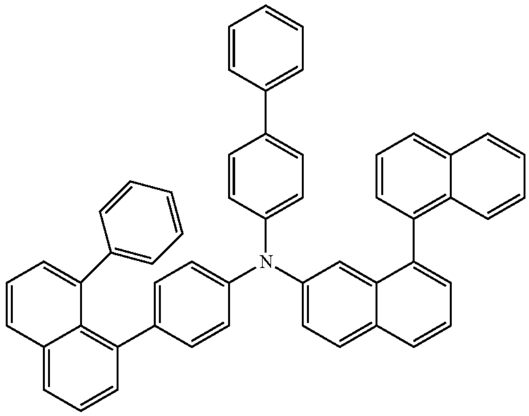
20
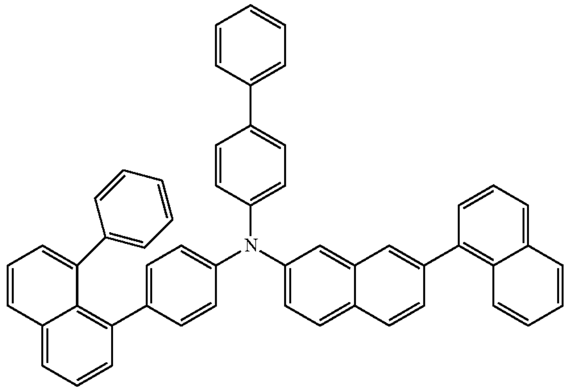
-continued
21
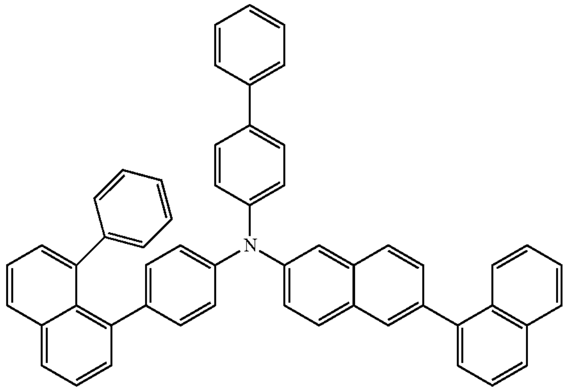
22
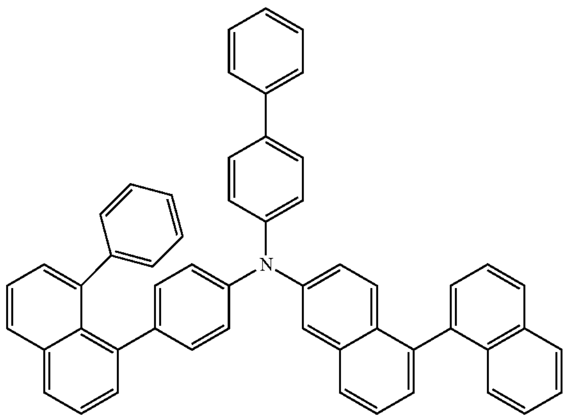
23
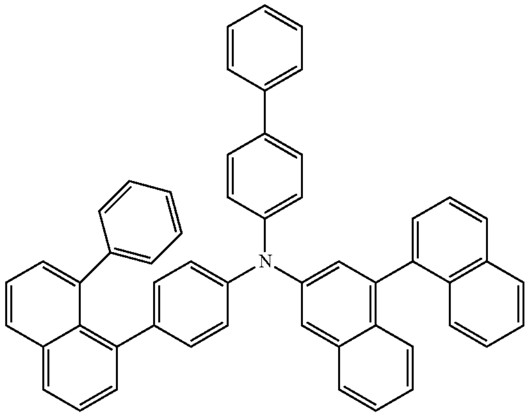

-continued
24
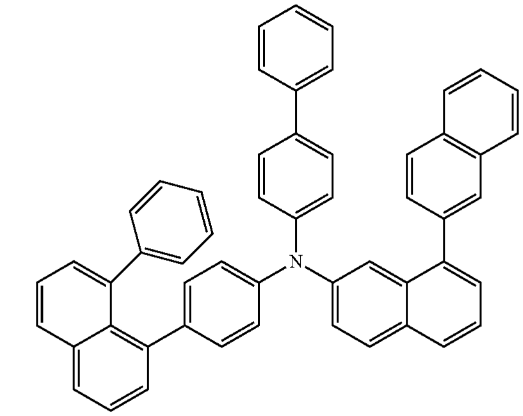
25
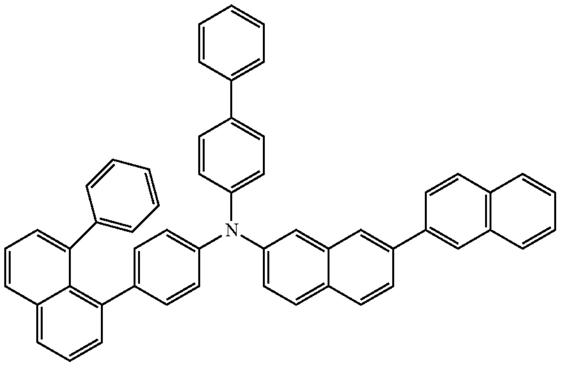
26
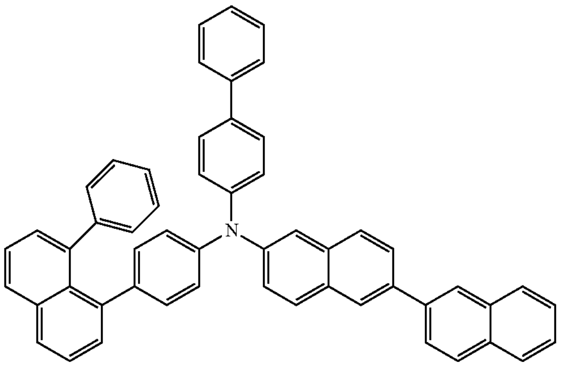
27
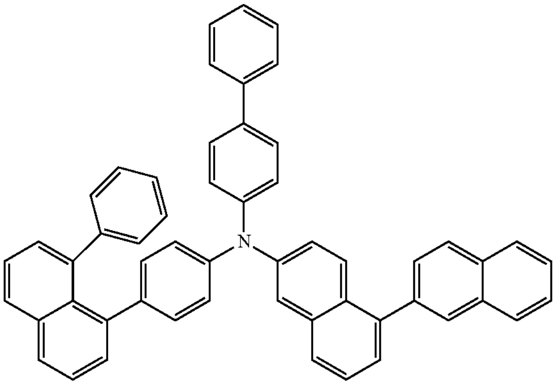
-continued
28
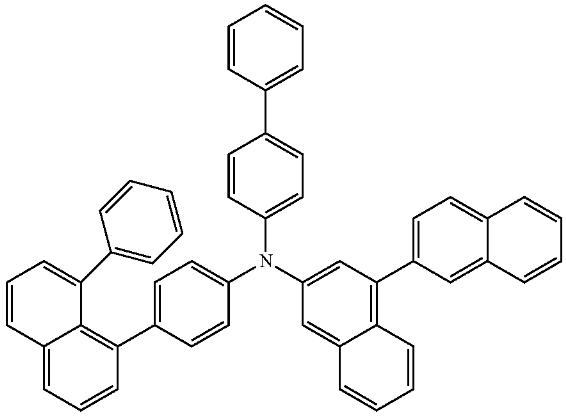
29
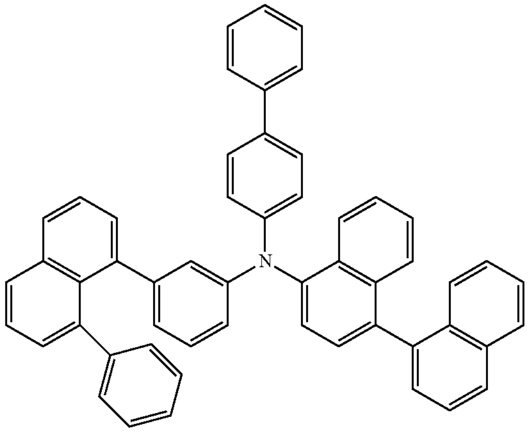
30
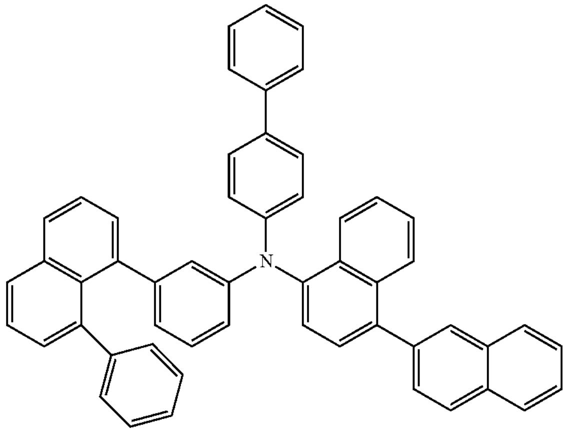

-continued
31
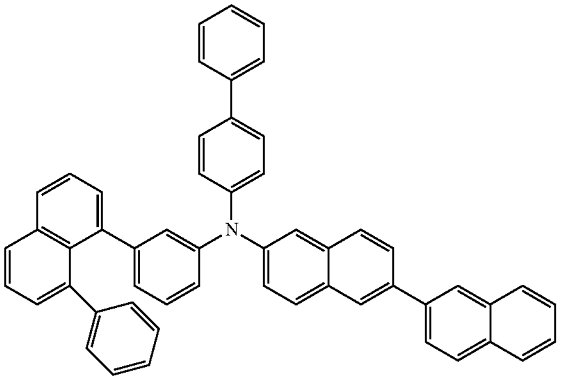
32
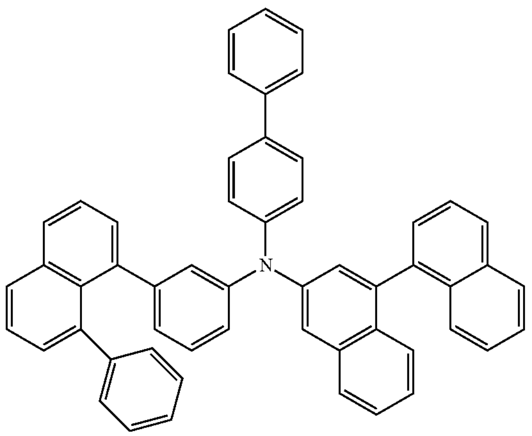
33
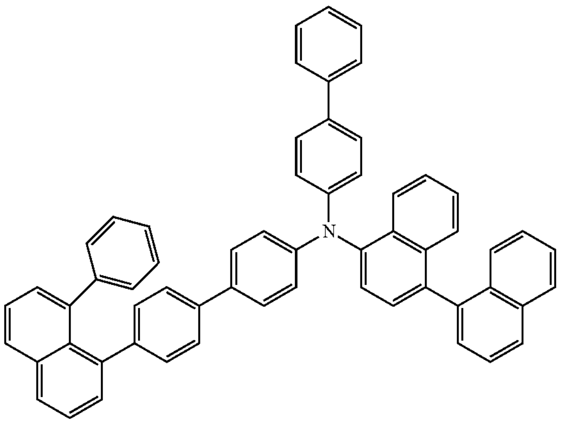
-continued
34
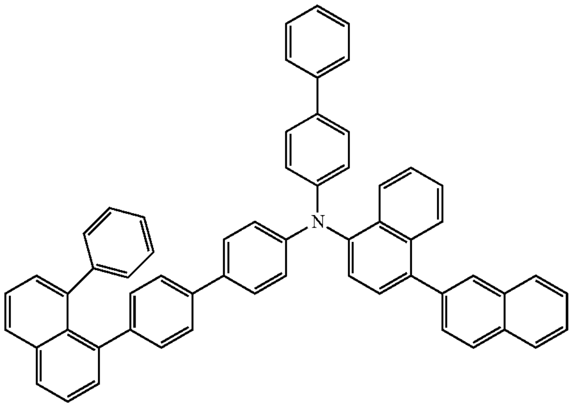
35
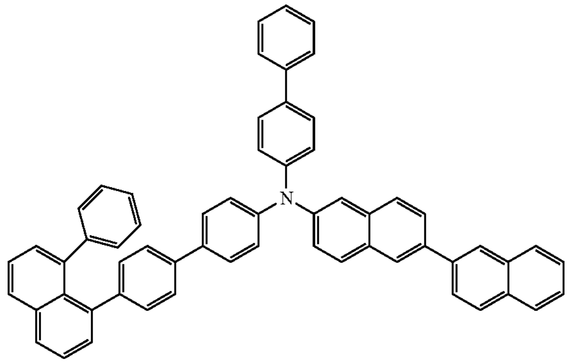
36
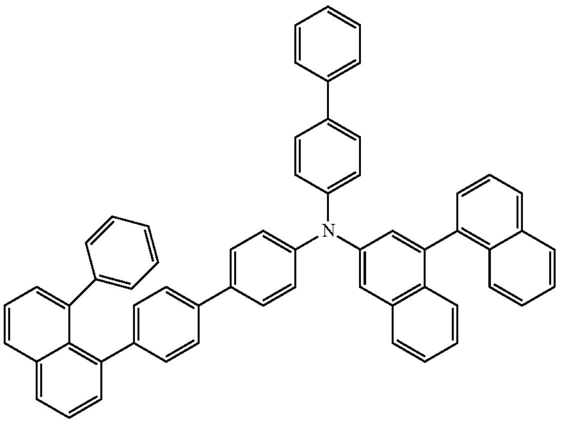

-continued
37
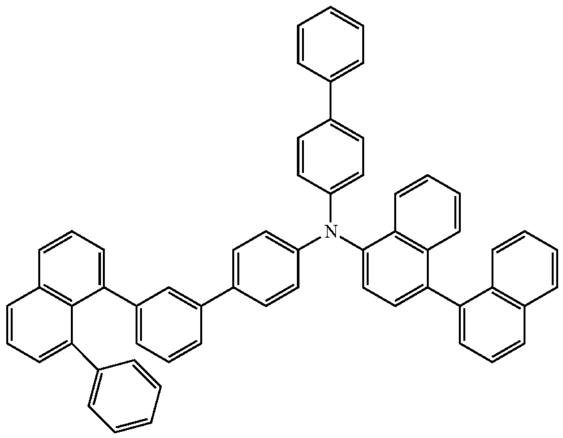
38
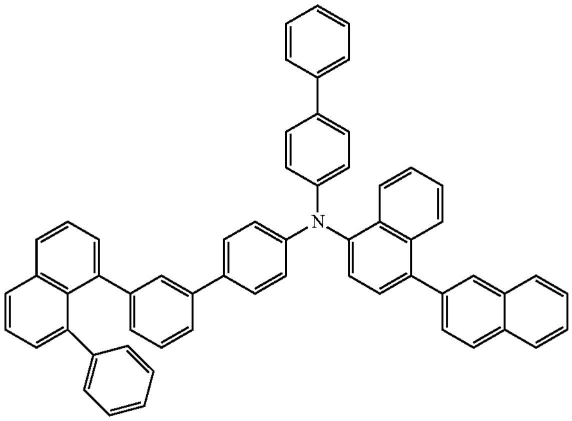
39
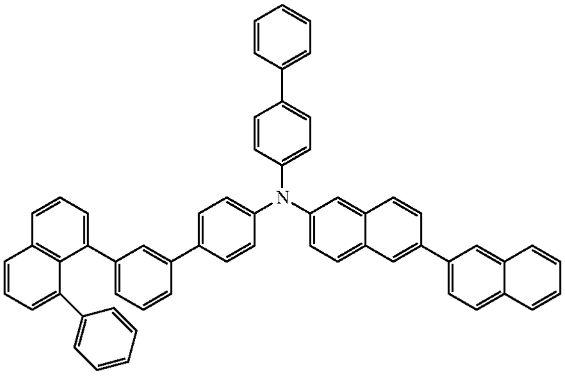
-continued
40
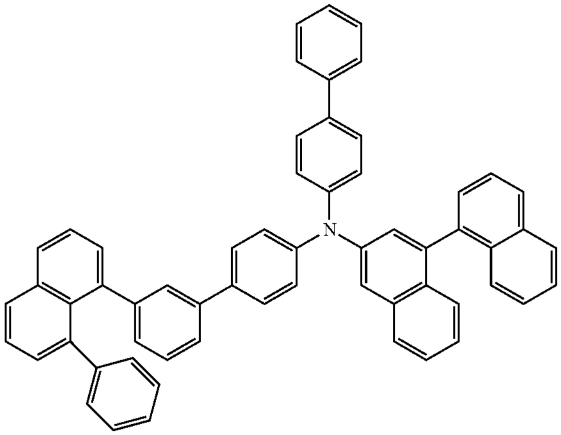
41
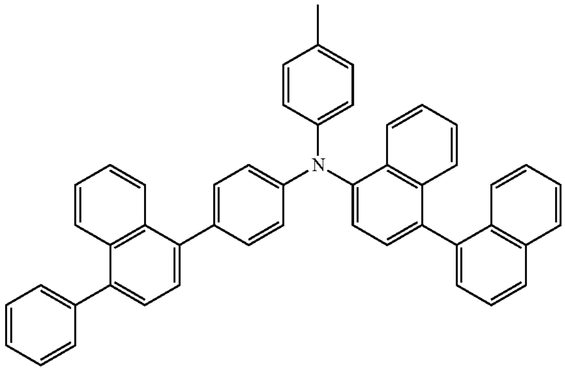
42
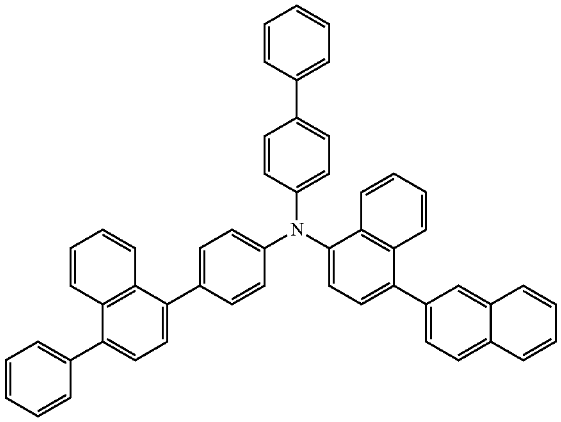

43
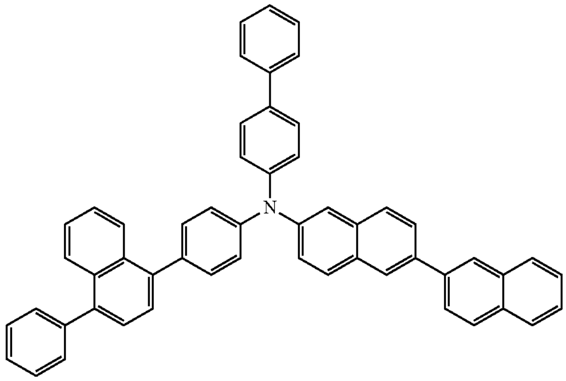
44
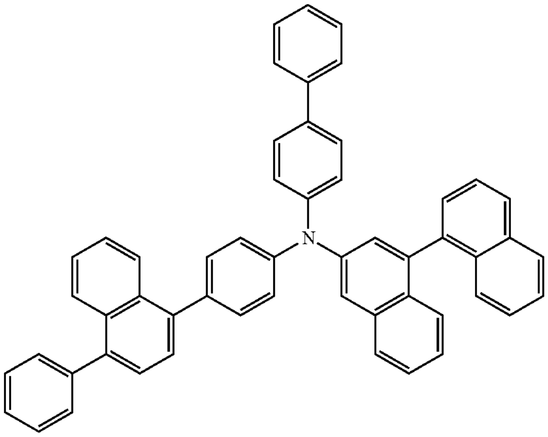
45
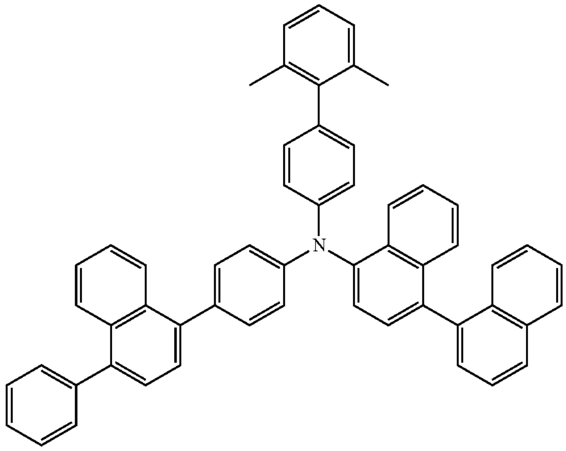
46
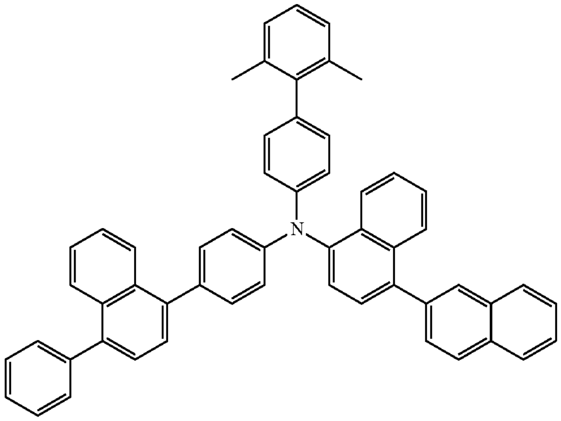
47
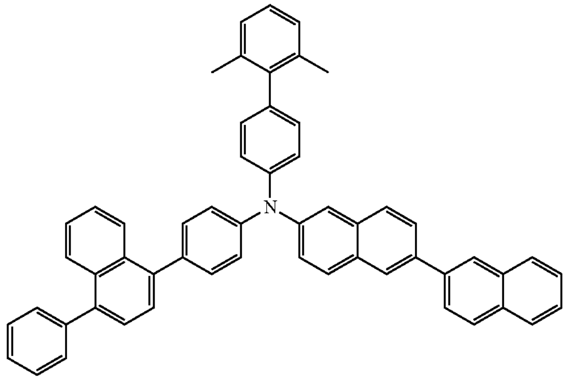
48
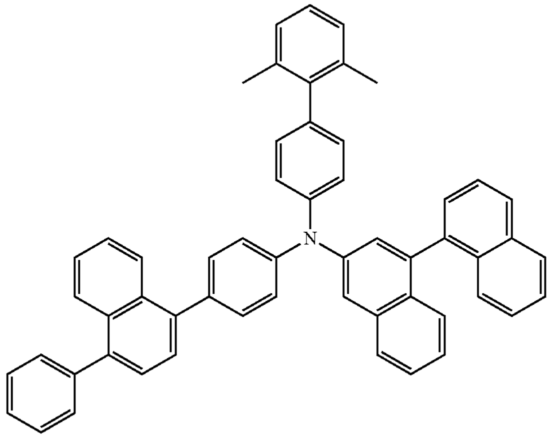

-continued
49
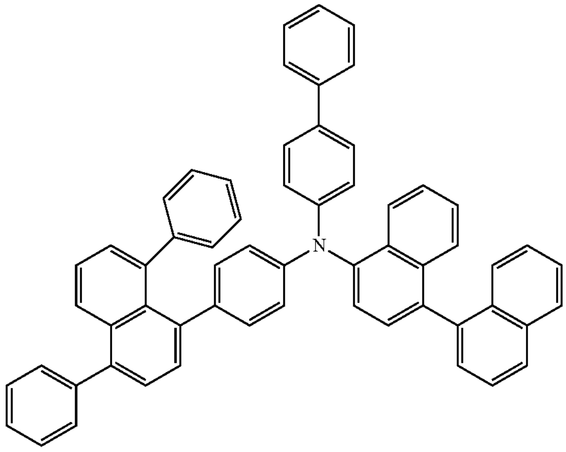
50
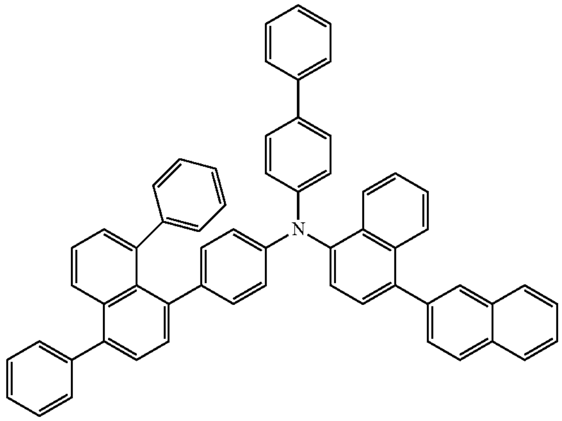
51
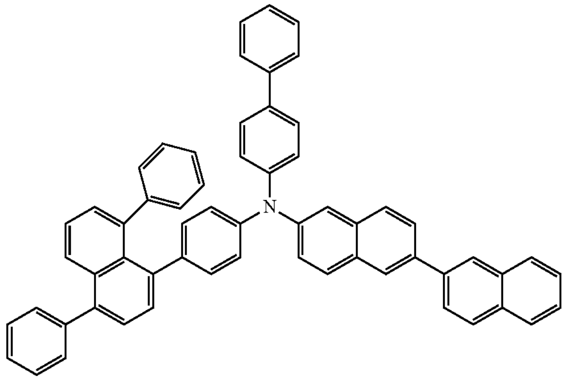
-continued
52
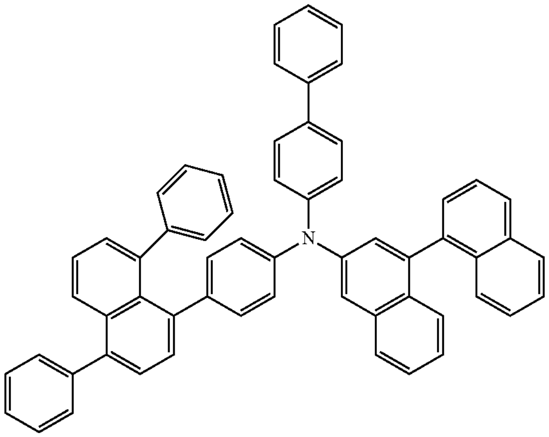
53
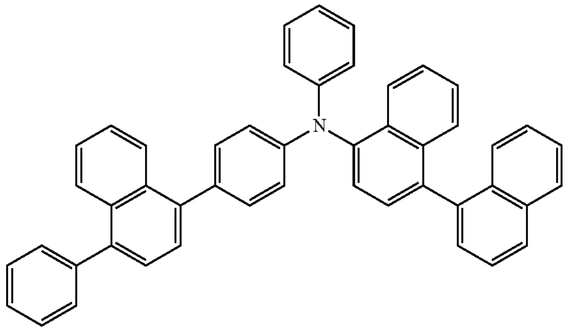
54
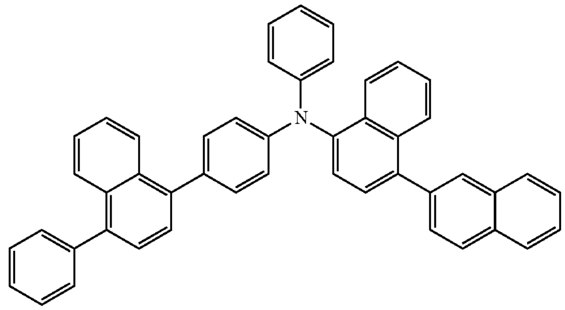
55
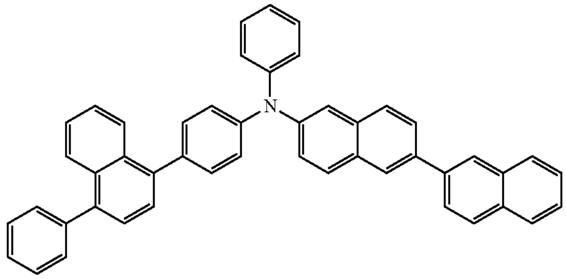

-continued
56
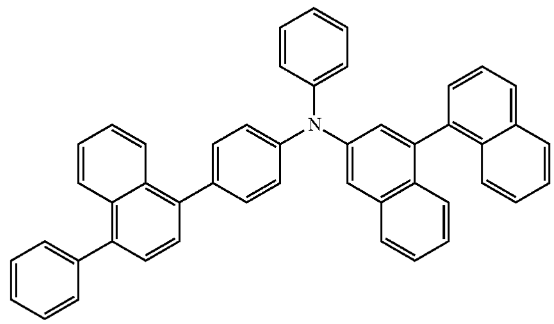
57
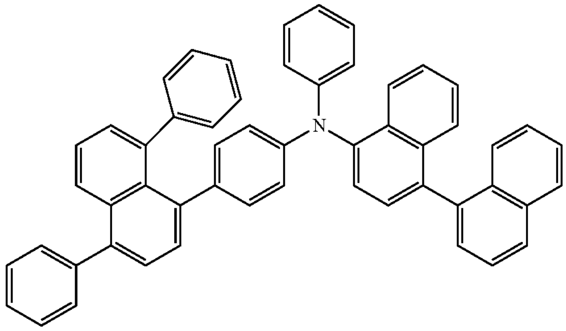
58
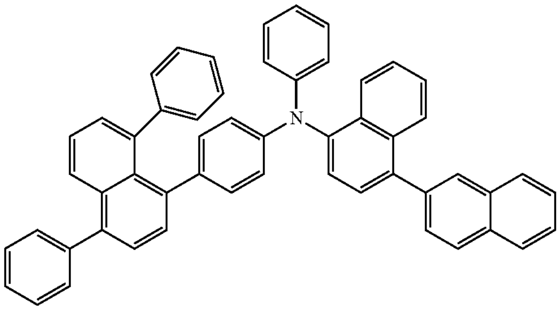
59
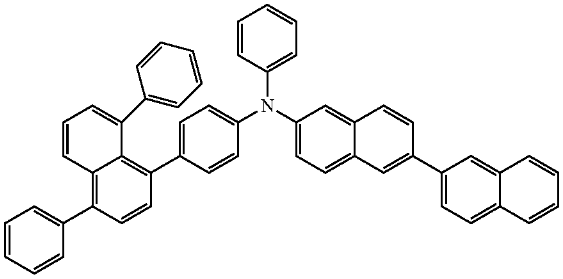
-continued
60
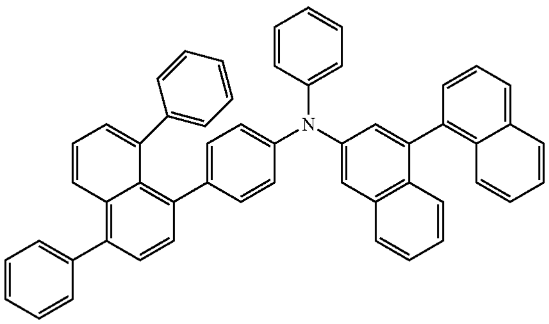
61
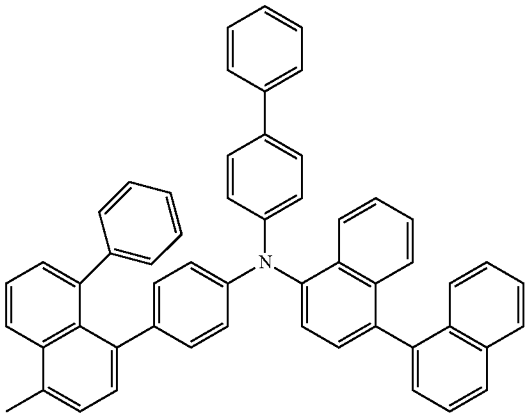
62
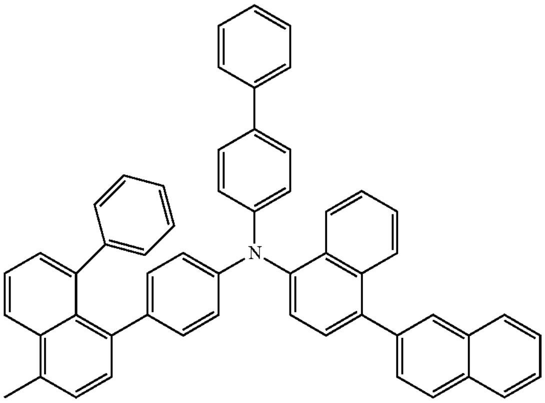
63
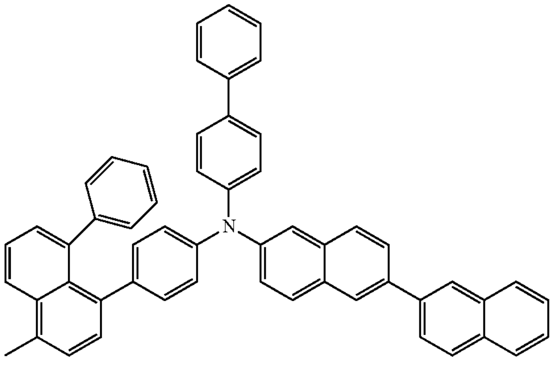

-continued
64
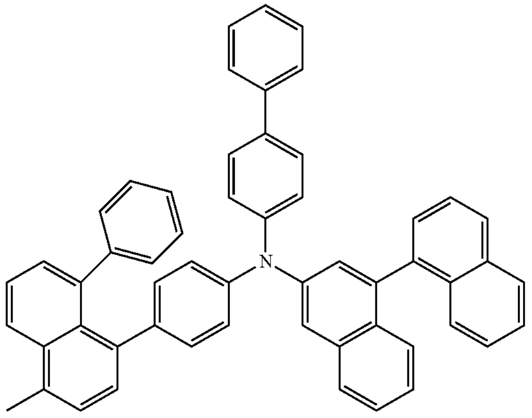
65
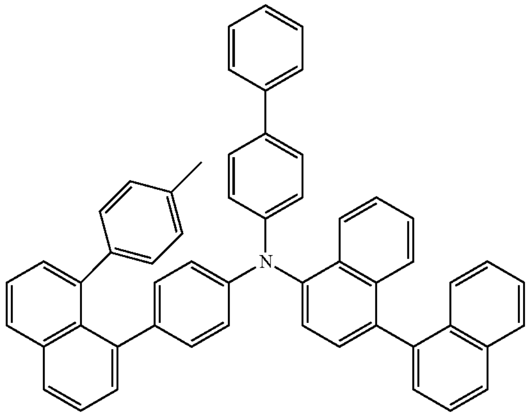
66
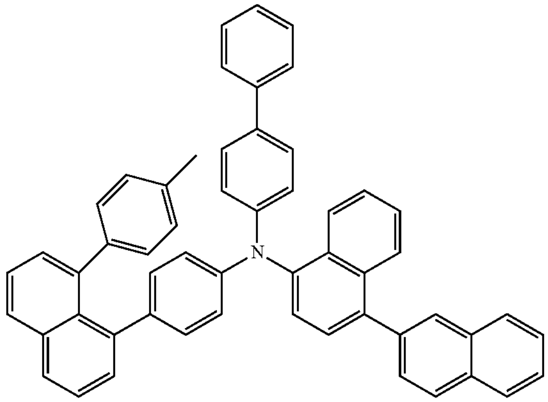
-continued
67
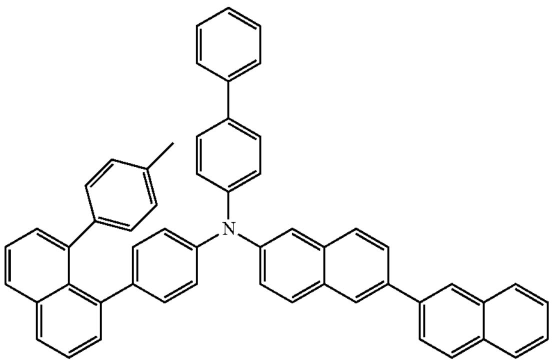
68
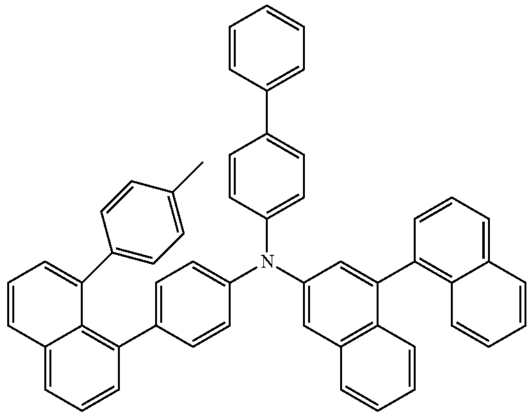
69
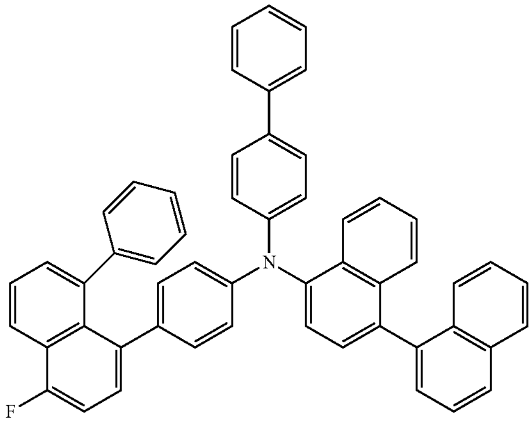

-continued
70
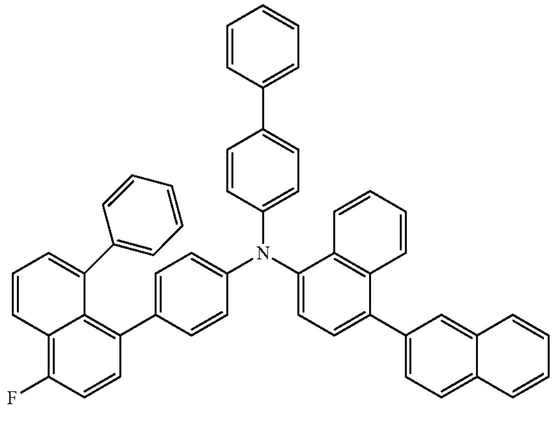
71
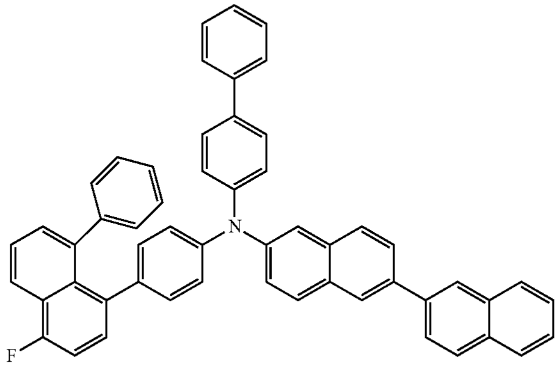
72
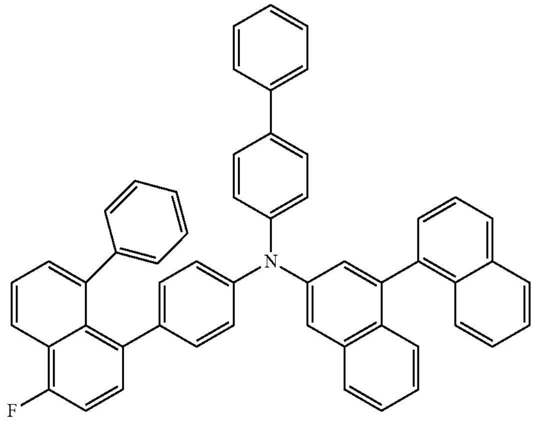
-continued
73
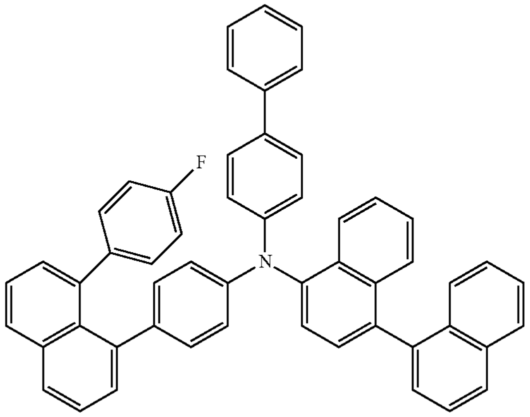
74
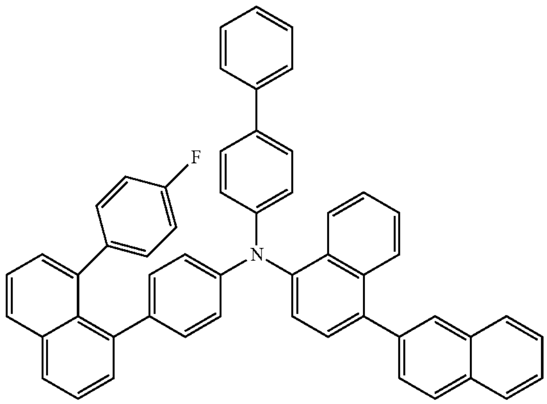
75
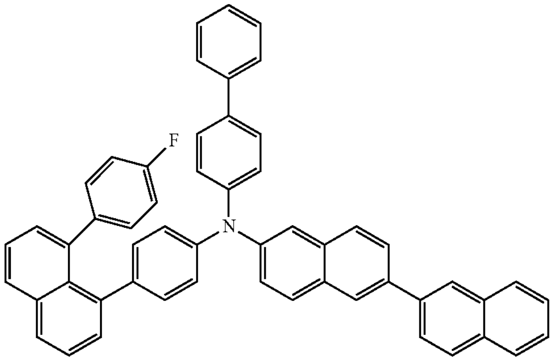

-continued
76
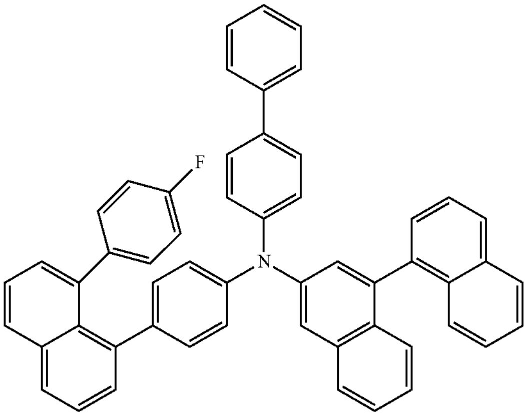
77
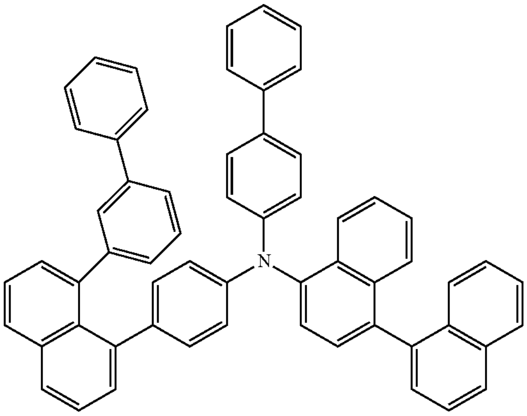
78
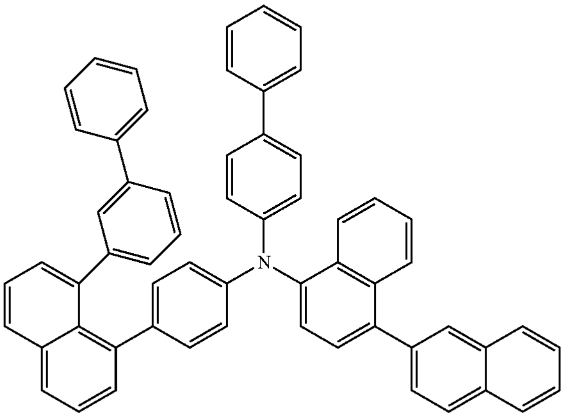
-continued
79
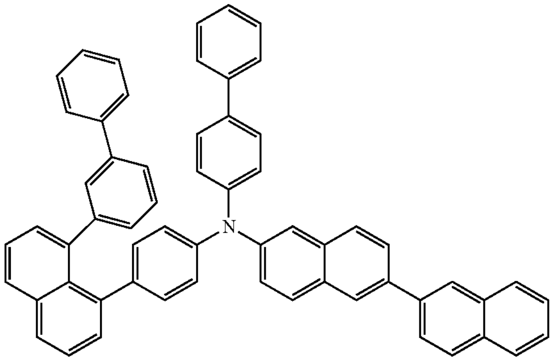
80
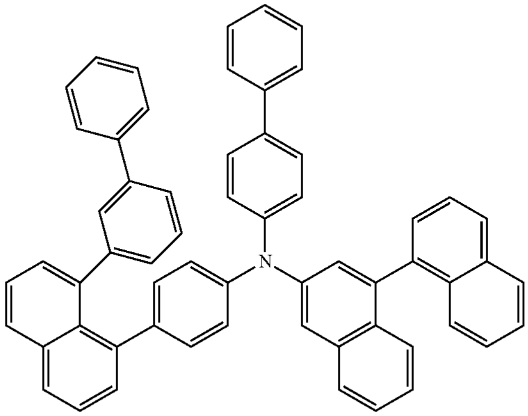
81
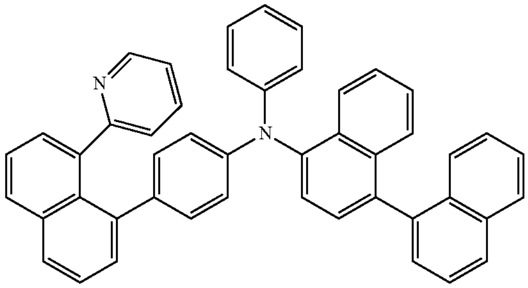
82
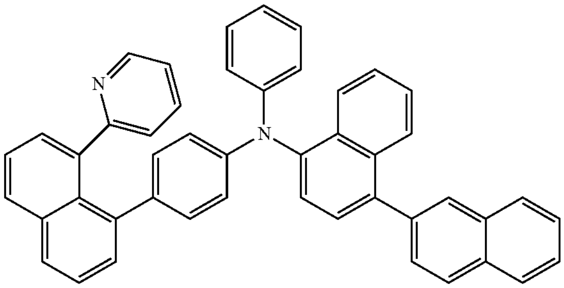

-continued
83
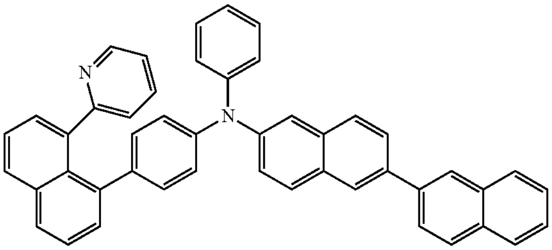
84
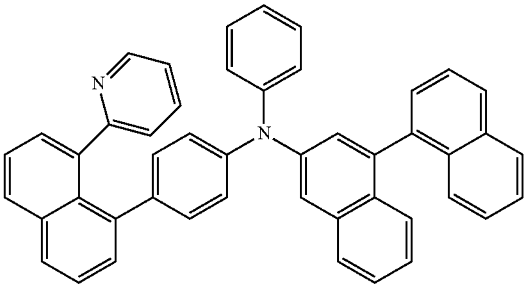
85
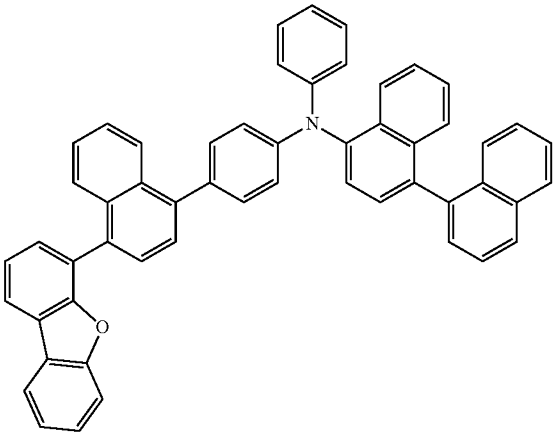
86
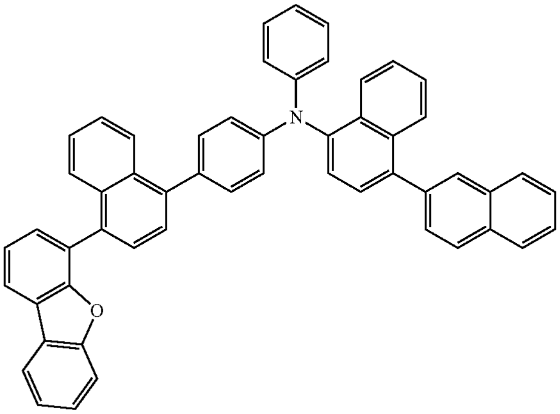
-continued
87
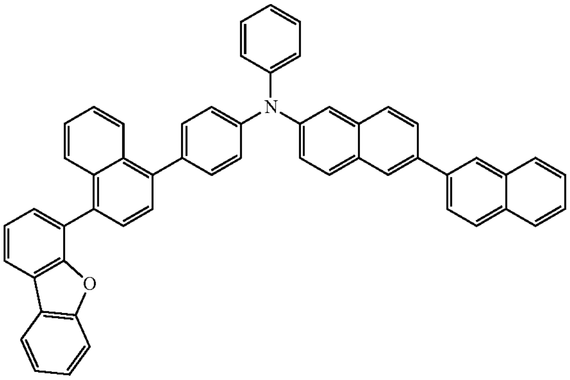
88
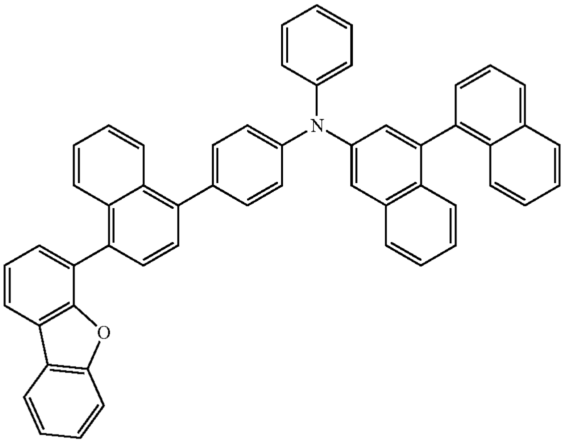
89
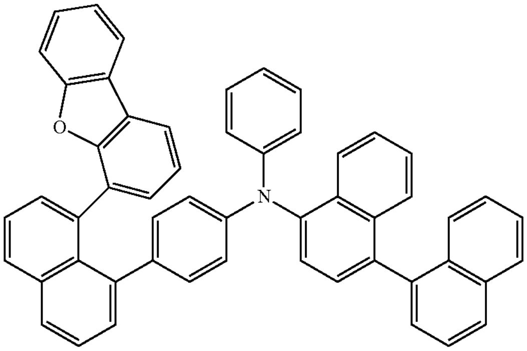
90
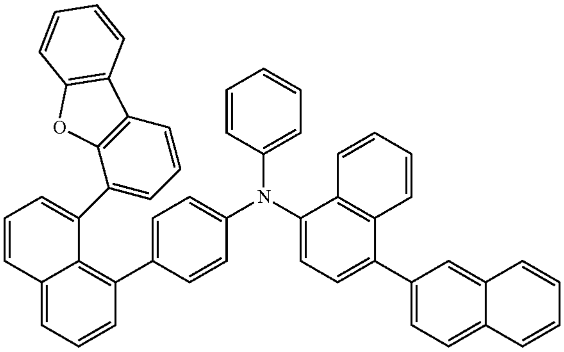

-continued
91
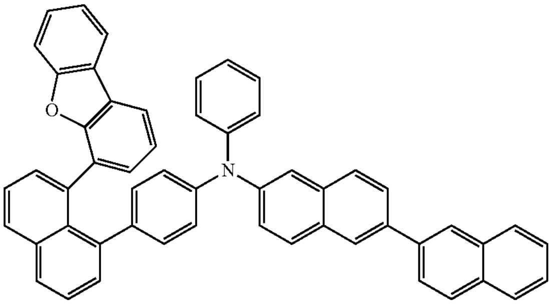
92
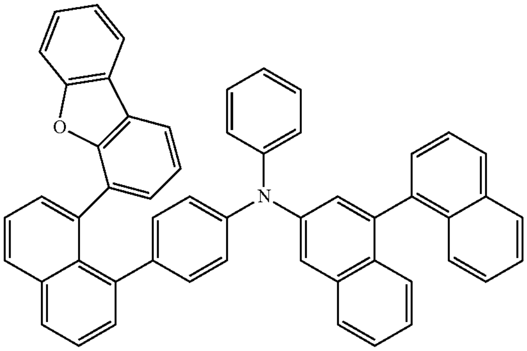
93
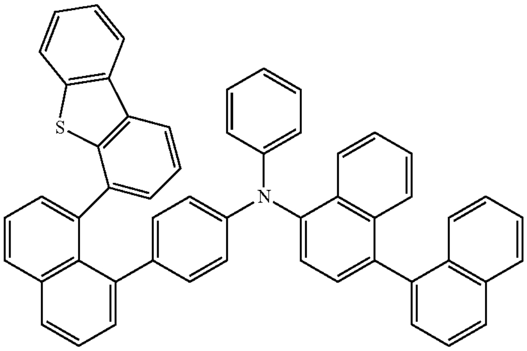
94
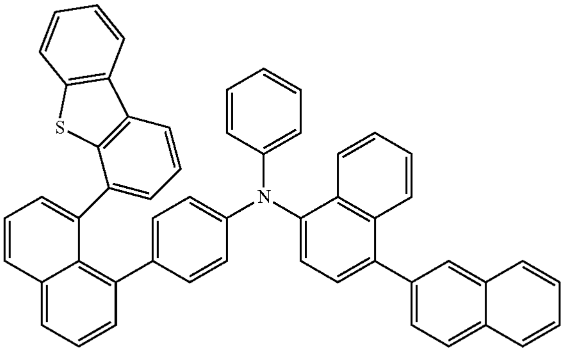
-continued
95
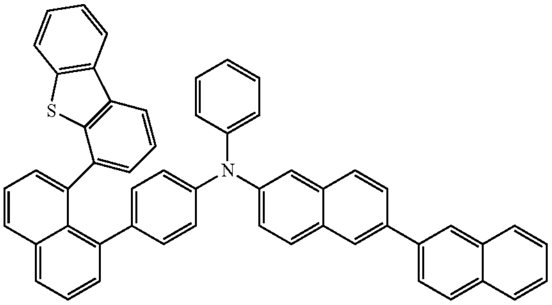
96
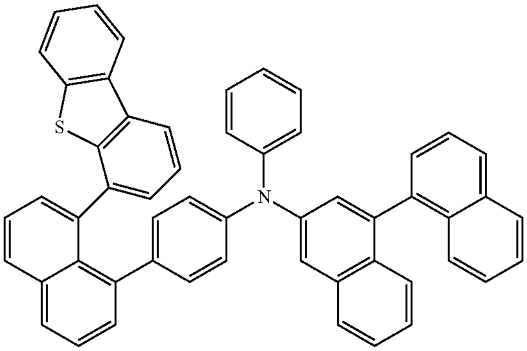
97
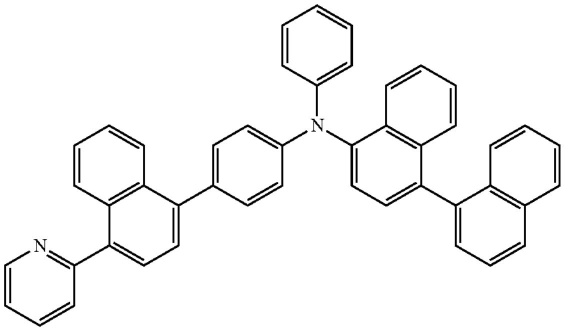
98
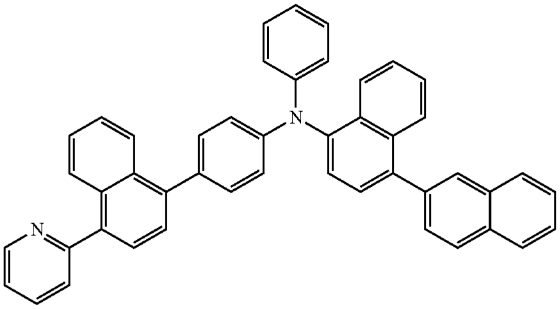

-continued
99
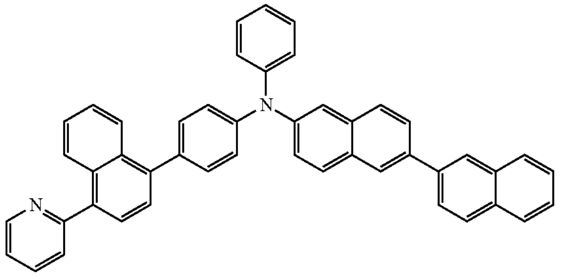
100
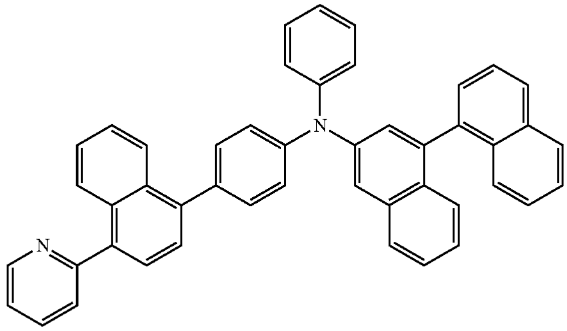
101
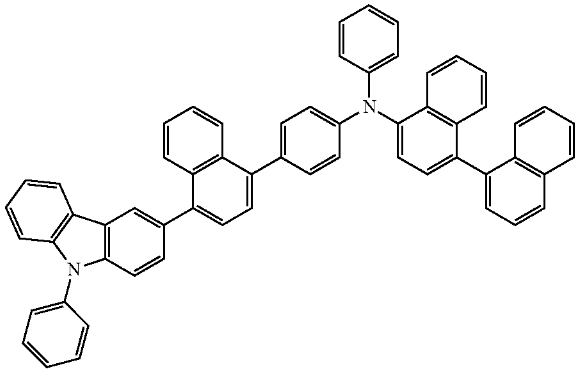
102
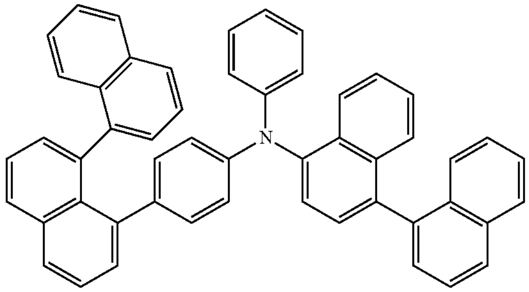
-continued
103
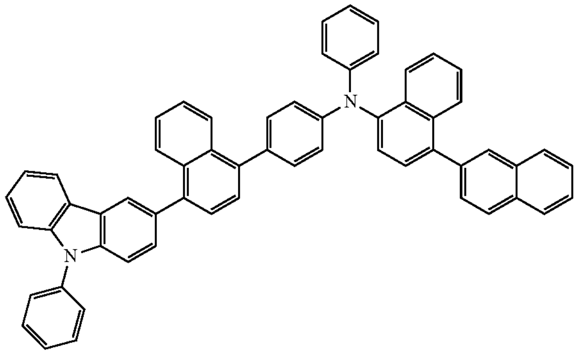
104
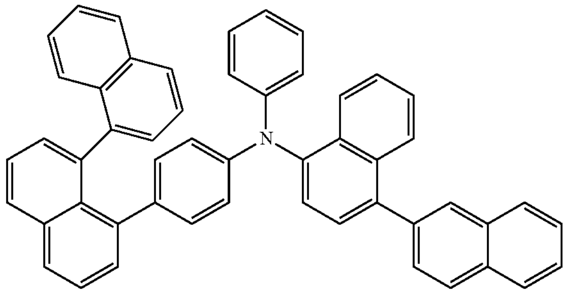
105
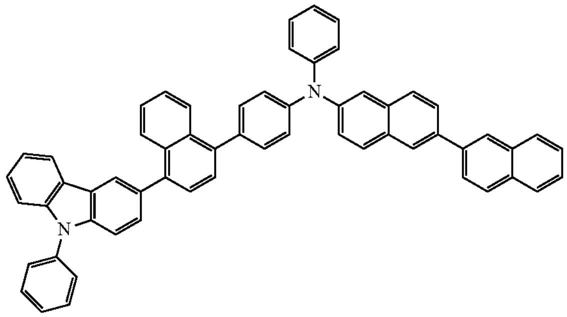
106
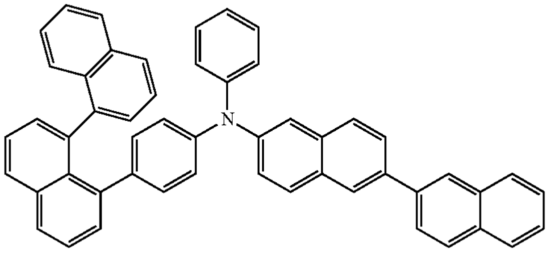

-continued
107
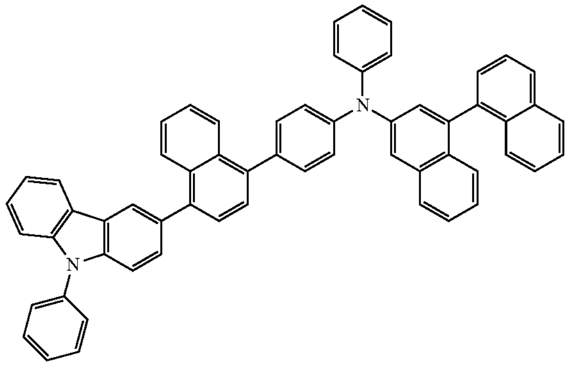
108
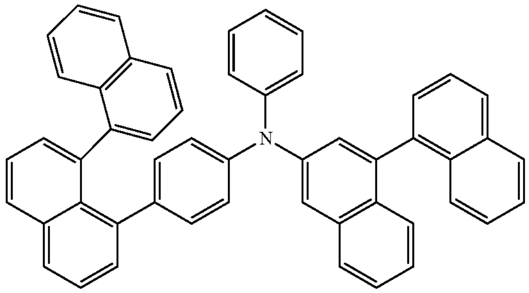
109
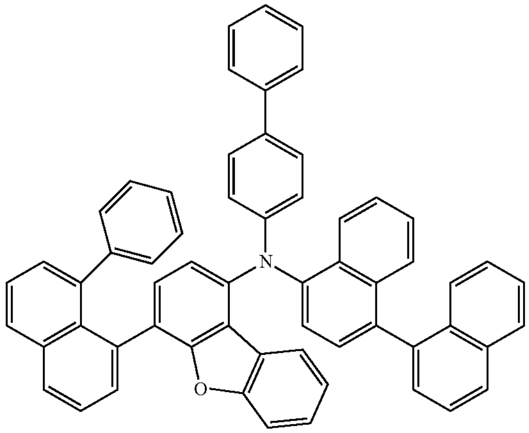
110
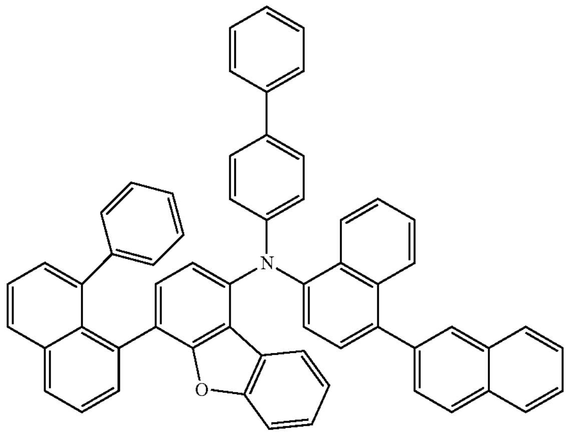
-continued
111
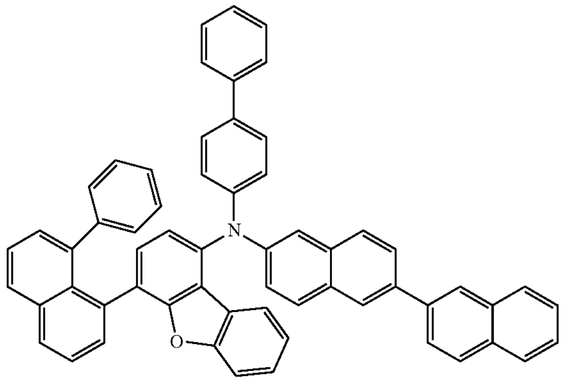
112
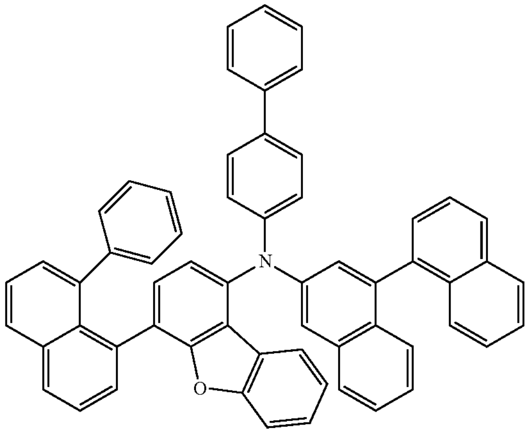
113
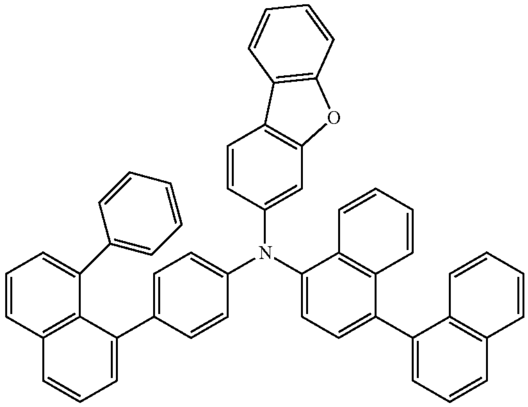

-continued
114
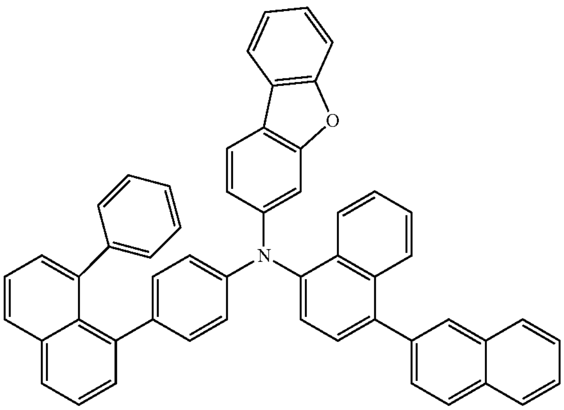
115
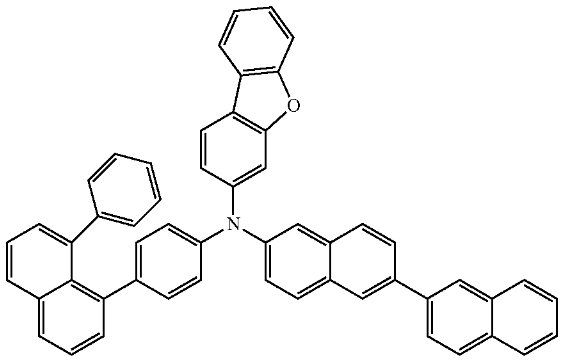
116
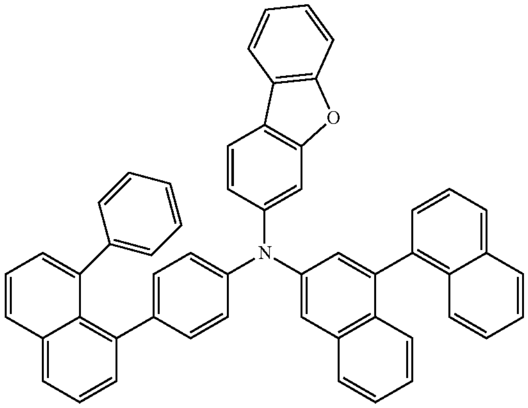
117
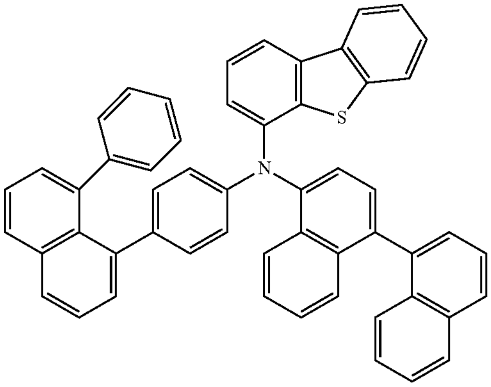
-continued
118
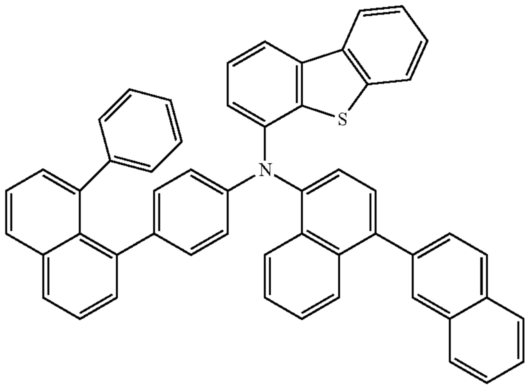
119
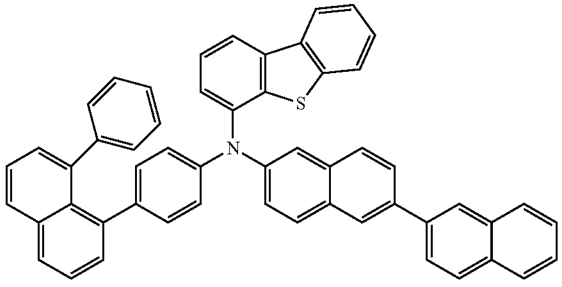
120
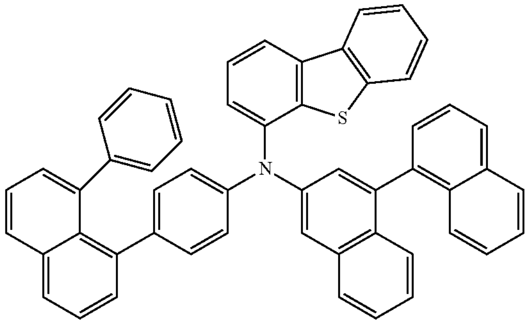
121
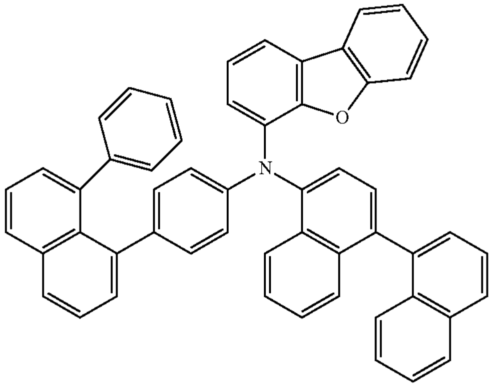

-continued
122
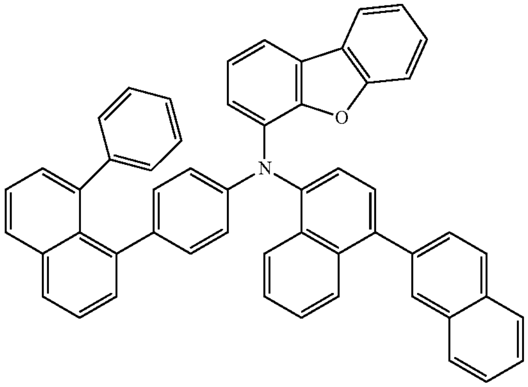
123
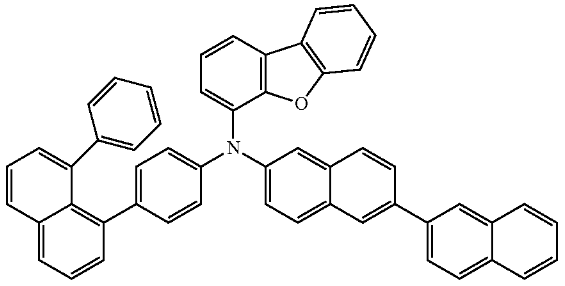
124
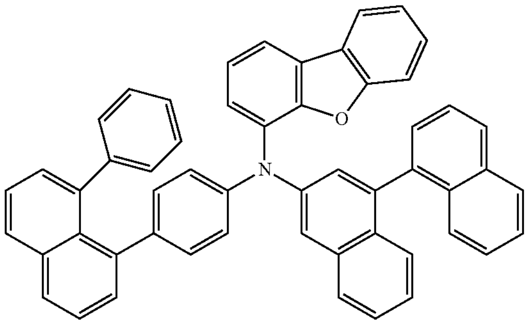
125
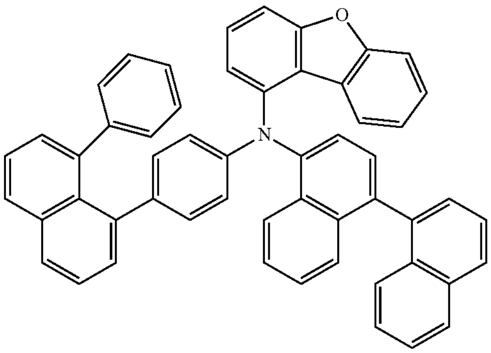
-continued
126
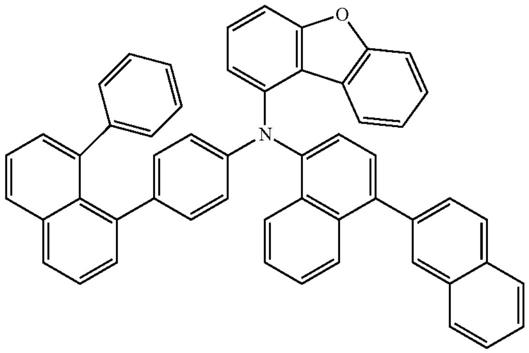
127
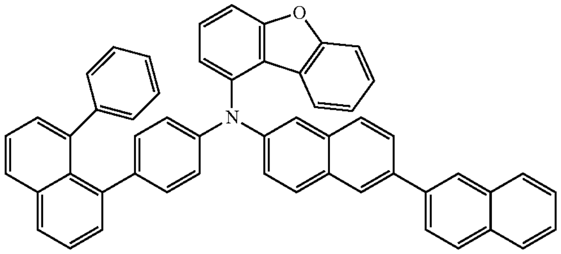
128
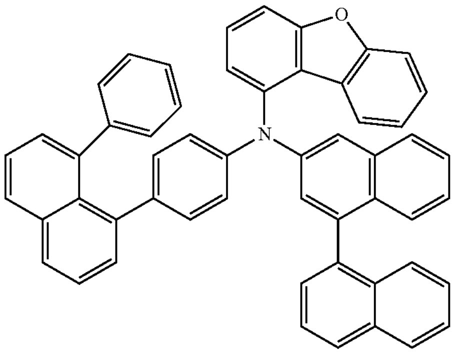
129
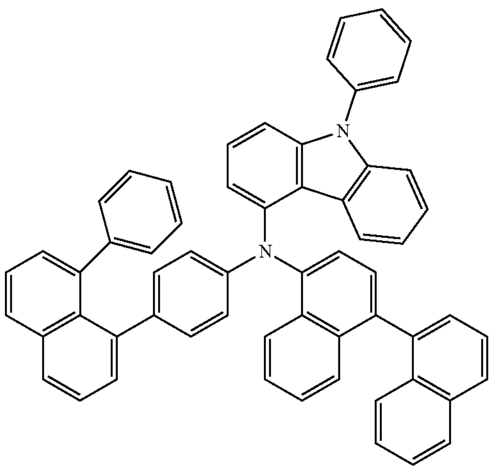

-continued
130
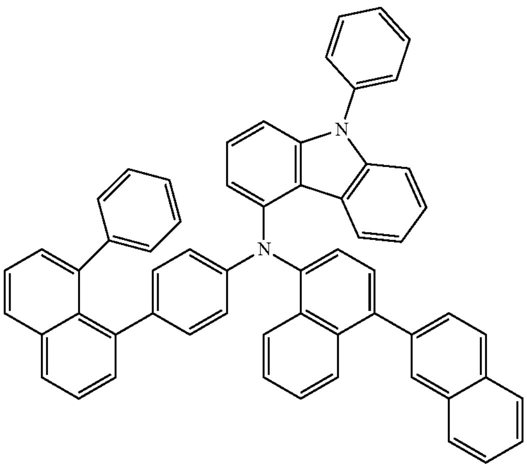
131
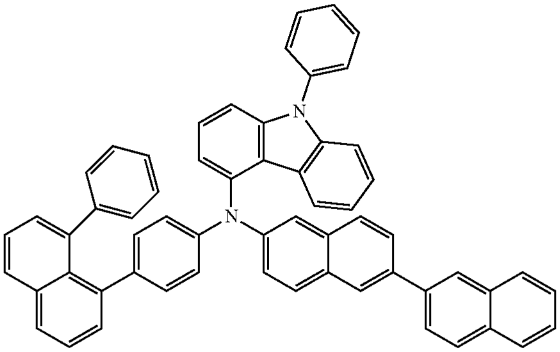
132
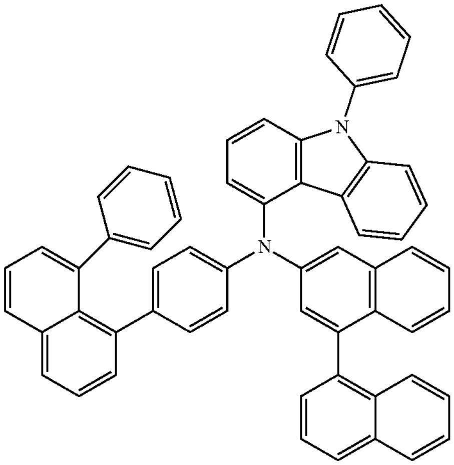
-continued
133
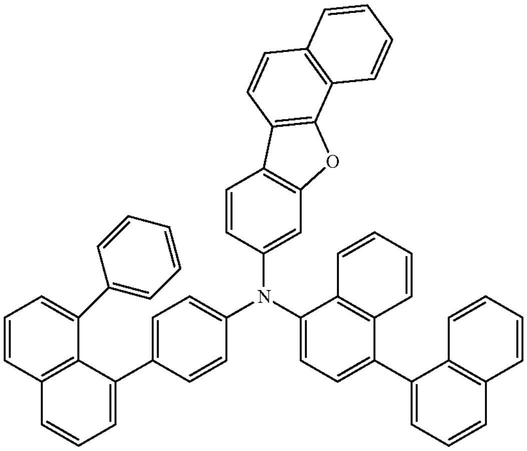
134
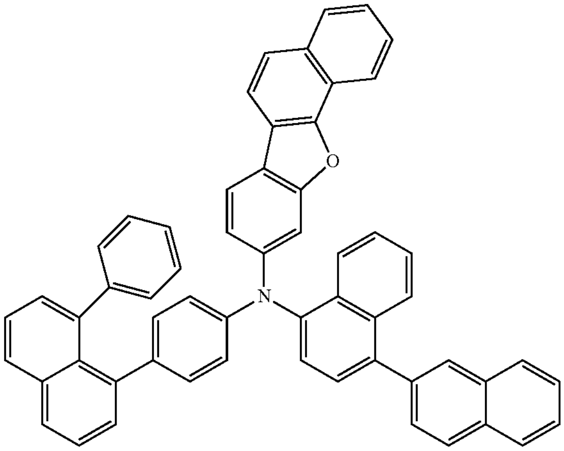
135
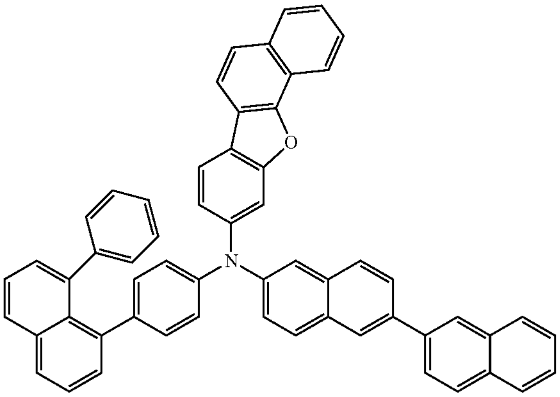

-continued
136
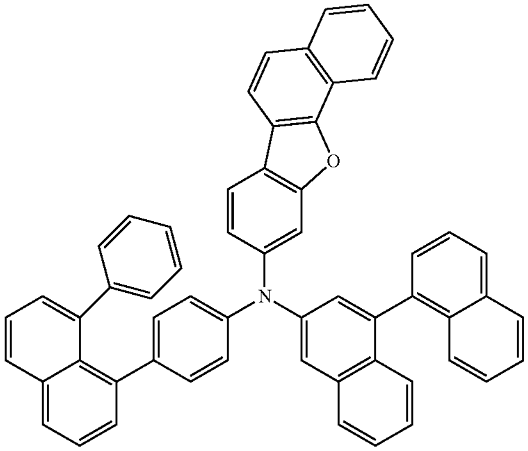
137
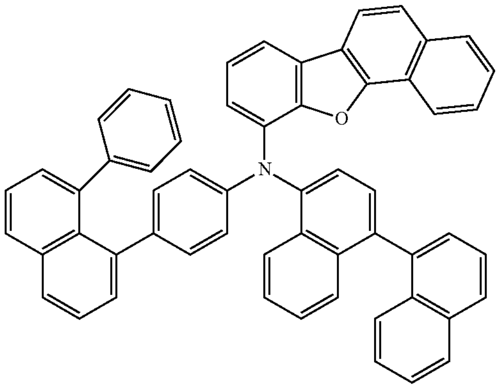
138
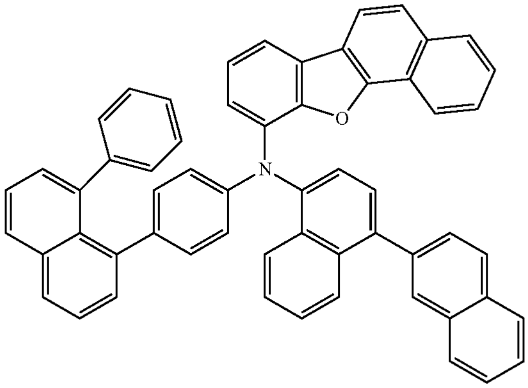
139
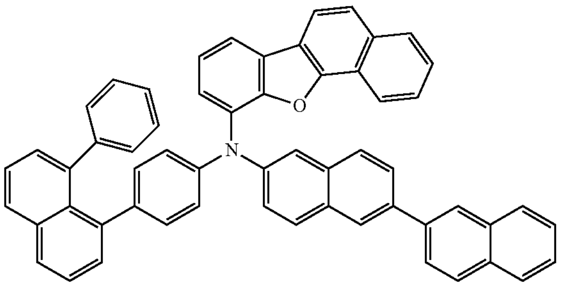
-continued
140
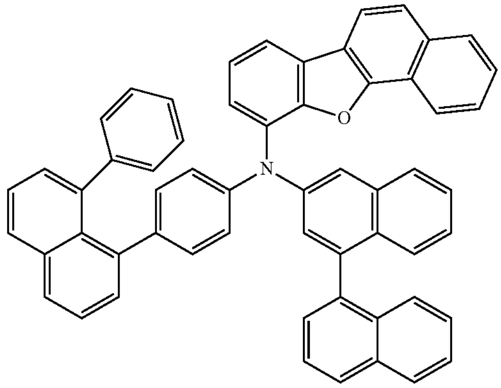
141
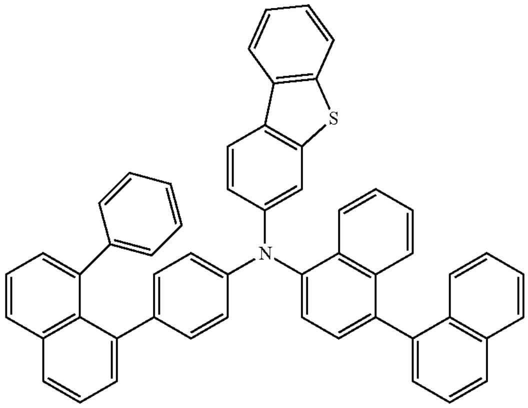
142
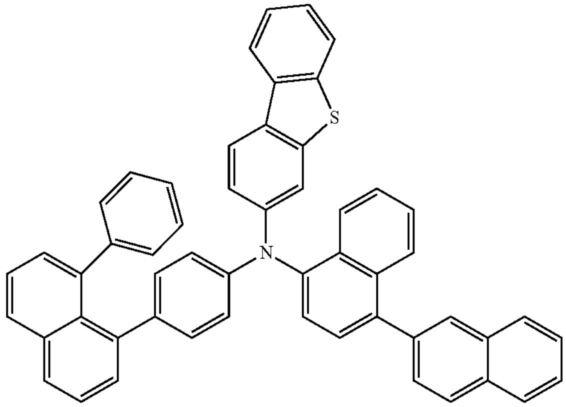
143
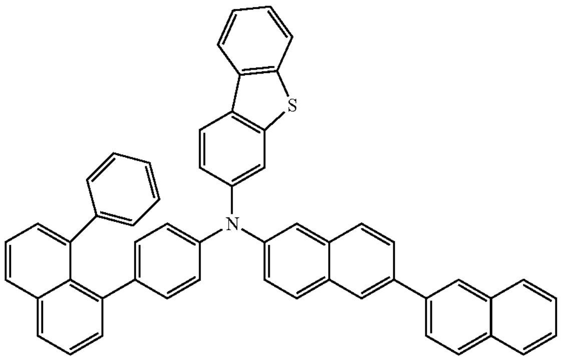

-continued
144
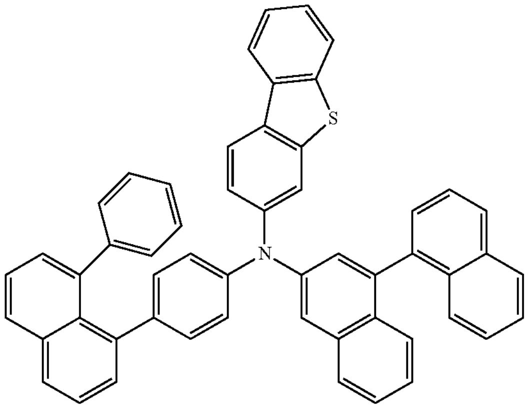
145
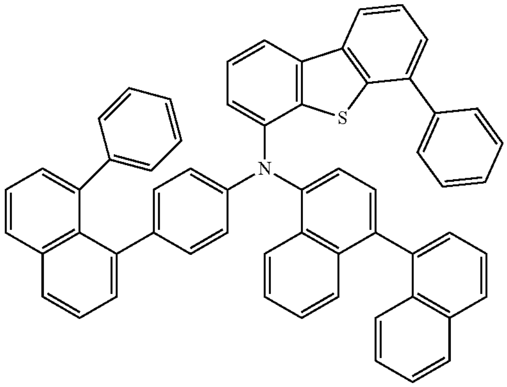
146
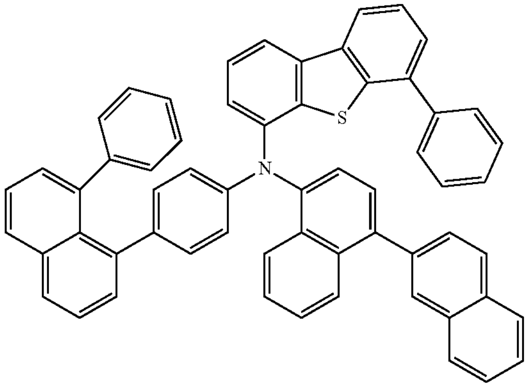
147
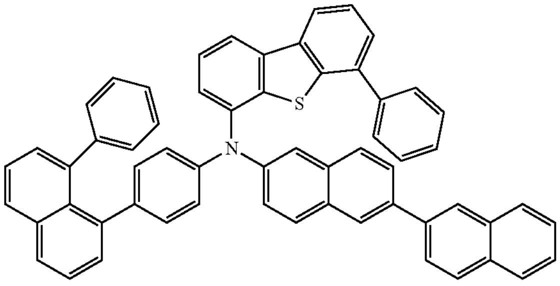
-continued
148
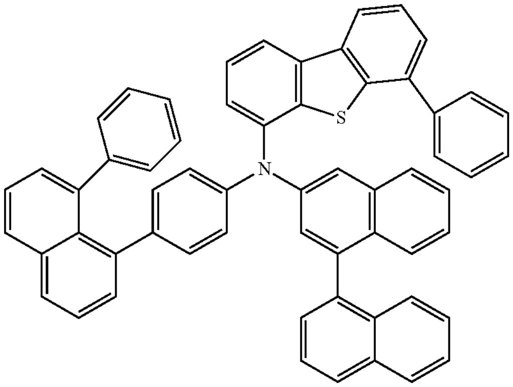
149
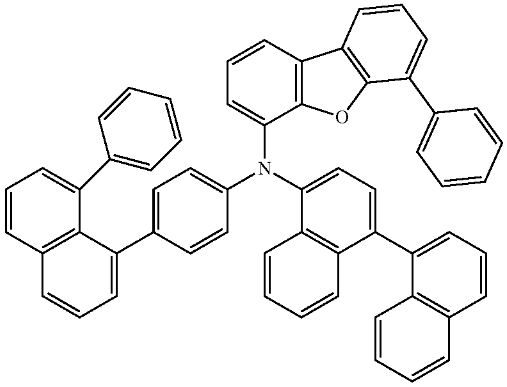
150
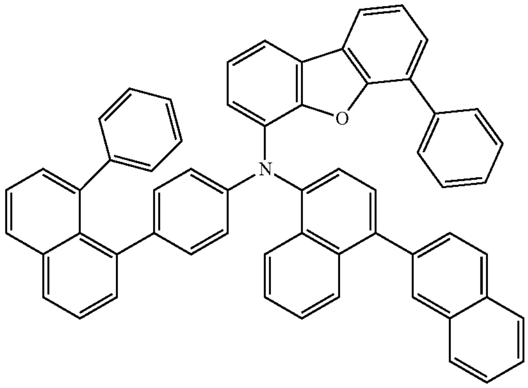
151
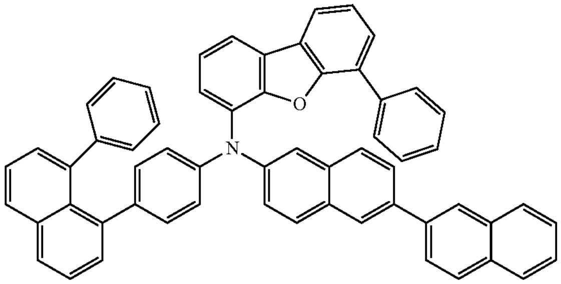

-continued
152
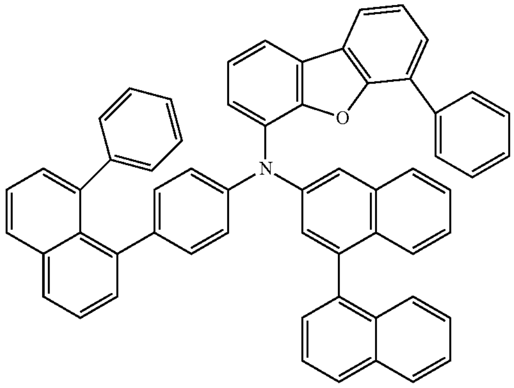
153
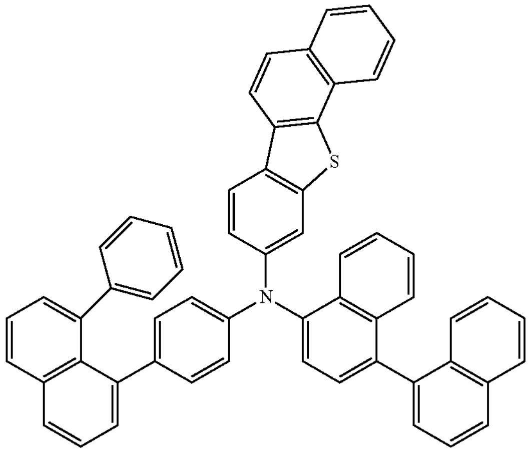
154
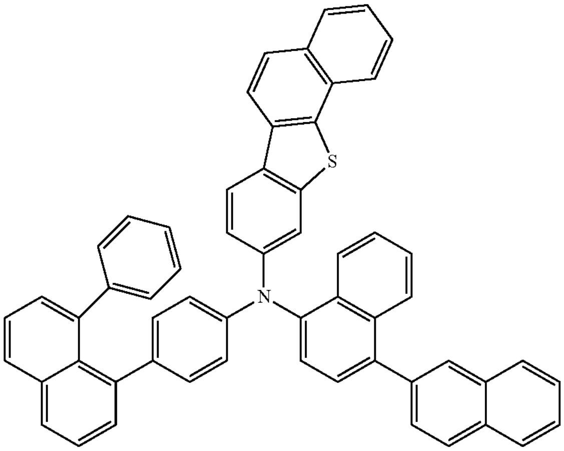
-continued
155
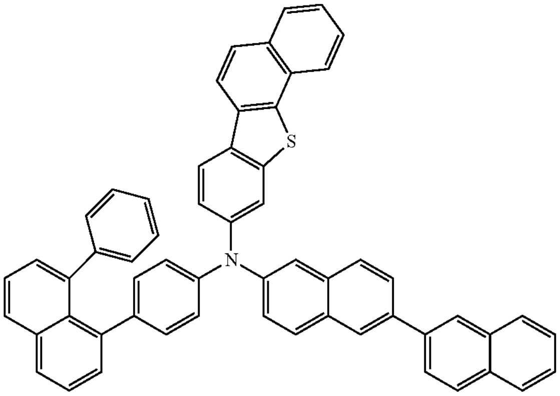
156
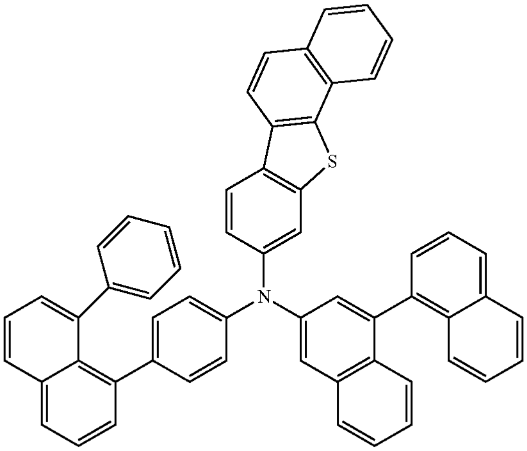
157
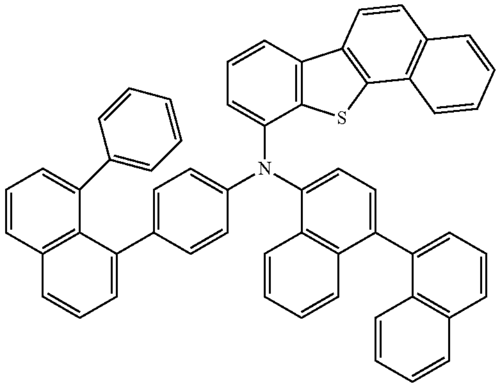

-continued
158
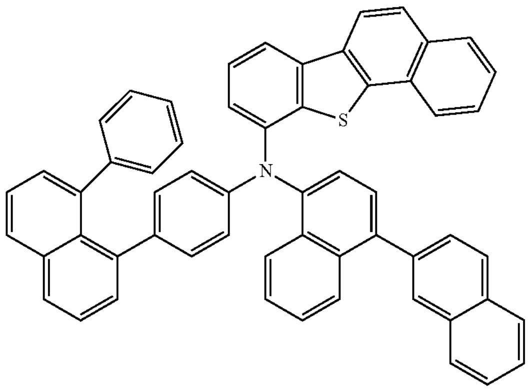
159
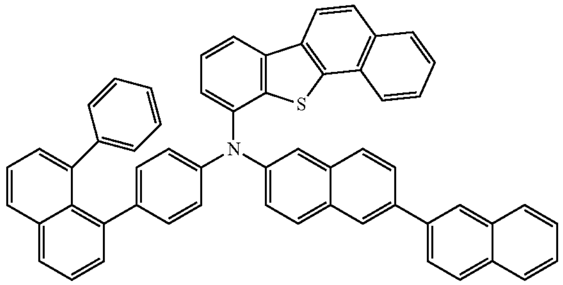
160
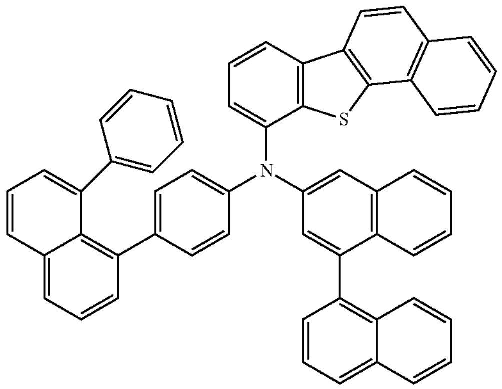
161
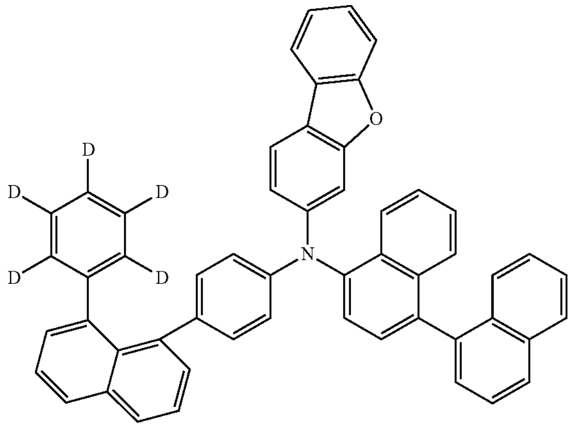
-continued
162
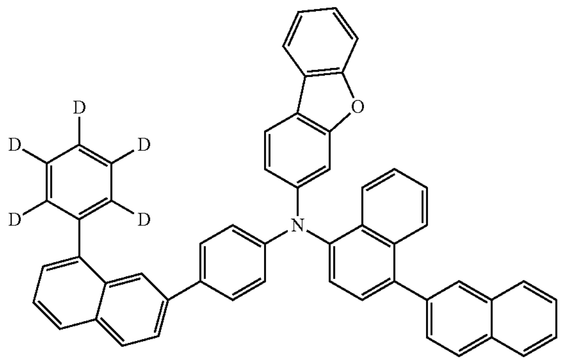
163
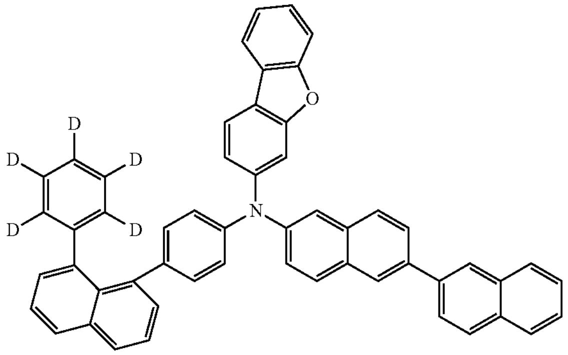
164
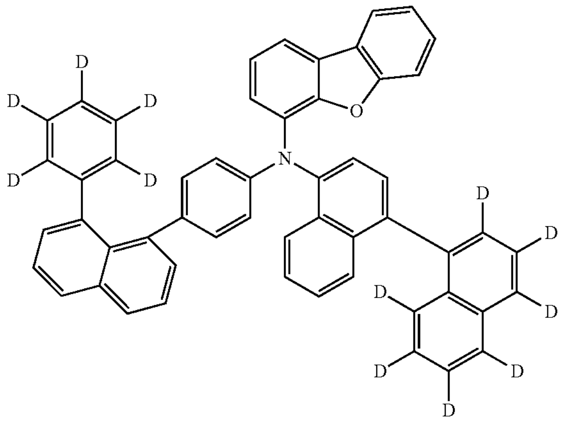
165
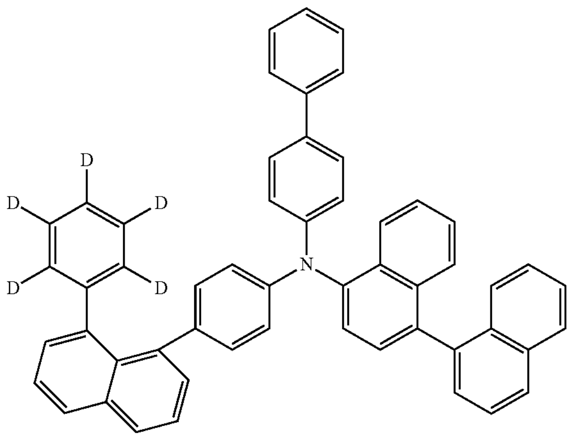

-continued
166
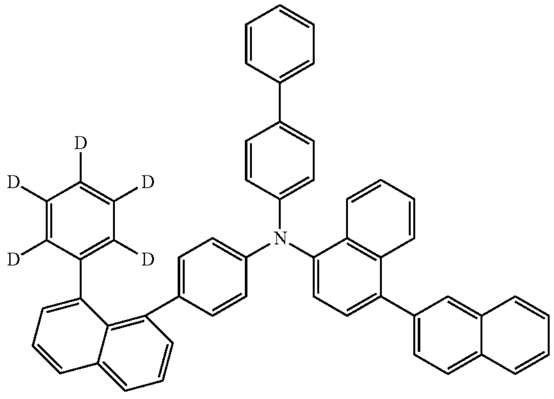
167
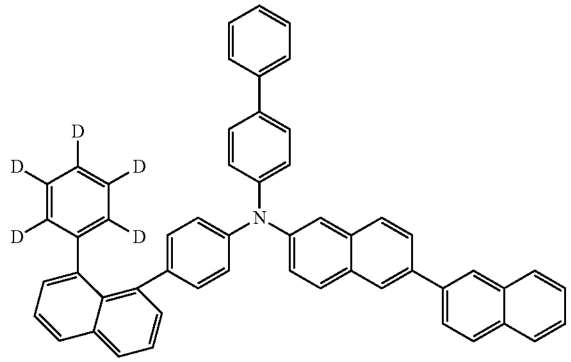
168
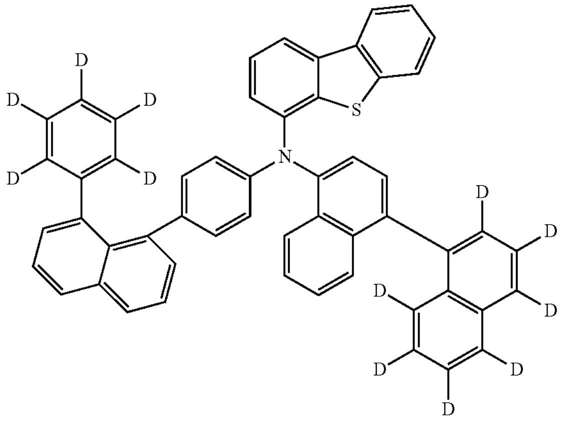
-continued
169
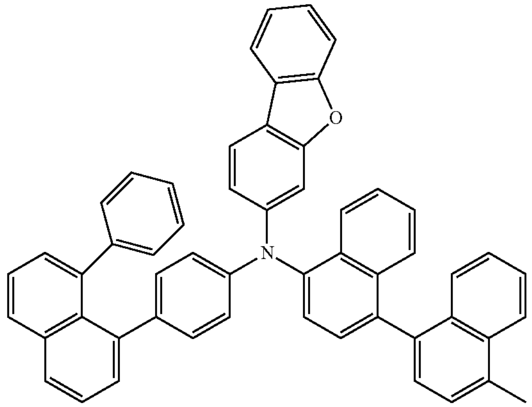
170
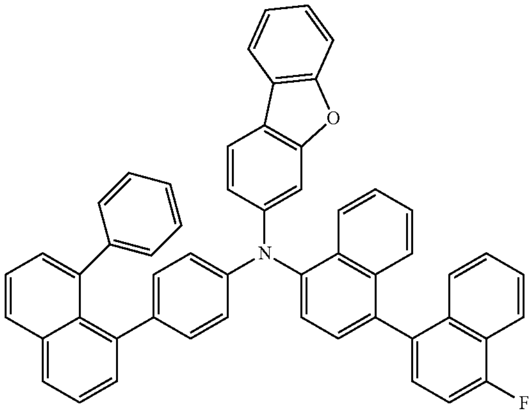
171
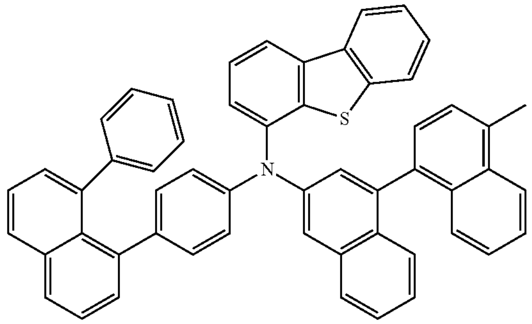
172
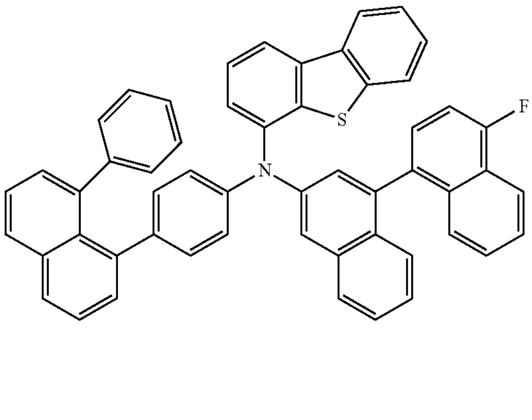

-continued
173
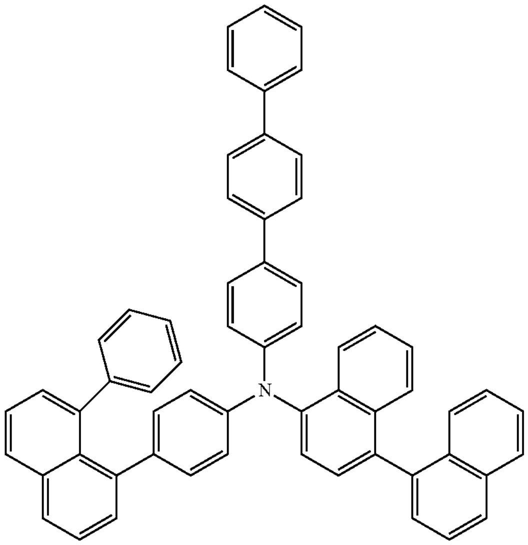
174
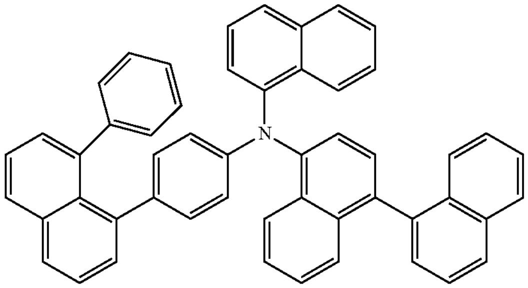
175
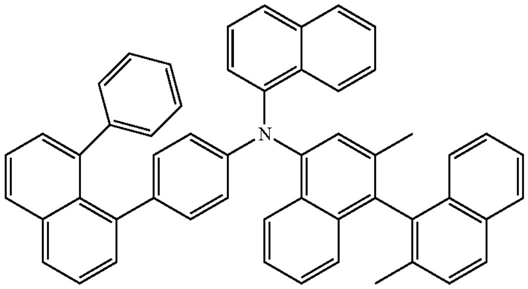
176
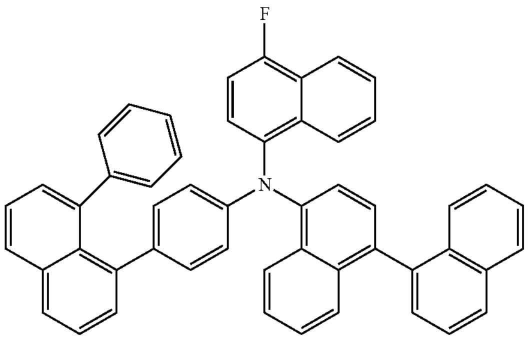
-continued
177
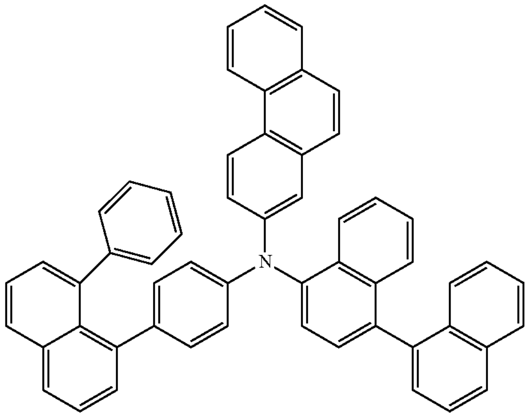
178
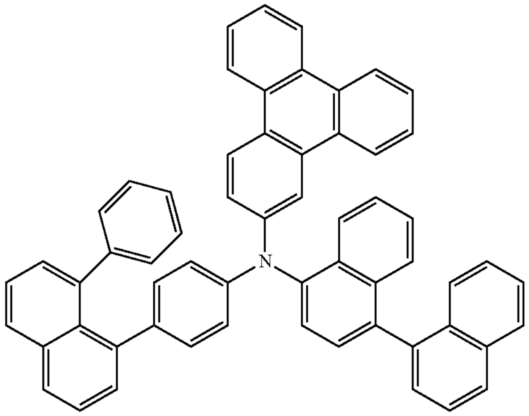
179
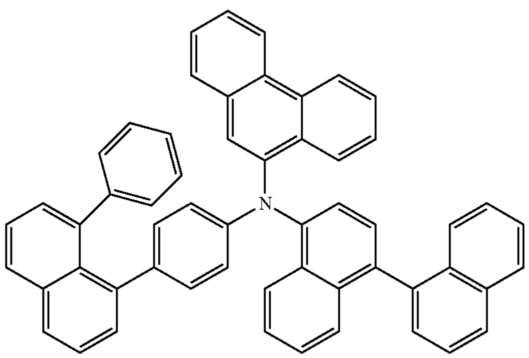

-continued
180
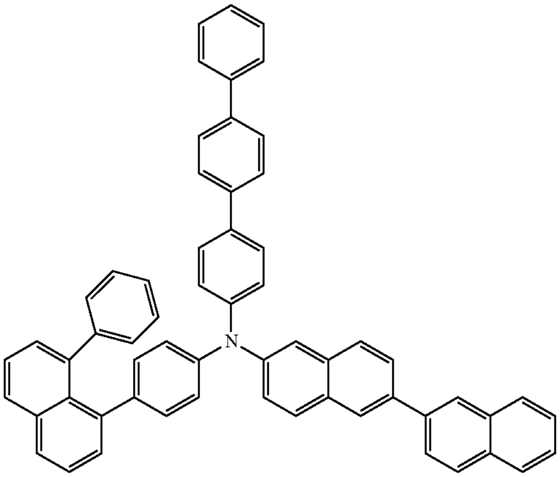
181
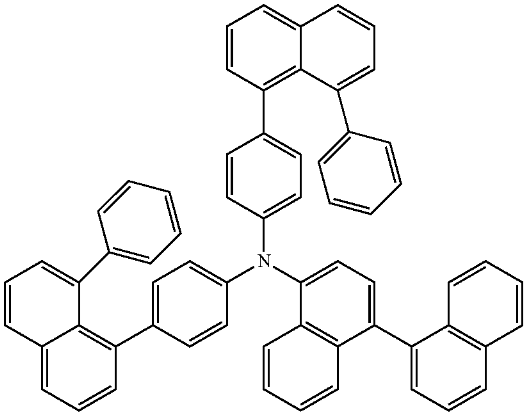
182
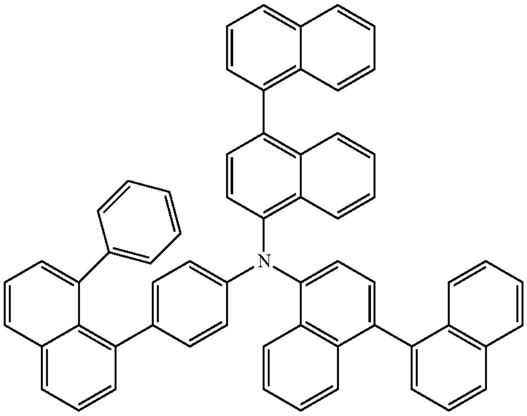
-continued
183
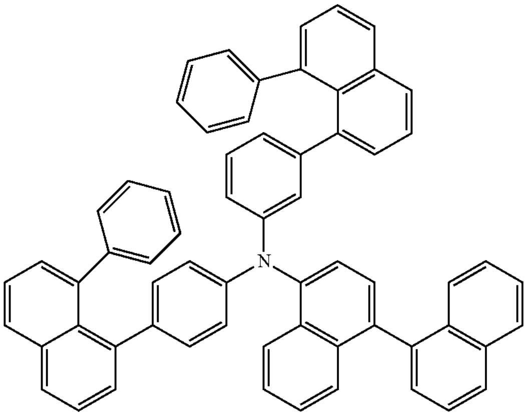
184
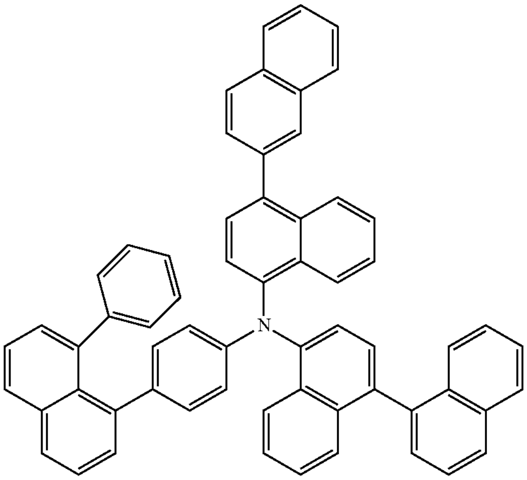
185
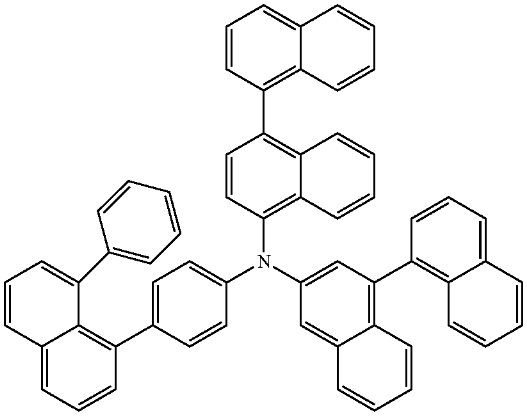

-continued
186
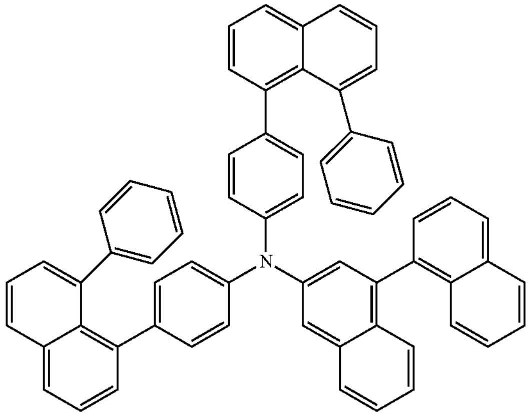
187
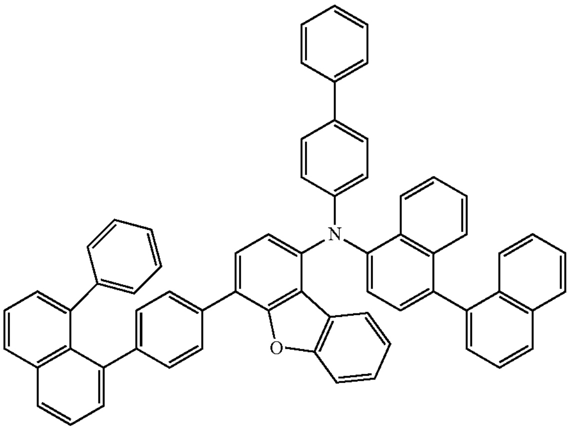
188
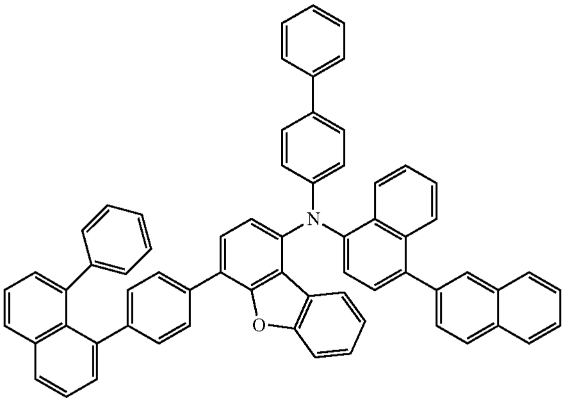
-continued
189
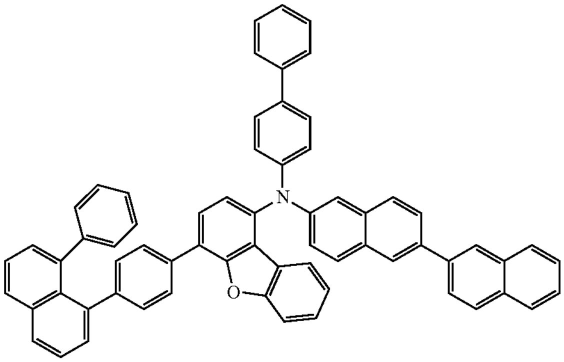
190
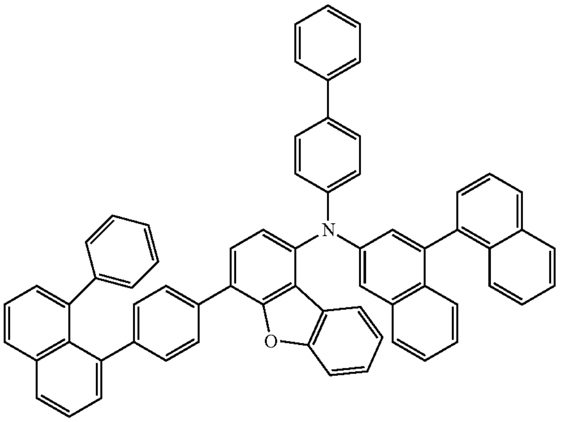
191
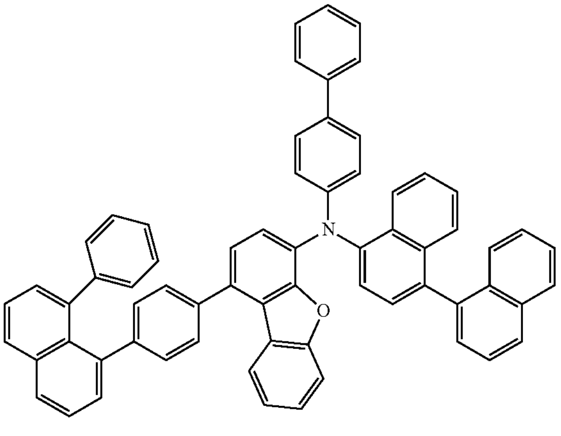

-continued
192
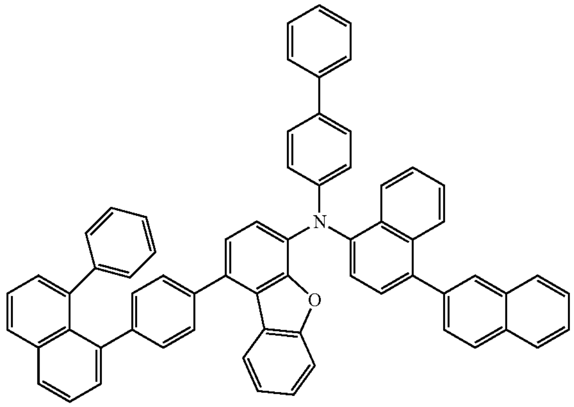
193
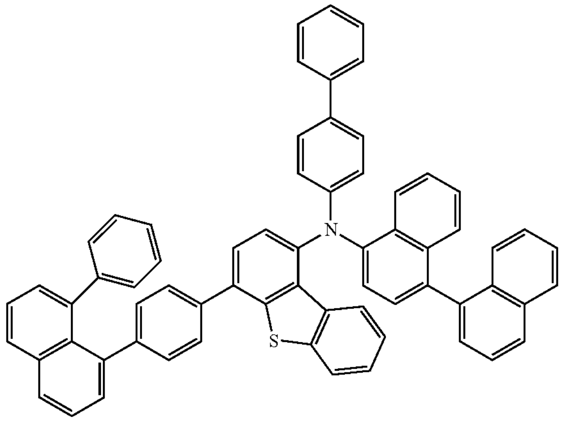
194
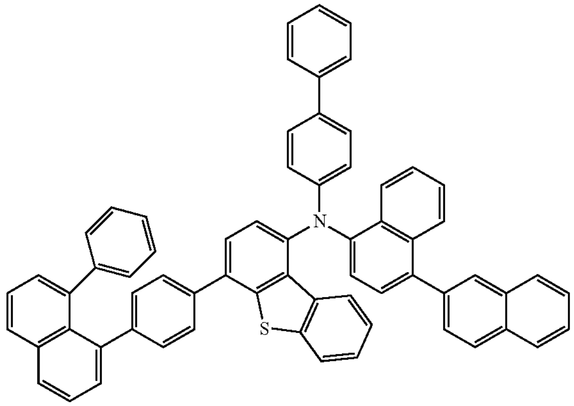
-continued
195
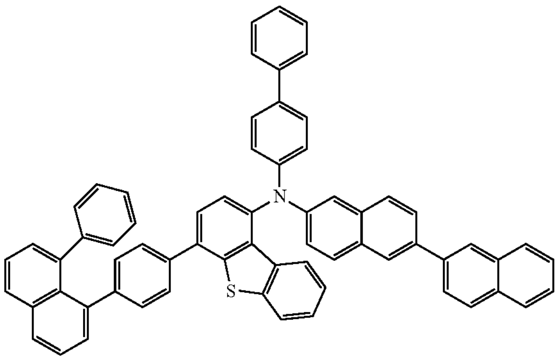
196
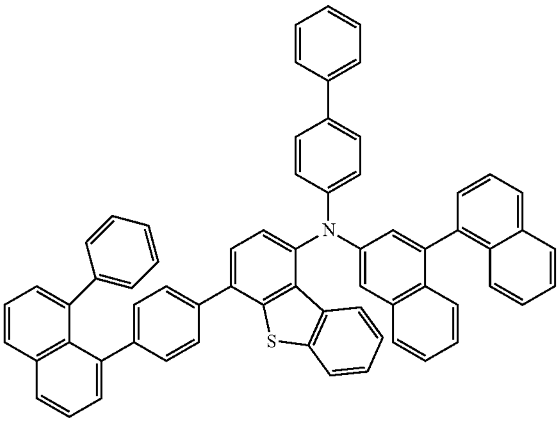
197
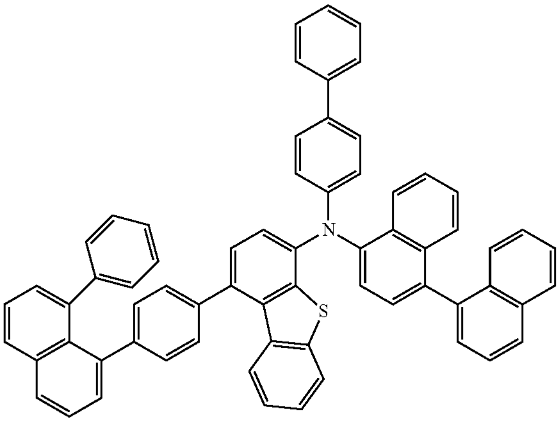

-continued
198
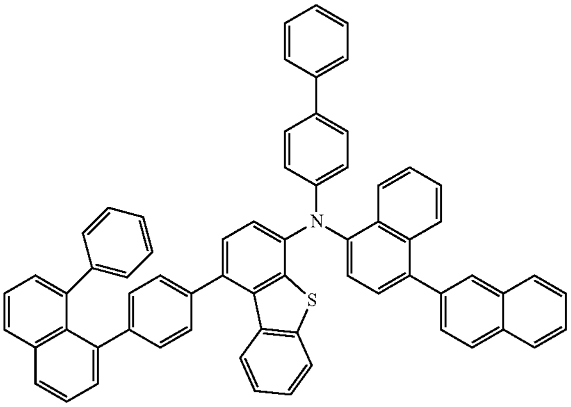
199
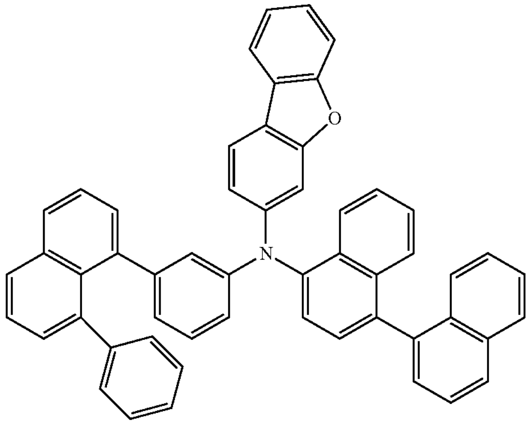
200
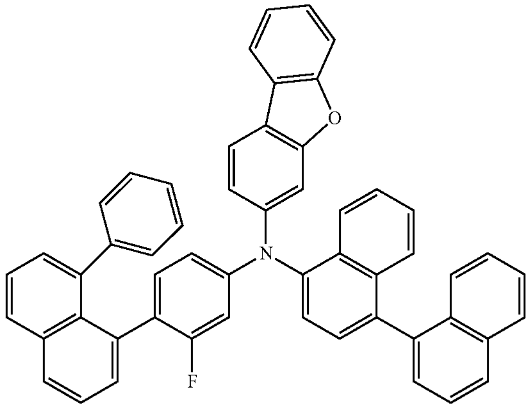
-continued
201
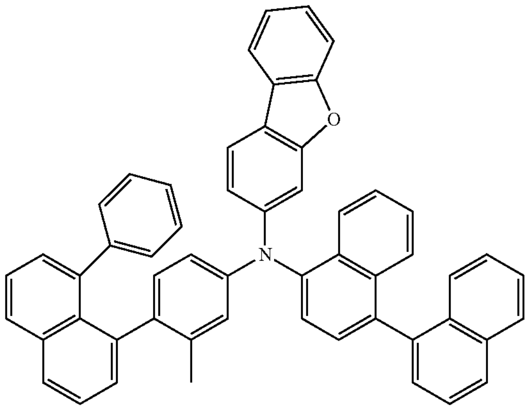
202
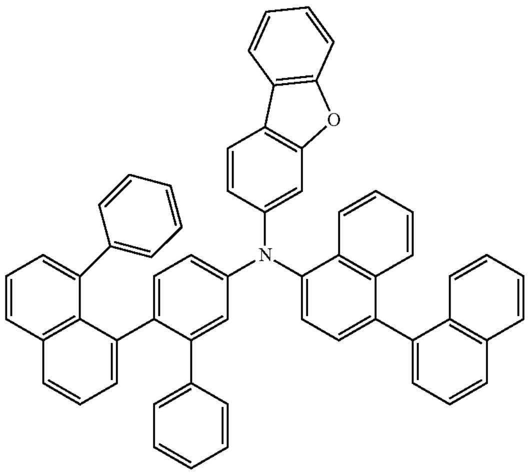
203
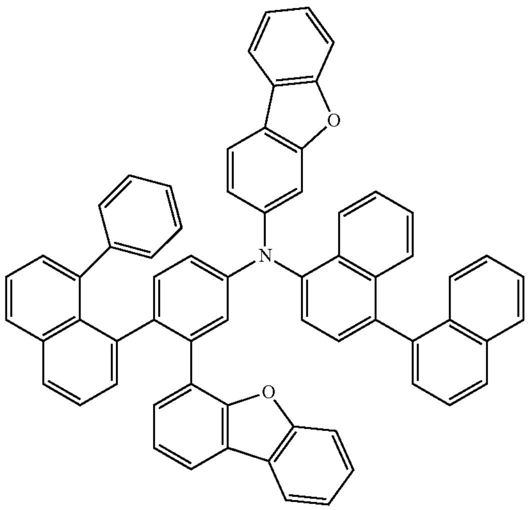

-continued
204
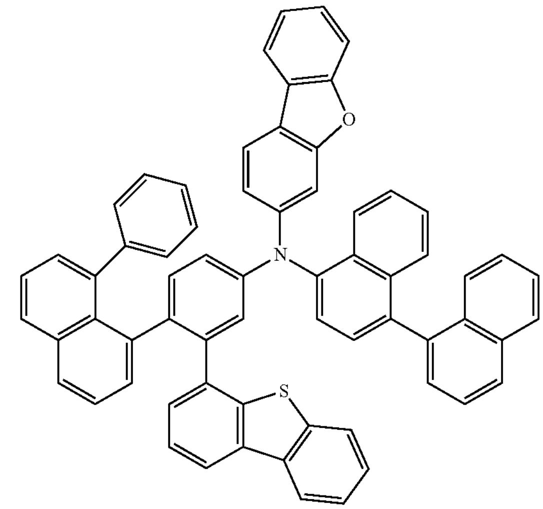
205
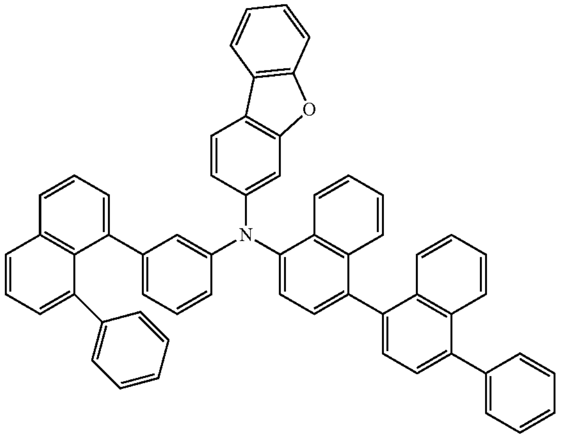
206
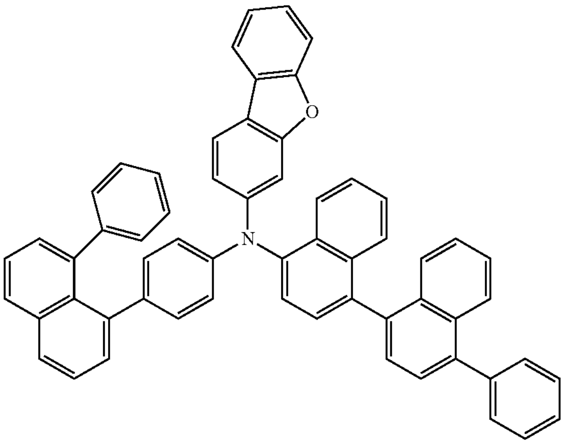
-continued
207
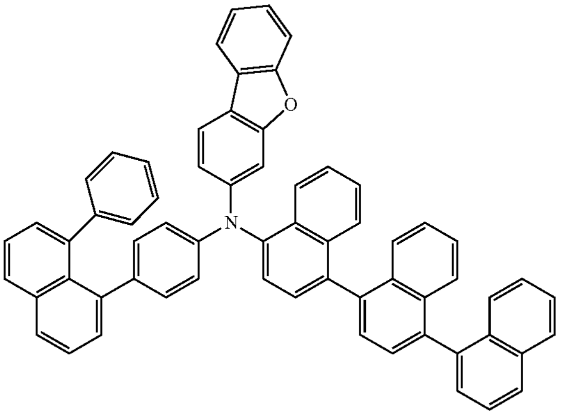
208
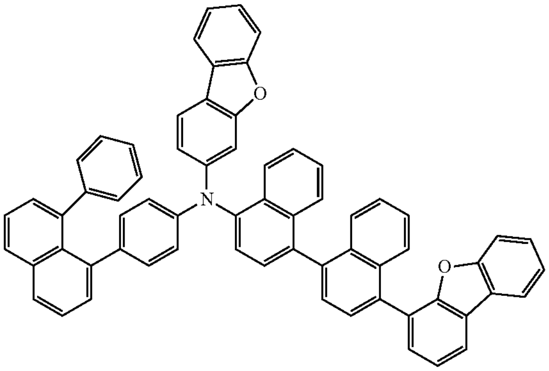
209
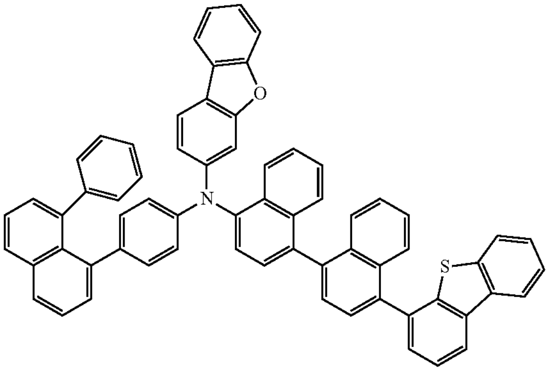
210
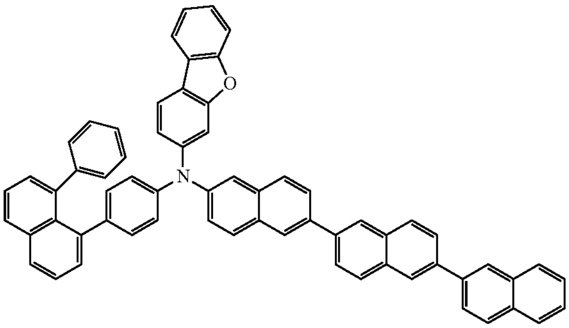

-continued

211

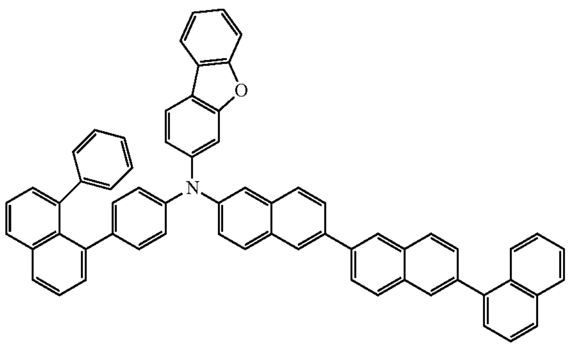

212

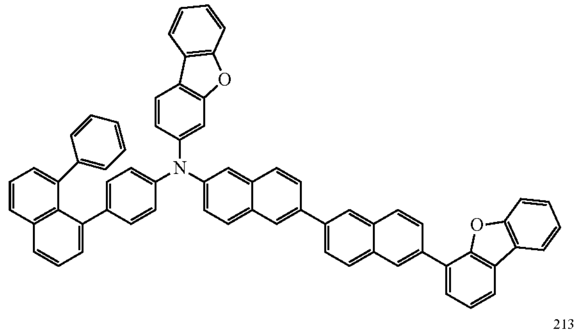

213

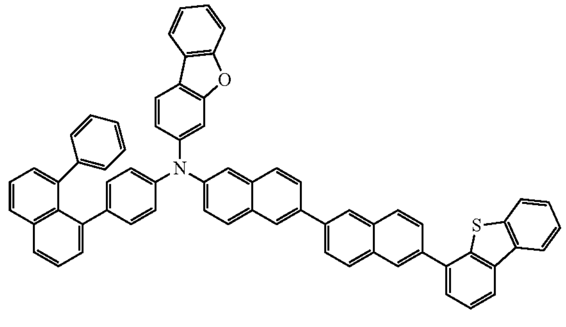

In Compound Group 1, D is a deuterium atom.

The amine compound of an embodiment may include a structure in which a phenylnaphthyl group and a binaphthyl group are directly or indirectly combined with a nitrogen atom. The amine compound of an embodiment may include a structure represented by Formula Z.

[Formula Z]

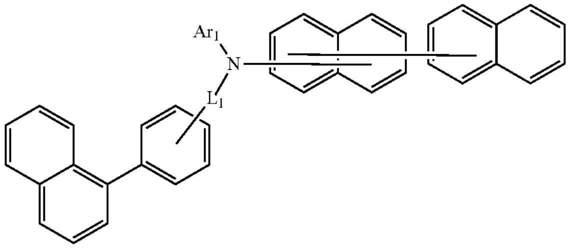

In Formula Z, $Ar_1$ and $L_1$ may be the same as defined in Formula 1. Formula Z may represent a case where a phenylnaphthyl group and a binaphthyl group are combined with a nitrogen atom. In the phenylnaphthyl group, at least one aryl group or at least one heteroaryl group may be bonded to the naphthyl group. Each of the aryl group and heteroaryl group may be substituted or unsubstituted. In the phenylnaphthyl group, the phenyl group may be combined with the nitrogen atom via $L_1$.

In the binaphthyl group, a naphthyl group among the two naphthyl groups may be directly bonded to the nitrogen atom. The amine compound of an embodiment including the binaphthyl group may show improved thermal stability properties. The binaphthyl group has a relatively high glass transition temperature, and may contribute to the improvement of the thermal stability of the amine compound. The amine compound of an embodiment including the phenylnaphthyl group substituted with an aryl group or a heteroaryl group, may show improved charge transport properties. Accordingly, the amine compound including the phenylnaphthyl group and the binaphthyl group may show excellent charge transport properties and thermal stability. The amine compound of an embodiment may be used as a material for a hole transport region of a light emitting device and may contribute to the improvement of the efficiency and life of the light emitting device.

The hole transport region HTR is provided on the first electrode EL1. The hole transport region HTR may include at least one of a hole injection layer HIL, a hole transport layer HTL, a buffer layer (not shown), an emission auxiliary layer (not shown), or an electron blocking layer EBL. At least one of the hole injection layer HIL, the hole transport layer HTL or the electron blocking layer EBL may include the amine compound of an embodiment.

A thickness of the hole transport region HTR may be, for example, in a range of about 50 Å to about 15,000 Å. The hole transport region HTR may be a layer formed of a single material, a layer formed of different materials, or a multilayer structure including layers formed of different materials.

For example, the hole transport region HTR may have the structure of a single layer of a hole injection layer HIL or a hole transport layer HTL, or may have a structure of a single layer formed using a hole injection material and a hole transport material. In another embodiment, the hole transport region HTR may have a structure of a layer formed of different materials, or a structure in which a hole injection layer HIL/hole transport layer HTL, a hole injection layer HIL/hole transport layer HTL/buffer layer (not shown), a hole injection layer HIL/buffer layer (not shown), a hole transport layer HTL/buffer layer (not shown), or a hole injection layer HIL/hole transport layer HTL/electron blocking layer EBL are stacked in its respective stated order from the first electrode EL1, but embodiments are not limited thereto.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may further include a compound represented by Formula H-1.

[Formula H-1]

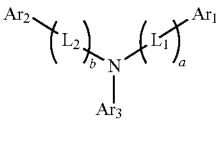

In Formula H-1, $L_1$ and $L_2$ may each independently be a direct linkage, a substituted or unsubstituted arylene group of 6 to 30 ring-forming carbon atoms, or a substituted or unsubstituted heteroarylene group of 2 to 30 ring-forming carbon atoms. In Formula H-1, a and b may each independently be an integer from 0 to 10. When a or b is 2 or more, multiple $L_1$ groups and $L_2$ groups may each independently be a substituted or unsubstituted arylene group of 6 to 30 ring-forming carbon atoms, or a substituted or unsubstituted heteroarylene group of 2 to 30 ring-forming carbon atoms.

In Formula H-1, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. In Formula H-1, $Ar_3$ may be a substituted or unsubstituted aryl group of 6 to 30 ring-forming carbon atoms.

The compound represented by Formula H-1 may be a monoamine compound. In another embodiment, the compound represented by Formula H-1 may be a diamine compound in which at least one of $Ar_1$ to $Ar_3$ may include an amine group as a substituent. For example, the compound represented by Formula H-1 may be a carbazole-based compound in which at least one of $Ar_1$ and $Ar_2$ may include a substituted or unsubstituted carbazole group, or a fluorene-based compound in which at least one of $Ar_1$ and $Ar_2$ may include a substituted or unsubstituted fluorene group.

The compound represented by Formula H-1 may be any one selected from Compound Group H. However, the compounds shown in Compound Group H are only example, and the compounds represented by Formula H-1 are not limited to Compound Group H.

[Compound Group H]

H-1-1

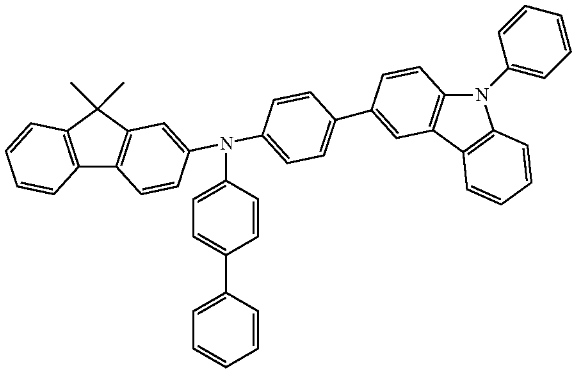

H-1-2

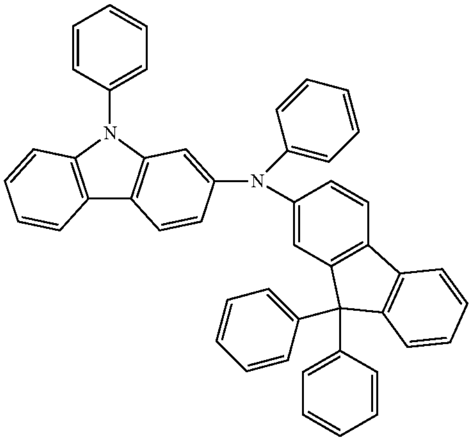

-continued

H-1-3

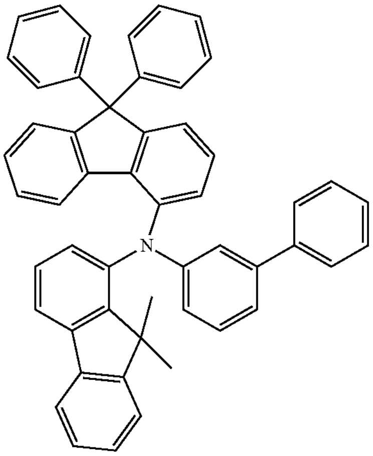

H-1-4

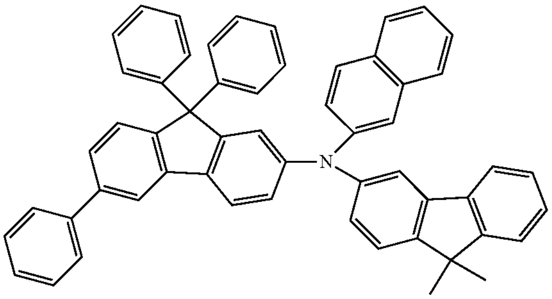

H-1-5

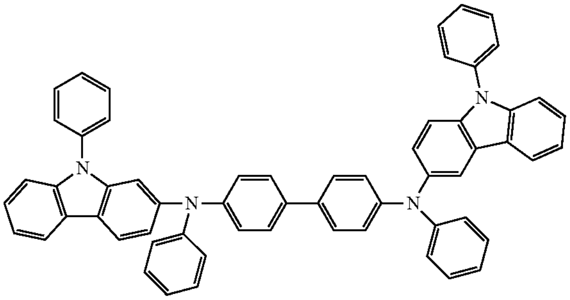

H-1-6

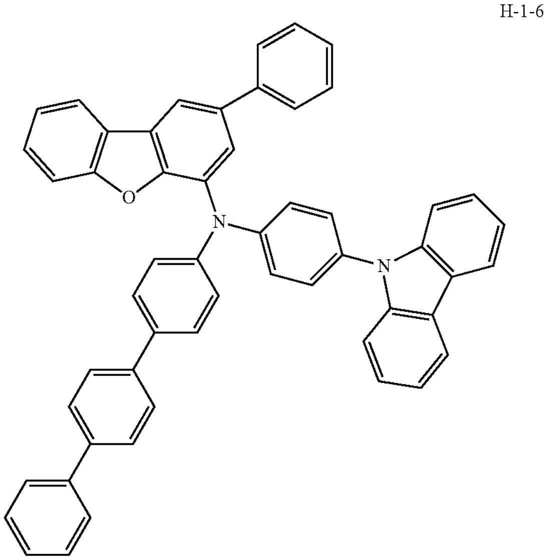

-continued
H-1-7
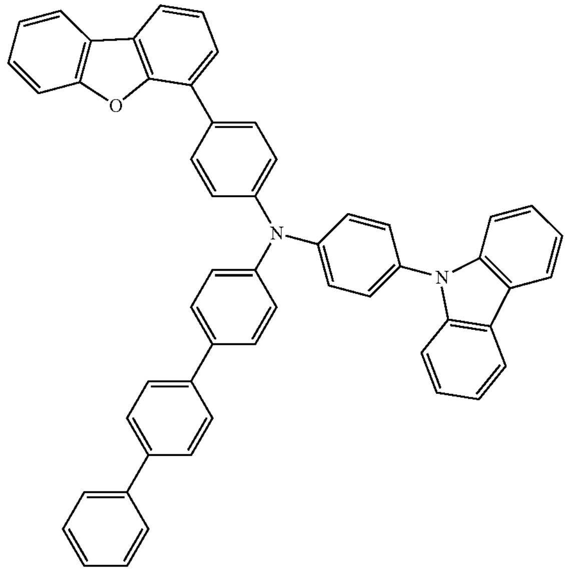
H-1-8
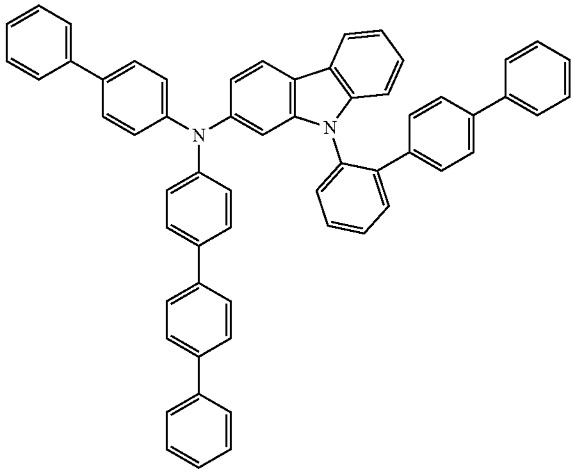
H-1-9
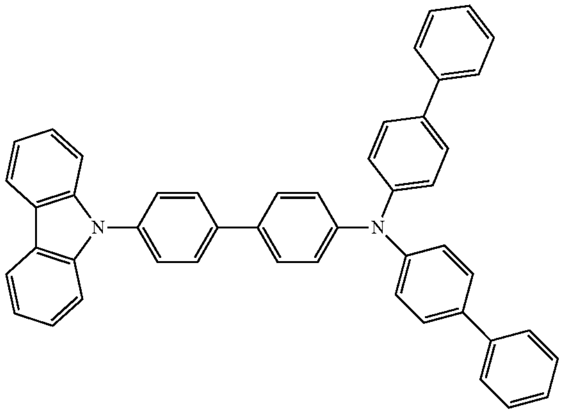
-continued
H-1-10
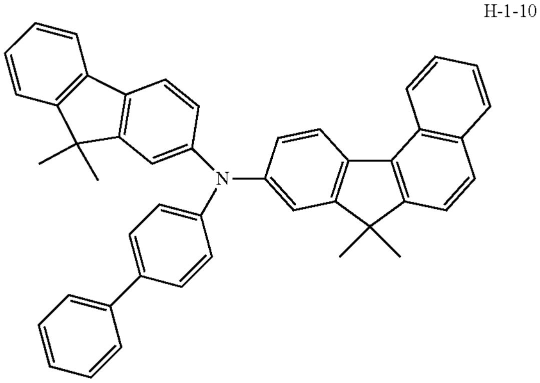
H-1-11
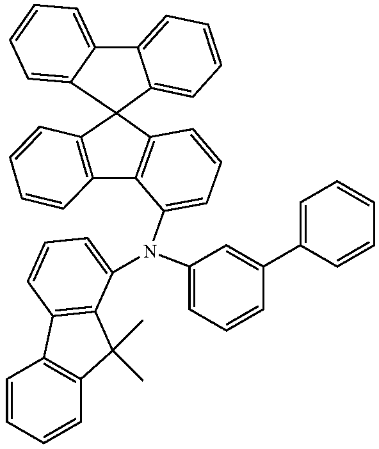
H-1-12
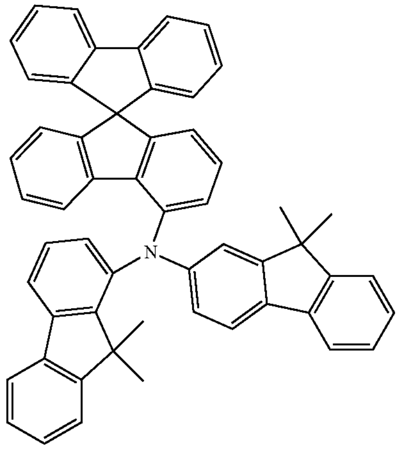
H-1-13
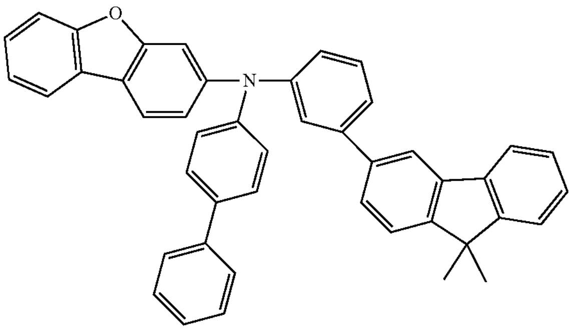

-continued

H-1-14

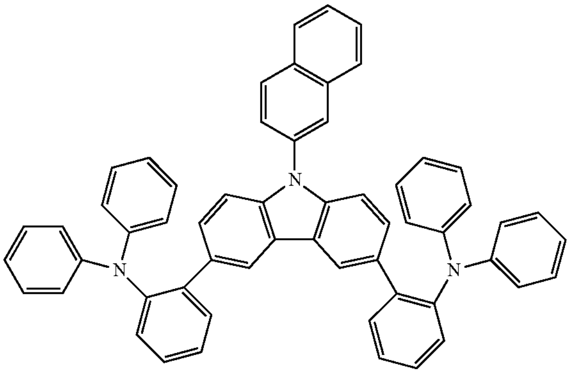

H-1-15

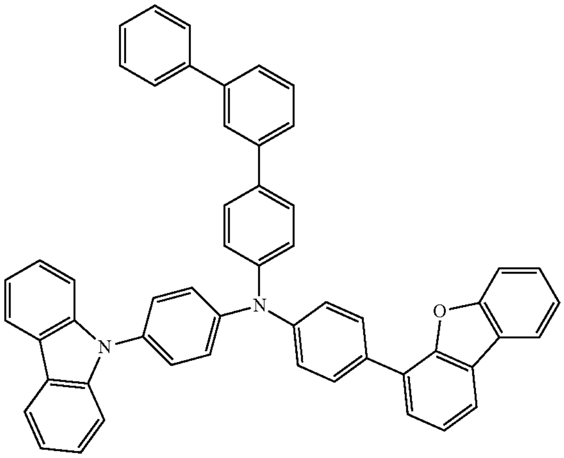

H-1-16

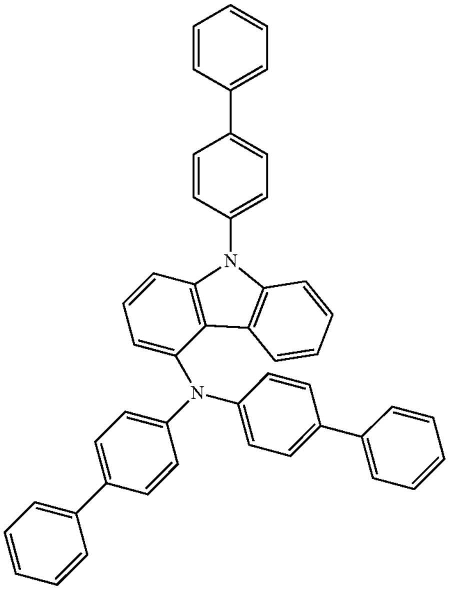

-continued

H-1-17

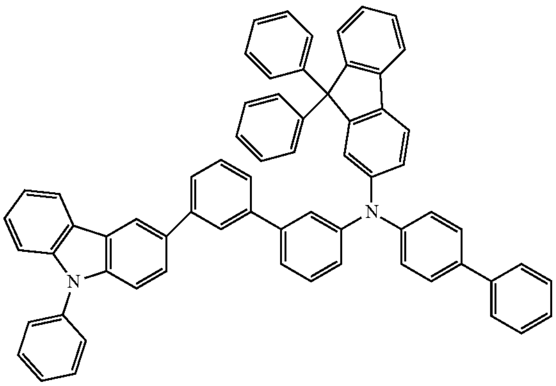

H-1-18

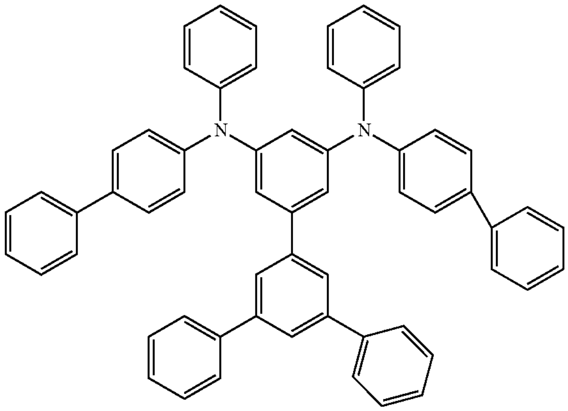

H-1-19

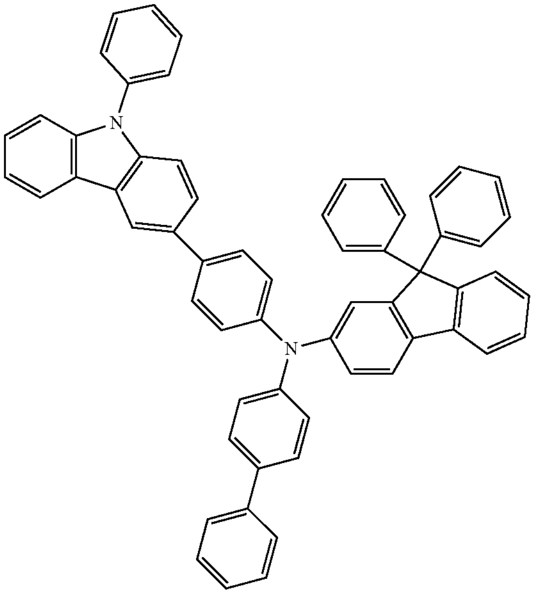

The hole transport region HTR may include a phthalocyanine compound such as copper phthalocyanine, $N^1$,$N^{1'}$-([1,1'-biphenyl]-4,4'-diyl)bis($N^1$-phenyl-tolylbenzene-1,4-diamine) (DNTPD), 4,4',4"-[tris(3-methylphenyl)phenylamino] triphenylamine (m-MTDATA), 4,4',4"-tris(N,N-diphenylamino)triphenylamine (TDATA), 4,4',4"-tris[N(2-naphthyl)-N-phenylamino]-triphenylamine (2-TNATA), poly(3,4-ethylenedioxythiophene)/poly(4-styrenesulfonate)

(PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium [tetrakis (pentafluorophenyl)borate], and dipyrazino[2,3-f:2',3'-h] quinoxaline-2,3,6,7,10,11-hexacarbonitrile (HATCN).

The hole transport region HTR may include carbazole derivatives such as N-phenyl carbazole and polyvinyl carbazole, fluorene-based derivatives, N,N'-bis(3-methylphenyl)-N,N'-diphenyl[1,1'-biphenyl]-4,4'-diamine (TPD), triphenylamine-based derivatives such as 4,4',4"-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine] (TAPC), 4,4'-bis[N,N'-(3-tolyl)amino]-3,3'-dimethylbiphenyl (HMTPD), 9-(4-tert-butylphenyl)-3,6-bis(triphenylsilyl)-9H-carbazole (CzSi), 9-phenyl-9H-3,9'-bicarbazole (CCP), 1,3-bis(N-carbazolyl)benzene (mCP), 1,3-bis(1,8-dimethyl-9H-carbazol-9-yl)benzene (mDCP), etc.

The hole transport region HTR may include the compounds of the hole transport region in at least one of a hole injection layer HIL, a hole transport layer HTL, or an electron blocking layer EBL.

A thickness of the hole transport region HTR may be in a range of about 100 Å to about 10,000 Å. For example, the thickness of the hole transport region HTR may be in a range of about 100 Å to about 5,000 Å. In case where the hole transport region HTR includes a hole injection layer HIL, a thickness of the hole injection layer HIL may be, for example, in a range of about 30 Å to about 1,000 Å. In case where the hole transport region HTR includes a hole transport layer HTL, a thickness of the hole transport layer HTL may be in a range of about 30 Å to about 1,000 Å. In case where the hole transport region HTR includes an electron blocking layer, a thickness of the electron blocking layer EBL may be in a range of about 10 Å to about 1,000 Å. If the thicknesses of the hole transport region HTR, the hole injection layer HIL, the hole transport layer HTL, and the electron blocking layer EBL satisfy the above-described ranges, satisfactory hole transport properties may be achieved without substantial increase of driving voltage.

The hole transport region HTR may further include a charge generating material to increase conductivity. The charge generating material may be dispersed uniformly or non-uniformly in the hole transport region HTR. The charge generating material may be, for example, a p-dopant. The p-dopant may include at least one of metal halide compounds, quinone derivatives, metal oxides, and cyano group-containing compounds, without limitation. For example, the p-dopant may include metal halide compounds such as CuI and RbI, quinone derivatives such as tetracyanoquinodimethane (TCNQ) and 2,3,5,6-tetrafluoro-7,7',8,8-tetracyanoquinodimethane (F4-TCNQ), metal oxides such as tungsten oxide and molybdenum oxide, cyano group-containing compounds such as dipyrazino[2,3-f:2',3'-h] quinoxaline-2,3,6,7,10,11-hexacarbonitrile (HATCN) and 4-[[2,3-bis[cyano-(4-cyano-2,3,5,6-tetrafluorophenyl)methylidene] cyclopropylidene]-cyanomethyl]-2,3,5,6-tetrafluorobenzonitrile (NDP9), etc., without limitation.

As described above, the hole transport region HTR may further include at least one of a buffer layer (not shown) or an electron blocking layer EBL, in addition to the hole injection layer HIL and the hole transport layer HTL. The buffer layer (not shown) may compensate for a resonance distance according to a wavelength of light emitted from an emission layer EML and may increase light emitting efficiency. Materials which may be included in the hole transport region HTR may be included in the buffer layer (not shown). The electron blocking layer EBL may block injection of electrons from an electron transport region ETR to a hole transport region HTR.

The emission layer EML is provided on the hole transport region HTR. The emission layer EML may have a thickness, for example, in a range of about 100 Å to about 1,000 Å. For example, the emission layer EML may have a thickness in a range of about 100 Å to about 300 Å. The emission layer EML may be a layer formed of a single material, a layer formed of different materials, or a multilayer structure having layers formed of different materials.

In the light emitting device ED of an embodiment, the emission layer EML may include anthracene derivatives, pyrene derivatives, fluoranthene derivatives, chrysene derivatives, dihydrobenzanthracene derivatives, or triphenylene derivatives. For example, the emission layer EML may include anthracene derivatives or pyrene derivatives.

In the light emitting devices ED of embodiments shown in each of FIG. 3 to FIG. 6, the emission layer EML may include a host and a dopant, and the emission layer EML may include a compound represented by Formula E-1. The compound represented by Formula E-1 may be used as a fluorescence host material.

[Formula E-1]

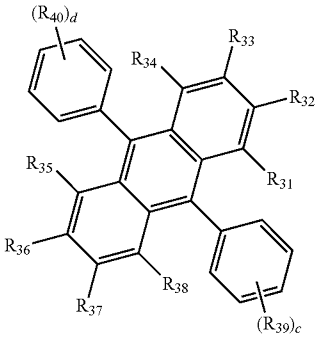

In Formula E-1, $R_{31}$ to $R_{40}$ may each independently be a hydrogen atom, a deuterium atom, a halogen atom, a substituted or unsubstituted silyl group, a substituted or unsubstituted thio group, a substituted or unsubstituted oxy group, a substituted or unsubstituted alkyl group of 1 to 10 carbon atoms, a substituted or unsubstituted alkenyl group of 2 to 10 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula E-1, $R_{31}$ to $R_{40}$ may be combined with an adjacent group to form a saturated hydrocarbon ring, an unsaturated hydrocarbon ring, a saturated heterocycle, or an unsaturated heterocycle.

In Formula E-1, c and d may each independently be an integer from 0 to 5.

The compound represented by Formula E-1 may be any one selected from Compound E1 to Compound E19.

E1
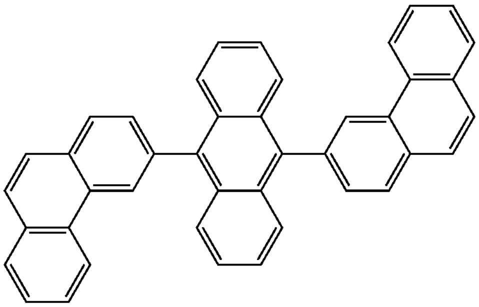
E2
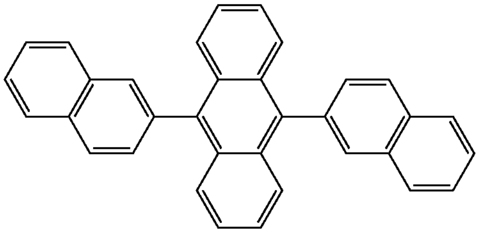
E3
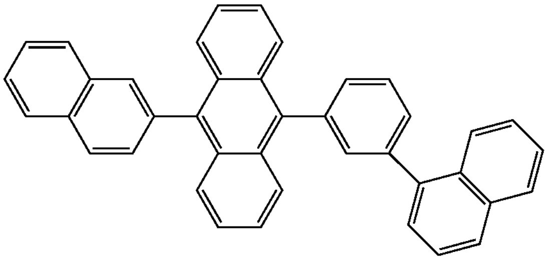
E4
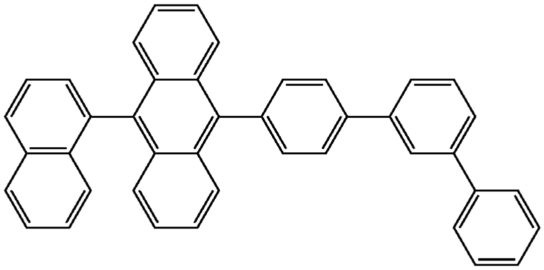
E5
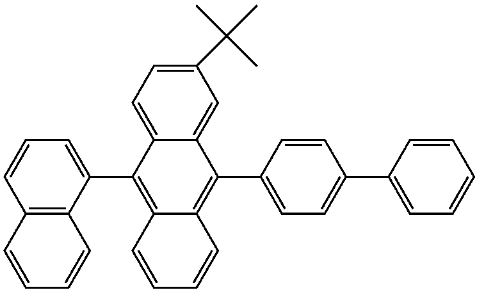
-continued
E6
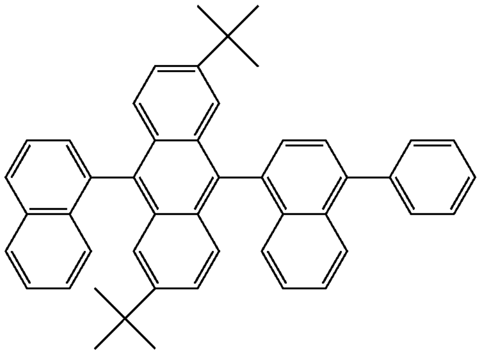
E7
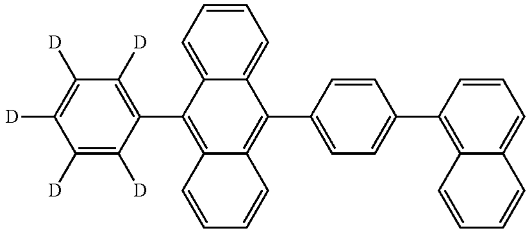
E8
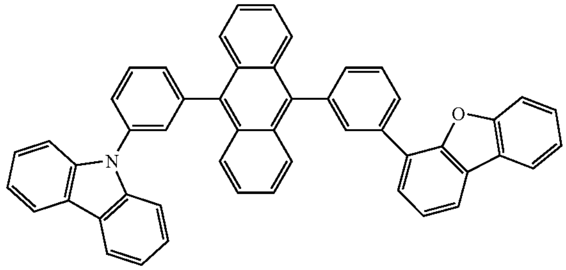
E9
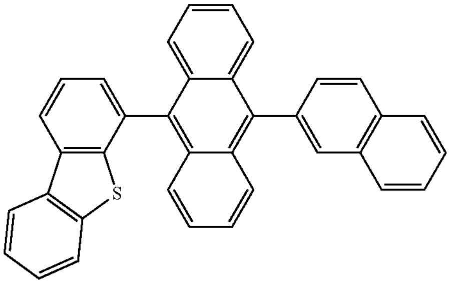
E10
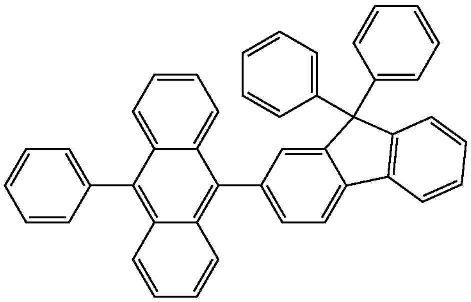

-continued
E11
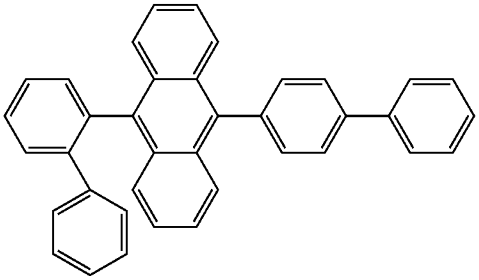
E12
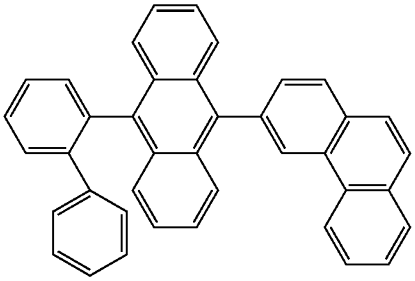
E13
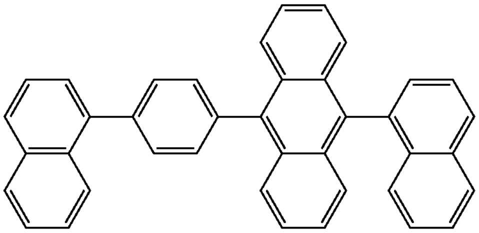
E14
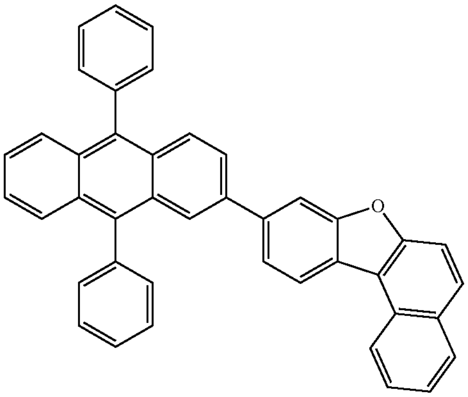
-continued
E15
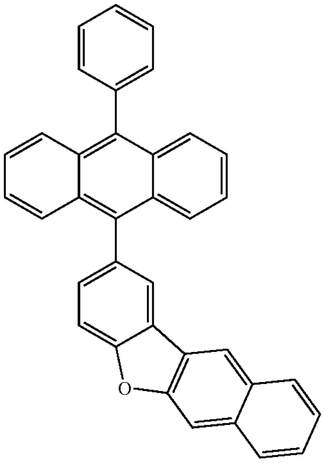
E16
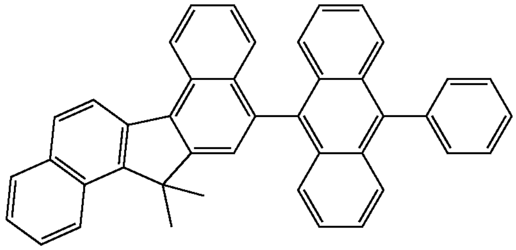
E17
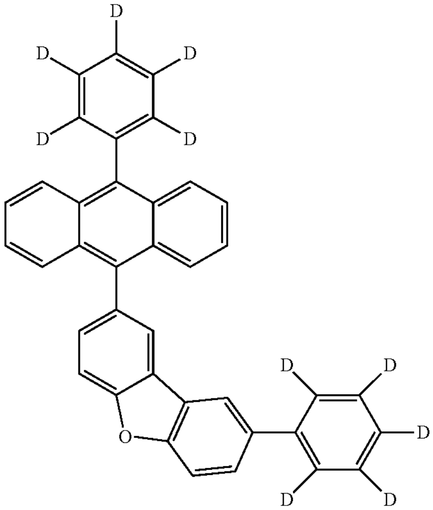
E18
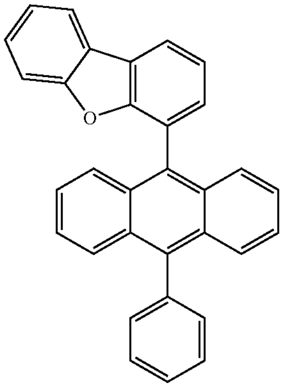

-continued

E19

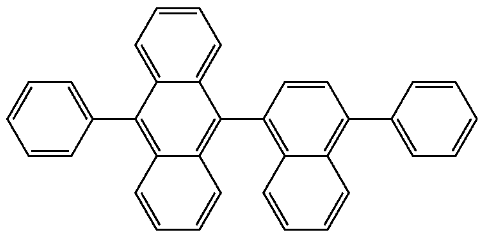

In an embodiment, the emission layer EML may include a compound represented by Formula E-2a or Formula E-2b. The compound represented by Formula E-2a or Formula E-2b may be used as a phosphorescence host material.

[Formula E-2a]

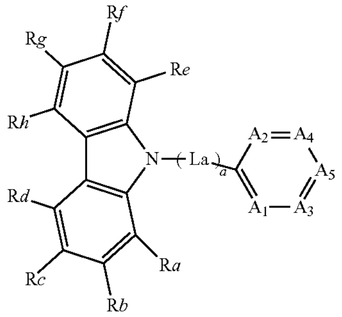

In Formula E-2b, a may be an integer from 0 to 10, and $L_a$ may be a direct linkage, a substituted or unsubstituted arylene group of 6 to 30 ring-forming carbon atoms, or a substituted or unsubstituted heteroarylene group of 2 to 30 ring-forming carbon atoms. When a is 2 or more, multiple $L_a$ groups may each independently be a substituted or unsubstituted arylene group of 6 to 30 ring-forming carbon atoms, or a substituted or unsubstituted heteroarylene group of 2 to 30 ring-forming carbon atoms.

In Formula E-2a, $A_1$ to $A_5$ may each independently be N or C(Ri). $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. $R_a$ to $R_i$ may be combined with an adjacent group to form a hydrocarbon ring or a heterocycle including N, O, S, etc. as a ring-forming atom.

In Formula E-2a, two or three of $A_1$ to $A_5$ may be N, and the remainder of $A_1$ to $A_5$ may be $C(R_i)$.

[Formula E-2b]

$$(Cbz1)-(L_b)_b-(Cbz2)$$

In Formula E-2b, Cbz1 and Cbz2 may each independently be an unsubstituted carbazole group, or a carbazole group substituted with an aryl group of 6 to 30 ring-forming carbon atoms. $L_b$ may be a direct linkage, a substituted or unsubstituted arylene group of 6 to 30 ring-forming carbon atoms, or a substituted or unsubstituted heteroarylene group of 2 to 30 ring-forming carbon atoms. In Formula E-2b, b may be an integer from 0 to 10, and when b is 2 or more, multiple $L_b$ groups may each independently be a substituted or unsubstituted arylene group of 6 to 30 ring-forming carbon atoms, or a substituted or unsubstituted heteroarylene group of 2 to 30 ring-forming carbon atoms.

The compound represented by Formula E-2a or Formula E-2b may be any one selected from Compound Group E-2. However, the compounds shown in Compound Group E-2 are only examples, and the compound represented by Formula E-2a or Formula E-2b is not limited to Compound Group E-2.

[Compound Group E-2]

E-2-1

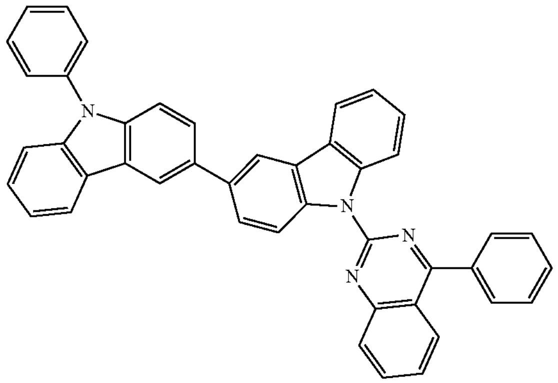

E-2-2

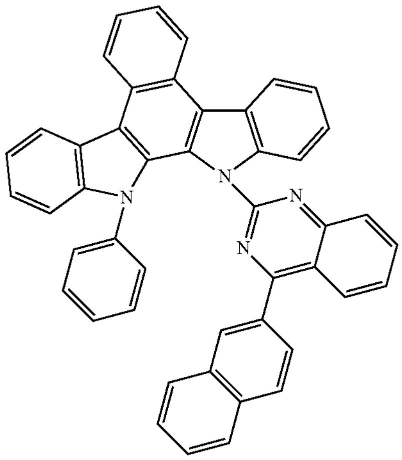

-continued
E-2-3
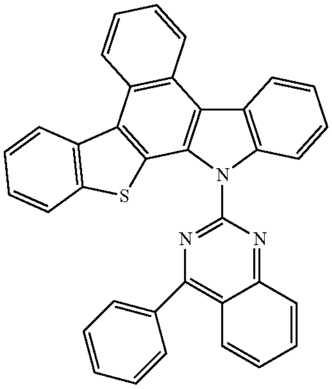
E-2-4
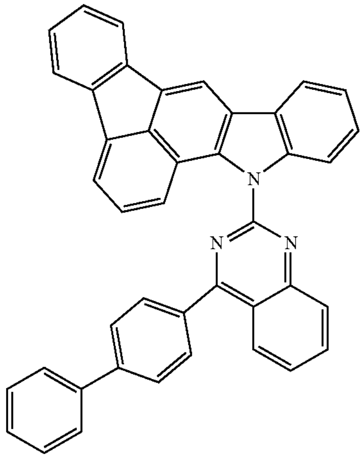
E-2-5
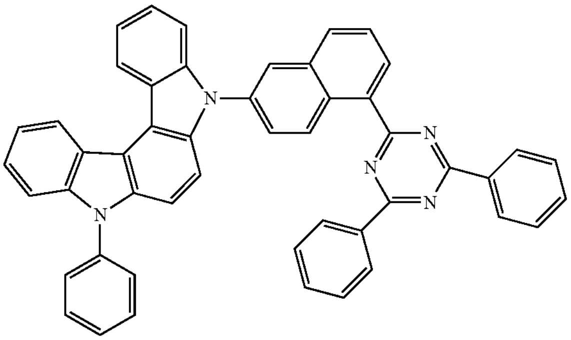
-continued
E-2-6
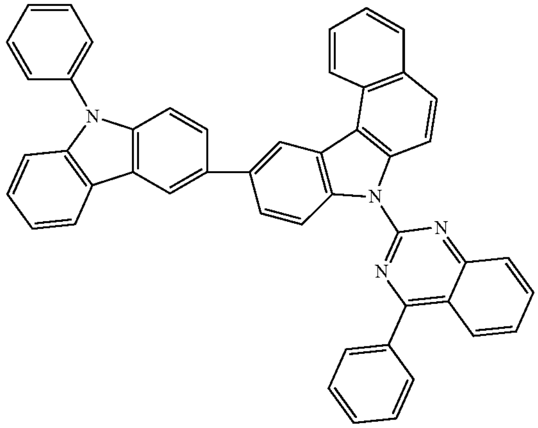
E-2-7
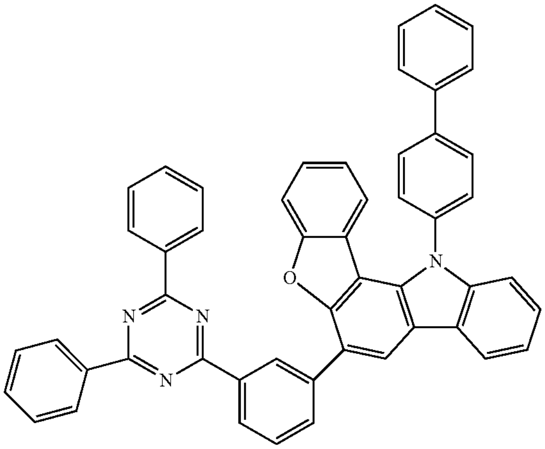
E-2-8
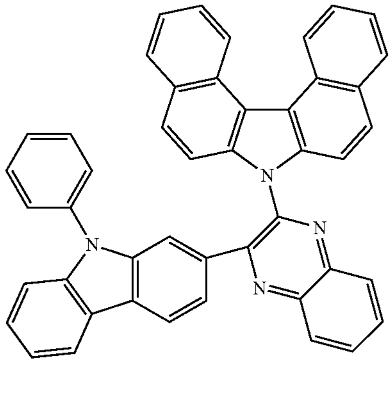

-continued
E-2-9
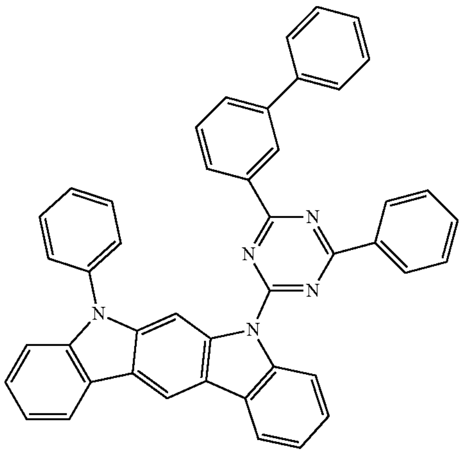
E-2-10
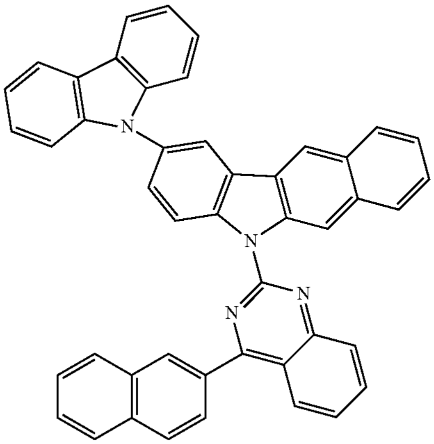
E-2-11
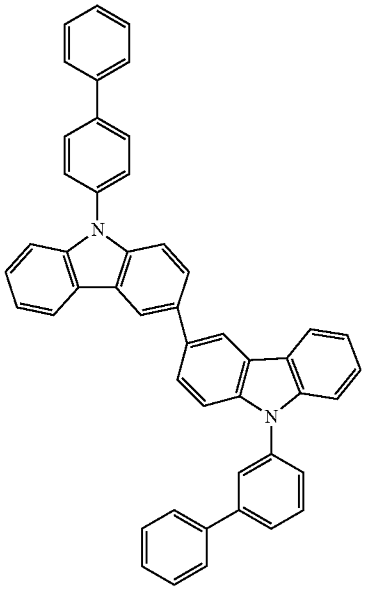
-continued
E-2-12
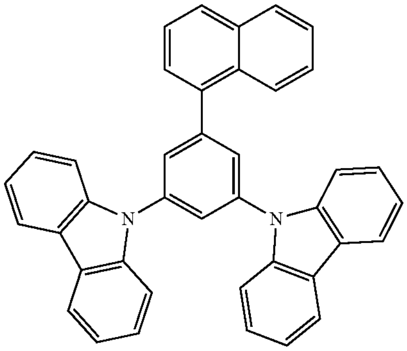
E-2-13
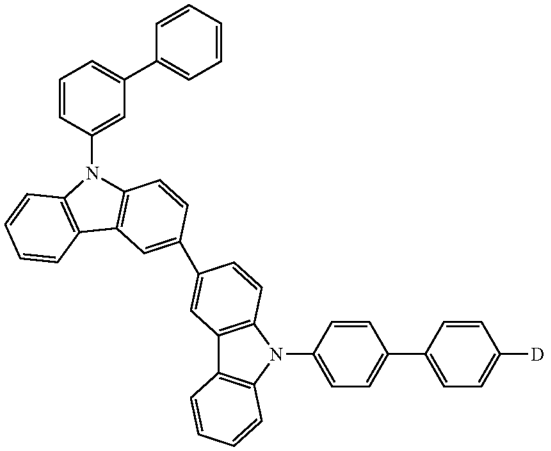
E-2-14
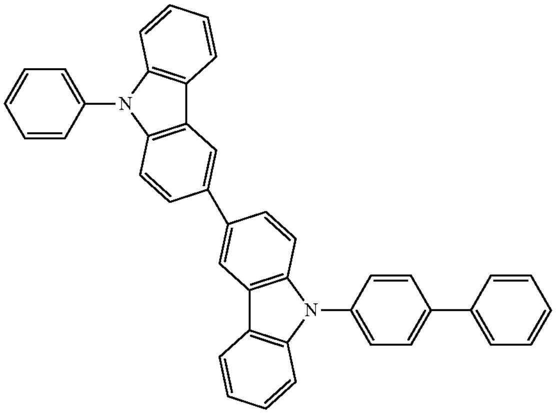
E-2-15
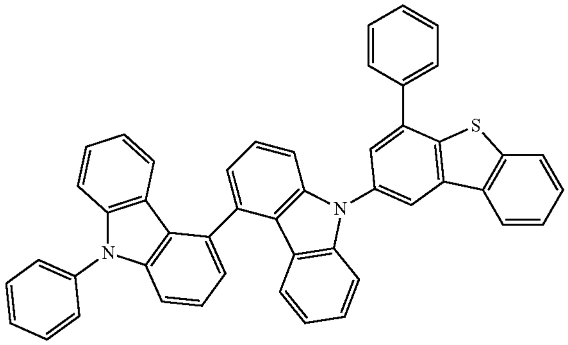

-continued
E-2-16
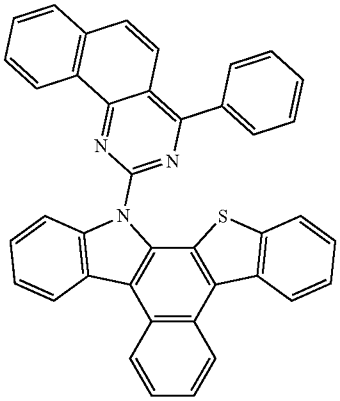
E-2-17
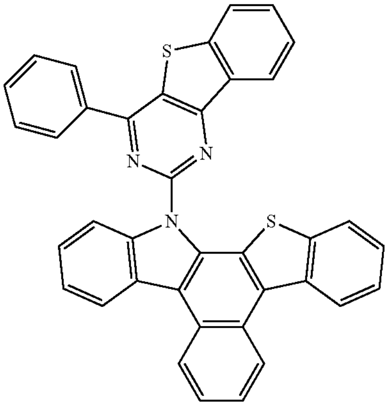
E-2-18
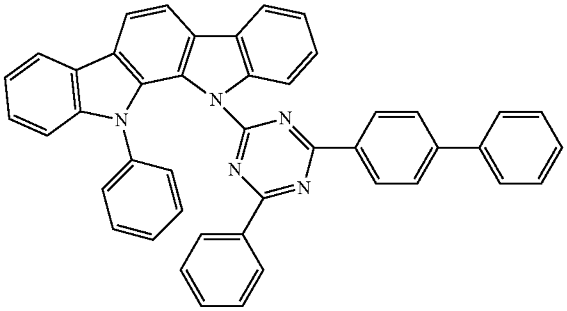
E-2-19
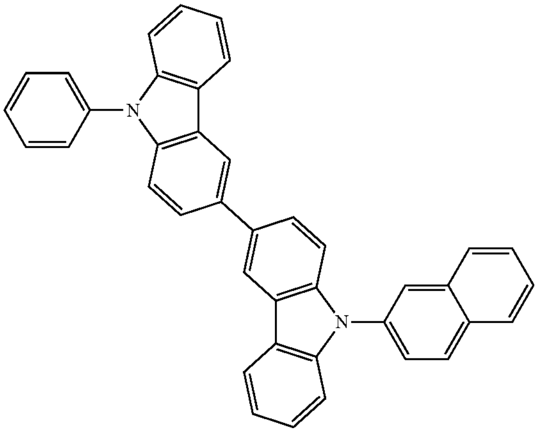
-continued
E-2-20
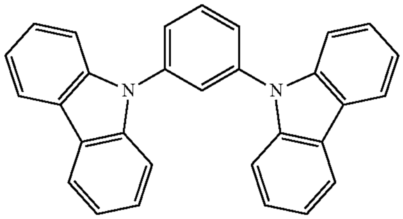
E-2-21
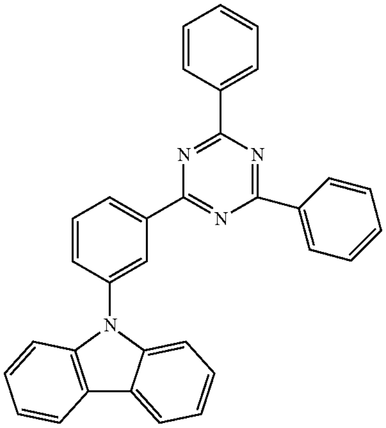
E-2-22
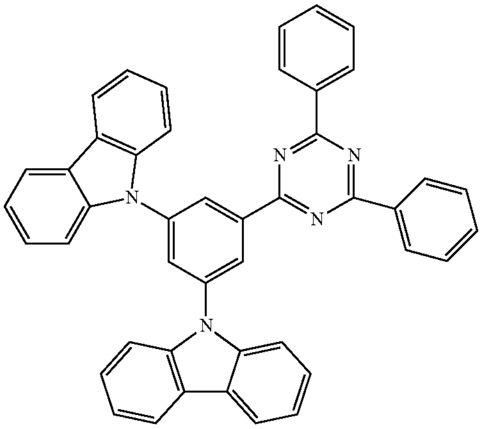
E-2-23
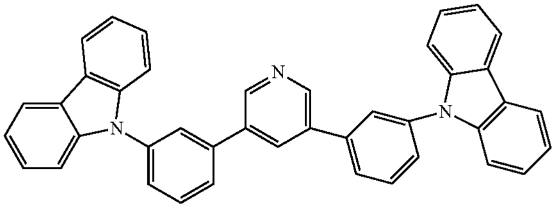

-continued

E-2-24

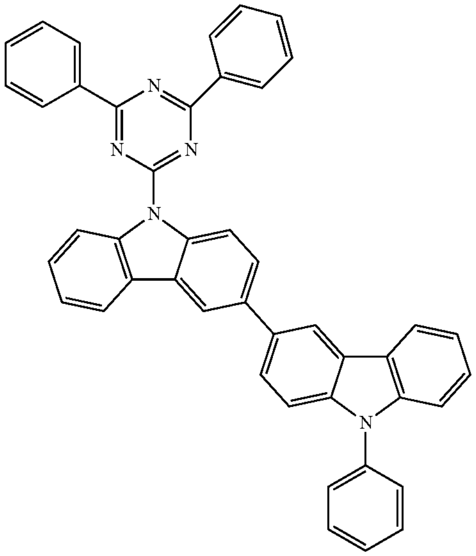

The emission layer EML may further include a common material in the art as a host material. For example, the emission layer EML may include as a host material, at least one of bis(4-(9H-carbazol-9-yl)phenyl)diphenyl silane (BCPDS), (4-(1-(4-(diphenylamino)phenyl)cyclohexyl)phenyl)diphenyl-phosphine oxide (POPCPA), bis[2-(diphenylphosphino)phenyl] ether oxide (DPEPO), 4,4'-bis(N-carbazolyl)-1,1'-biphenyl (CBP), 1,3-bis(carbazol-9-yl) benzene (mCP), 2,8-bis(diphenylphosphoryl)dibenzo[b,d]furan (PPF), 4,4',4"-tris(carbazol-9-yl)-triphenylamine (TCTA), or 1,3,5-tris(1-phenyl-1H-benzo[d]imidazole-2-yl) benzene (TPBi). However, embodiments are not limited thereto. For example, tris(8-hydroxyquinolino)aluminum ($Alq_3$), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis (triphenyl silyl)benzene (UGH2), hexaphenylcyclotrisiloxane ($DPSiO_3$), octaphenylcyclotetra siloxane ($DPSiO_4$), etc. may be used as the host material.

The emission layer EML may include a compound represented by Formula M-a or Formula M-b. The compound represented by Formula M-a or Formula M-b may be used as a phosphorescence dopant material.

[Formula M-a]

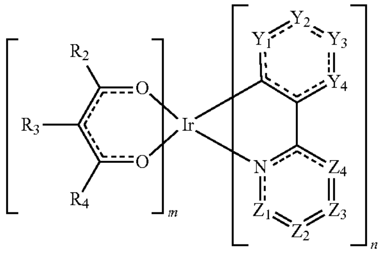

In Formula M-a, $Y_1$ to $Y_4$ and $Z_1$ to $Z_4$ may each independently be $C(R_1)$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula M-a, m may be 0 or 1, and n may be 2 or 3. In Formula M-a, when m is 0, n may be 3, and when m is 1, n may be 2.

The compound represented by Formula M-a may be used as a phosphorescence dopant. The compound represented by Formula M-a may be any one selected from Compounds M-a1 to M-a25. However, Compounds M-a1 to M-a25 are only examples, and the compound represented by Formula M-a is not limited to Compounds M-a1 to M-a25.

M-a1

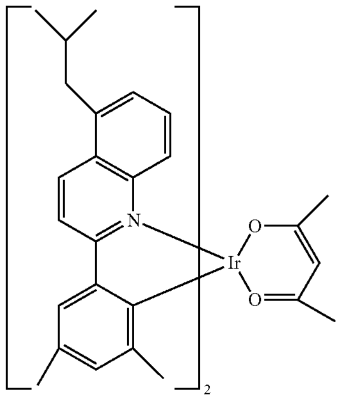

M-a2

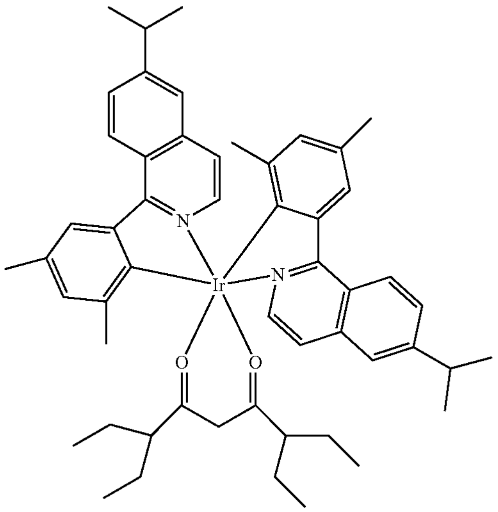

M-a3

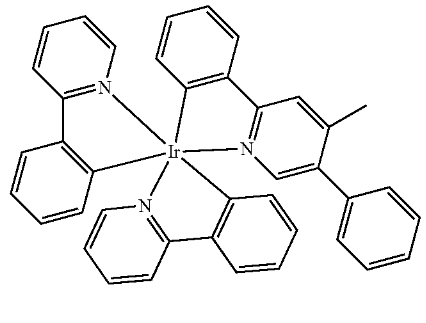

-continued
M-a4
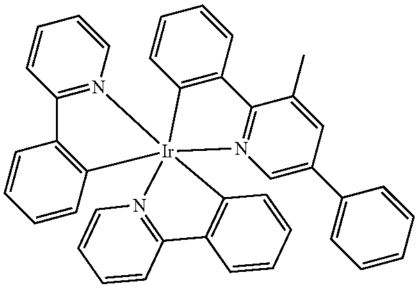
M-a5
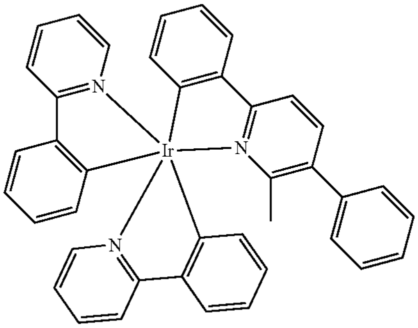
M-a6
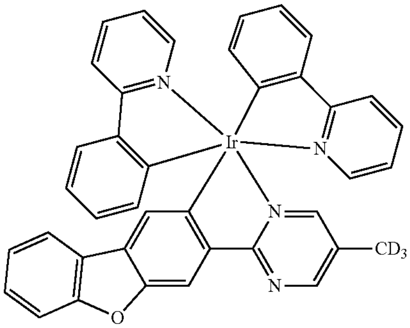
M-a7
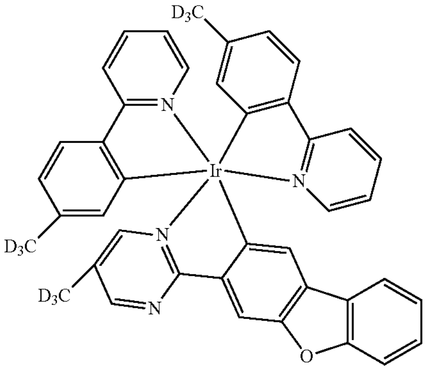
M-a8
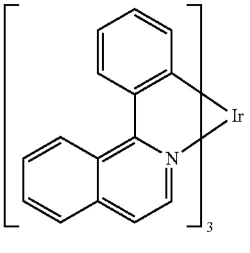
-continued
M-a9
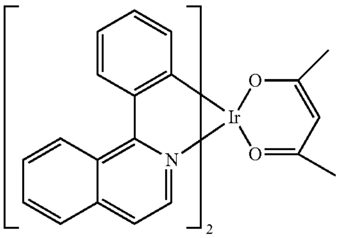
M-a10
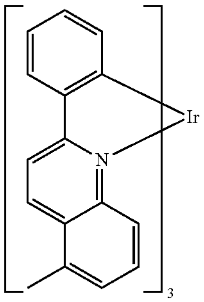
M-a11
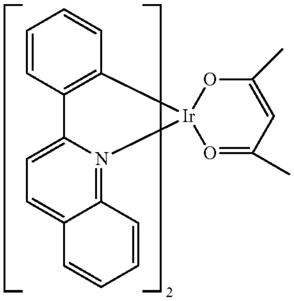
M-a12
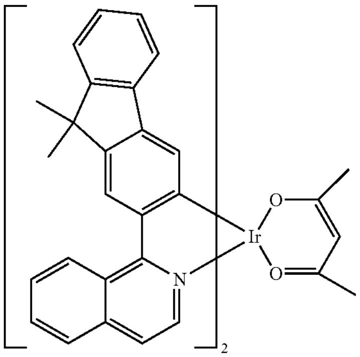
M-a13
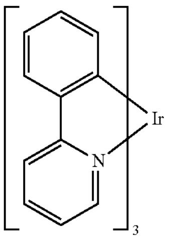

-continued
M-a14
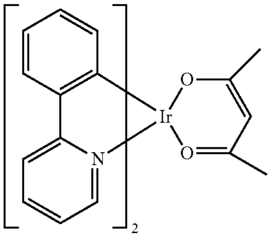
M-a15
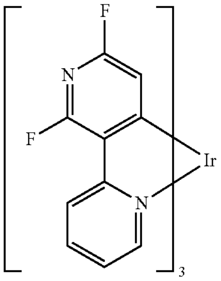
M-a16
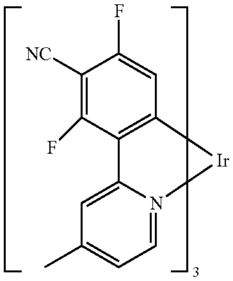
M-a17
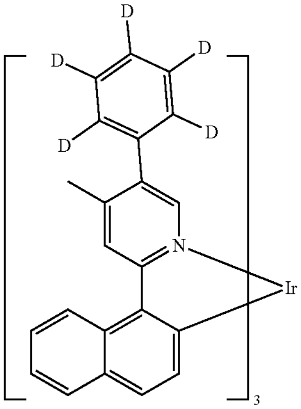
M-a18
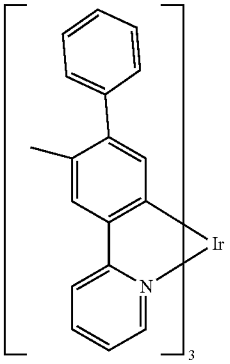
-continued
M-a19
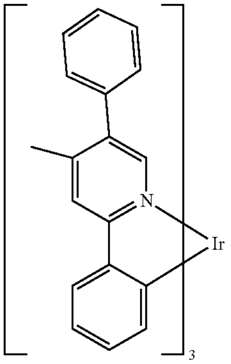
M-a20
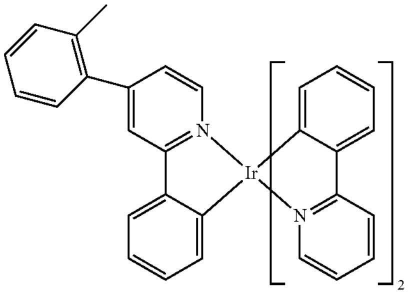
M-a21
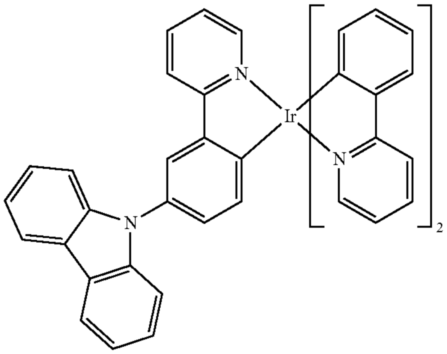
M-a22
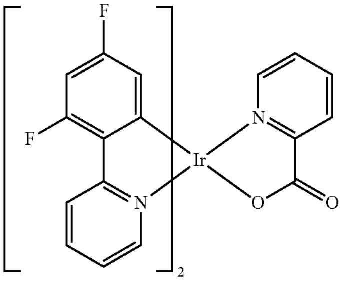
M-a23
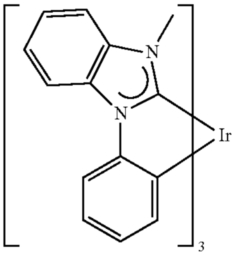

-continued

M-a24

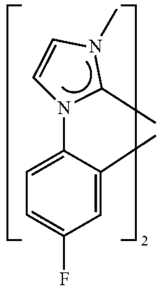

M-a25

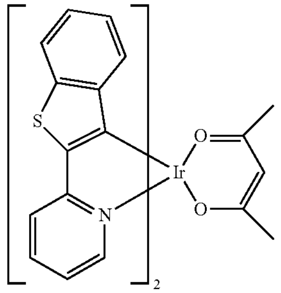

Compound M-a1 and Compound M-a2 may be used as red dopant materials, and Compound M-a3 to Compound M-a7 may be used as green dopant materials.

[Formula M-b]

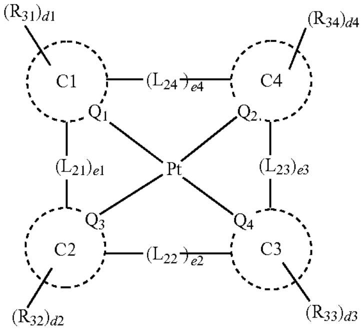

In Formula M-b, $Q_1$ to $Q_4$ may each independently be C or N, C1 to C4 may each independently be a substituted or unsubstituted hydrocarbon ring of 5 to 30 ring-forming carbon atoms, or a substituted or unsubstituted heterocycle of 2 to 30 ring-forming carbon atoms. $L_{21}$ to $L_{24}$ may each independently be a direct linkage, *—O—*, *—S—*,

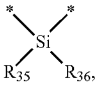 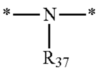 , 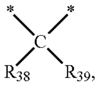, 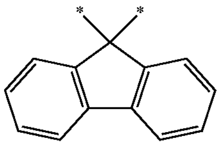 , a substituted or unsubstituted divalent alkyl group of 1 to 20 carbon atoms, a substituted or unsubstituted arylene group of 6 to 30 ring-forming carbon atoms, or a substituted or unsubstituted heteroarylene group of 2 to 30 ring-forming carbon atoms, and e1 to e4 may each independently be 0 or 1. In Formula M-b, Rai to $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring, and d1 to d4 may each independently be an integer from 0 to 4.

The compound represented by Formula M-b may be used as a blue phosphorescence dopant or a green phosphorescence dopant.

The compound represented by Formula M-b may be any one selected from Compounds M-b-1 to M-b-11. However, Compounds M-b-1 to M-b-11 are only examples, and the compound represented by Formula M-b is not limited to Compounds M-b-1 to M-b-11.

M-b-1

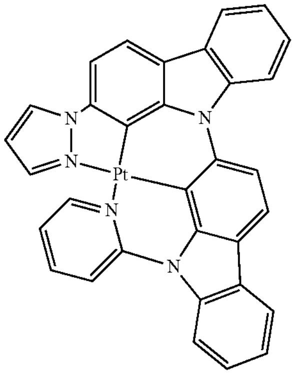

M-b-2

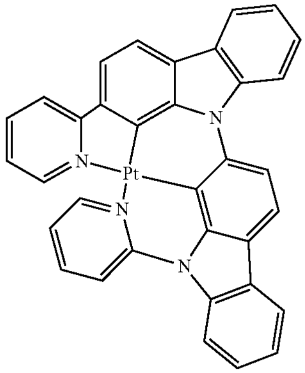

M-b-3

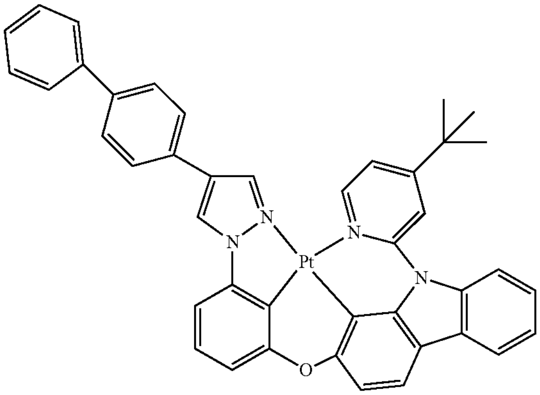

-continued

M-b-4

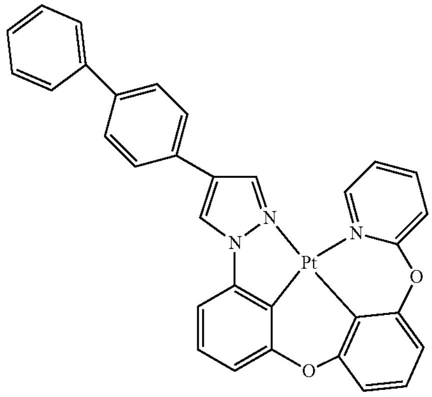

M-b-5

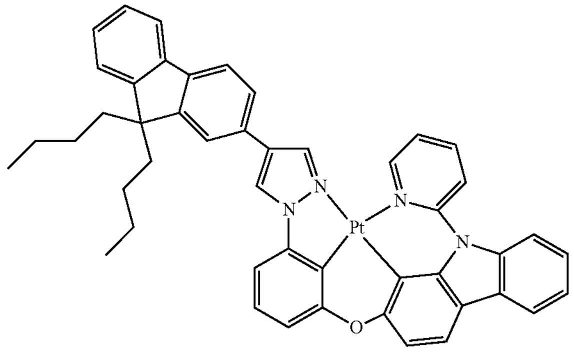

M-b-6

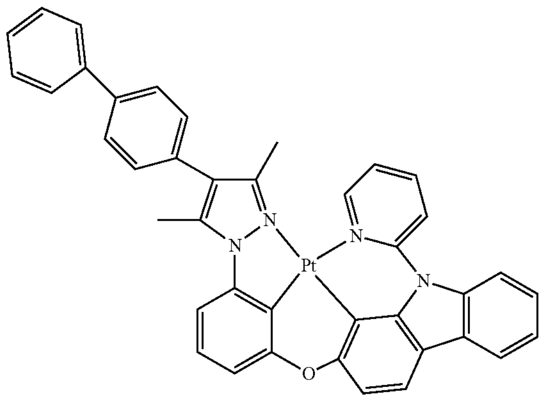

M-b-7

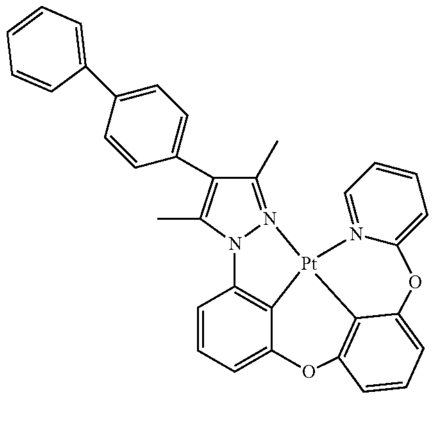

-continued

M-b-8

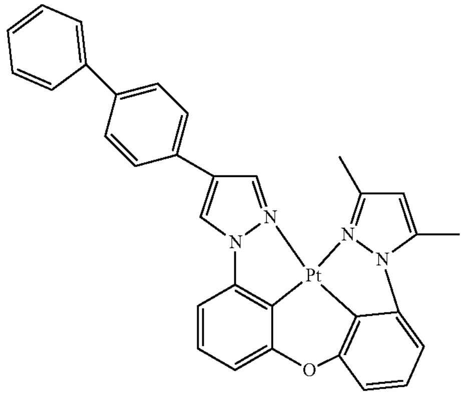

M-b-9

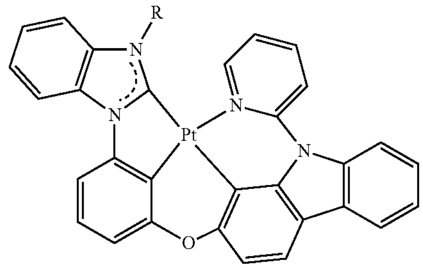

M-b-10

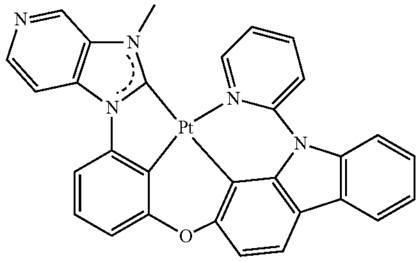

M-b-11

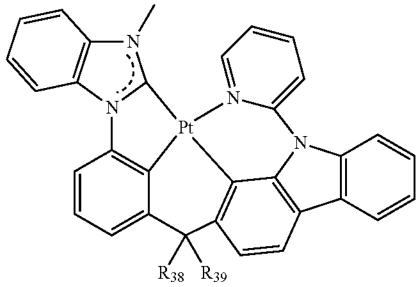

In Compounds M-b-1 to M-b-11, R, $R_{38}$, and $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

The emission layer EML may include any one of Formula F-a to Formula F-c. The compounds represented by Formula F-a to Formula F-c may be used as fluorescence dopant materials.

[Formula F-a]

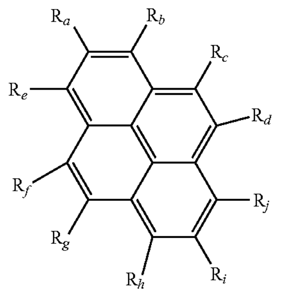

In Formula F-a, two selected from $R_a$ to $R_j$ may each independently be substituted with a group represented by *—$NAr_1Ar_2$. The remainder of $R_a$ to $R_j$ which are not substituted with *—$NAr_1Ar_2$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In the group represented by *—$NAr_1Ar_2$, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. For example, at least one of $Ar_1$ and $Ar_2$ may be a heteroaryl group including O or S as a ring-forming atom.

[Formula F-b]

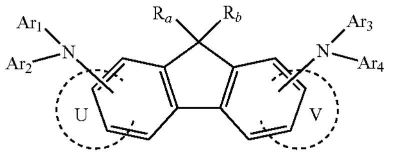

In Formula F-b, $R_a$ and $R_b$ may each independently be a hydrogen atom, a deuterium atom, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula F-b, $Ar_1$ to $Ar_4$ may each independently be a substituted or unsubstituted aryl group of 6 to 30 ring-forming carbon atoms, or a substituted or unsubstituted heteroaryl group of 2 to 30 ring-forming carbon atoms.

In Formula F-b, U and V may each independently be a substituted or unsubstituted hydrocarbon ring of 5 to 30 ring-forming carbon atoms, or a substituted or unsubstituted heterocycle of 2 to 30 ring-forming carbon atoms.

In Formula F-b, the number of rings represented by U and V may each independently be 0 or 1. For example, in Formula F-b, if the number of U or V is 1, a fused ring may be present at the part designated by U or V, and if the number of U or V is 0, a ring may not be present at the part designated by U or V. When the number of U is 0 and the number of V is 1, or if the number of U is 1 and the number of V is 0, a fused ring having the fluorene core of Formula F-b may be a ring compound with four rings. When the number of both U and V is 0, the fused ring of Formula F-b may be a ring compound with three rings. When the number of both U and V is 1, a fused ring having the fluorene core of Formula F-b may be a ring compound with five rings.

[Formula F-c]

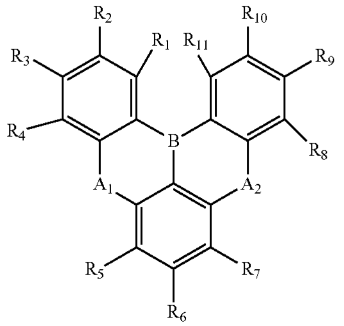

In Formula F-c, $A_1$ and $A_2$ may each independently be O, S, Se, or $N(R_m)$, and $R_m$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In Formula F-c, $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

In Formula F-c, $A_1$ and $A_2$ may each independently be combined with an adjacent ring to form a fused ring. For example, when $A_1$ and $A_2$ are each independently $N(R_m)$, $A_1$ may be combined with $R_4$ or $R_5$ to form a ring. For example, $A_2$ may be combined with $R_7$ or $R_8$ to form a ring.

In an embodiment, the emission layer EML may include as a dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi), and 4,4'-bis[2-(4-(N,N-diphenylamino)phenyl)vinyl]biphenyl (DPAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, and 1,4-bis(N,N-diphenylamino)pyrene), etc.

The emission layer EML may include a phosphorescence dopant material. For example, the phosphorescence dopant may include a metal complex including iridium (Ir), platinum (Pt), osmium (Os), gold (Au), titanium (Ti), zirconium (Zr), hafnium (Hf), europium (Eu), terbium (Tb) or thulium (Tm). For example, iridium(III) bis(4,6-difluorophenylpyridinato-N,C2')picolinate (FIrpic), bis(2,4-difluorophenylpyridinato)-tetrakis(1-pyrazolyl)borate iridium(III) (Fir6), or platinum octaethyl porphyrin (PtOEP) may be used as the phosphorescence dopant. However, embodiments are not limited thereto.

The emission layer EML may include a quantum dot material. The quantum dot may be a Group II-VI compound, a Group III-VI compound, a Group compound, a Group III-V compound, a Group III-II-V compound, a Group IV-VI compound, a Group IV element, a Group IV compound, and combinations thereof.

The Group II-VI compound may be a binary compound selected from the group consisting of CdSe, CdTe, CdS, ZnS, ZnSe, ZnTe, ZnO, HgS, HgSe, HgTe, MgSe, MgS, and mixtures thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof; a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and mixtures thereof; or any combination thereof.

The Group III-VI compound may be a binary compound such as $In_2S_3$, and $In_2Se_3$; a ternary compound such as $InGaS_3$, and $InGaSe_3$; or any combination thereof.

The Group compound may be a ternary compound selected from the group consisting of AgInS, $AgInS_2$, CuInS, $CuInS_2$, $AgGaS_2$, $CuGaS_2$, $CuGaO_2$, $AgGaO_2$, $AgAlO_2$ and mixtures thereof; a quaternary compound such as $AgInGaS_2$, and $CuInGaS_2$; or any combination thereof.

The Group III-V compound may be a binary compound selected from the group consisting of GaN, GaP, GaAs, GaSb, AlN, AlP, AlAs, AlSb, InN, InP, InAs, InSb, and mixtures thereof; a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and mixtures thereof; a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof; or any combination thereof. The Group III-V compound may further include a Group II metal. For example, InZnP, etc. may be selected as a Group III-II-V compound.

The Group IV-VI compound may be a binary compound selected from the group consisting of SnS, SnSe, SnTe, PbS, PbSe, PbTe, and mixtures thereof; a ternary compound selected from the group consisting of SnSeS, SnSeTe, SnSTe, PbSeS, PbSeTe, PbSTe, SnPbS, SnPbSe, SnPbTe, and mixtures thereof; a quaternary compound selected from the group consisting of SnPbSSe, SnPbSeTe, SnPbSTe, and mixtures thereof; or any combination thereof. The Group IV element may be selected from the group consisting of Si, Ge, and a mixture thereof. The Group IV compound may be a binary compound selected from the group consisting of SiC, SiGe, and a mixture thereof.

A binary compound, a ternary compound, or a quaternary compound may be present in a particle at a uniform concentration or may be present in a particle at a partially different concentration distribution state. In an embodiment, the quantum dot may have a core/shell structure in which one quantum dot surrounds another quantum dot. The interface of the core and the shell may have a concentration gradient in which the concentration of an element that is present in the shell decreases toward the core.

In embodiments, the quantum dot may have a core-shell structure including a core including a nanocrystal and a shell surrounding the core. The shell of the quantum dot may be a protection layer that prevents chemical deformation of the core to maintain semiconductor properties and/or may be a charging layer that imparts electrophoretic properties to the quantum dot. The shell may be a single layer or a multilayer. Examples of the shell of the quantum dot may include a metal oxide, a non-metal oxide, a semiconductor compound, or combinations thereof.

For example, the metal oxide or non-metal oxide may include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$ and NiO; or a ternary compound such as $MgAl_2O_4$, $CoFe_2O_4$, $NiFe_2O_4$ and $CoMn_2O_4$, but embodiments are not limited thereto.

The semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments are not limited thereto.

The quantum dot may have a full width of half maximum (FWHM) of an emission wavelength spectrum equal to or less than about 45 nm. For example, the quantum dot may have a FWHM of an emission wavelength spectrum equal to or less than about 40 nm. For example, the quantum dot may have a FWHM of an emission wavelength spectrum equal to or less than about 30 nm. Within these ranges, color purity or color reproducibility may be improved. Light emitted through the quantum dot may be emitted in all directions, and light viewing angle properties may be improved.

The shape of the quantum dot may be a shape that is used in the art, without limitation. For example, a quantum dot may have a spherical shape, a pyramidal shape, a multi-arm shape, or a cubic shape, or the quantum dot may be in the form of a nanoparticle, a nanotube, a nanowire, a nanofiber, a nanoplate, etc.

The quantum dot may control the color of light emitted according to a particle size thereof, and accordingly, the quantum dot may have various emission colors such as blue, red, and green.

In the light emitting device ED of an embodiment, as shown in FIG. 3 to FIG. 6, an electron transport region ETR is provided on the emission layer EML. The electron transport region ETR may include at least one of a hole blocking layer HBL, an electron transport layer ETL or an electron injection layer EIL. However, embodiments are not limited thereto.

The electron transport region ETR may be a layer formed of a single material, a layer formed of different materials, or a multilayer structure having layers formed of different materials.

For example, the electron transport region ETR may have a single layer structure of an electron injection layer EIL or an electron transport layer ETL, or a single layer structure formed of an electron injection material and an electron transport material. The electron transport region ETR may have a single layer structure formed of different materials, or may have a structure in which an electron transport layer ETL/electron injection layer EIL, or a hole blocking layer HBL/electron transport layer ETL/electron injection layer EIL are stacked in its respective stated order from the emission layer EML, but embodiments are not limited thereto. A thickness of the electron transport region ETR may be, for example, in a range of about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

The electron transport region ETR may include a compound represented by Formula ET-1.

[Formula ET-1]

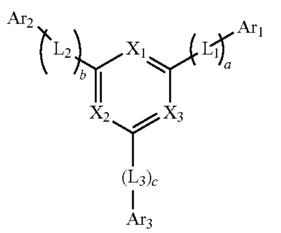

In Formula ET-1, at least one of $X_1$ to $X_3$ may be N, and the remainder of $X_1$ to $X_3$ may be $C(R_a)$. $R_a$ may be a hydrogen atom, a deuterium atom, a substituted or unsubstituted alkyl of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In Formula ET-1, $Ar_1$ to $Ar_3$ may each independently be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula ET-1, a to c may each independently be an integer from 0 to 10. In Formula ET-1, $L_1$ to $L_3$ may each independently be a direct linkage, a substituted or unsubstituted arylene group of 6 to 30 ring-forming carbon atoms, or a substituted or unsubstituted heteroarylene group of 2 to 30 ring-forming carbon atoms. When a to c are 2 or more, $L_1$ to $L_3$ may each independently be a substituted or unsubstituted arylene group of 6 to 30 ring-forming carbon atoms, or a substituted or unsubstituted heteroarylene group of 2 to 30 ring-forming carbon atoms.

The electron transport region ETR may include an anthracene-based compound. However, embodiments are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri (1-phenyl-1H-benzo[d]imidazol-2-yl) benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1, O8)-(1,1'-biphenyl-4-olato)aluminum (BAlq), berylliumbis(benzoquinolin-10-olate ($Bebq_2$), 9,10-di(naphthalene-2-yl)anthracene (ADN), 1,3-bis[3,5-di(pyridin-3-yl)phenyl]benzene (BmPyPhB), and mixtures thereof, without limitation.

The electron transport region ETR may include at least one of Compounds ET1 to ET36.

ET1

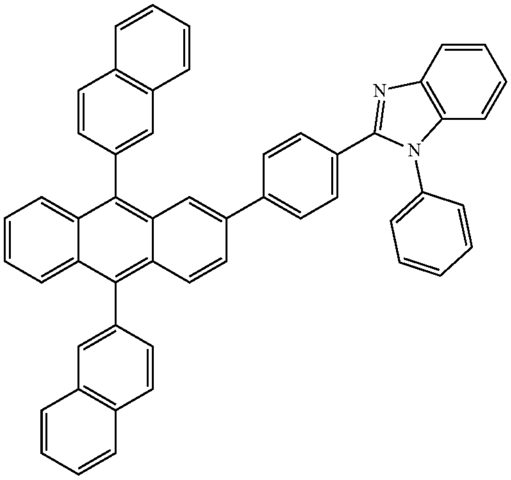

ET2

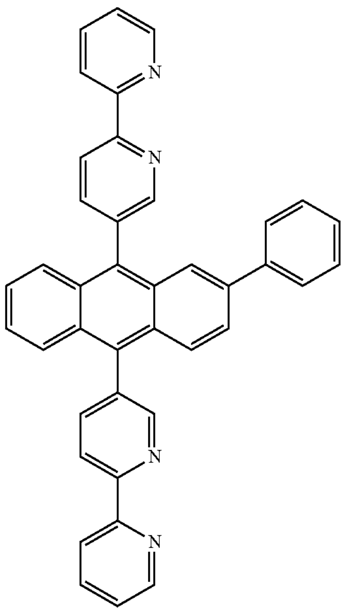

ET3

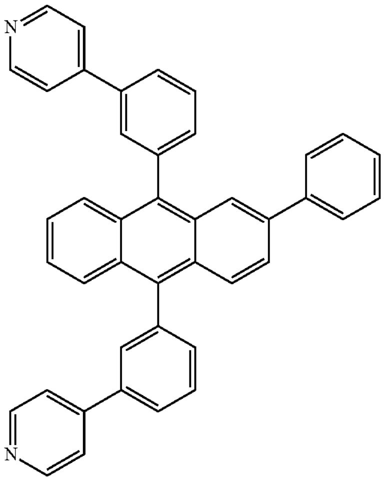

-continued
ET4
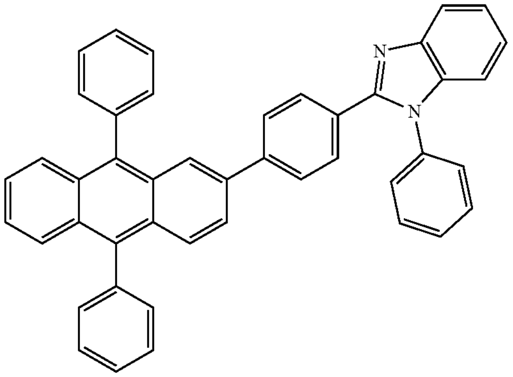
ET5
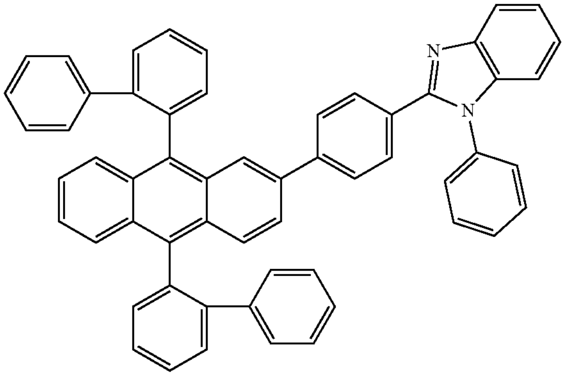
ET6
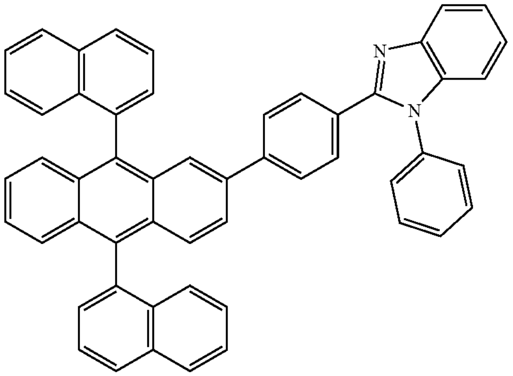
-continued
ET7
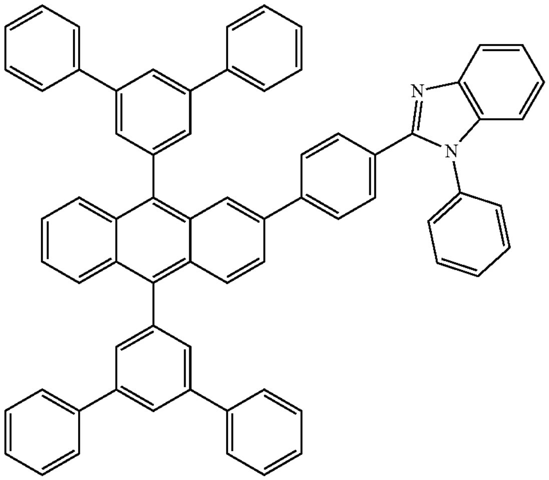
ET8
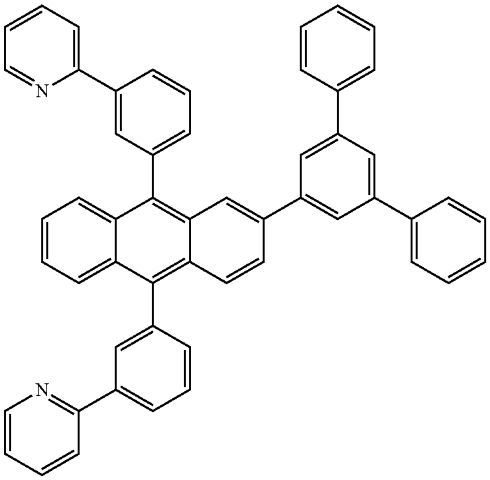
ET9
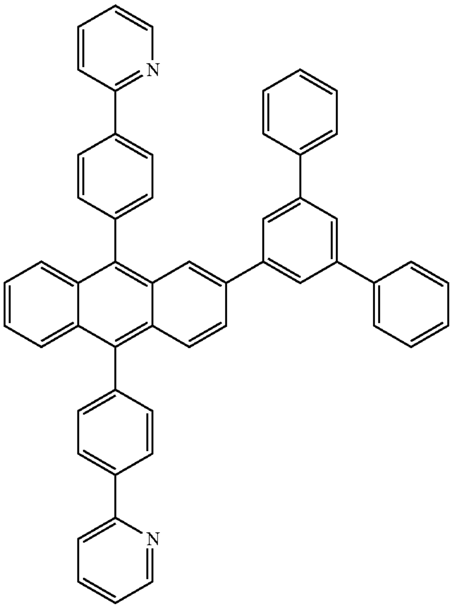

-continued
ET10
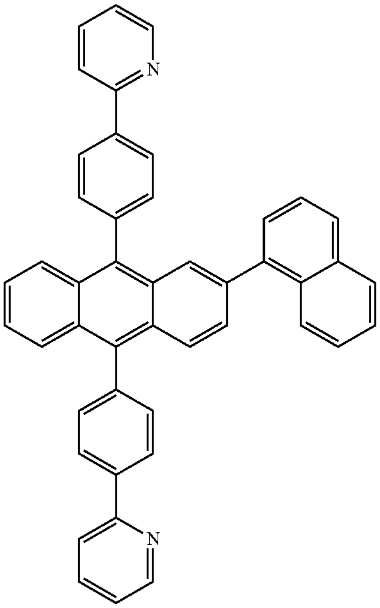
ET11
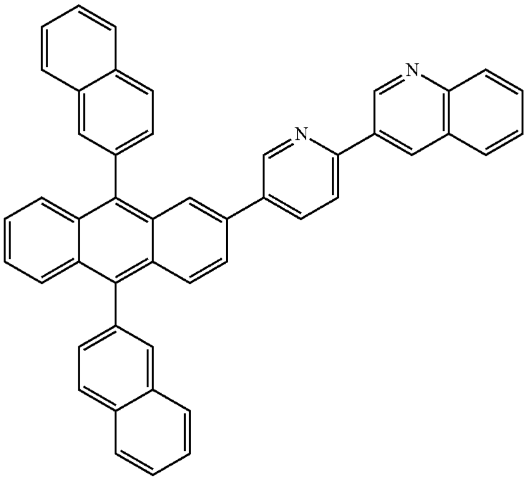
ET12
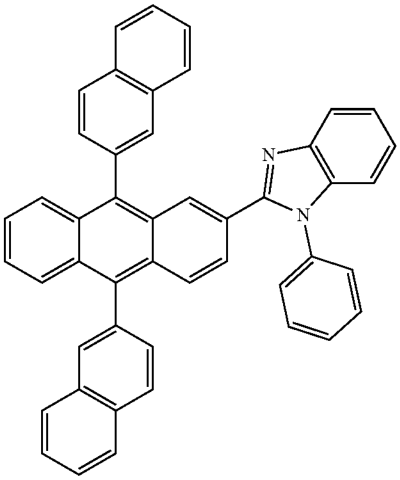
-continued
ET13
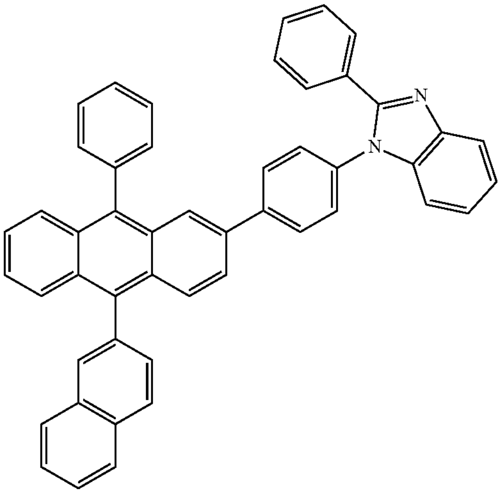
E14
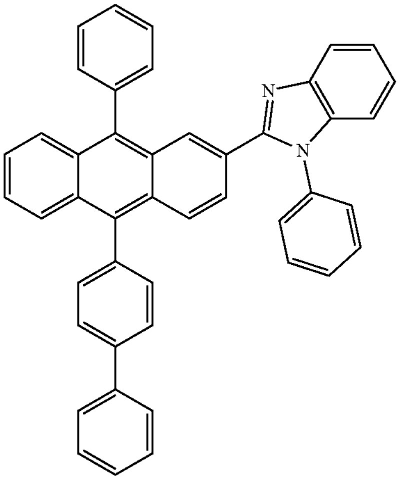
E15
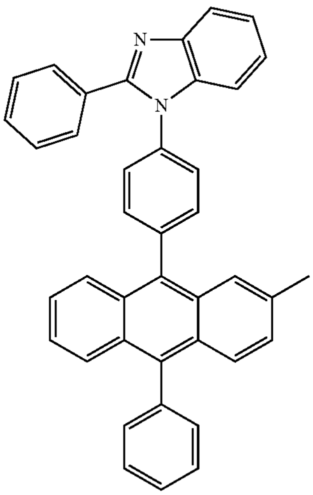

-continued
E16
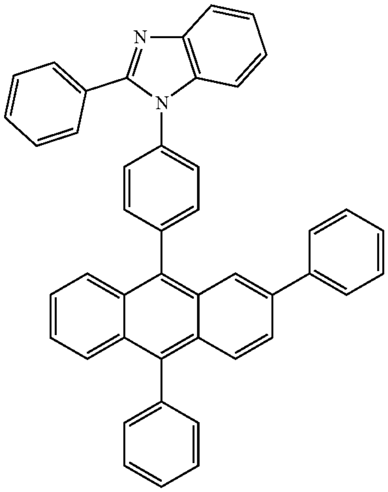
ET17
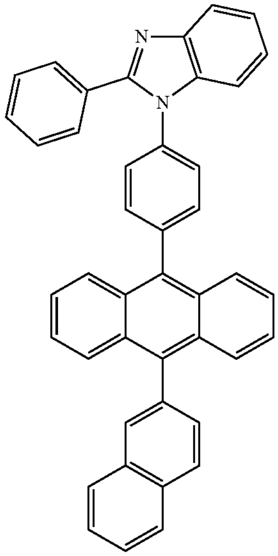
ET18
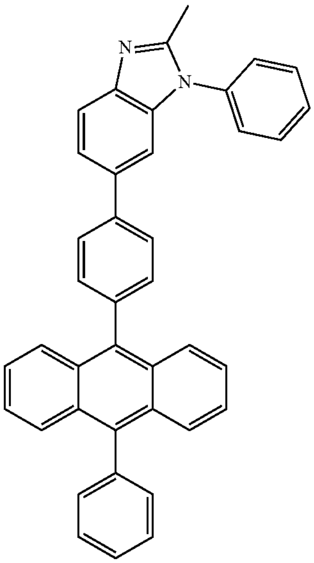
-continued
ET19
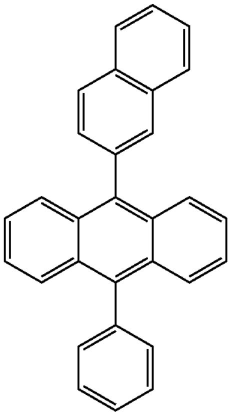
ET20
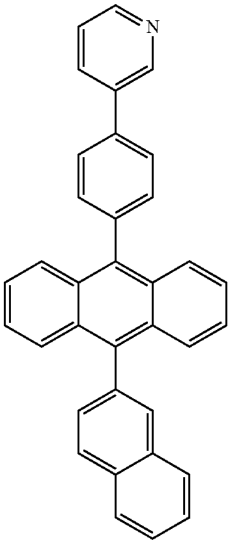
ET21
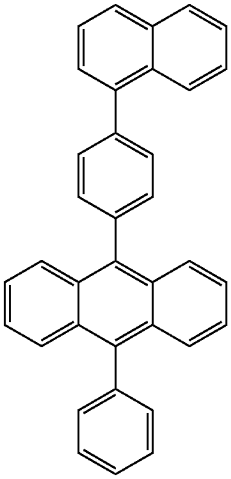

-continued
ET22
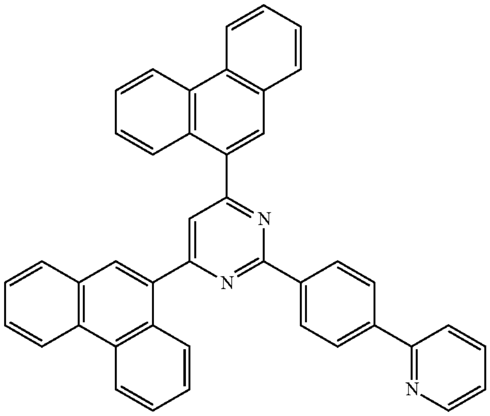
ET23
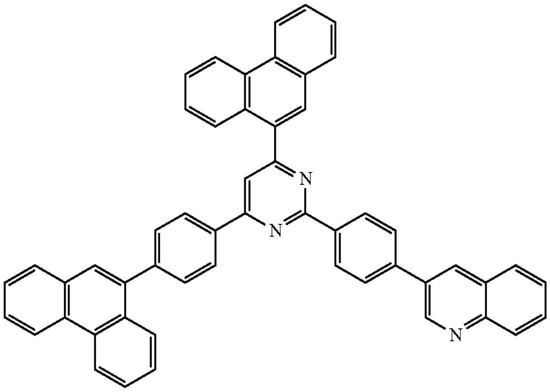
ET24
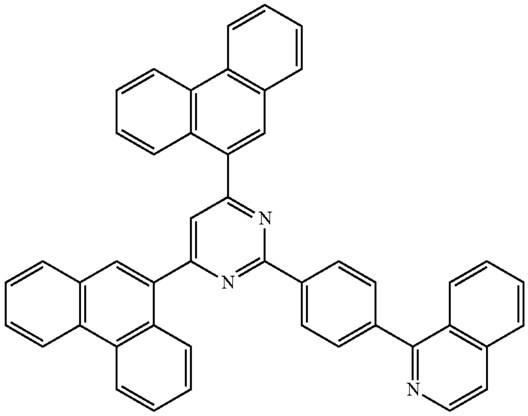
-continued
ET25
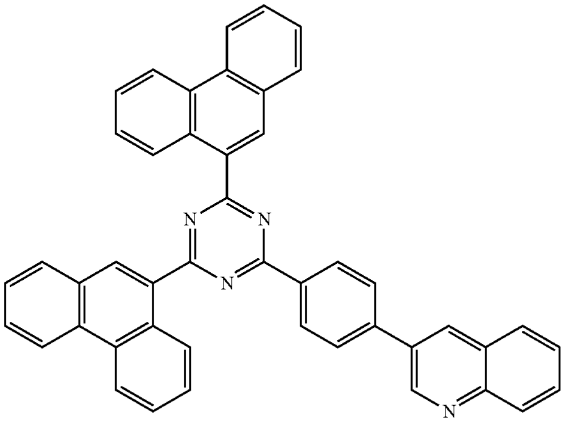
ET26
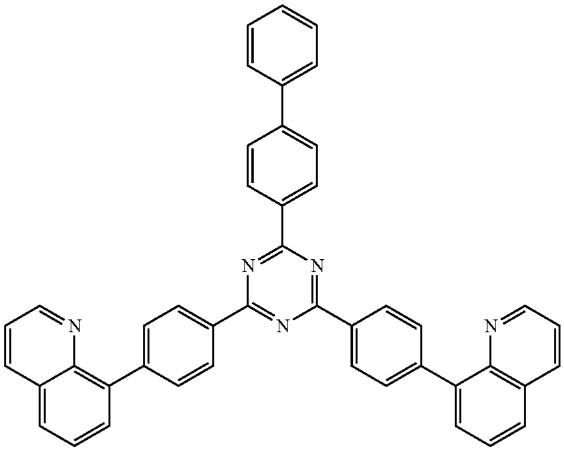
ET27
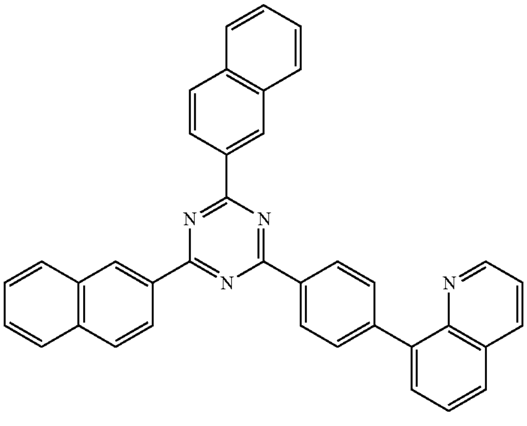

-continued
ET28
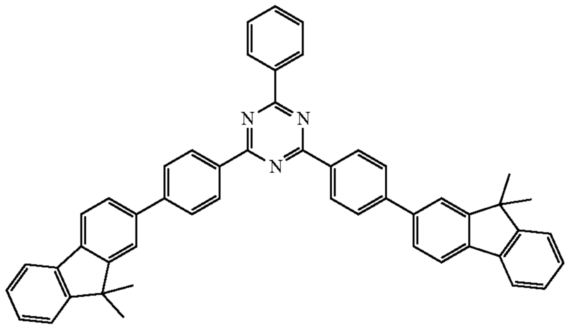
ET29
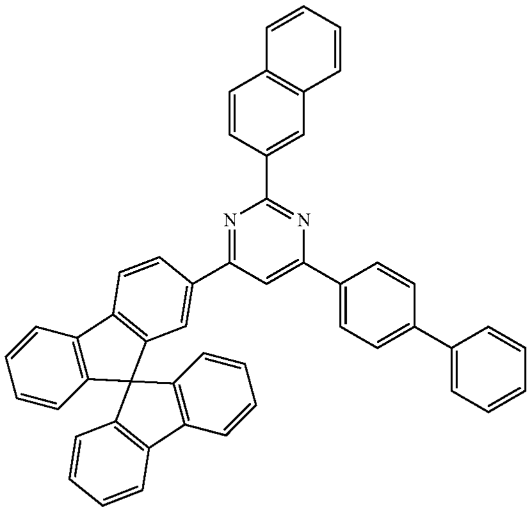
ET30
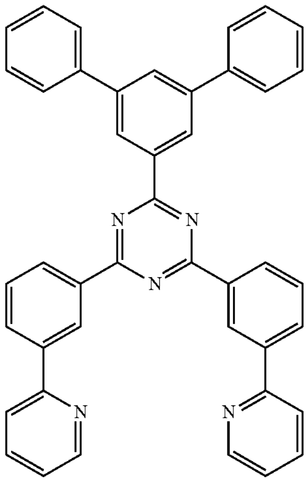
-continued
ET31
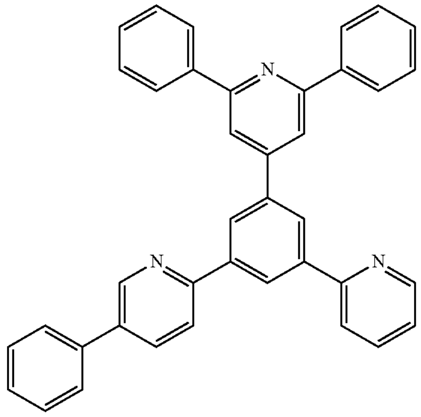
ET32
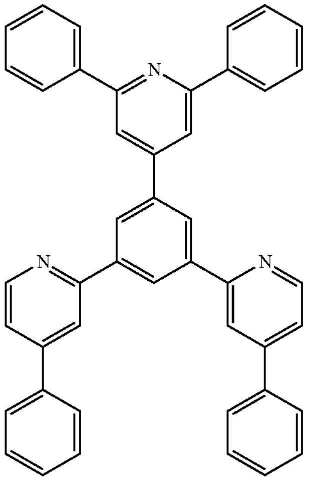
ET33
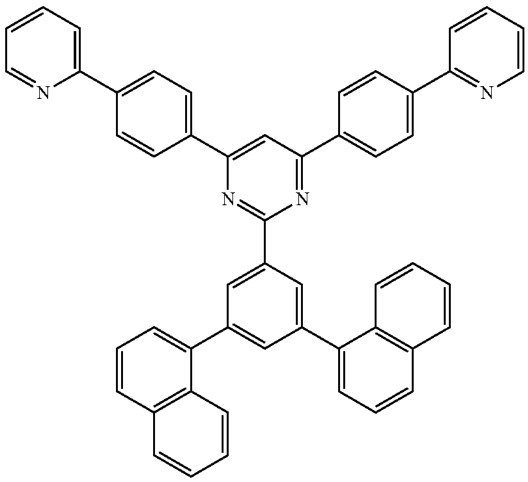

-continued

ET34

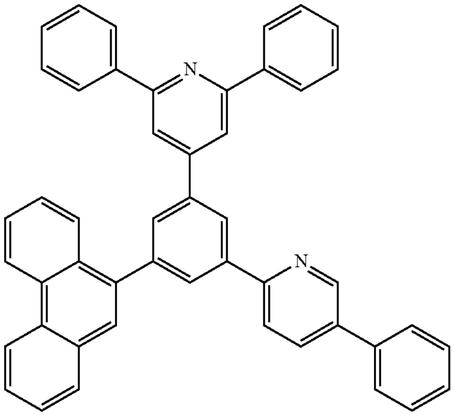

ET35

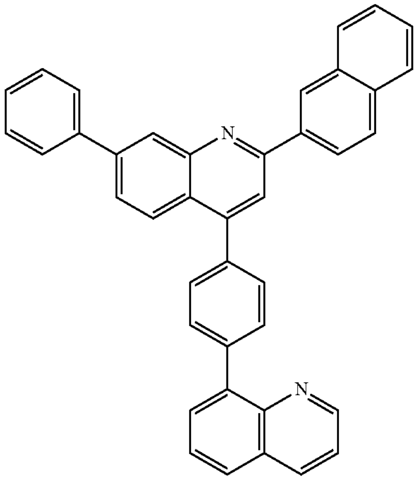

ET36

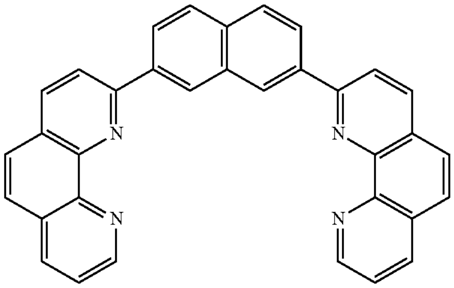

The electron transport region ETR may include a metal halide such as LiF, NaCl, CsF, RbCl, RbI, CuI and KI, a lanthanide metal such as Yb, or a co-deposited material of a metal halide and a lanthanide metal. For example, the electron transport region ETR may include KI:Yb, RbI:Yb, etc., as a co-deposited material. The electron transport region ETR may include a metal oxide such as $Li_2O$ and BaO, or 8-hydroxy-lithium quinolate (Liq). However, embodiments are not limited thereto. The electron transport region ETR may be formed using a mixture material of an electron transport material and an insulating organo metal salt. The organo metal salt may be a material having an energy band gap equal to or greater than about 4 eV. For example, the organo metal salt may include metal acetates, metal benzoates, metal acetoacetates, metal acetylacetonates, or metal stearates.

The electron transport region ETR may include at least one of 2,9-dimethyl-4,7-diphenyl-1,10-phenanthroline (BCP), diphenyl(4-triphenylsilyl)phenyl)phosphine oxide (TSPO1), or 4,7-diphenyl-1,10-phenanthroline (Bphen) in addition to the aforementioned materials. However, embodiments are not limited thereto.

The electron transport region ETR may include the compounds of the electron transport region in at least one of an electron injection layer EIL, an electron transport layer ETL, or a hole blocking layer HBL.

If the electron transport region ETR includes an electron transport layer ETL, a thickness of the electron transport layer ETL may be in a range of about 100 Å to about 1,000 Å. For example, the thickness of the electron transport layer ETL may be in a range of about 150 Å to about 500 Å. If the thickness of the electron transport layer ETL satisfies the above-described range, satisfactory electron transport properties may be obtained without a substantial increase of driving voltage. If the electron transport region ETR includes an electron injection layer EIL, a thickness of the electron injection layer EIL may be in a range of about 1 Å to about 100 Å. For example, the thickness of the electron injection layer EIL may be in a range of about 3 Å to about 90 Å. If the thickness of the electron injection layer EIL satisfies the above described range, satisfactory electron injection properties may be obtained without a substantial increase of driving voltage.

The second electrode EL2 is provided on the electron transport region ETR. The second electrode EL2 may be a common electrode. The second electrode EL2 may be a cathode or an anode, but embodiments are not limited thereto. For example, if the first electrode EL1 is an anode, the second cathode EL2 may be a cathode, and if the first electrode EL1 is a cathode, the second electrode EL2 may be an anode.

The second electrode EL2 may be a transmissive electrode, a transflective electrode, or a reflective electrode. If the second electrode EL2 is a transmissive electrode, the second electrode EL2 may include a transparent metal oxide, for example, ITO, IZO, ZnO, ITZO, etc.

If the second electrode EL2 is a transflective electrode or a reflective electrode, the second electrode EL2 may include Ag, Mg, Cu, Al, Pt, Pd, Au, Ni, Nd, Ir, Cr, $L_1$, Ca, LiF/Ca, LiF/Al, Mo, Ti, Yb, W, compounds thereof, or mixtures thereof (for example, AgMg, AgYb, or MgYb). In another embodiment, the second electrode EL2 may have a multi-layered structure including a reflective layer or a transflective layer formed using the above-described materials and a transparent conductive layer formed using ITO, IZO, ZnO, ITZO, etc. For example, the second electrode EL2 may include the aforementioned metal materials, combinations of two or more metal materials selected from the aforementioned metal materials, or oxides of the aforementioned metal materials.

Although not shown in the drawings, the second electrode EL2 may be electrically connected to an auxiliary electrode. If the second electrode EL2 is electrically connected to the auxiliary electrode, the resistance of the second electrode EL2 may decrease.

In an embodiment, the light emitting device ED may further include a capping layer CPL disposed on the second electrode EL2. The capping layer CPL may be a multilayer or a single layer.

In an embodiment, the capping layer CPL may include an organic layer or an inorganic layer. For example, if the capping layer CPL includes an inorganic material, the inorganic material may include an alkali metal compound such as LiF, an alkaline earth metal compound such as $MgF_2$, SiON, SiNx, SiOy, etc.

For example, if the capping layer CPL includes an organic material, the organic material may include a-NPD, NPB, TPD, m-MTDATA, $Alq_3$, CuPc, N4,N4,N4',N4'-tetra(biphenyl-4-yl) biphenyl-4,4'-diamine (TPD15), 4,4',4"-tris(carbazol sol-9-yl) triphenylamine (TCTA), etc., or may include an epoxy resin, or acrylate such as methacrylate.

The capping layer CPL may include at least one of Compounds P1 to P5, but embodiments are not limited thereto.

P1

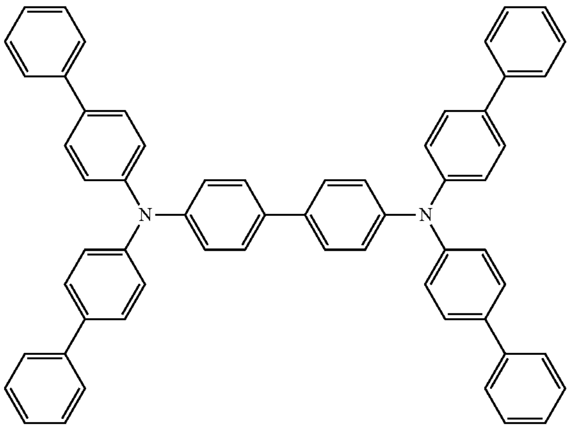

P2

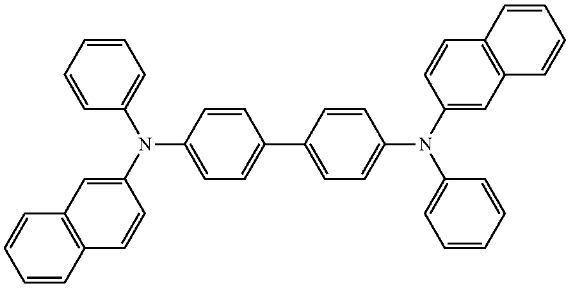

P3

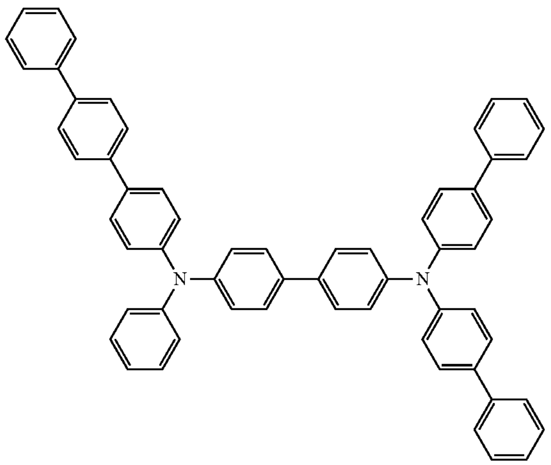

-continued

P4

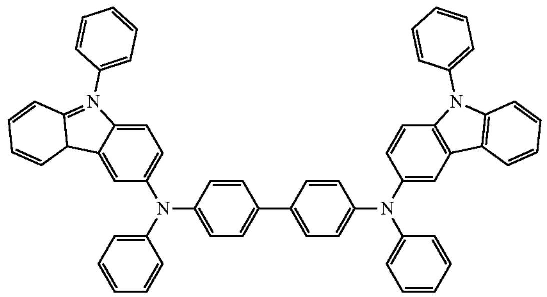

P5

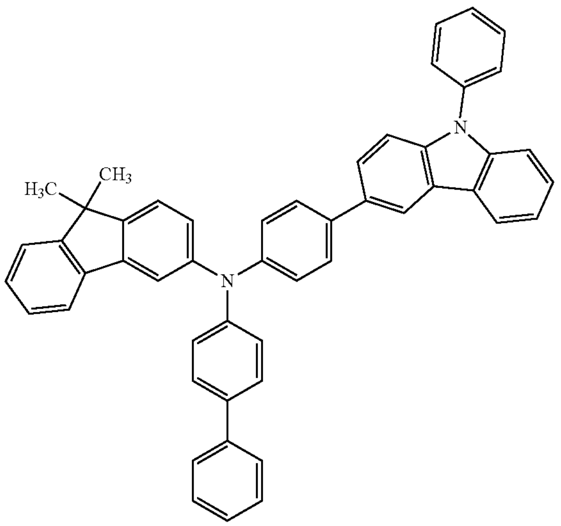

A refractive index of the capping layer CPL may be equal to or greater than about 1.6. For example, the capping layer CPL may have a refractive index equal to or greater than about 1.6 with respect to light in a wavelength range of about 550 nm to about 660 nm.

Figure 7:
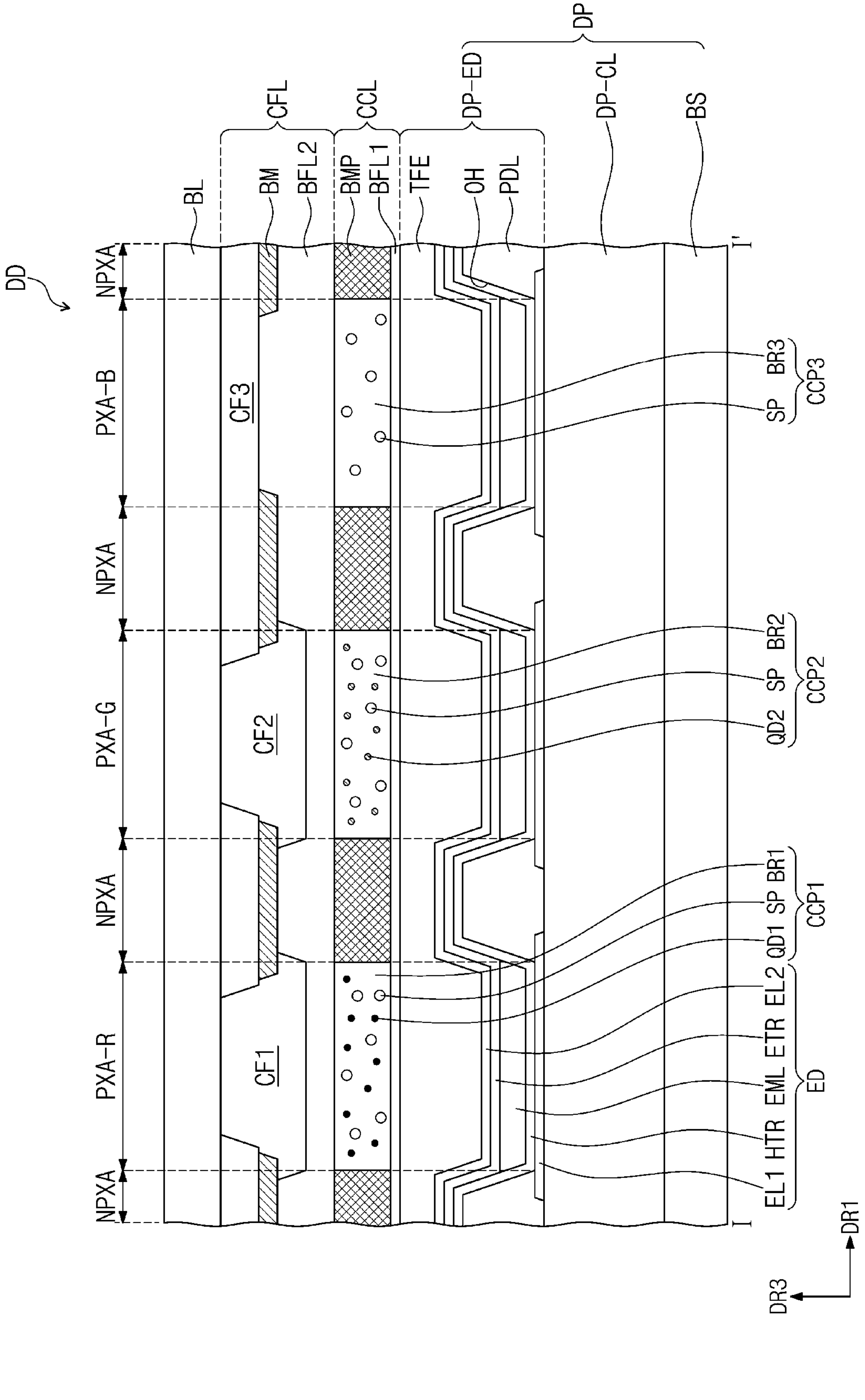
FIG. 7 is a schematic cross-sectional view showing a display apparatus according to an embodiment.
Figure 8:
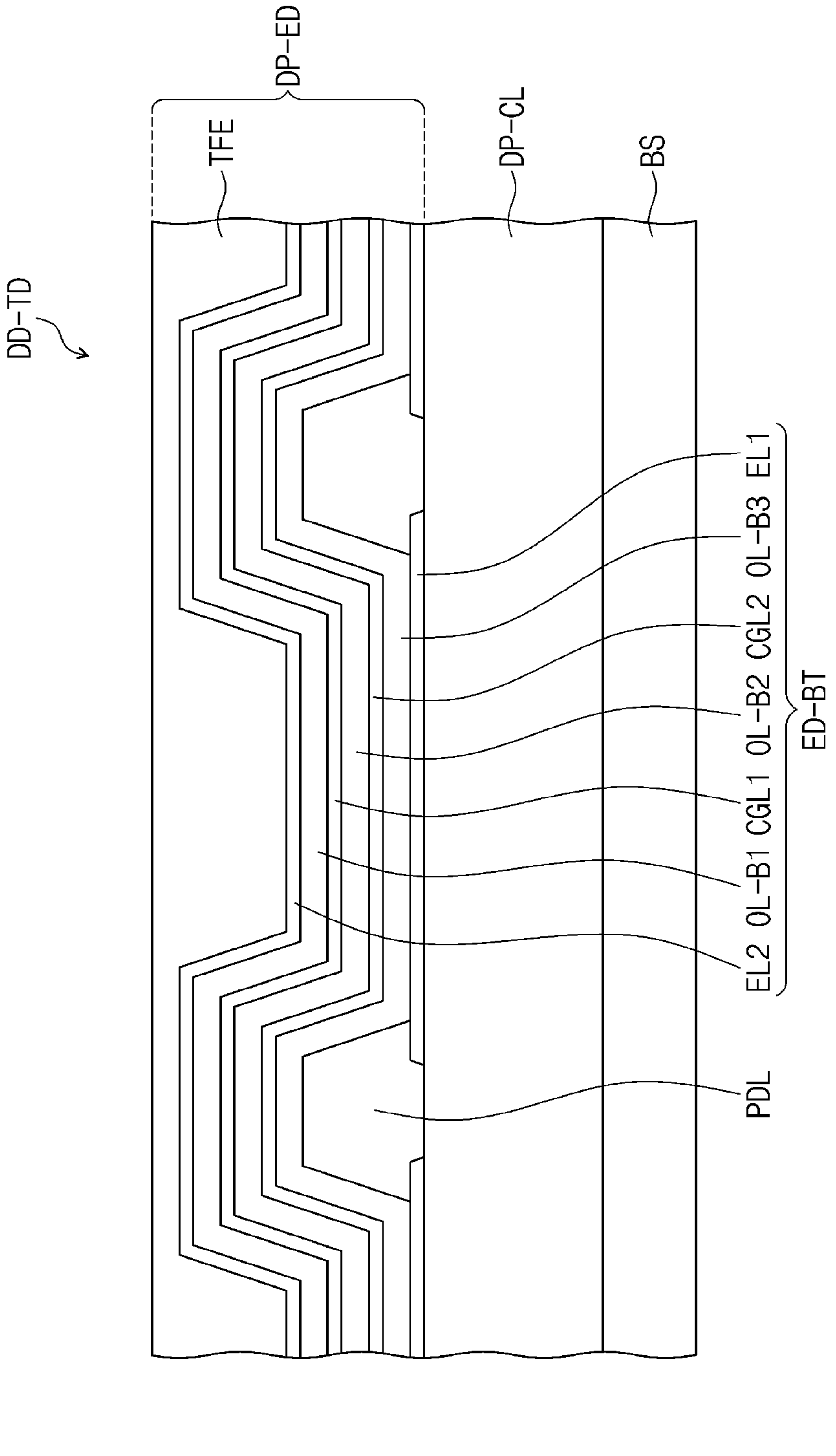
FIG. 8 is a schematic cross-sectional view showing a display apparatus according to an embodiment.

FIG. 7 and FIG. 8 are each a schematic cross-sectional view of a display apparatus according to embodiments. In the explanation on the display apparatuses of embodiments according to FIG. 7 and FIG. 8, the overlapping parts with the explanation on FIG. 1 to FIG. 6 will not be explained again, and the different features will be explained.

Referring to FIG. 7, the display apparatus DD according to an embodiment may include a display panel DP including a display device layer DP-ED, a light controlling layer CCL disposed on the display panel DP, and a color filter layer CFL.

In an embodiment shown in FIG. 7, the display panel DP may include a base layer BS, a circuit layer DP-CL provided on the base layer BS, and a display device layer DP-ED, and the display device layer DP-ED may include a light emitting device ED.

The light emitting device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. A structure of the light emitting device according to FIG. 3 to FIG. 6 may be applied to the structure of the light emitting device ED shown in FIG. 7.

Referring to FIG. 7, the emission layer EML may be disposed in openings OH defined in a pixel definition layer PDL. For example, the emission layer EML which is divided by the pixel definition layer PDL and correspondingly provided to each of the luminous areas PXA-R, PXA-G, and PXA-B may emit light in a same wavelength region. In the display apparatus DD of an embodiment, the emission layer EML may emit blue light. Although not shown in the drawings, in an embodiment, the emission layer EML may be provided as a common layer for all luminous areas PXA-R, PXA-G and PXA-B.

The light controlling layer CCL may be disposed on the display panel DP. The light controlling layer CCL may include a light converter. The light converter may include a quantum dot or a phosphor. The light converter may convert the wavelength of a provided light and may emit the converted light. For example, the light controlling layer CCL may be a layer including a quantum dot or a layer including a phosphor.

The light controlling layer CCL may include light controlling parts CCP1, CCP2, and CCP3. The light controlling parts CCP1, CCP2, and CCP3 may be separated from one another.

Referring to FIG. 7, a partition pattern BMP may be disposed between the separated light controlling parts CCP1, CCP2, and CCP3, but embodiments are not limited thereto. FIG. 7 illustrates that the partition pattern BMP does not overlap the light controlling parts CCP1, CCP2, and CCP3, but at least a portion of the edge of the light controlling parts CCP1, CCP2, and CCP3 may overlap the partition pattern BMP.

The light controlling layer CCL may include a first light controlling part CCP1 including a first quantum dot QD1 that converts first color light provided from the light emitting device ED into second color light, a second light controlling part CCP2 including a second quantum dot QD2 that converts first color light into third color light, and a third light controlling part CCP3 that transmits first color light.

In an embodiment, the first light controlling part CCP1 may provide red light which is the second color light, and the second light controlling part CCP2 may provide green light which is the third color light. The third light controlling part CCP3 may transmit and provide blue light, which is the first color light provided from the light emitting device ED. For example, the first quantum dot QD1 may be a red quantum dot, and the second quantum dot QD2 may be a green quantum dot. The same descriptions as provided above with respect to quantum dots may be applied to the quantum dots QD1 and QD2.

The light controlling layer CCL may further include a scatterer SP. The first light controlling part CCP1 may include the first quantum dot QD1 and the scatterer SP, the second light controlling part CCP2 may include the second quantum dot QD2 and the scatterer SP, and the third light controlling part CCP3 may not include a quantum dot but may include the scatterer SP.

The scatterer SP may be an inorganic particle. For example, the scatterer SP may include at least one of $TiO_2$, ZnO, $Al_2O_3$, $SiO_2$, and hollow silica. The scatterer SP may include at least one of $TiO_2$, ZnO, $Al_2O_3$, $SiO_2$, and hollow silica, or may be a mixture of two or more materials selected from $TiO_2$, ZnO, $Al_2O_3$, $SiO_2$, and hollow silica.

The first light controlling part CCP1, the second light controlling part CCP2, and the third light controlling part CCP3 may each include base resins BR1, BR2, and BR3 dispersing the quantum dots QD1 and QD2 and the scatterer SP. In an embodiment, the first light controlling part CCP1 may include the first quantum dot QD1 and the scatterer SP dispersed in the first base resin BR1, the second light controlling part CCP2 may include the second quantum dot QD2 and the scatterer SP dispersed in the second base resin BR2, and the third light controlling part CCP3 may include the scatterer particle SP dispersed in the third base resin BR3. The base resins BR1, BR2, and BR3 may each be a medium in which the quantum dots QD1 and QD2 and the scatterer SP are dispersed, and may be composed of various resin compositions which may be generally referred to as a binder. For example, the base resins BR1, BR2, and BR3 may each independently be acrylic resins, urethane-based resins, silicone-based resins, epoxy-based resins, etc. The base resins BR1, BR2, and BR3 may each be transparent resins. In an embodiment, the first base resin BR1, the second base resin BR2, and the third base resin BR3 may be the same as or different from each other.

The light controlling layer CCL may include a barrier layer BFL1. The barrier layer BFL1 may play the role of blocking the penetration of moisture and/or oxygen (hereinafter, will be referred to as "humidity/oxygen"). The barrier layer BFL1 may block the exposure of the light controlling parts CCP1, CCP2, and CCP3 to humidity/oxygen. The barrier layer BFL1 may cover the light controlling parts CCP1, CCP2, and CCP3. The barrier layer BFL2 may be provided between the light controlling parts CCP1, CCP2, and CCP3 and a color filter layer CFL.

The barrier layers BFL1 and BFL2 may each include at least one inorganic layer. For example, the barrier layers BFL1 and BFL2 may each be formed by including an inorganic material. For example, the barrier layers BFL1 and BFL2 may each independently include silicon nitride, aluminum nitride, zirconium nitride, titanium nitride, hafnium nitride, tantalum nitride, silicon oxide, aluminum oxide, titanium oxide, tin oxide, cerium oxide, silicon oxynitride, or a metal thin film securing light transmittance. The barrier layers BFL1 and BFL2 may each further include an organic layer. The barrier layers BFL1 and BFL2 may each be formed of a single layer or of multiple layers.

In the display apparatus DD of an embodiment, the color filter layer CFL may be disposed on the light controlling layer CCL. In an embodiment, the color filter layer CFL may be disposed directly on the light controlling layer CCL. For example, the barrier layer BFL2 may be omitted.

The color filter layer CFL may include a light blocking part BM and filters CF1, CF2, and CF3. The color filter layer CFL may include a first filter CF1 that transmits second color light, a second filter CF2 that transmits third color light, and a third filter CF3 that transmits first color light. For example, the first filter CF1 may be a red filter, the second filter CF2 may be a green filter, and the third filter CF3 may be a blue filter. Each of the filters CF1, CF2, and CF3 may include a polymer photosensitive resin and a pigment or dye. The first filter CF1 may include a red pigment or dye, the second filter CF2 may include a green pigment or dye, and the third filter CF3 may include a blue pigment or dye. However, embodiments are not limited thereto, and the third filter CF3 may not include a pigment or dye. The third filter CF3 may include a polymer photosensitive resin and not include a pigment or dye. The third filter CF3 may be transparent. The third filter CF3 may be formed using a transparent photosensitive resin.

In an embodiment, the first filter CF1 and the second filter CF2 may each be a yellow filter. The first filter CF1 and the second filter CF2 may be provided in one body without distinction.

The light blocking part BM may be a black matrix. The light blocking part BM may include an organic light blocking material or an inorganic light blocking material including a black pigment or a black dye. The light blocking part BM may prevent light leakage and may divide the boundaries among adjacent filters CF1, CF2, and CF3. In an embodiment, the light blocking part BM may be formed as a blue filter.

The first to third filters CF1, CF2, and CF3 may be disposed corresponding to each of a red luminous area PXA-R, green luminous area PXA-G, and blue luminous area PXA-B, respectively.

A base substrate BL may be disposed on the color filter layer CFL. The base substrate BL may provide a base surface on which the color filter layer CFL, the light controlling layer CCL, etc. are disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawing, in an embodiment, the base substrate BL may be omitted.

FIG. 8 is a schematic cross-sectional view showing a portion of the display apparatus according to an embodiment. In FIG. 8, a schematic cross-sectional view of a portion corresponding to the display panel DP in FIG. 7 is shown. In a display apparatus DD-TD of an embodiment, the light emitting device ED-BT may include light emitting structures OL-B1, OL-B2, and OL-B3. The light emitting device ED-BT may include a first electrode EL1 and an oppositely disposed second electrode EL2, and the light emitting structures OL-B1, OL-B2, and OL-B3 stacked in a thickness direction between the first electrode EL1 and the second electrode EL2. Each of the light emitting structures OL-B1, OL-B2, and OL-B3 may include an emission layer EML (FIG. 7), and a hole transport region HTR and an electron transport region ETR disposed with the emission layer EML (FIG. 7) therebetween.

For example, the light emitting device ED-BT included in the display apparatus DD-TD of an embodiment may be a light emitting device having a tandem structure and including multiple emission layers.

In an embodiment shown in FIG. 8, light emitted from the light emitting structures OL-B1, OL-B2, and OL-B3 may be all blue light. However, embodiments are not limited thereto, and light emitted from the light emitting structures OL-B1, OL-B2, and OL-B3 may have wavelength regions which are different from each other. For example, the light emitting device ED-BT including the light emitting structures OL-B1, OL-B2, and OL-B3 emitting light in different wavelength regions may emit white light.

Charge generating layers CGL1 and CGL2 may be disposed between neighboring light emitting structures among OL-B1, OL-B2, and OL-B3. The charge generating layers CGL1 and CGL2 may each independently include a p-type charge generating layer and/or an n-type charge generating layer.

Hereinafter, the amine compound according to an embodiment and the light emitting device of an embodiment will be explained with reference to the Examples and the Comparative Examples. The Examples below are only illustrations for understanding the disclosure, and the scope thereof is not limited thereto.

EXAMPLES

1. Synthesis of Amine Compound of an Embodiment

A synthesis method of an amine compound according to an embodiment will be explained by illustrating the synthesis methods of Compounds 3, 7, 32, 36, 113, 117, 129, 187, 202, and 206. The synthesis methods of the amine compounds explained hereinafter are only provided as examples, and the synthesis method of the compound according to an embodiment is not limited to the examples below.

(1) Synthesis of Compound 3

Amine Compound 3 according to an embodiment may be synthesized, for example, by the steps of Reaction 1-1 to Reaction 1-4 below.

[Reaction 1-1]

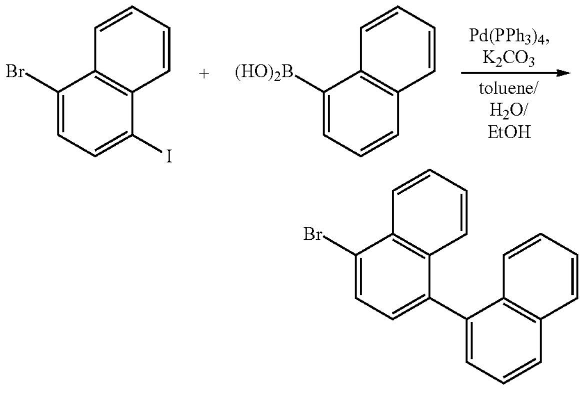

A

<Synthesis of Compound A>

Under Ar atmosphere, to a 2 L, three-neck flask, 1-bromo-4-iodonaphthalene (30.0 g), 1-naphthaleneboronic acid (15.5 g), tetrakis(triphenylphosphine)palladium(0) (Pd $(PPh_3)_4$, 5.2 g), and potassium carbonate ($K_2CO_3$, 25 g) were added and dissolved in a mixture solvent of toluene, water and ethanol (volume ratio of 10:2:1, 500 mL), followed by heating and stirring at about 80° C. for about 12 hours. Water was added to the reaction solution, and extraction with dichloromethane ($CH_2Cl_2$) was performed. Organic layers were collected and dried with magnesium sulfate ($MgSO_4$), and the solvent was removed by distillation under a reduced pressure. The crude product thus obtained was separated by silica gel column chromatography to obtain 16.5 g of Compound A (yield 55%). The molecular weight of Compound A measured by FAB-MS was 333.

[Reaction 1-2]

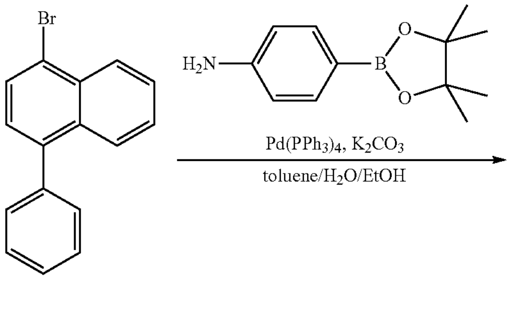

-continued

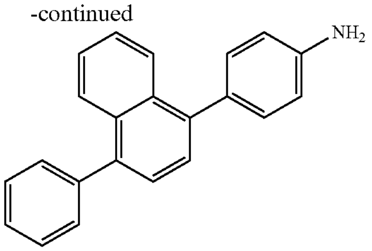

E

<Synthesis of Compound E>

By a same method as the synthesis method of Compound A, except for using 1-bromo-4-phenylnaphthalene (10.0 g) instead of 1-bromo-4-iodonaphthalene (30.0 g), and using 4-(4,4,5,5-tetramethyl-1,3,2-dioxaborolan-2-yl)aniline (7.7 g) instead of 1-naphthaleneboronic acid (15.5 g), 7.62 g of Compound E was obtained. The molecular weight of Compound E measured by FAB-MS was 295.

[Reaction 1-3]

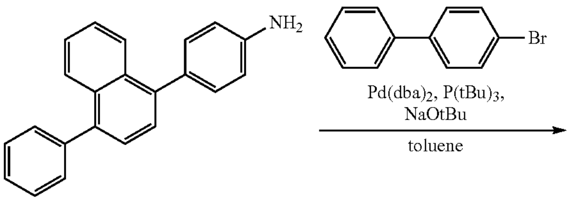

E

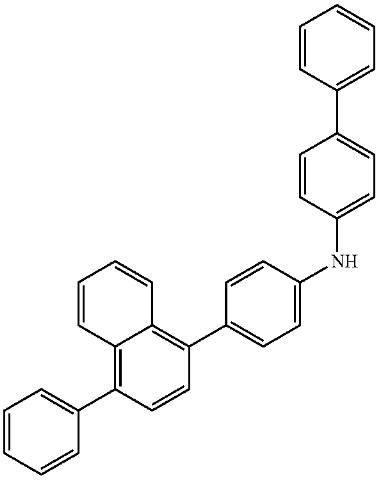

K

<Synthesis of Compound K>

Under Ar atmosphere, to a 200 mL, three-neck flask, Compound E (5.0 g), 4-bromobiphenyl (3.94 g), bis(dibenzylideneacetone)palladium(0) ($Pd(dba)_2$, 0.5 g), and sodium tert-butoxide (NaOtBu, 1.6 g) were added and dissolved in toluene (90 mL), and tri-tert-butylphosphine ($P(tBu)_3$, 2.0 M in toluene, 0.8 mL) was added thereto, followed by heating and refluxing for about 4 hours. Water was added to the reaction solution, and extraction with dichloromethane was performed. Organic layers were collected and dried with magnesium sulfate, and the solvent was removed by distillation under a reduced pressure. The crude product thus obtained was separated by silica gel column chromatography to obtain 4.92 g of Compound K (yield 65%). The molecular weight of Compound K measured by FAB-MS was 447.

[Reaction 1-4]

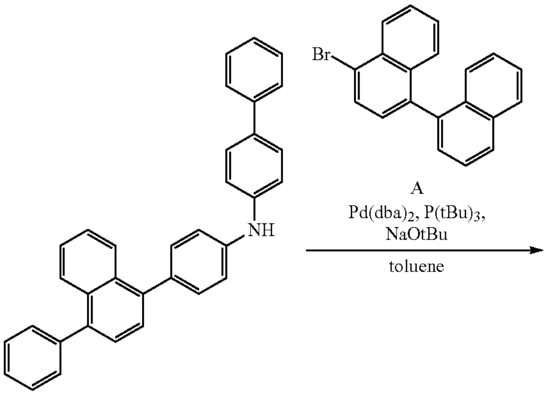

K

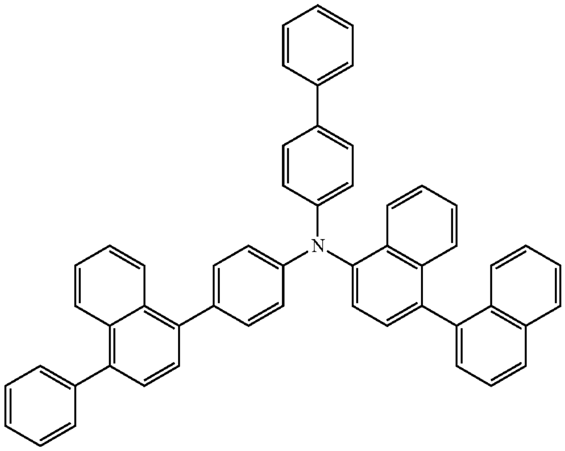

3

<Synthesis of Compound 3>

Under Ar atmosphere, to a 200 mL, three-neck flask, Compound K (3.0 g), Compound A (2.23 g), $Pd(dba)_2$ (0.2 g), and NaOtBu (1.0 g) were added and dissolved in toluene (50 mL), and $P(tBu)_3$, (2.0 M in toluene, 0.3 mL) was added thereto, followed by heating and refluxing for about 6 hours. Water was added to the reaction solution, and extraction with dichloromethane was performed. Organic layers were collected and dried with magnesium sulfate, and the solvent was removed by distillation under a reduced pressure. The crude product thus obtained was separated by silica gel column chromatography to obtain 3.99 g of Compound 3 (yield 85%). The molecular weight of Compound 3 measured by FAB-MS was 699.

(2) Synthesis of Compound 7

Amine Compound 7 according to an embodiment may be synthesized, for example, by the steps of Reaction 2-1 to Reaction 2-4 below.

[Reaction 2-1]

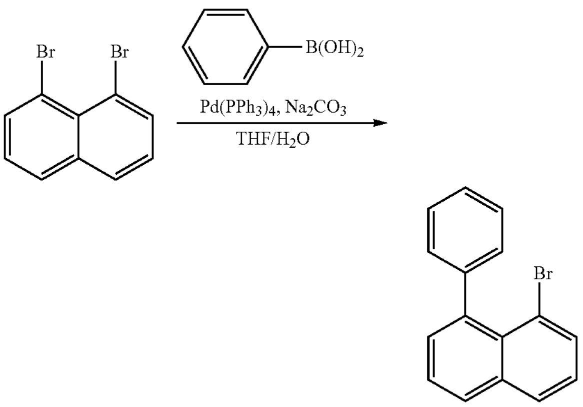

F

<Synthesis of Compound F>

Under Ar atmosphere, to a 1 L, three-neck flask, 1,8-dibromonaphthalene (20.0 g), phenylboronic acid (8.52 g), $Pd(PPh_3)_4$ (4.0 g), and sodium carbonate ($Na_2CO_3$, 15 g) were added and dissolved in a mixture solvent of THF and water (volume ratio of 8:2, 350 mL), followed by heating and stirring at about 70° C. for about 10 hours. Water was added to the reaction solution, and extraction with dichloromethane was performed. Organic layers were collected and dried with magnesium sulfate, and the solvent was removed by distillation under a reduced pressure. The crude product thus obtained was separated by silica gel column chromatography to obtain 14.8 g of Compound F (yield 75%). The molecular weight of Compound F measured by FAB-MS was 283.

[Reaction 2-2]

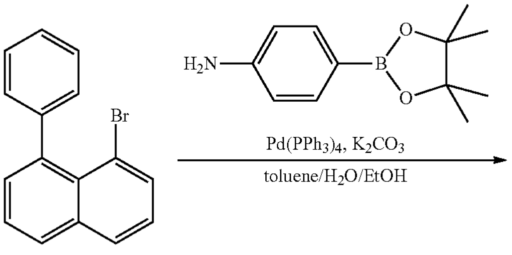

F

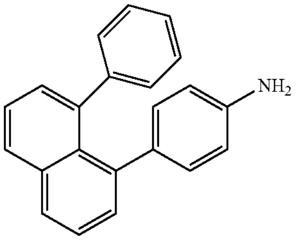

J

<Synthesis of Compound J>

By a same method as the synthesis method of Compound A, except for using Compound F (5.0 g) instead of 1-bromo-4-iodonaphthalene (30.0 g), and using 4-(4,4,5,5-tetramethyl-1,3,2-dioxaborolan-2-yl)aniline (3.8 g) instead of 1-naphthaleneboronic acid (15.5 g), 2.09 g of Compound J (yield 40%) was obtained. The molecular weight of Compound J measured by FAB-MS was 295.

[Reaction 2-3]

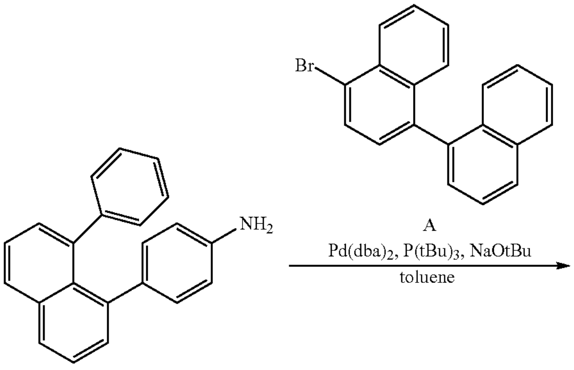

A

J

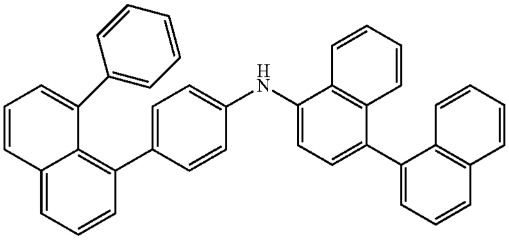

L

<Synthesis of Compound L>

By a same method as the synthesis method of Compound K, except for using Compound J (10.0 g) instead of Compound E (5.0 g), and using Compound A (11.3 g) instead of 4-bromobiphenyl (3.94 g), 14.5 g of Compound L (yield 78%) was obtained. The molecular weight of Compound L measured by FAB-MS was 547.

[Reaction 2-4]

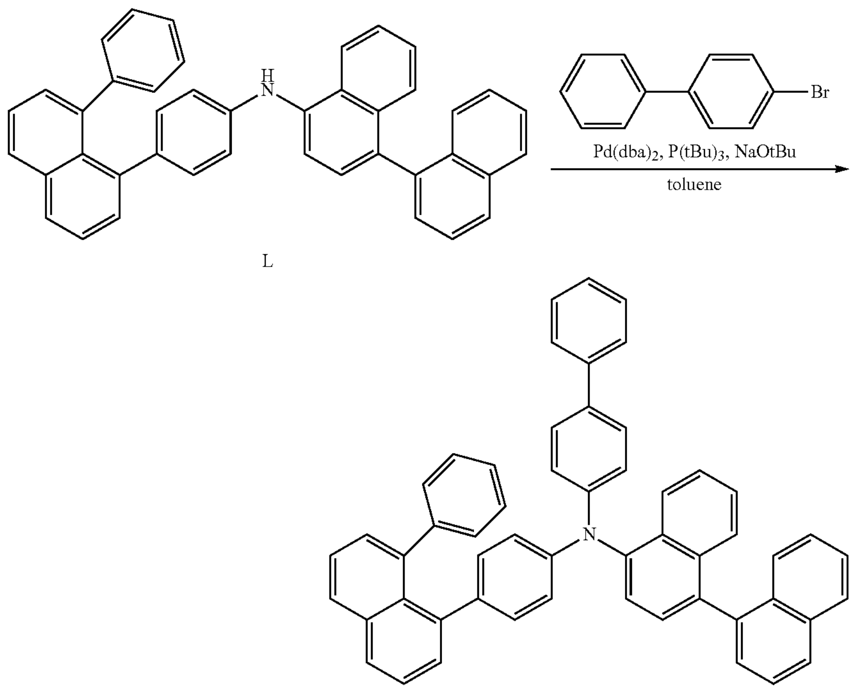

L

7

<Synthesis of Compound 7>

By a same method as the synthesis method of Compound 3, except for using Compound L (3.0 g) instead of Compound K (3.0 g), and using 4-bromobiphenyl (1.28 g) instead of Compound A (2.23 g), 2.95 g of Compound 7 (yield 77%) was obtained. The molecular weight of Compound 7 measured by FAB-MS was 699.

(3) Synthesis of Compound 32

Amine Compound 32 according to an embodiment may be synthesized, for example, by the steps of Reaction 3-1 to Reaction 3-4 below.

[Reaction 3-1]

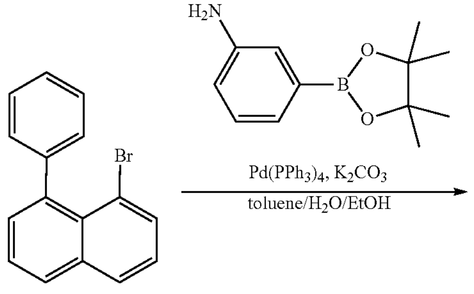

F

-continued

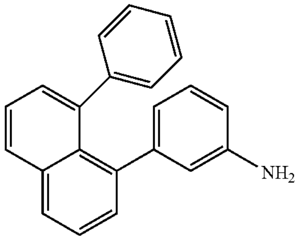

I

<Synthesis of Compound I>

By a same method as the synthesis method of Compound A, except for using Compound F (5.0 g) instead of 1-bromo-4-iodonaphthalene (30.0 g), and using 3-(4,4,5,5-tetramethyl-1,3,2-dioxaborolan-2-yl)aniline (3.87 g) instead of 1-naphthaleneboronic acid (15.5 g), 2.87 g of Compound I (yield 55%) was obtained. The molecular weight of Compound I measured by FAB-MS was 295.

[Reaction 3-2]

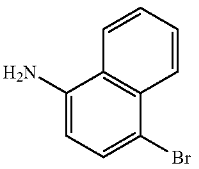

+

-continued

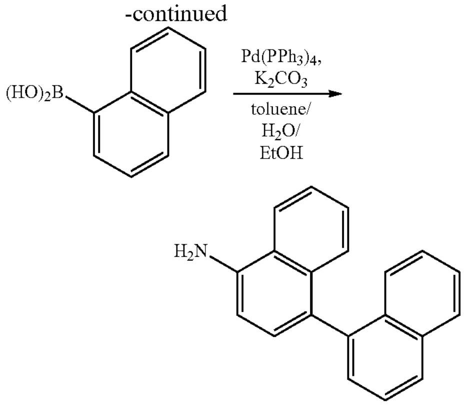

B

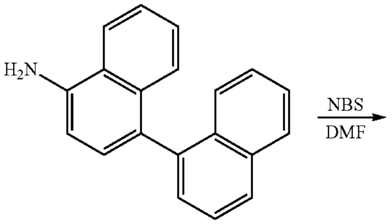

B

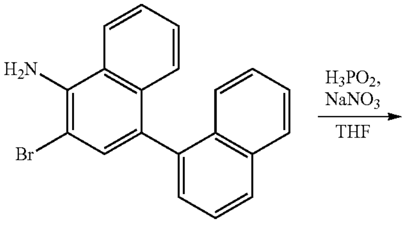

C

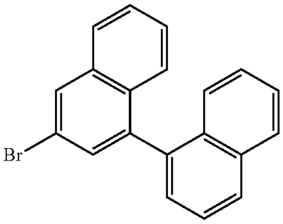

D

<Synthesis of Compound B>

By a same method as the synthesis method of Compound A, except for using 4-bromo-1-naphthylamine (30.0 g) instead of 1-bromo-4-iodonaphthalene (30.0 g), and using 1-naphthaleneboronic acid (23.2 g) instead of 1-naphthaleneboronic acid (15.5 g), 25.8 g of Compound B (yield 72%) was obtained. The molecular weight of Compound B measured by FAB-MS was 269.

<Synthesis of Compound C>

Under Ar atmosphere, to a 1 L, three-neck flask, Compound B (20.0 g) was added, dissolved in DMF (150 mL), and stirred. A DMF solution (70 mL) in which N-bromosuccinimide (13.2 g) was dissolved was added thereto dropwise at about 0° C., followed by stirring at room temperature for about 12 hours. The reaction solution was poured into water (2 L), and a solid precipitated was obtained by filtering. The solid thus obtained was separated by silica gel column chromatography to obtain 15.5 g of Compound C (yield 60%). The molecular weight of Compound C measured by FAB-MS was 348.

<Synthesis of Compound D>

Under Ar atmosphere, to a 1 L, three-neck flask, Compound C (15.0 g) was added and dissolved in THF (200 mL). While stirring at about 0° C., hypophosphorous acid ($H_3PO_2$, 50 g) and sodium nitrite ($NaNO_3$, 8.9 g) were added and stirred at about 0° C. for about 4 hours. After stirring at room temperature for about 12 hours, water was added, and an aqueous solution of 2 M sodium hydroxide (NaOH) was added until pH reached 10. Extraction with dichloromethane was performed, organic layers were collected and dried with magnesium sulfate, and the solvent was removed by distillation under a reduced pressure. The crude product thus obtained was separated by silica gel column chromatography to obtain 5.02 g of Compound D (yield 35%). The molecular weight of Compound D measured by FAB-MS was 333.

[Reaction 3-3]

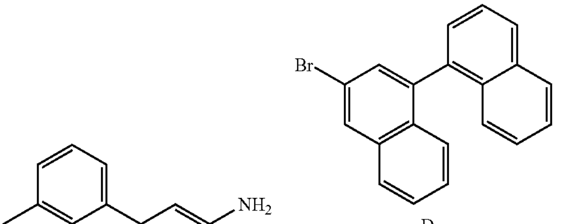

D

I

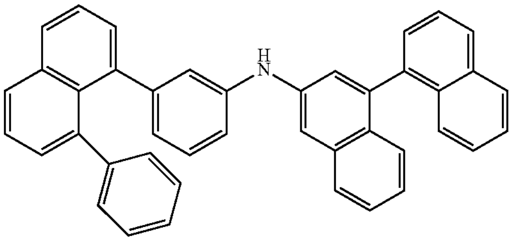

M

<Synthesis of Compound M>

By a same method as the synthesis method of Compound K, except for using Compound I (5.0 g) instead of Compound E (5.0 g), and using Compound D (5.64 g) instead of 4-bromobiphenyl (3.94 g), 6.30 g of Compound M (yield 68%) was obtained. The molecular weight of Compound M measured by FAB-MS was 547.

[Reaction 3-4]

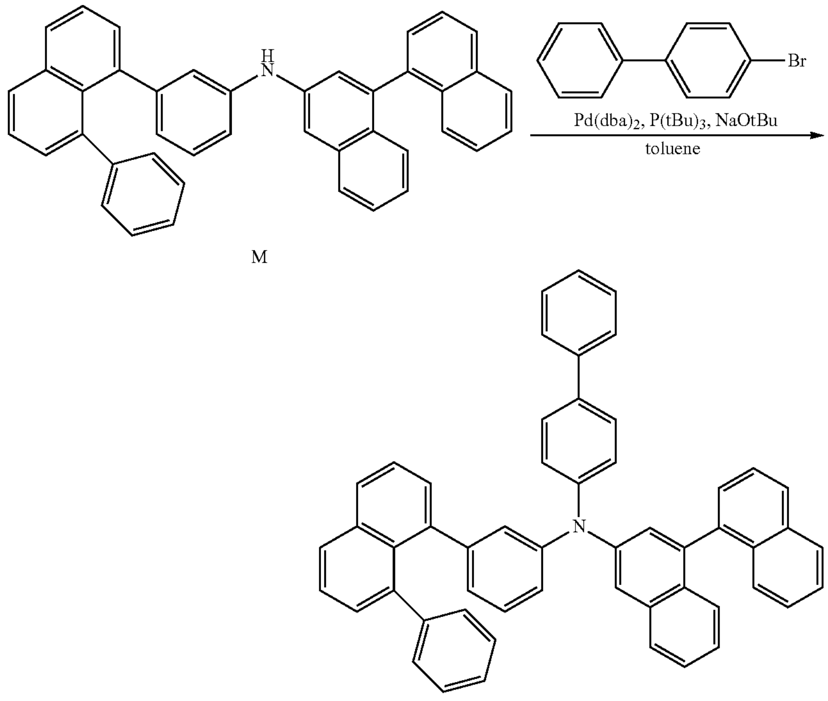

M

32

<Synthesis of Compound 32>

By a same method as the synthesis method of Compound 3, except for using Compound M (3.0 g) instead of Compound K (3.0 g), and using 4-bromobiphenyl (1.28 g) instead of Compound A (2.23 g), 3.22 g of Compound 32 (yield 84%) was obtained. The molecular weight of Compound 32 measured by FAB-MS was 699.

(4) Synthesis of Compound 36

Amine Compound 36 according to an embodiment may be synthesized, for example, by the steps of Reaction 4-1 to Reaction 4-3 below.

[Reaction 4-1]

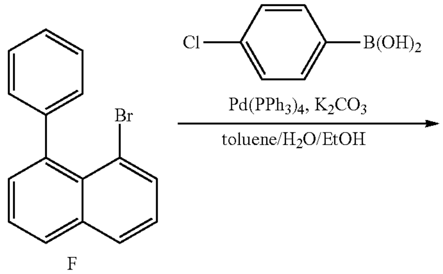

F

-continued

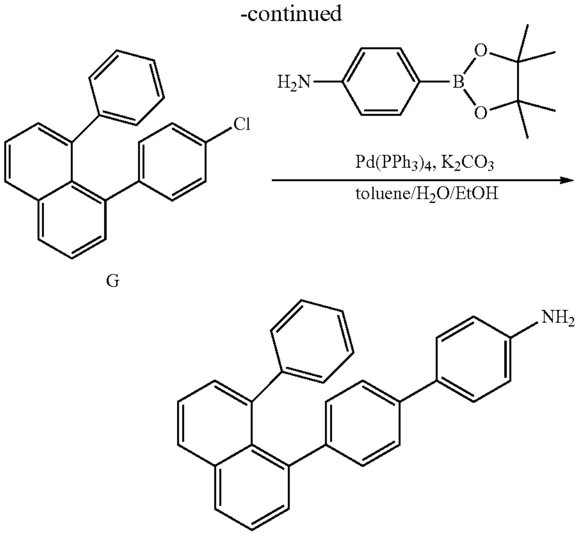

G

H

<Synthesis of Compound G>

Under Ar atmosphere, to a 300 mL, three-neck flask, Compound F (5.0 g), 4-chlorophenylboronic acid (2.76 g), $Pd(PPh_3)_4$ (1.0 g), and $K_2CO_3$ (4.9 g) were added and dissolved in a mixture solvent of toluene, water, and ethanol (volume ratio of 10:2:1, 100 mL), followed by heating and stirring at about 80° C. for about 10 hours. Water was added to the reaction solution, extraction with dichloromethane was performed, and organic layers were collected and dried with magnesium sulfate. The solvent was removed by distillation under a reduced pressure. The crude product thus obtained was separated by silica gel column chromatography to obtain 3.17 g of Compound G (yield 57%). The molecular weight of Compound G measured by FAB-MS was 314.

<Synthesis of Compound H>

By a same method as the synthesis method of Compound A, except for using Compound G (5.0 g) instead of 1-bromo-4-iodonaphthalene (30.0 g), and using 4-(4,4,5,5-tetramethyl-1,3,2-dioxaborolan-2-yl)aniline (3.48 g) instead of 1-naphthaleneboronic acid (15.5 g), 4.48 g of Compound H (yield 76%) was obtained. The molecular weight of Compound H measured by FAB-MS was 371.

[Reaction 4-2]

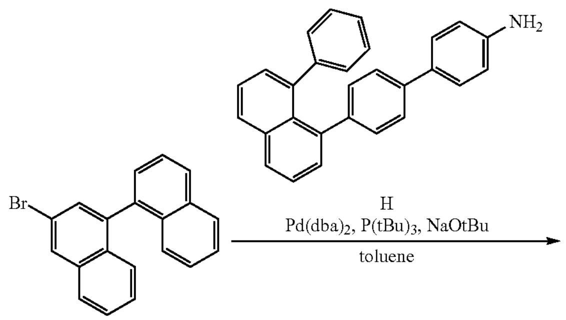

D

-continued

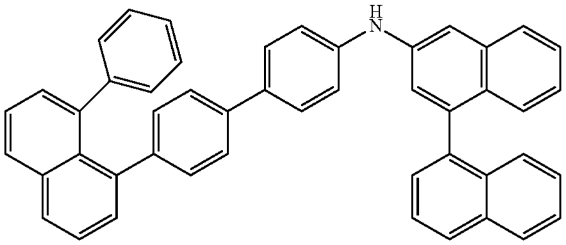

N

<Synthesis of Compound N>

By a same method as the synthesis method of Compound K, except for using Compound D (3.0 g) instead of Compound E (5.0 g), and using Compound H (3.34 g) instead of 4-bromobiphenyl (3.94 g), 3.93 g of Compound N (yield 70%) was obtained. The molecular weight of Compound N measured by FAB-MS was 623.

[Reaction 4-3]

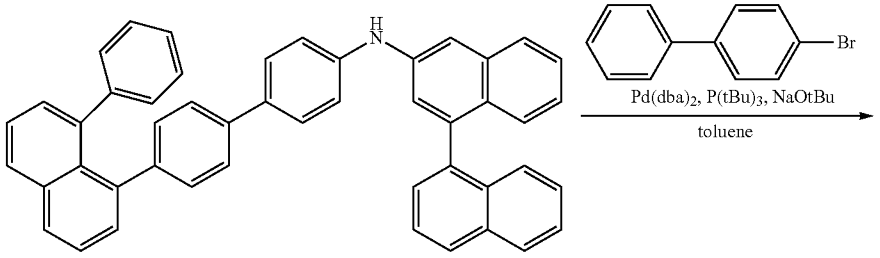

N

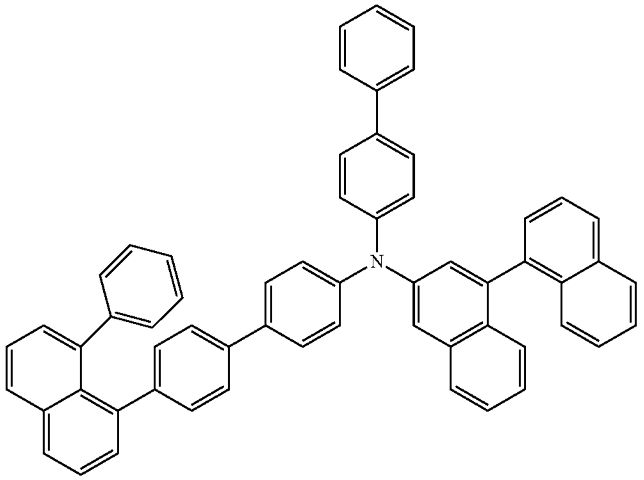

<Synthesis of Compound 36>

By a same method as the synthesis method of Compound 3, except for using Compound N (3.0 g) instead of Compound K (3.0 g), and using 4-bromobiphneyl (1.12 g) instead of Compound A (2.23 g), 2.61 g of Compound 36 (yield 70%) was obtained. The molecular weight of Compound 36 measured by FAB-MS was 775.

(5) Synthesis of Compound 113

Amine Compound 113 according to an embodiment may be synthesized, for example, by the step of Reaction 5 below.

[Reaction 5]

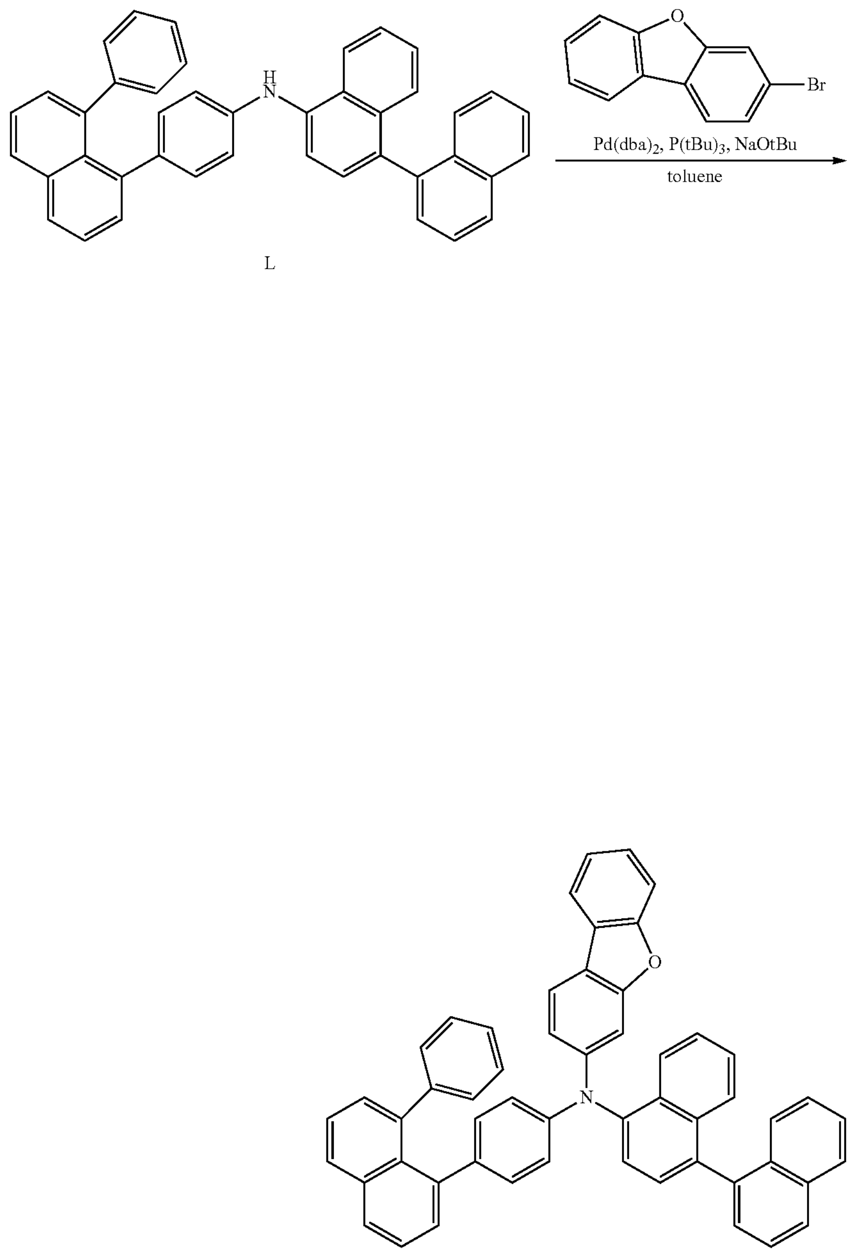

L

113

By a same method as the synthesis method of Compound 3, except for using Compound L (3.0 g) instead of Compound K (30.0 g), and using 3-bromodibenzofuran (1.35 g) instead of Compound A (2.23 g), 2.62 g of Compound 113 (yield 67%) was obtained. The molecular weight of Compound 113 measured by FAB-MS was 713.

(6) Synthesis of Compound 117

Amine Compound 117 according to an embodiment may be synthesized, for example, by the step of Reaction 6 below.

[Reaction 6]

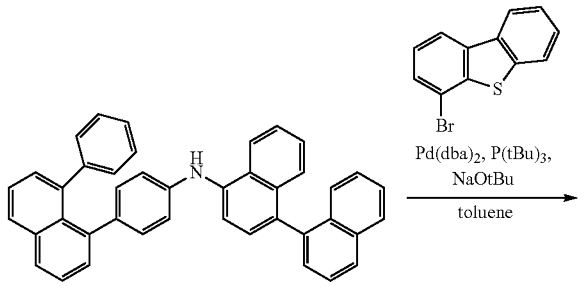

L

-continued

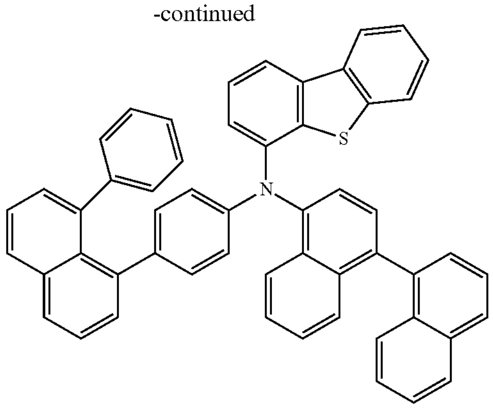

117

By a same method as the synthesis method of Compound 3, except for using Compound L (3.0 g) instead of Compound K (3.0 g), and using 4-bromodibenzothiophene (1.44 g) instead of Compound A (2.23 g), 2.56 g of Compound 117 (yield 64%) was obtained. The molecular weight of Compound 117 measured by FAB-MS was 729.

(7) Synthesis of Compound 129

Amine Compound 129 according to an embodiment may be synthesized, for example, by the step of Reaction 7 below.

[Reaction 7]

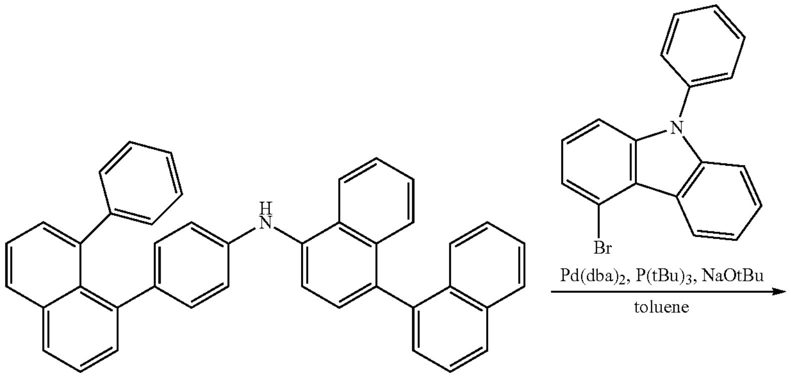

L

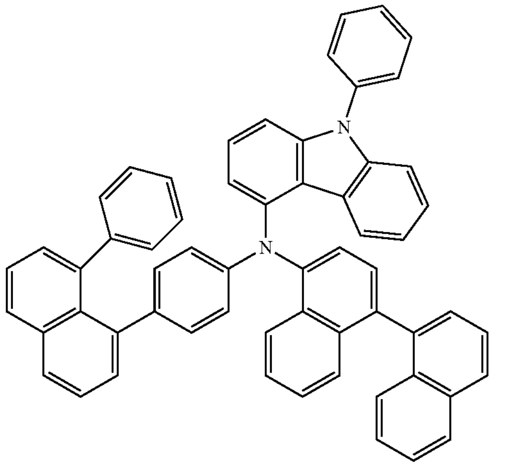

129

By a same method as the synthesis method of Compound 3, except for using Compound L (3.0 g) instead of Compound K (3.0 g), and using 4-bromocarbazole (1.76 g) instead of Compound A (2.23 g), 2.59 g of Compound 129 (yield 60%) was obtained. The molecular weight of Compound 129 measured by FAB-MS was 788.

(8) Synthesis of Compound 187

Amine Compound 187 according to an embodiment may be synthesized, for example, by the steps of Reaction 8-1 to Reaction 8-4 below.

[Reaction 8-1]

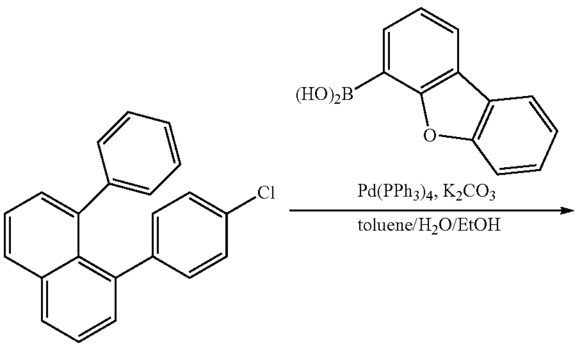

G

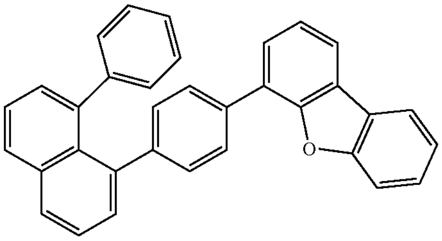

O

<Synthesis of Compound O>

By a same method as the synthesis method of Compound A, except for using Compound G (10.0 g) instead of 1-bromo-4-iodonaphthalene (30.0 g), and using dibenzofuran-4-ylboronic acid (6.7 g) instead of 1-naphthaleneboronic acid (15.5 g), 11.3 g of Compound O (yield 80%) was obtained. The molecular weight of Compound O measured by FAB-MS was 446.

[Reaction 8-2]

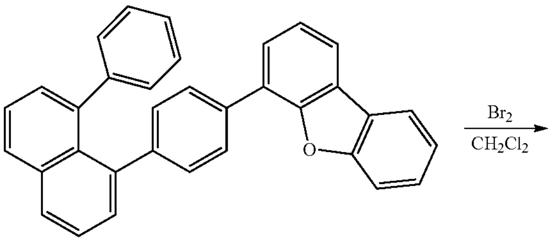

O

-continued

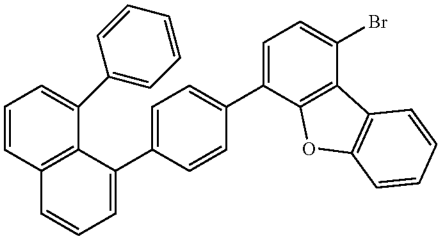

P

<Synthesis of Compound P>

Under Ar atmosphere, to a 500 mL, three-neck flask, Compound 0 (10.0 g) was added, dissolved in dichloromethane (100 mL), and stirred at about 0° C. A solution (50 mL) in which $Br_2$ (3.8 g) was dissolved was slowly added thereto. After stirring at room temperature for about 3 hours, a $NaHCO_3$ aqueous solution was added thereto, and extraction with dichloromethane was performed. Organic layers were collected and dried with magnesium sulfate, and the solvent was removed by distillation under a reduced pressure. The crude product thus obtained was washed with acetone to obtain 10.12 g of Compound P (yield 86%). The molecular weight of Compound P measured by FAB-MS was 525.

[Reaction 8-3]

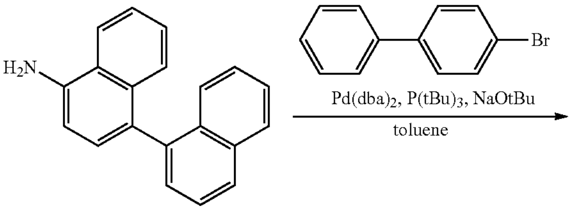

B

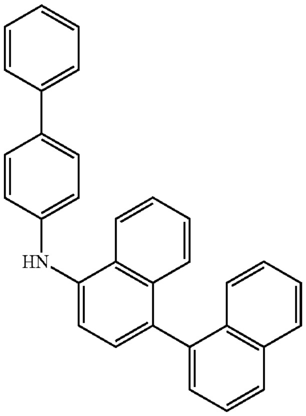

Q

<Synthesis of Compound Q>

By a same method as the synthesis method of Compound K, except for using Compound B (5.0 g) instead of Compound E (5.0 g), and using 4-bromobiphenyl (4.3 g) instead of 4-bromobiphenyl (3.94 g), 6.1 g of Compound Q (yield 78%) was obtained. The molecular weight of Compound Q measured by FAB-MS was 421.

[Reaction 8-4]

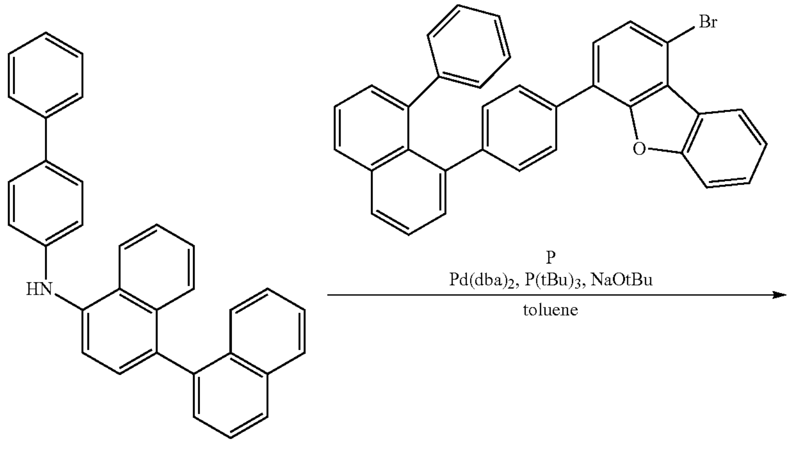

Q

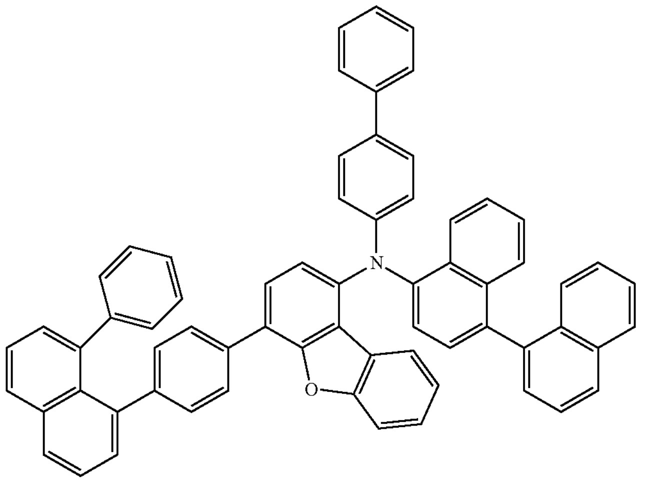

187

<Synthesis of Compound 187>

By a same method as the synthesis method of Compound 3, except for using Compound Q (3.0 g) instead of Compound K (3.0 g), and using Compound P (3.7 g) instead of Compound A (2.23 g), 4.01 g of Compound 187 (yield 65%) was obtained. The molecular weight of Compound 187 measured by FAB-MS was 866.

(9) Synthesis of Compound 202

Amine Compound 202 according to an embodiment may be synthesized, for example, by the steps of Reaction 9-1 to Reaction 9-4 below.

[Reaction 9-1]

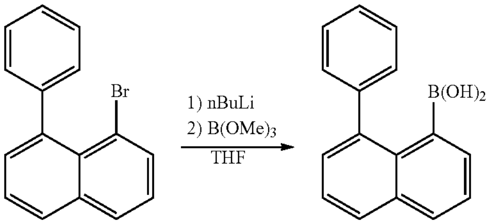

F R

<Synthesis of Compound R>

Under Ar atmosphere, to a 500 mL, three-neck flask, Compound F (10.0 g) was added, dissolved in tetrahydrofuran (THF, 100 mL), and cooled to about −78° C. A hexane solution including n-BuLi (1.6 M, 33 mL) was added thereto dropwise, and stirred for about 1 hour. $B(OMe)_3$ (19.8 g) was added, and stirred at about −78° C. for about 1 hour and at room temperature for about 3 hours. Water was added to the reaction solution, extraction with dichloromethane was performed, and organic layers were collected and dried with magnesium sulfate. The solvent was removed by distillation under a reduced pressure. The crude product thus obtained was washed with hexane to obtain 6.22 g of Compound R (yield 71%). The molecular weight of Compound R measured by FAB-MS was 248.

[Reaction 9-2]

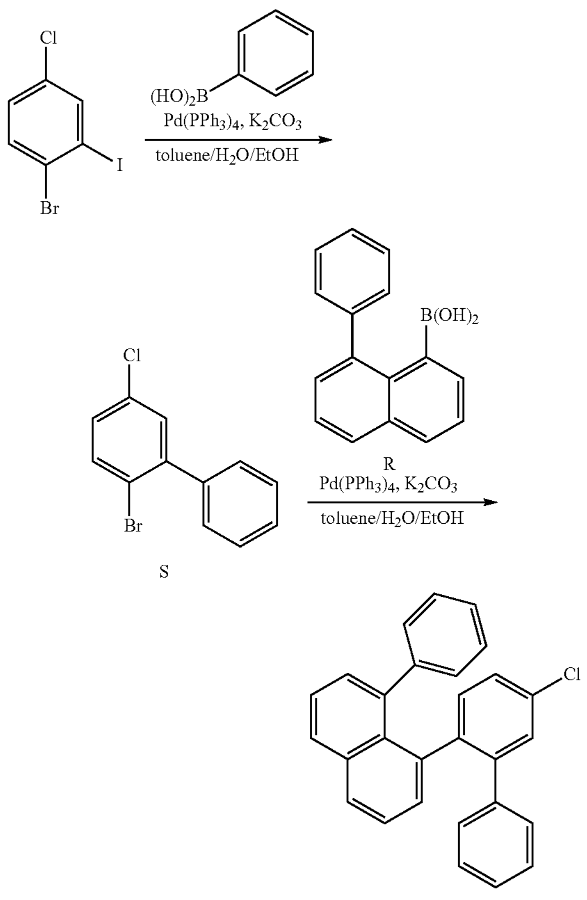

T

<Synthesis of Compound S>

By a same method as the synthesis method of Compound A, except for using 1-bromo-4-chloro-2-iodobenzene (200.0 g) instead of 1-bromo-4-iodonaphthalene (30.0 g), and using phenylboronic acid (7.7 g) instead of 1-naphthaleneboronic acid (15.5 g), 13.49 g of Compound S (yield 80%) was obtained. The molecular weight of Compound S measured by FAB-MS was 267.

<Synthesis of Compound T>

By a same method as the synthesis method of Compound S, except for using Compound S (10.0 g) instead of 1-bromo-4-chloro-2-iodobenzene (20.0 g), and using Compound R (9.3 g) instead of phenylboronic acid (7.7 g), 9.20 g of Compound T (yield 63%) was obtained. The molecular weight of Compound T measured by FAB-MS was 390.

[Reaction 9-3]

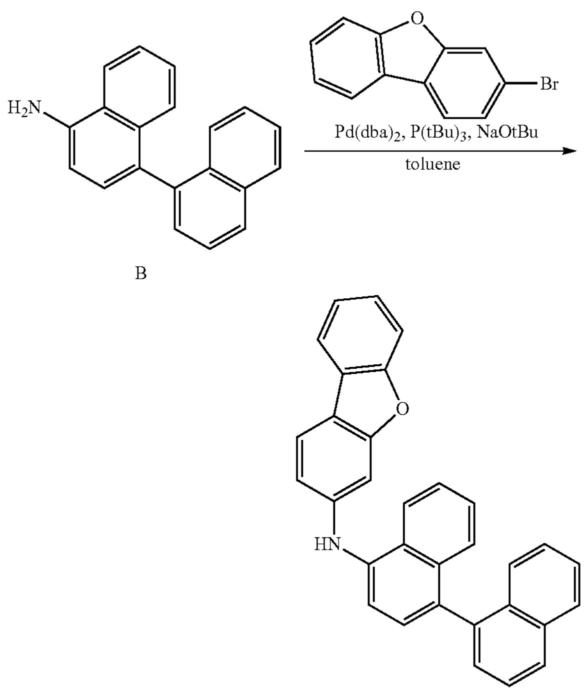

U

<Synthesis of Compound U>

By a same method as the synthesis method of Compound K, except for using Compound B (5.0 g) instead of Compound E (5.0 g), and using 3-bromodibenzofuran (4.6 g) instead of 4-bromobiphenyl (3.94 g), 6.79 g of Compound U (yield 84%) was obtained. The molecular weight of Compound U measured by FAB-MS was 435.

[Reaction 9-4]

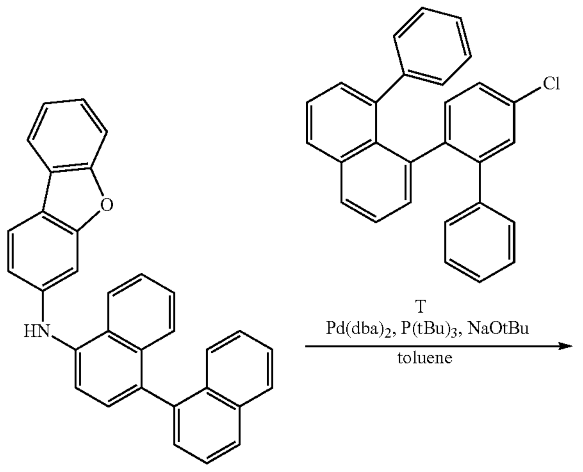

U

-continued

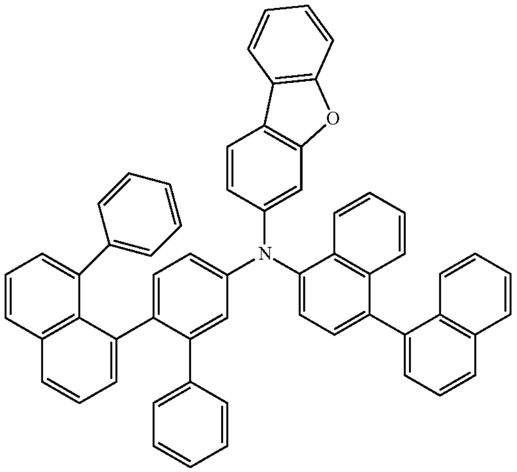

202

<Synthesis of Compound 202>

By a same method as the synthesis method of Compound 3, except for using Compound U (3.0 g) instead of Compound K (3.0 g), and using Compound T (2.7 g) instead of Compound A (2.23 g), 4.03 g of Compound 202 (yield 74%) was obtained. The molecular weight of Compound 202 measured by FAB-MS was 789.

(10) Synthesis of Compound 206

Amine Compound 206 according to an embodiment may be synthesized, for example, by the steps of Reaction 10-1 to Reaction 10-3 below.

[Reaction 10-1]

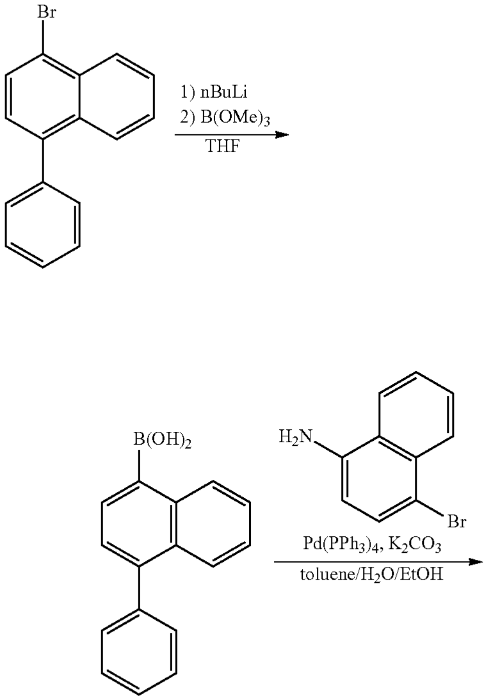

V

-continued

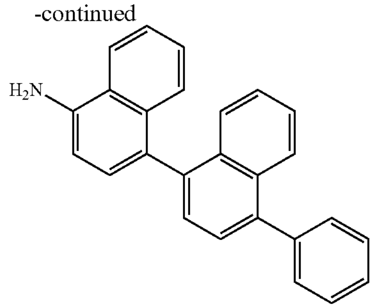

W

<Synthesis of Compound V>

By a same method as the synthesis method of Compound R, except for using 1-bromo-4-iodonaphthalene (10.0 g) instead of Compound F (10.0 g), 6.48 g of Compound V (yield 74%) was obtained. The molecular weight of Compound V measured by FAB-MS was 248.

<Synthesis of Compound W>

By a same method as the synthesis method of Compound A, except for using Compound V (5.0 g) instead of 1-bromo-4-iodonaphthalene (30.0 g) and using 4-bromo-1-naphthylamine (4.5 g) instead of naphthaleneboronic acid (15.5 g), 3.83 g of Compound W (yield 55%) was obtained. The molecular weight of Compound W measured by FAB-MS was 345.

[Reaction 10-2]

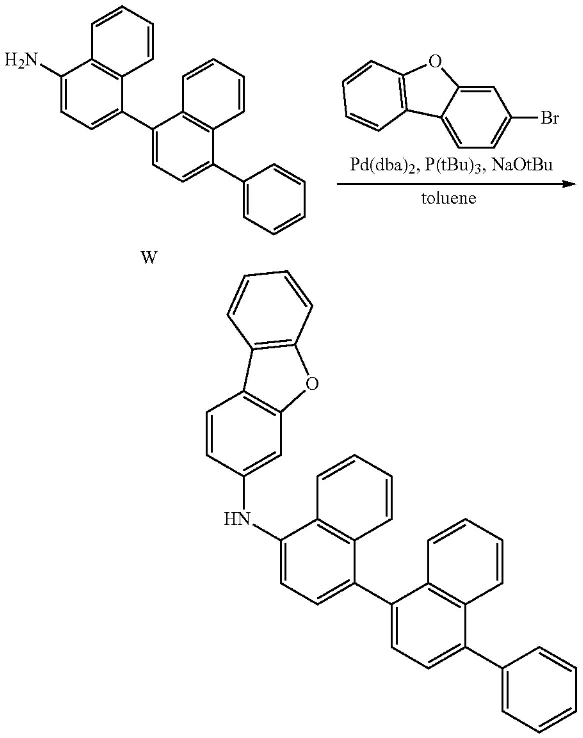

X

<Synthesis of Compound X>

By a same method as the synthesis method of Compound K, except for using Compound W (3.0 g) instead of Compound E (5.0 g), and using 3-bromodibenzofuran (2.1 g) instead of 4-bromobiphenyl (3.94 g), 3.55 g of Compound X (yield 80%) was obtained. The molecular weight of Compound X measured by FAB-MS was 511.

[Reaction 10-3]

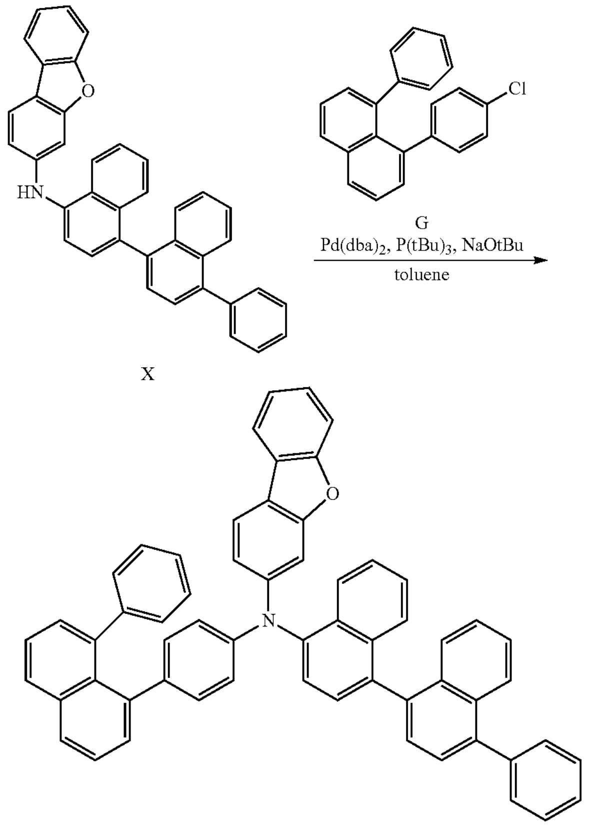

X

G

206

<Synthesis of Compound 206>

By a same method as the synthesis method of Compound 3, except for using Compound X (3.0 g) instead of Compound K (3.0 g), and using Compound G (1.8 g) instead of Compound A (2.23 g), 3.75 g of Compound 206 (yield 81%) was obtained. The molecular weight of Compound 206 measured by FAB-MS was 789.

2. Manufacture and Evaluation of Light Emitting Device (1) Manufacture of Light Emitting Device A light emitting device including the amine compound of an Example or a Comparative Example in a hole transport layer was manufactured by a method below. By using the amine compounds of embodiments, Compounds 3, 7, 32, 36, 113, 117, 129, 187, 202, and 206 as materials for hole transport layers, light emitting devices of Examples 1 to 10 were manufactured. The light emitting devices of Comparative Examples 1 to 7 were manufactured using Comparative Compound X-1 to Comparative Compound X-7 in hole transport layers.

On a glass substrate, ITO of a thickness of about 1500 Å was patterned, and washed with ultrapure water and ultrasonic waves, and exposed to UV for about 30 minutes and treated with ozone. 2-TNATA was deposited to a thickness of about 600 Å, and the Example Compound or the Comparative Compound was deposited to a thickness of about 300 Å to form a hole transport region.

ADN and TBP in a ratio of 3:97 was co-deposited to form an emission layer with a thickness of about 250 Å. On the emission layer, a layer was formed using $Alq_3$ to a thickness of about 250 Å, and a layer was formed using LiF to a thickness of about 10 Å to form an electron transport region. A second electrode was formed using Al to a thickness of about 1000 Å. In the Examples, the hole transport region, the emission layer, the electron transport region, and the second electrode were formed using a vacuum deposition apparatus.

2-TNATA, TBP, ADN, and $Alq_3$ used for the manufacture of the light emitting devices are materials that are common in the art, and commercially available materials were used after purification.

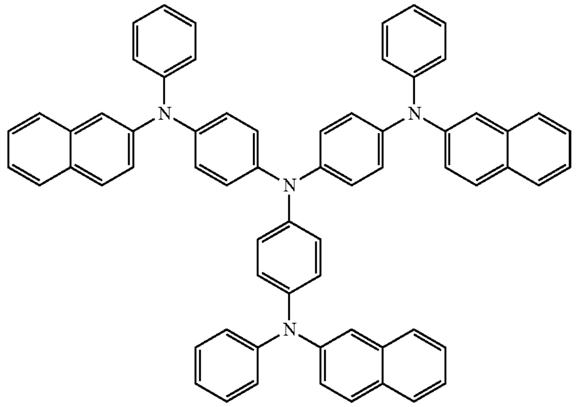

2-TNATA

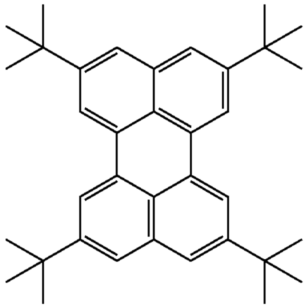

TBP

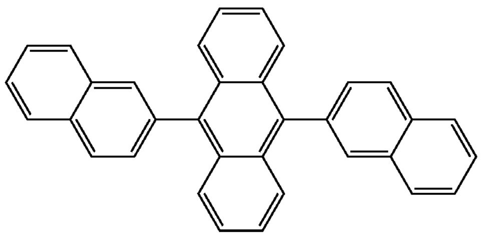

ADN

-continued
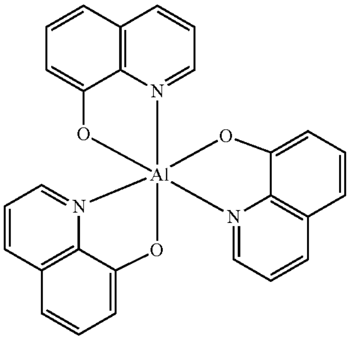
Alq3
The compounds used in Examples 1 to 10, and Comparative Examples 1 to 7 are shown in Table 2.
TABLE 2
| | | |
|---|---|---|
| Compound 3 | 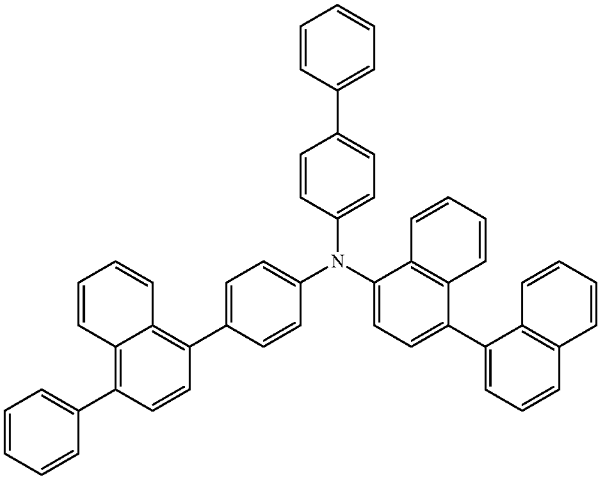 [SMILES: c1ccc(-c2ccc(N(c3ccc(-c4ccc(-c5ccccc5)c5ccccc45)cc3)c3ccc(-c4cccc5ccccc45)c4ccccc34)cc2)cc1] | 3 |
| Compound 7 | 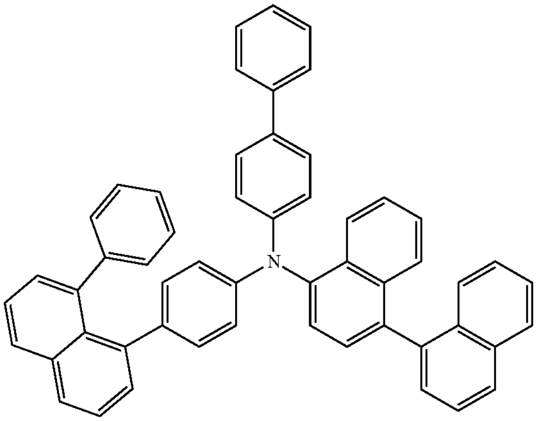 [SMILES: c1ccc(-c2ccc(N(c3ccc(-c4cccc5cccc(-c6ccccc6)c45)cc3)c3ccc(-c4cccc5ccccc45)c4ccccc34)cc2)cc1] | 7 |

TABLE 2-continued
Compound 32 32
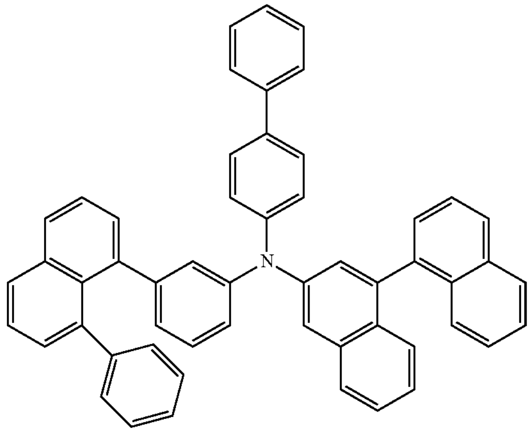 [SMILES: c1ccc(-c2ccc(N(c3cccc(-c4cccc5cccc(-c6ccccc6)c45)c3)c3cc(-c4cccc5ccccc45)c4ccccc4c3)cc2)cc1]
Compound 36 36
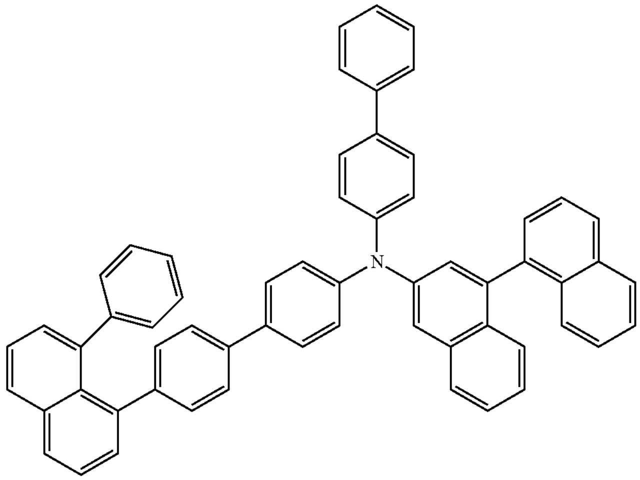 [SMILES: c1ccc(-c2ccc(N(c3ccc(-c4ccc(-c5cccc6cccc(-c7ccccc7)c56)cc4)cc3)c3cc(-c4cccc5ccccc45)c4ccccc4c3)cc2)cc1]
Compound 113 113
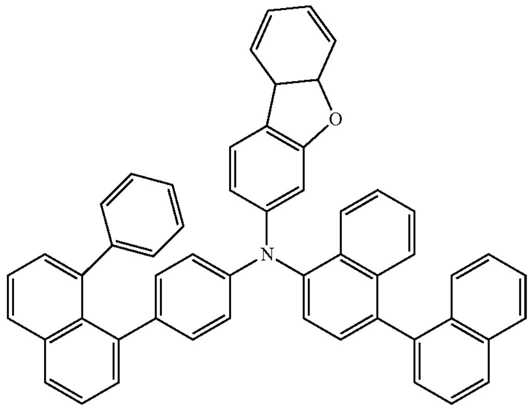 [SMILES: C1=CC2Oc3cc(N(c4ccc(-c5cccc6cccc(-c7ccccc7)c56)cc4)c4ccc(-c5cccc6ccccc56)c5ccccc45)ccc3C2C=C1]

TABLE 2-continued
Compound 117 117
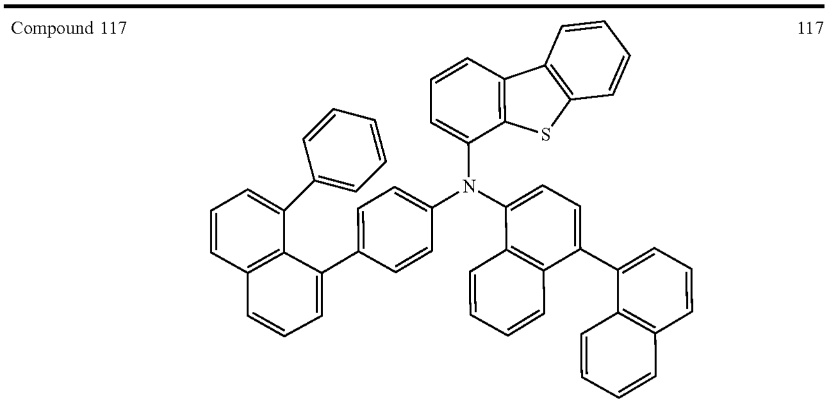
Compound 129 129
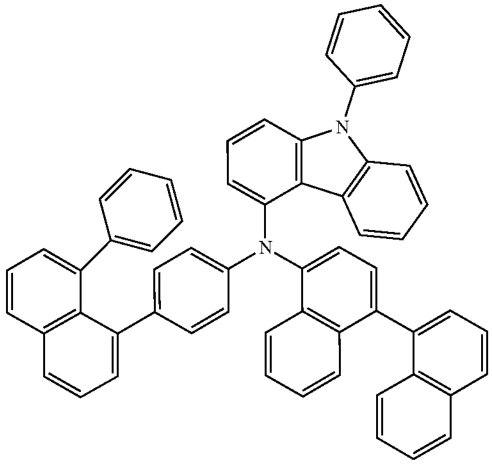 [SMILES: c1ccc(-c2cccc3cccc(-c4ccc(N(c5ccc(-c6cccc7ccccc67)c6ccccc56)c5cccc6c5c5ccccc5n6-c5ccccc5)cc4)c23)cc1]
Compound 187 187
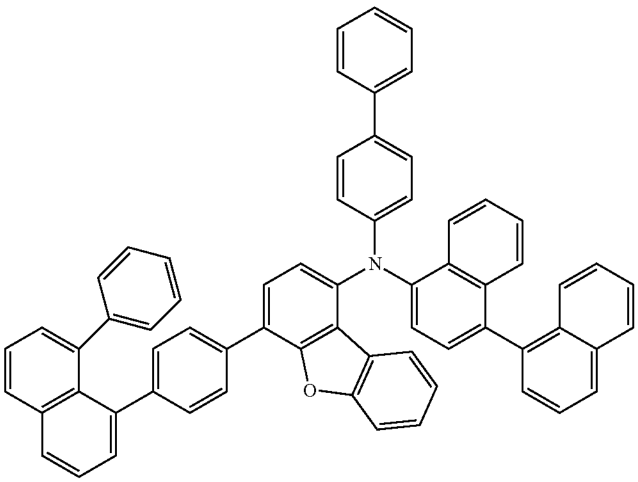 [SMILES: c1ccc(-c2ccc(N(c3ccc(-c4cccc5ccccc45)c4ccccc34)c3ccc(-c4ccc(-c5cccc6cccc(-c7ccccc7)c56)cc4)c4oc5ccccc5c34)cc2)cc1]

TABLE 2-continued
Compound 202
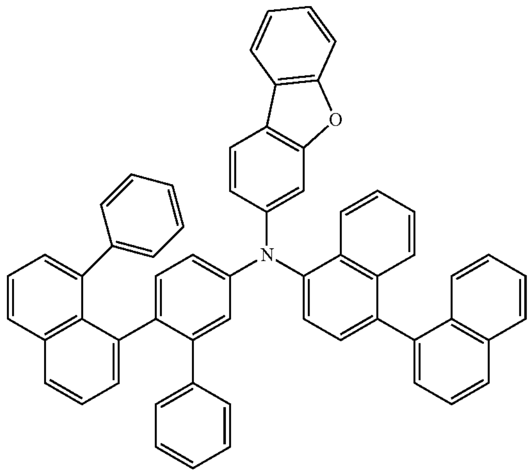 [SMILES: c1ccc(-c2cc(N(c3ccc4c(c3)oc3ccccc34)c3ccc(-c4cccc5ccccc45)c4ccccc34)ccc2-c2cccc3cccc(-c4ccccc4)c23)cc1]
202
Compound 206
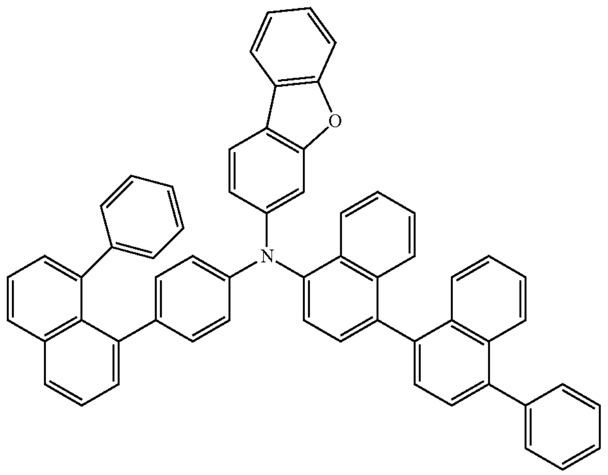 [SMILES: c1ccc(-c2ccc(-c3ccc(N(c4ccc(-c5cccc6cccc(-c7ccccc7)c56)cc4)c4ccc5c(c4)oc4ccccc45)c4ccccc34)c3ccccc23)cc1]
206
Comparative Compound X-1
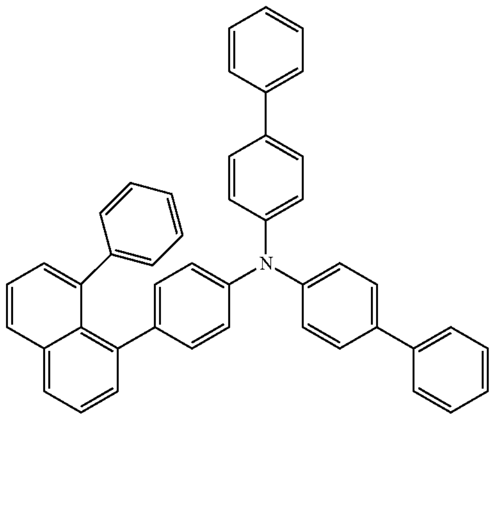 [SMILES: c1ccc(-c2ccc(N(c3ccc(-c4ccccc4)cc3)c3ccc(-c4cccc5cccc(-c6ccccc6)c45)cc3)cc2)cc1]
X-1

TABLE 2-continued
Comparative Compound X-2
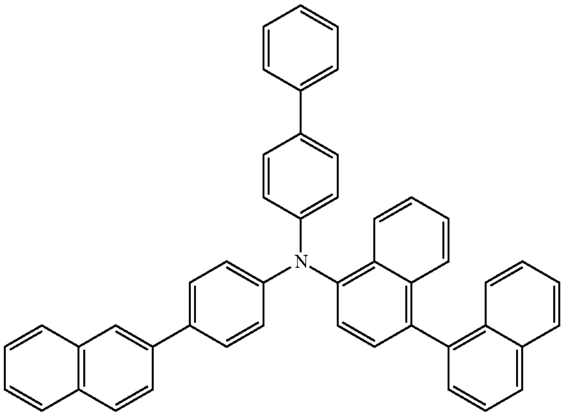 [SMILES: c1ccc(-c2ccc(N(c3ccc(-c4ccc5ccccc5c4)cc3)c3ccc(-c4cccc5ccccc45)c4ccccc34)cc2)cc1]
X-2
Comparative Compound X-3
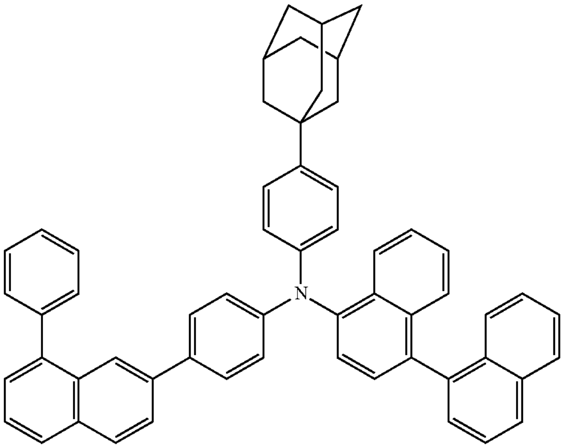 [SMILES: c1ccc(-c2cccc3ccc(-c4ccc(N(c5ccc(C67CC8CC9(CC(C8)(C9)C6)C7)cc5)c5ccc(-c6cccc7ccccc67)c6ccccc56)cc4)cc23)cc1]
X-3
Comparative Compound X-4
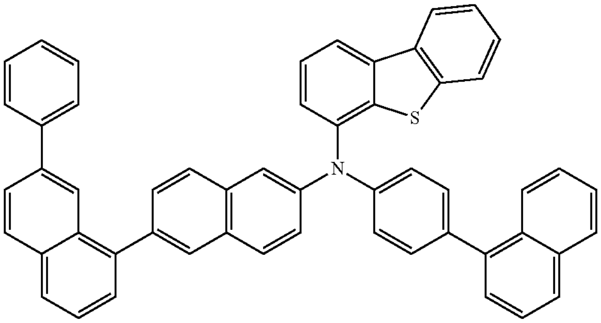 [SMILES: c1ccc(-c2ccc3cccc(-c4ccc5cc(N(c6ccc(-c7cccc8ccccc78)cc6)c6cccc7c6sc6ccccc67)ccc5c4)c3c2)cc1]
X-4
Comparative Compound X-5
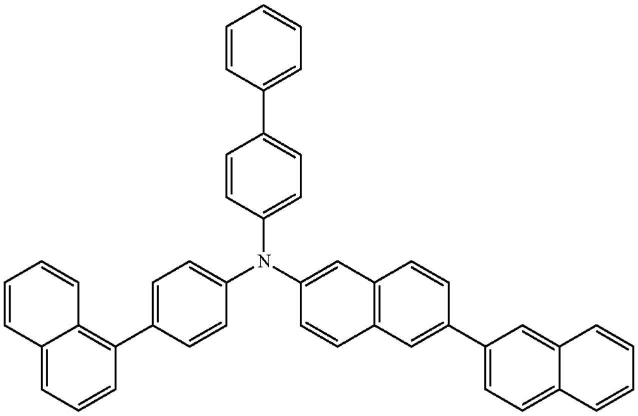 [SMILES: c1ccc(-c2ccc(N(c3ccc(-c4cccc5ccccc45)cc3)c3ccc4cc(-c5ccc6ccccc6c5)ccc4c3)cc2)cc1]
X-5

TABLE 2-continued

| | | |
|---|---|---|
| Comparative Compound X-6 | 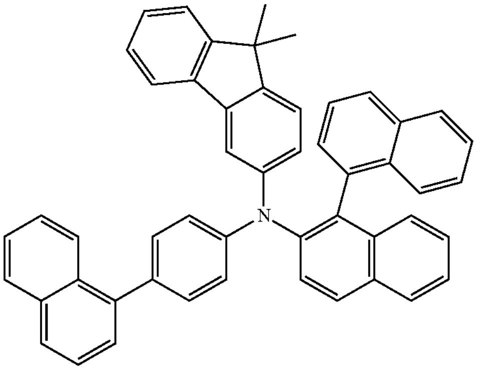 [SMILES: CC1(C)c2ccccc2-c2cc(N(c3ccc(-c4cccc5ccccc45)cc3)c3ccc4ccccc4c3-c3cccc4ccccc34)ccc21] | X-6 |
| Comparative Compound X-7 | 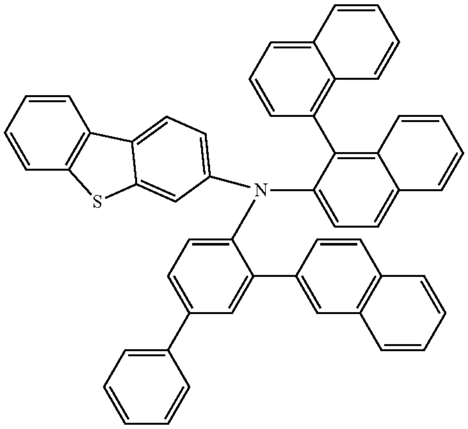 [SMILES: c1ccc(-c2ccc(N(c3ccc4c(c3)sc3ccccc34)c3ccc4ccccc4c3-c3cccc4ccccc34)c(-c3ccc4ccccc4c3)c2)cc1] | X-7 |

3. Evaluation of Properties of Light Emitting Device

In Table 3, the evaluation results of the light emitting devices according to Examples 1 to 10, and Comparative Examples 1 to 7 are shown. In Table 3, emission efficiency and device life are relative values. Emission efficiency and device life are relative values with 100% of the emission efficiency and device life of the light emitting device of Comparative Example 1. Emission efficiency is a relative value by measuring an emission efficiency value at a current density of about 10 mA/$cm^2$. When measuring emission efficiency, a light distribution measurement system of C9920-11 of Hamamatsu Photonics Co. was used. The device life (LT50) represents a relative time required for reducing the brightness of a light emitting device to half.

TABLE 3

| Device manufacturing example | Hole transport layer material | Emission efficiency (%) | Device life ($LT_{50}$) |
|---|---|---|---|
| Example 1 | Compound 3 | 106% | 110% |
| Example 2 | Compound 7 | 104% | 180% |
| Example 3 | Compound 32 | 110% | 120% |
| Example 4 | Compound 36 | 108% | 140% |
| Example 5 | Compound 113 | 102% | 180% |
| Example 6 | Compound 117 | 104% | 150% |
| Example 7 | Compound 129 | 102% | 150% |
| Example 8 | Compound 187 | 105% | 110% |
| Example 9 | Compound 202 | 102% | 120% |
| Example 10 | Compound 206 | 103% | 150% |
| Comparative Example 1 | Comparative Compound X-1 | 100% | 100% |
| Comparative Example 2 | Comparative Compound X-2 | 99% | 105% |

TABLE 3-continued

| Device manufacturing example | Hole transport layer material | Emission efficiency (%) | Device life ($LT_{50}$) |
|---|---|---|---|
| Comparative Example 3 | Comparative Compound X-3 | 98% | 70% |
| Comparative Example 4 | Comparative Compound X-4 | 98% | 80% |
| Comparative Example 5 | Comparative Compound X-5 | 95% | 105% |
| Comparative Example 6 | Comparative Compound X-6 | 98% | 50% |
| Comparative Example 7 | Comparative Compound X-7 | 100% | 40% |

Referring to Table 3, it could be found that the light emitting devices of Examples 1 to 10 showed better device life and emission efficiency when compared to the light emitting devices of Comparative Examples 1 to 7. The light emitting devices of Examples 1 to 10 include Compounds 3, 7, 32, 36, 113, 117, 129, 187, 202 and 206, which are the amine compounds of embodiments in hole transport layers.

When compared to the light emitting devices of Comparative Examples 1 to 7, it could be found that the light emitting devices of Examples 1 to 10 showed improved device life by about 1.1 times. It could be found that the light emitting device of Example 2 showed improved life by about 1.8 times when compared to the light emitting device of Comparative Example 1. Compounds 3, 7, 32, 36, 113, 117, 129, 187, 202 and 206, which are the amine compounds of embodiments, include a binaphthyl group and may show relatively high thermal stability. Accordingly, the light emitting devices of Examples 1 to 10 including Compounds 3, 7, 32, 36, 113, 117, 129, 187, 202 and 206 are thought to show long-life characteristics. Accordingly, the light emitting device including the amine compound of an embodiment in a hole transport region is thought to show high efficiency and long-life characteristics.

The light emitting device of Comparative Example 1 includes Comparative Compound X-1. Different from the amine compound of an embodiment, Comparative Compound X-1 does not include a phenylnaphthyl group and is thought to show relatively low thermal stability when compared to the Example Compounds.

The light emitting device of Comparative Example 2 includes Comparative Compound X-2, and the light emitting device of Comparative Example 4 includes Comparative Compound X-4. The light emitting device of Comparative Example 5 includes Comparative Compound X-5. Different from the amine compound of an embodiment, in Comparative Compound X-2, Comparative Compound X-4 and Comparative Compound X-5, no substituent other than a hydrogen atom is combined with the naphthyl group of a phenylnaphthyl group. Comparative Compound X-2, Comparative Compound X-4, and Comparative Compound X-5, which do not include a phenylnaphthyl group had low hole transport properties, and it is thought that the light emitting devices of Comparative Examples 2, 4 and 5 became light emitting devices having greater amounts of electrons than holes.

The light emitting device of Comparative Example 3 includes Comparative Compound X-3, and the light emitting device of Comparative Example 6 includes Comparative Compound X-6. It is thought that Comparative Compound X-3 and Comparative Compound X-6 include quaternary carbon, and the stability of the compounds was reduced. Since the stability of the compounds was reduced, the light emitting devices of Comparative Examples 3 and 6 showed short life.

The light emitting device of Comparative Example 7 includes Comparative Compound X-7, and in Comparative Compound X-7, no substituent other than a hydrogen atom is combined with the naphthyl group of a phenylnaphthyl group. Comparative Compound X-7 has a structure in which both a binaphthyl group and a phenylnaphthyl group are sterically bent. Due to the steric hindrance of the binaphthyl group and the phenylnaphthyl group, it is thought that the stability of Comparative Compound X-7 was reduced. According to the reduction of the stability of the compound, it is thought that the light emitting device of Comparative Example 7 showed short life.

The amine compound of an embodiment includes a phenylnaphthyl group and a binaphthyl group bonded to a nitrogen atom, and the phenylnaphthyl group may be substituted with at least one among an aryl group and a heteroaryl group. An amine compound including the phenylnaphthyl group may show relatively high hole transport properties. An amine compound including the binaphthyl group may show improved thermal stability. Accordingly, the amine compound of an embodiment may contribute to the increase of the efficiency and life of a light emitting device.

The light emitting device of an embodiment may include a first electrode, a second electrode, and at least one functional layer disposed between the first electrode and the second electrode. The at least one functional layer includes the amine compound of an embodiment, and the amine compound of an embodiment may include a phenylnaphthyl group and a binaphthyl group. Accordingly, a light emitting device including the amine compound of an embodiment may show improved efficiency and life characteristics.

The light emitting device of an embodiment includes the amine compound of an embodiment in a hole transport region and may show high efficiency and long-life characteristics.

The amine compound of an embodiment may improve the emission efficiency and device life of a light emitting device.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the following claims.

What is claimed is:

1. A light emitting device, comprising:

a first electrode;

a second electrode disposed on the first electrode; and at least one functional layer disposed between the first electrode and the second electrode, the at least one functional layer comprising an amine compound represented by the Formula 1:

[Formula 1]

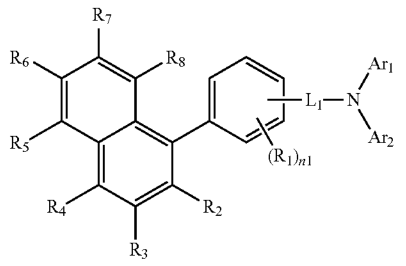

wherein in Formula 1, $L_1$ is direct linkage, a substituted or unsubstituted arylene group of 6 to 15 ring-forming carbon atoms, or a substituted or unsubstituted heteroarylene group of 2 to 15 ring-forming carbon atoms, $Ar_1$ is a phenyl group substituted with a substituted or unsubstituted alkyl group, a phenyl group substituted with a substituted or unsubstituted phenyl group, a phenyl group substituted with a substituted or unsubstituted naphthyl group, an unsubstituted phenyl group, a substituted or unsubstituted naphthyl group, a substituted or unsubstituted terphenyl group, a substituted or unsubstituted phenanthrene group, a substituted or unsubstituted triphenylene group, a substituted or unsubstituted carbazole group, a substituted or unsubstituted dibenzofuran group, a substituted or unsubstituted dibenzothiophene group, a substituted or unsubstituted naphthobenzofuran group, or a substituted or unsubstituted benzonaphthothiophene group, wherein $Ar_1$ does not include an adamantyl group, $Ar_2$ is a group represented by Formula 2, n1 is an integer from 0 to 4, $R_1$ is a hydrogen atom, a deuterium atom, a halogen atom, a substituted or unsubstituted oxy group, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms, or is combined with an adjacent group to form a ring, at least one of $R_2$ to $R_8$ is a substituted or unsubstituted aryl group of 6 to 30 ring-forming carbon atoms, or a substituted or unsubstituted heteroaryl group of 2 to 30 ring-forming carbon atoms, and the remainder of $R_2$ to $R_8$ are each independently a hydrogen atom, a deuterium atom, a halogen atom, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms:

[Formula 2]

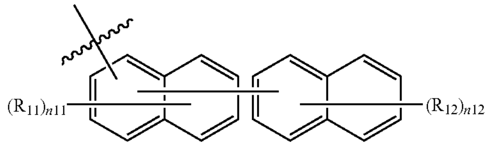

wherein in Formula 2, n11 is an integer from 0 to 6, n12 is an integer from 0 to 7, and $R_{11}$ and $R_{12}$ are each independently a hydrogen atom, a deuterium atom, a halogen atom, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms.

2. The light emitting device of claim 1, wherein the amine compound represented by Formula 1 is represented by Formula 1-A1 or Formula 1-A2:

[Formula 1-A1]

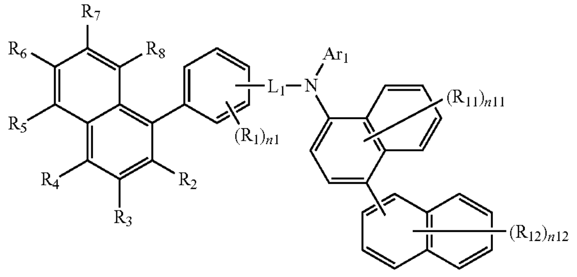

-continued

[Formula 1-A2]

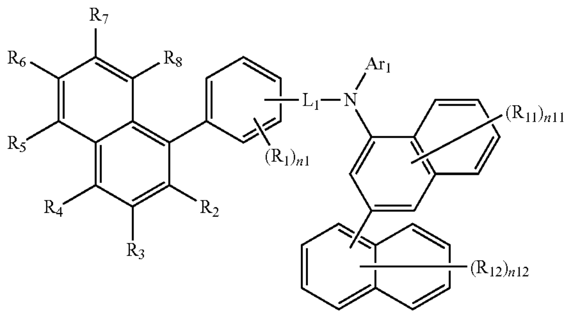

wherein in Formula 1-A1 and Formula 1-A2, $Ar_1$, $L_1$, n1, n11, n12, $R_1$ to $R_8$, $R_{11}$, and $R_{12}$ are the same as defined in Formula 1 and Formula 2.

3. The light emitting device of claim 1, wherein the amine compound represented by Formula 1 is represented by Formula 1-B1 or Formula 1-B2:

[Formula 1-B1]

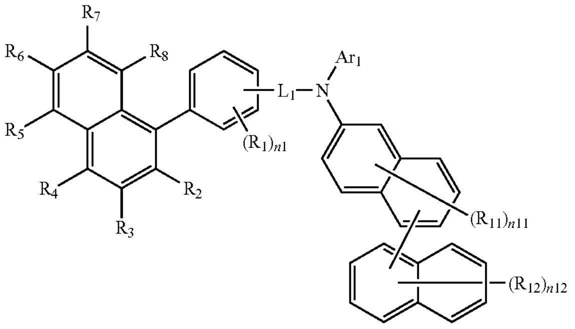

[Formula 1-B2]

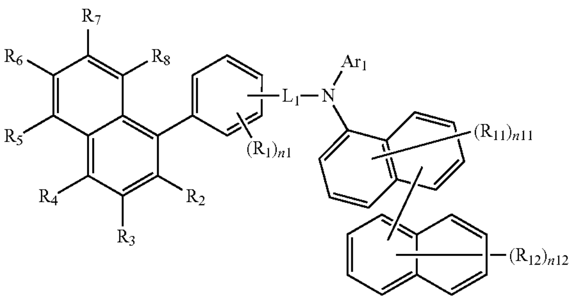

wherein in Formula 1-B1 and Formula 1-B2, $Ar_1$, $L_1$, n1, n11, n12, $R_1$ to $R_8$, $R_{11}$, and $R_{12}$ are the same as defined in Formula 1 and Formula 2.

4. The light emitting device of claim 1, wherein the amine compound represented by Formula 1 is represented by Formula 1-C1 or Formula 1-C2:

[Formula 1-C1]

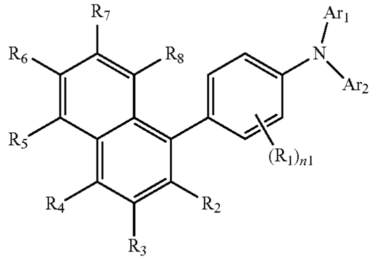

[Formula 1-C2]

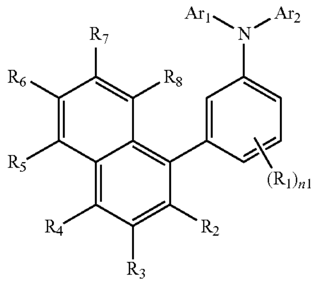

wherein in Formula 1-C1 and Formula 1-C2, $Ar_1$, $Ar_2$, n1, and $R_1$ to $R_8$ are the same as defined in Formula 1.

5. The light emitting device of claim 1, wherein $Ar_1$ is a group represented by one of Ar1-1 to Ar1-6:

Ar1-1

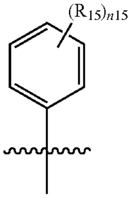

Ar1-2

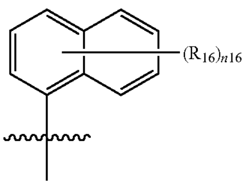

Ar1-3

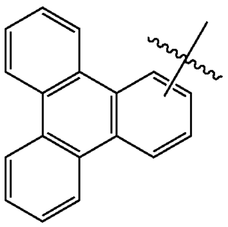

Ar1-4

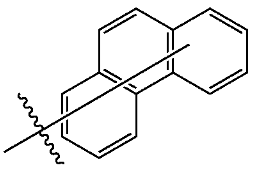

-continued

Ar1-5

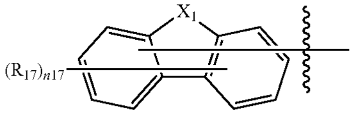

Ar1-6

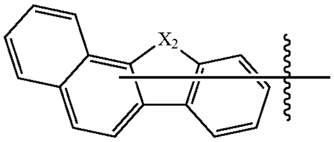

wherein in Ar1-1, n15 is an integer from 0 to 5, and $R_{15}$ is a hydrogen atom, a substituted or unsubstituted alkyl group of 1 to 10 carbon atoms, a substituted or unsubstituted phenyl group, or a substituted or unsubstituted naphthyl group, wherein in Ar1-2, n16 is an integer from 0 to 7, and $R_{16}$ is a hydrogen atom, a halogen atom, or a substituted or unsubstituted aryl group of 6 to 30 ring-forming carbon atoms, wherein in Ar1-5, $X_1$ is $N(R_{18})$, O, or S, n17 is an integer from 0 to 7, and $R_{17}$ and $R_{18}$ are each independently a hydrogen atom, or a substituted or unsubstituted aryl group of 6 to 30 ring-forming carbon atoms, wherein in Ar1-6, $X_2$ is O or S.

6. The light emitting device of claim 1, wherein at least one of $R_1$ to $R_8$ comprises a deuterium atom as a substituent, or at least one of $R_{11}$ and $R_{12}$ is a deuterium atom.

7. The light emitting device of claim 1, wherein at least one of $R_4$ and $R_8$ is a substituted or unsubstituted phenyl group, a substituted or unsubstituted naphthyl group, a substituted or unsubstituted pyridine group, a substituted or unsubstituted carbazole group, a substituted or unsubstituted dibenzofuran group, or a substituted or unsubstituted dibenzothiophene group.

8. The light emitting device of claim 1, wherein the at least one functional layer comprises:

an emission layer;

a hole transport region disposed between the first electrode and the emission layer; and an electron transport region disposed between the emission layer and the second electrode, and the hole transport region comprises the amine compound.

9. The light emitting device of claim 8, wherein the hole transport region comprises:

a hole injection layer disposed on the first electrode;

a hole transport layer disposed on the hole injection layer; and an electron blocking layer disposed on the hole transport layer, and at least one of the hole injection layer, the hole transport layer, and the electron blocking layer comprises the amine compound.

10. The light emitting device of claim 1, wherein the amine compound is one selected from Compound Group 1:

[Compound Group 1]
1
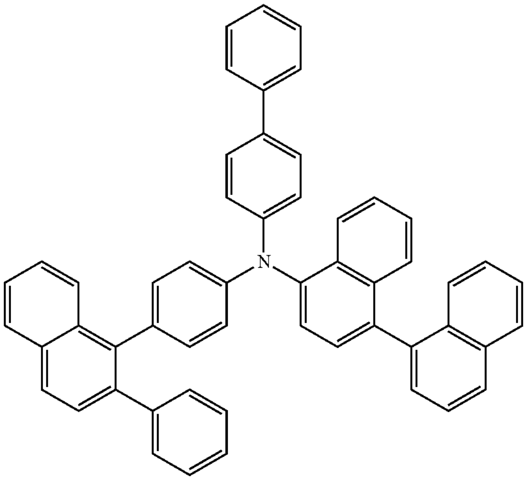
2
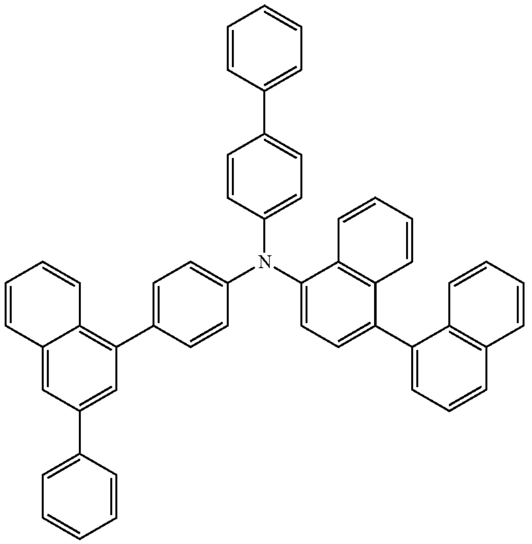
3
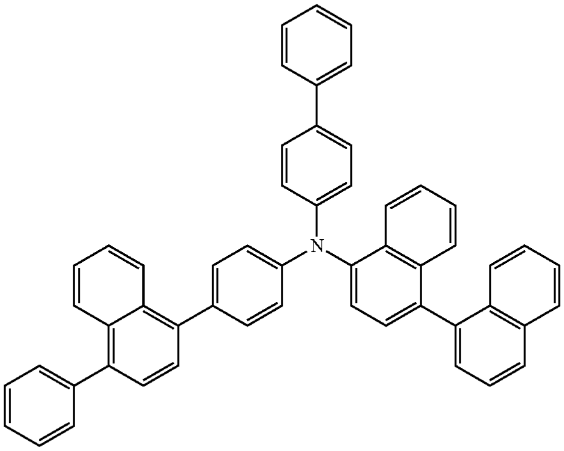
4
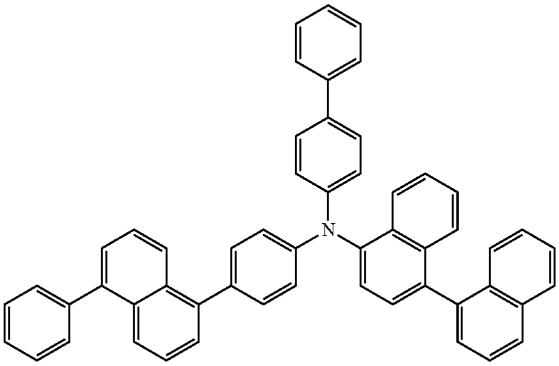
5
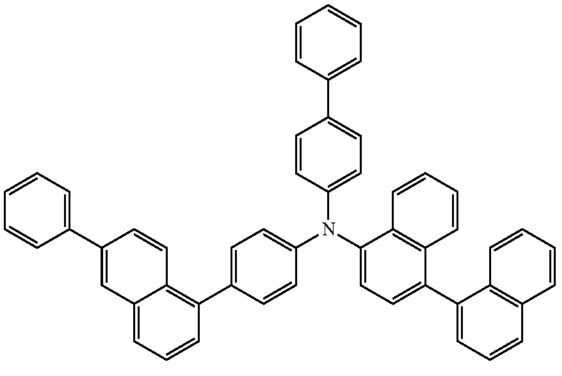
6
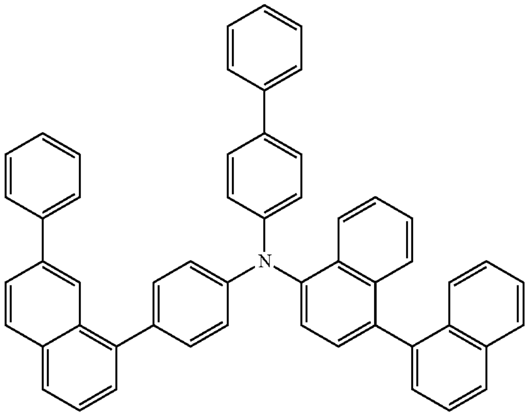

-continued
7
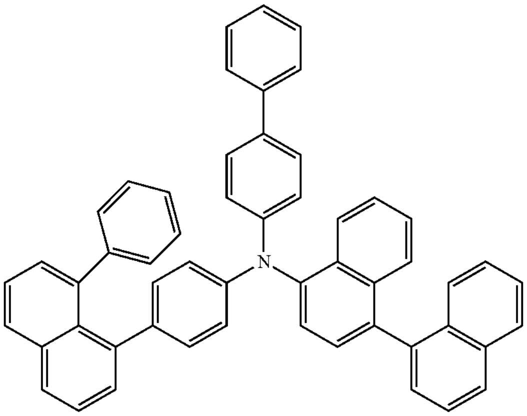
8
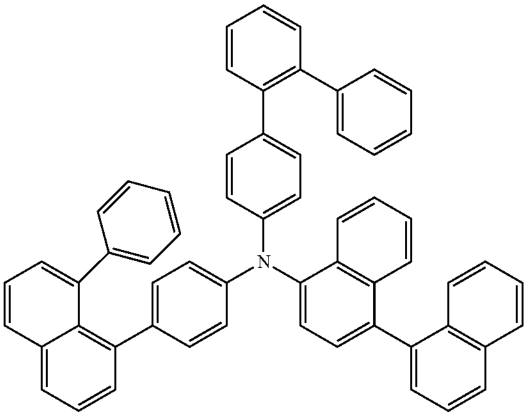
9
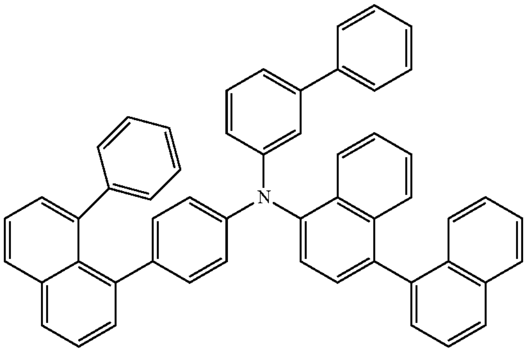
10
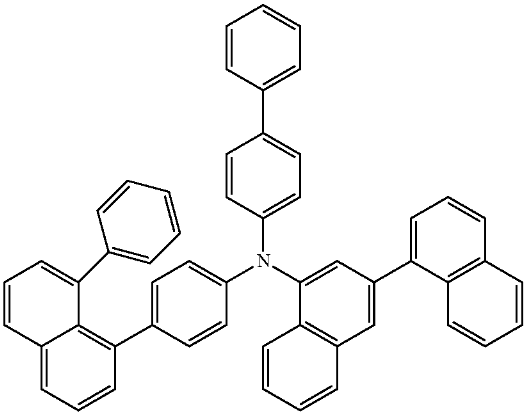
11
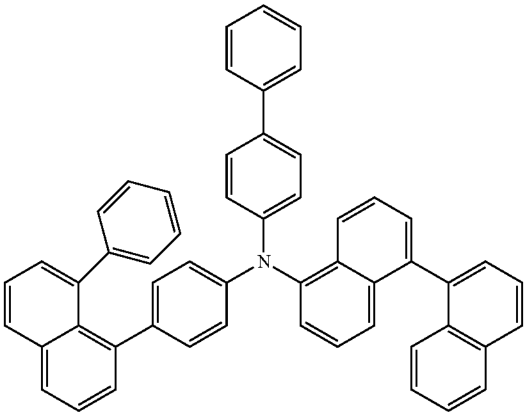
12
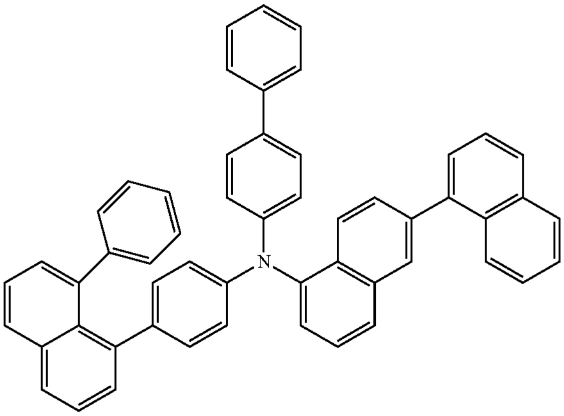

-continued
13
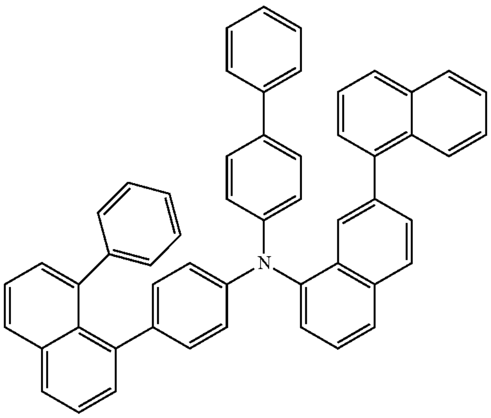
14
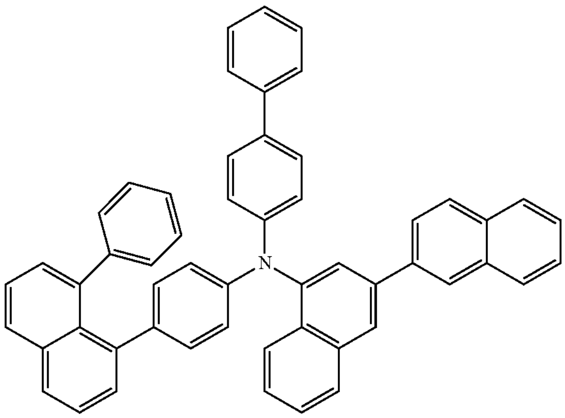
15
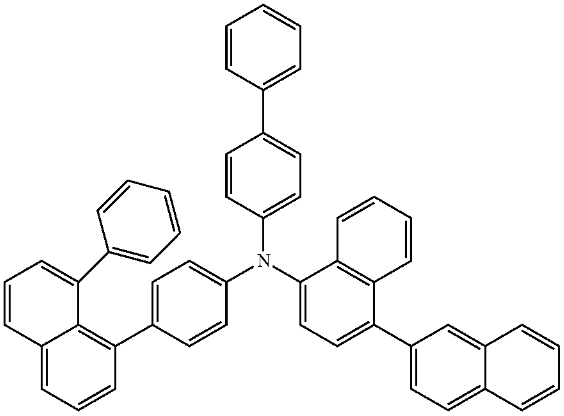
16
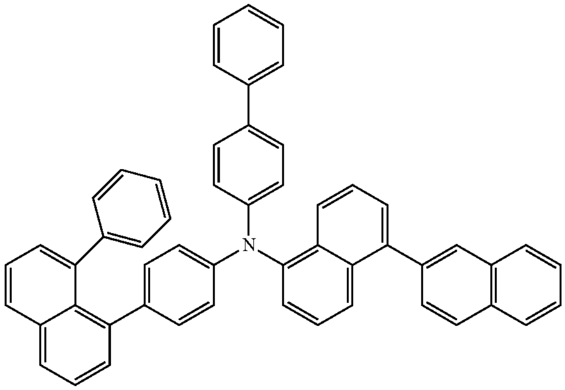
17
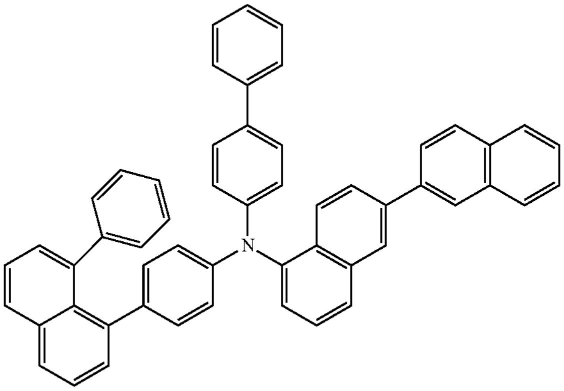
18
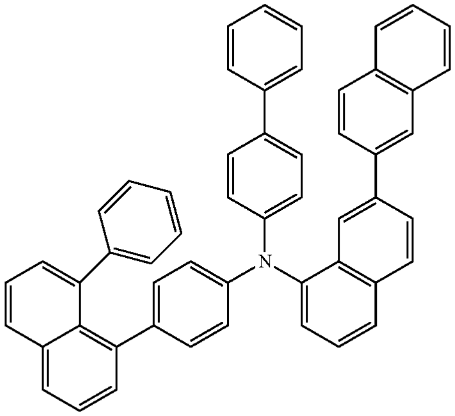

-continued
19
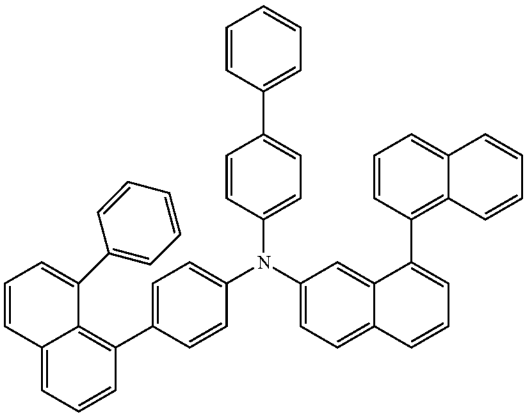
20
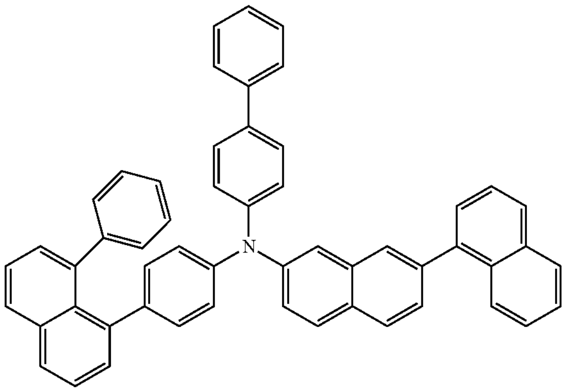
21
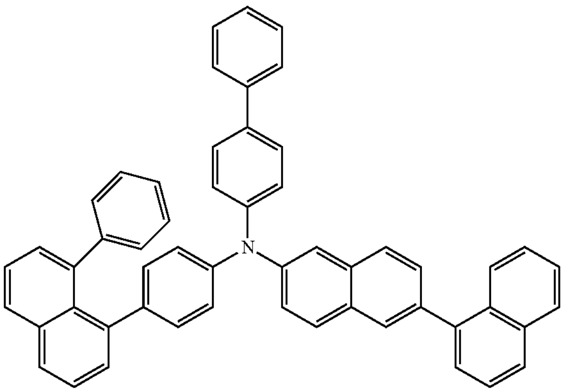
22
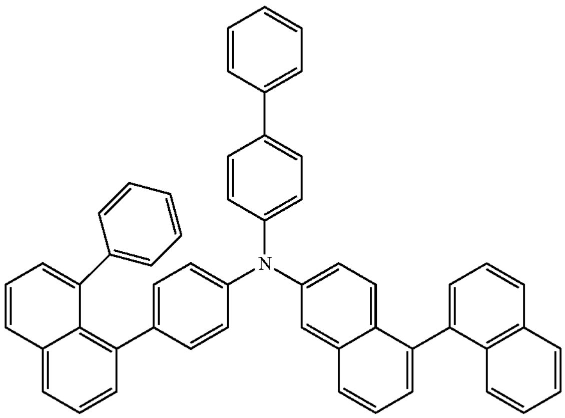
23
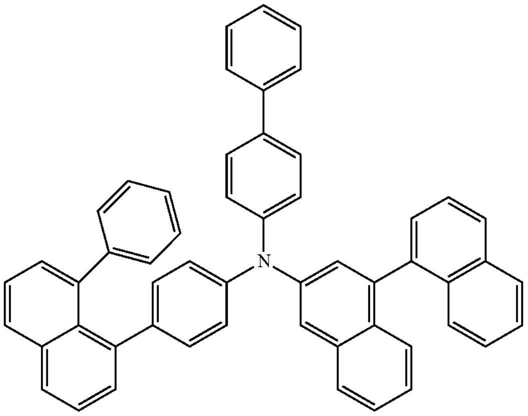
24
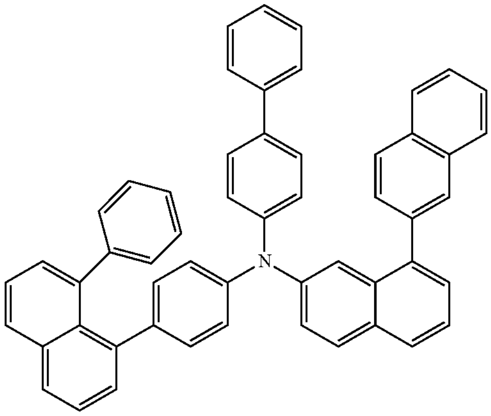

-continued
25
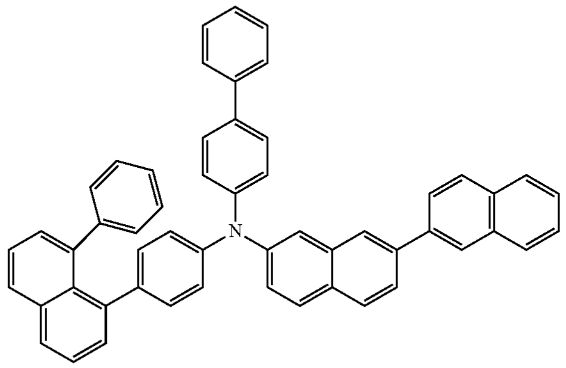
26
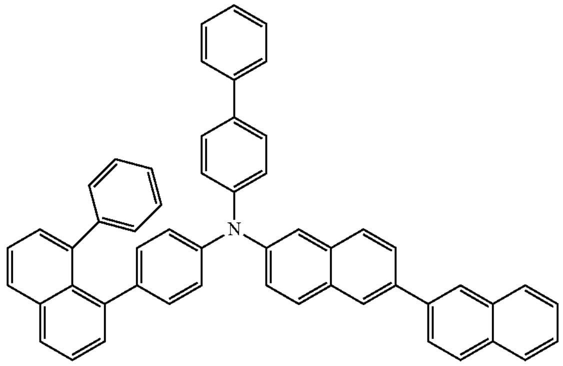
27
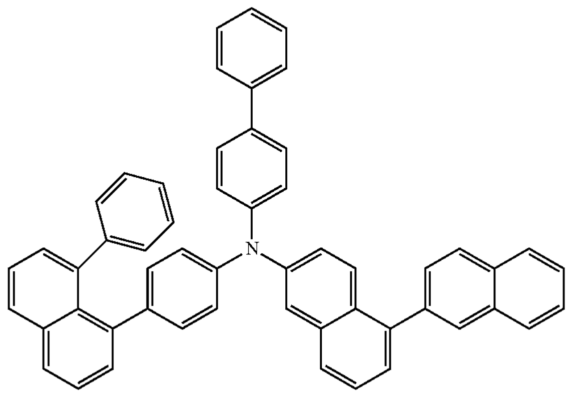
28
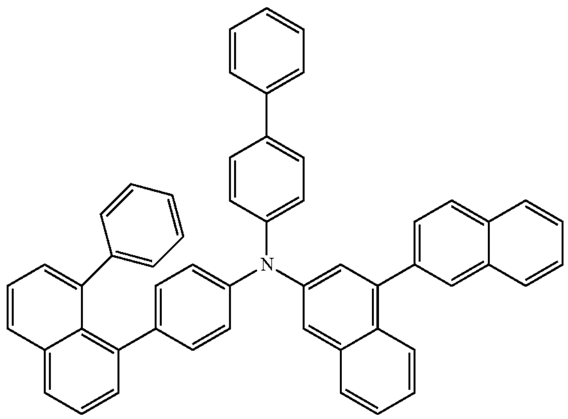
29
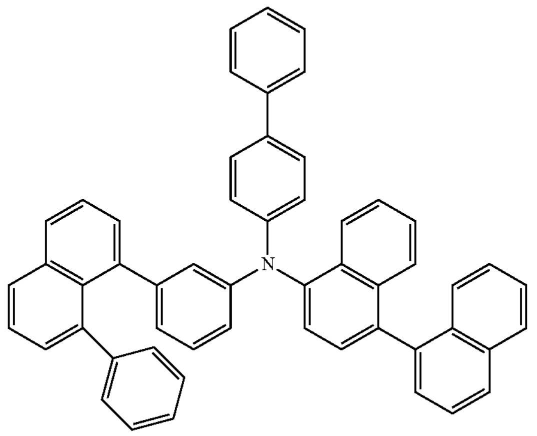
30
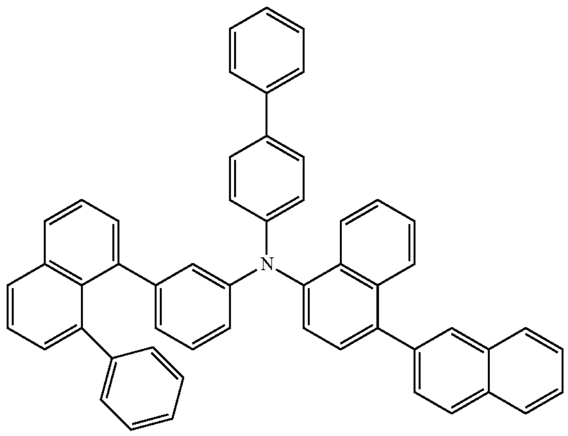

-continued
31
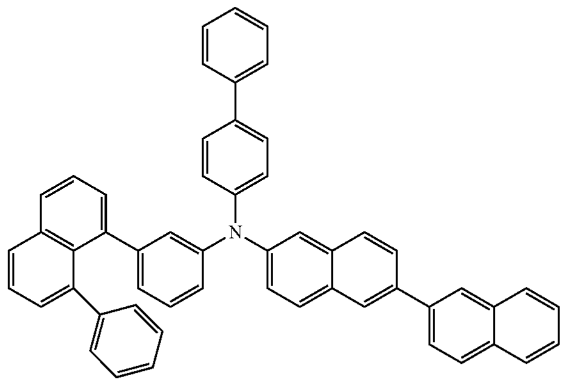
32
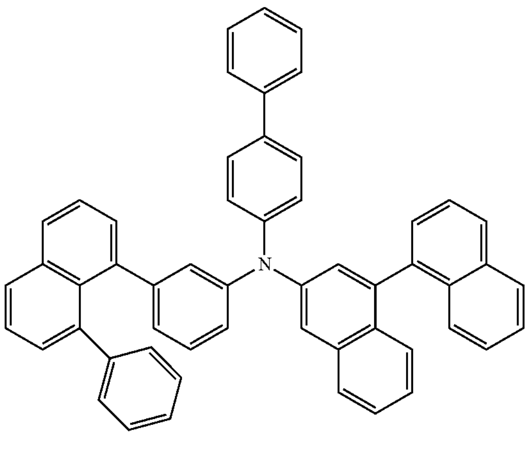
33
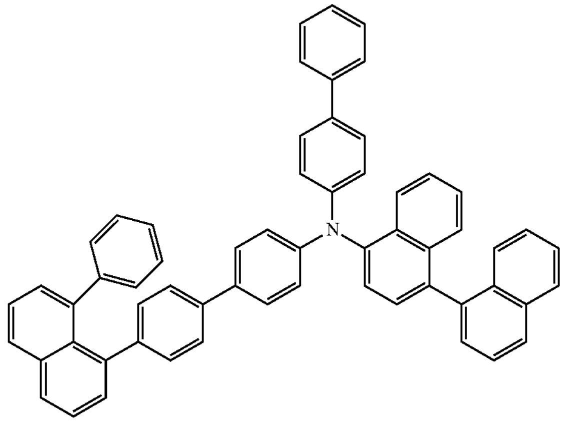
34
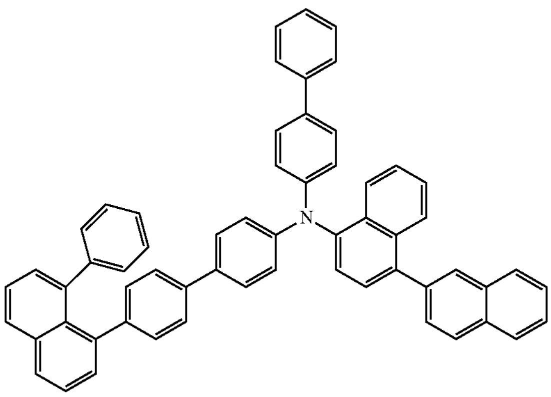
35
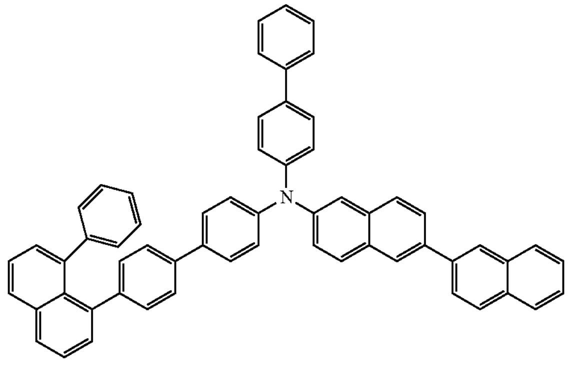
36
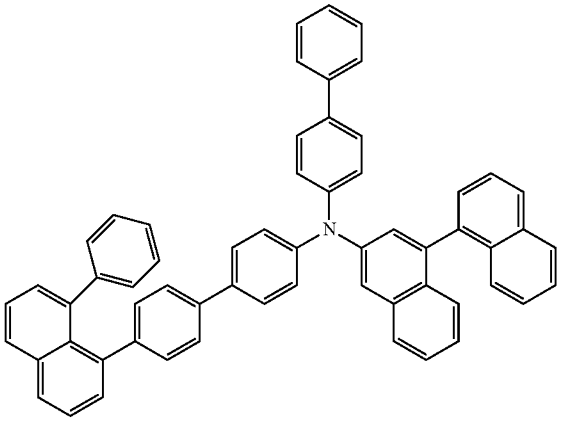

-continued
37
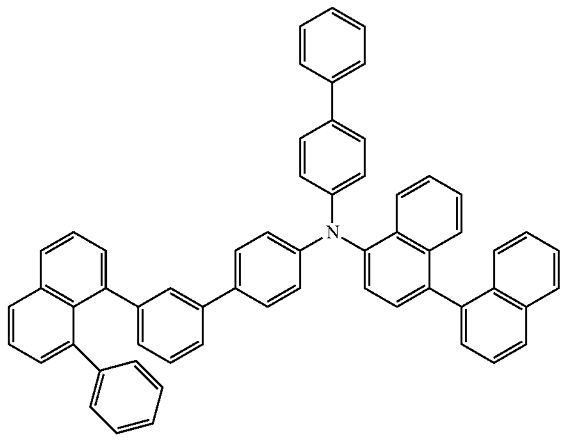
38
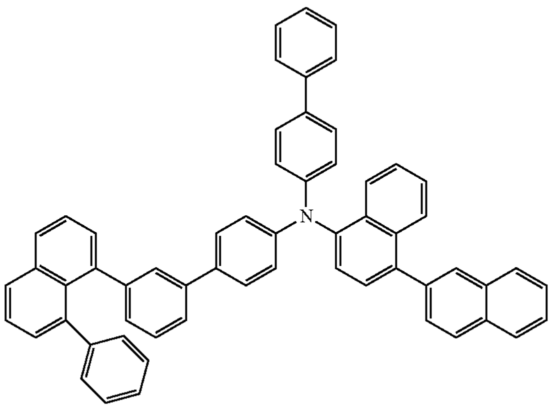
39
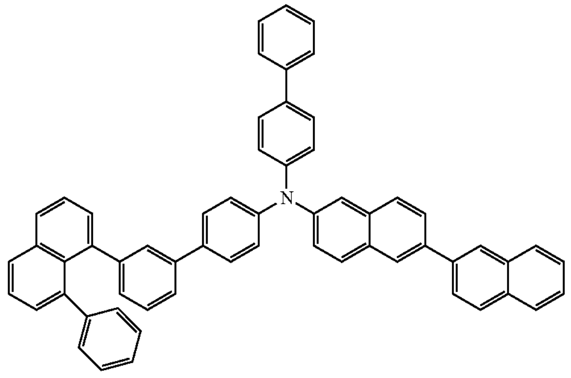
40
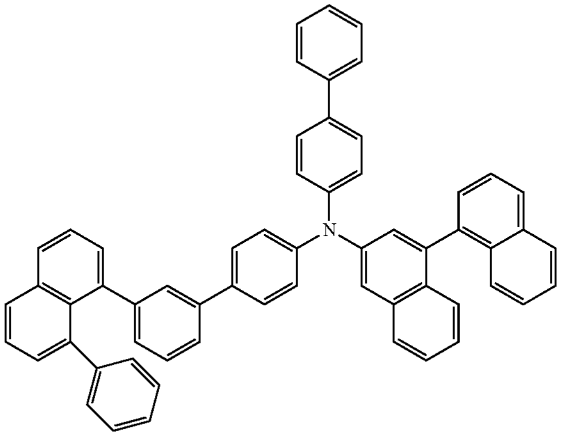
41
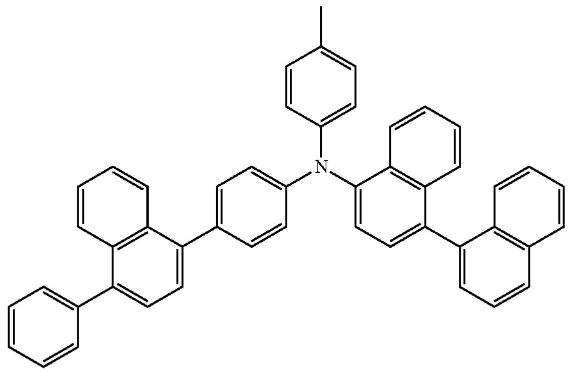
42
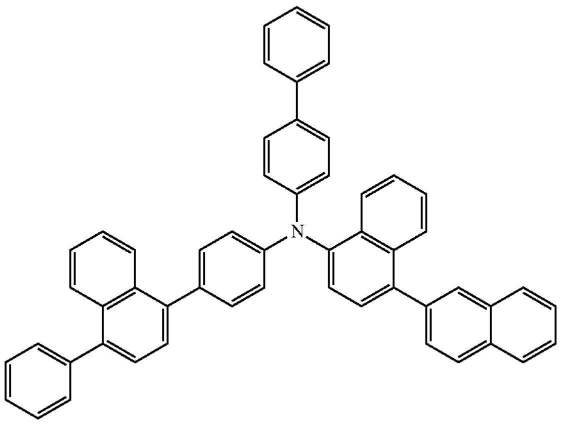

-continued
43
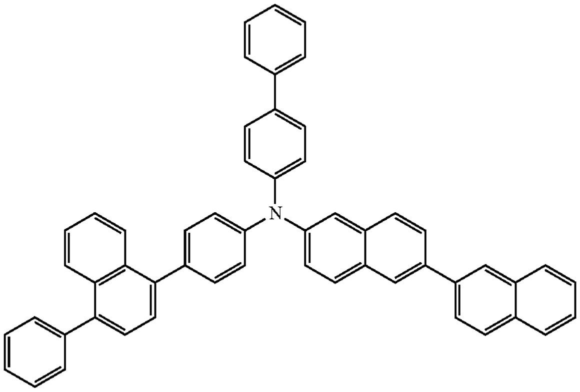
44
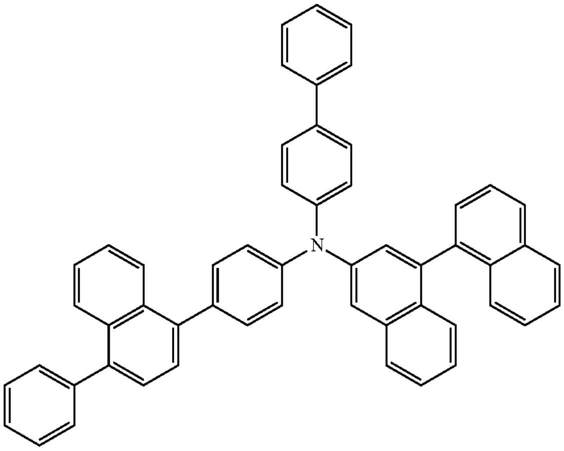
45
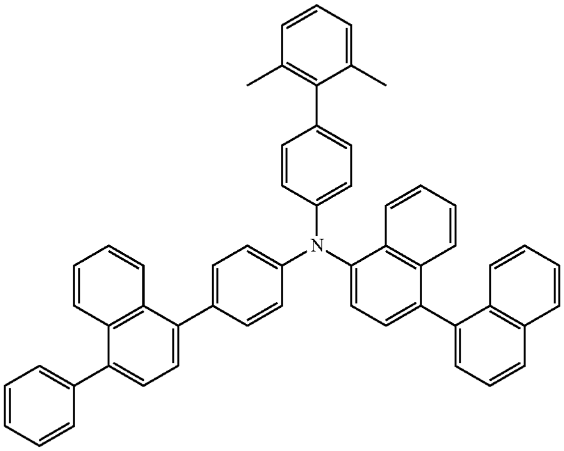
46
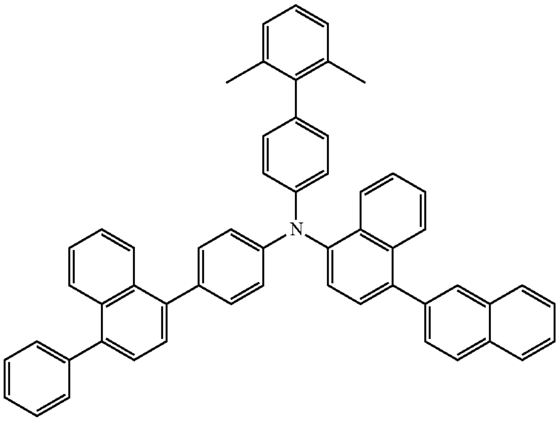
47
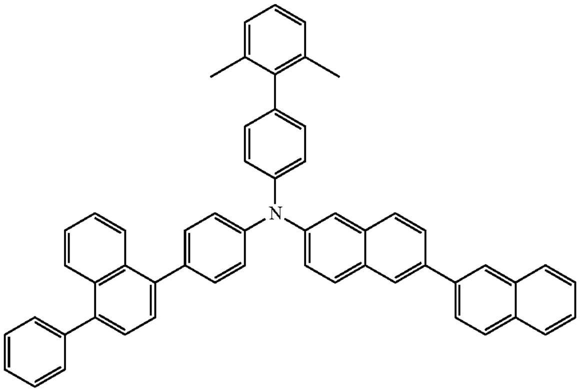
48
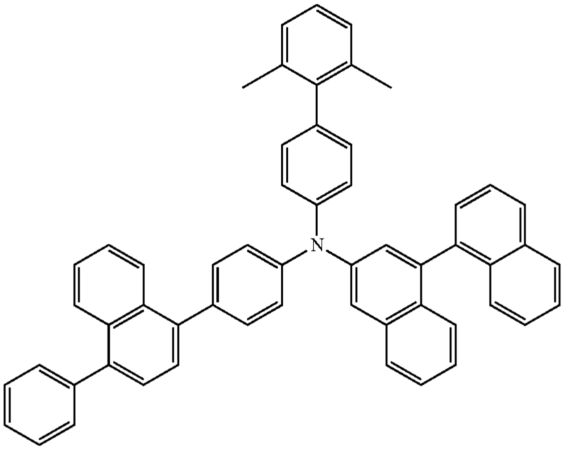

-continued
49
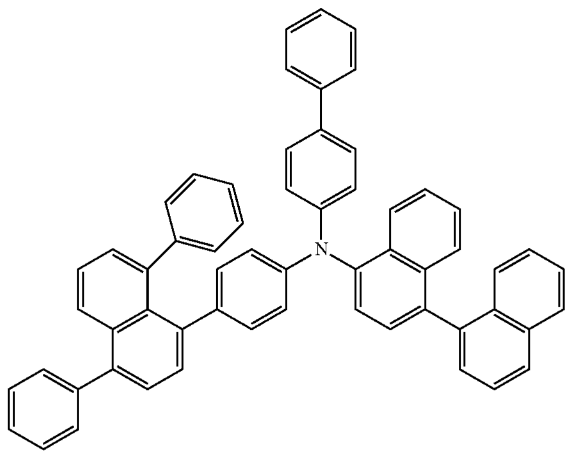
50
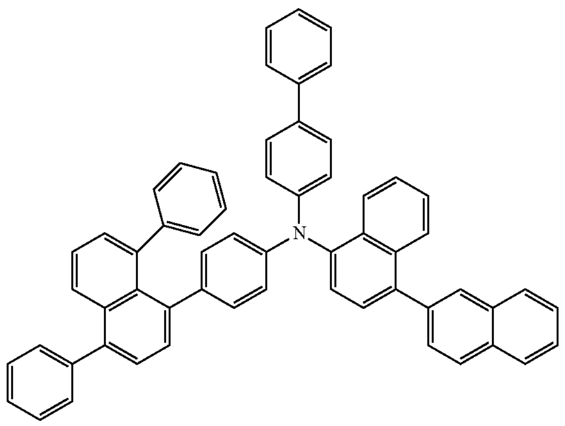
51
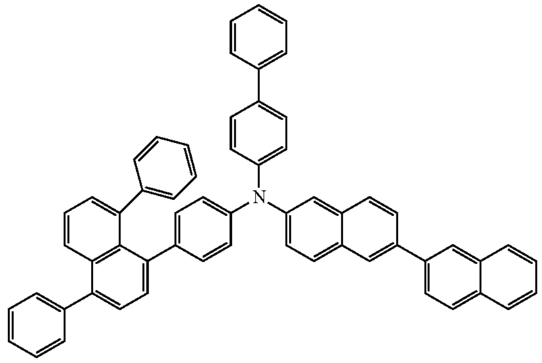
52
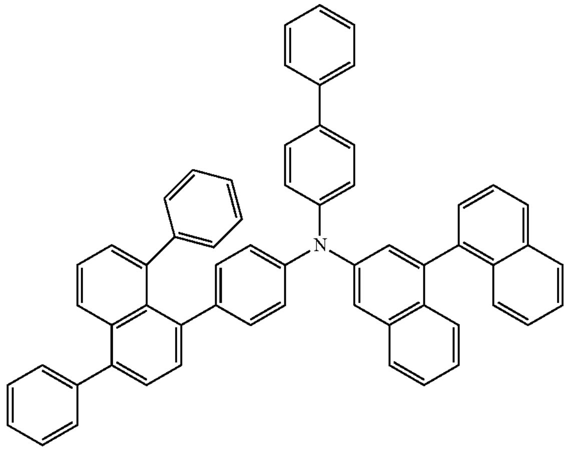
53
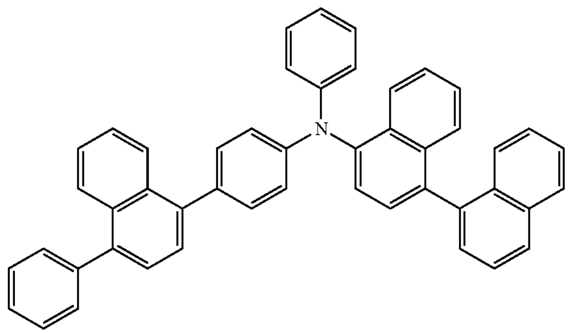
54
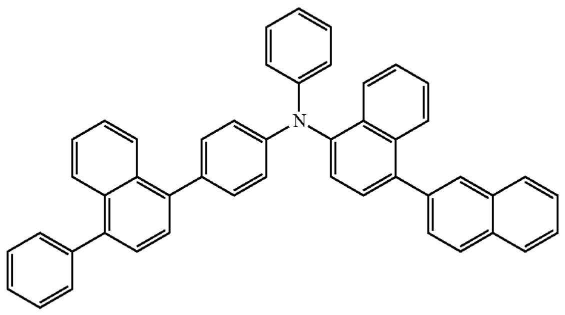
55
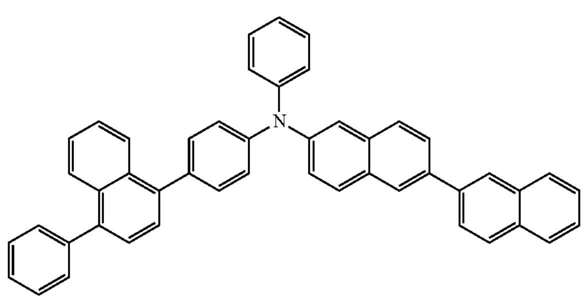
56
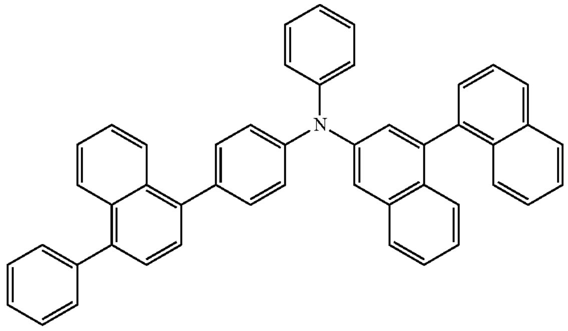

-continued
57
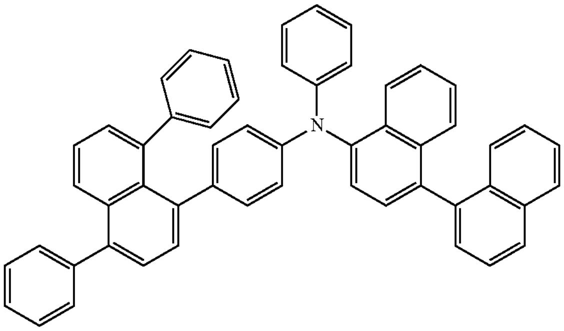
58
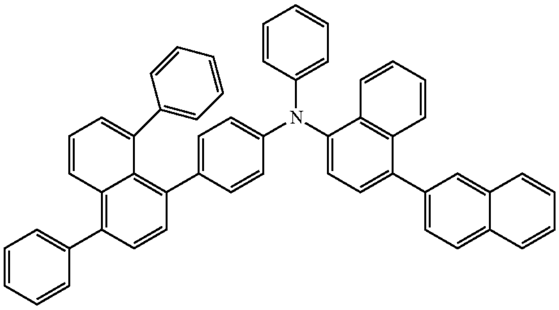
59
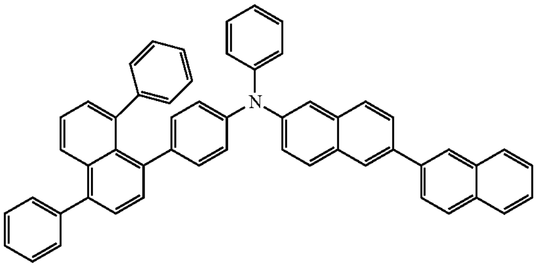
60
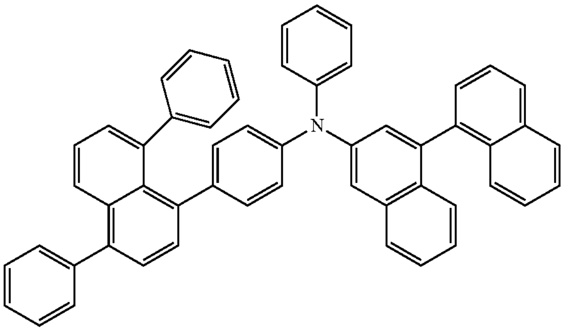
61
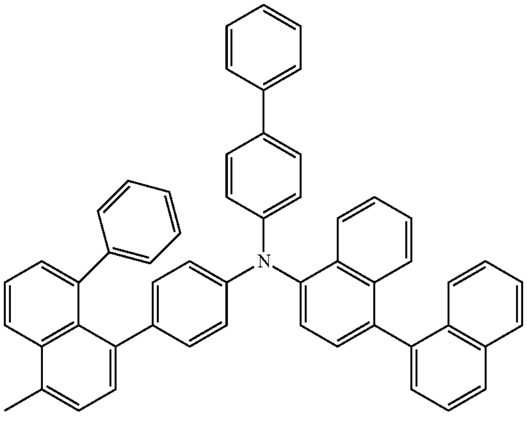
62
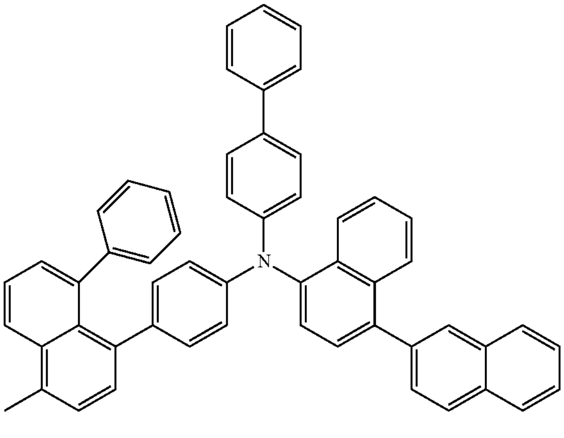
63
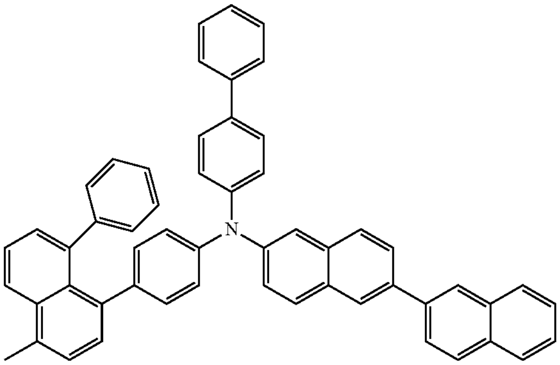
64
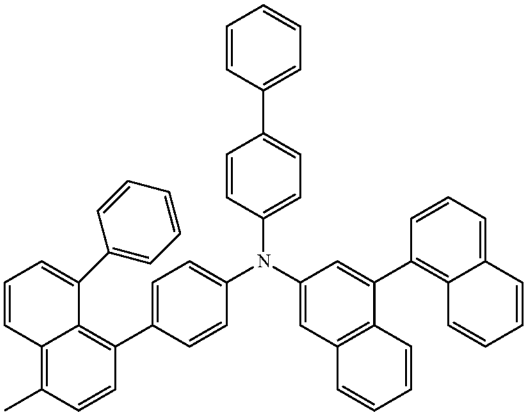

-continued
65
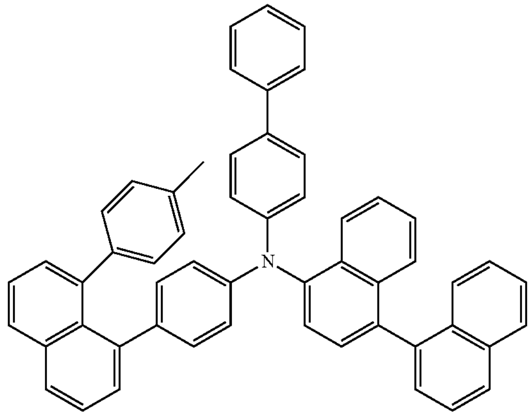
66
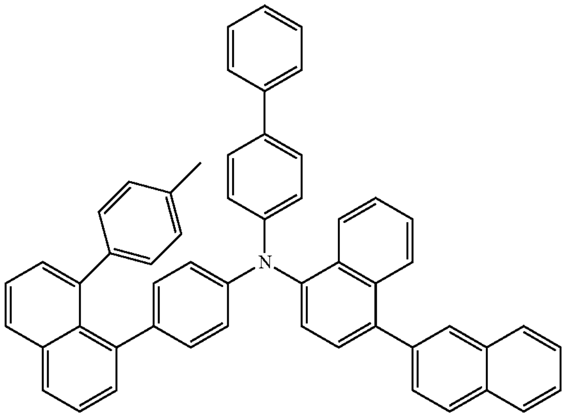
67
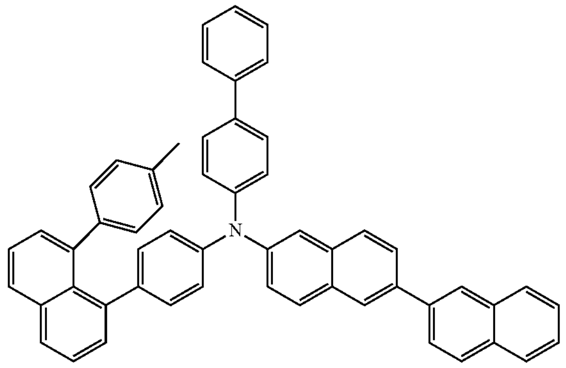
68
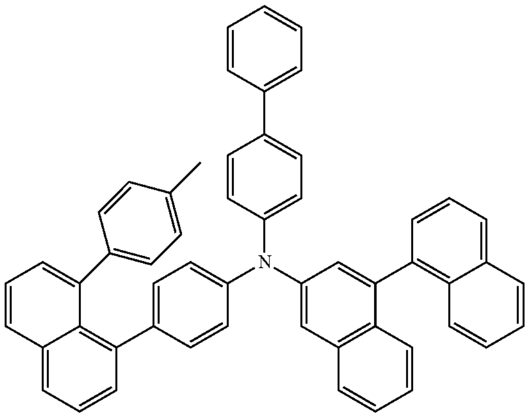
69
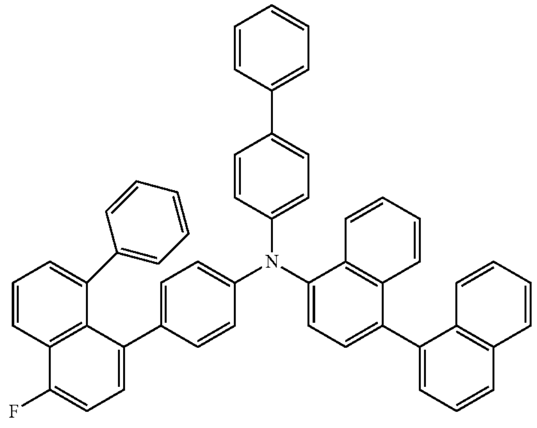
70
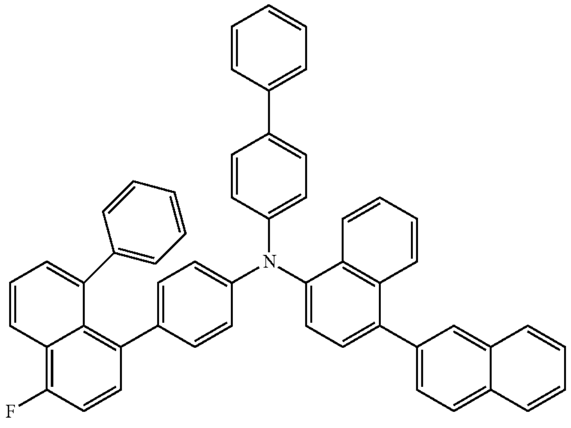

-continued
71
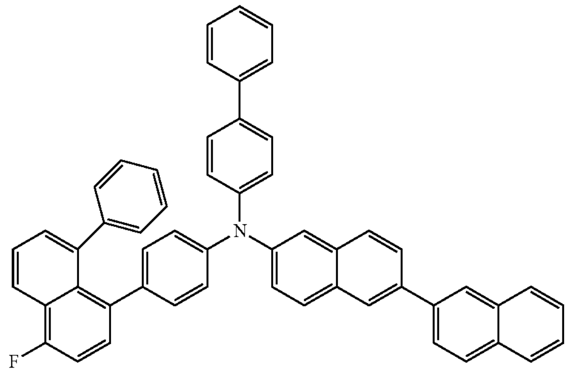
72
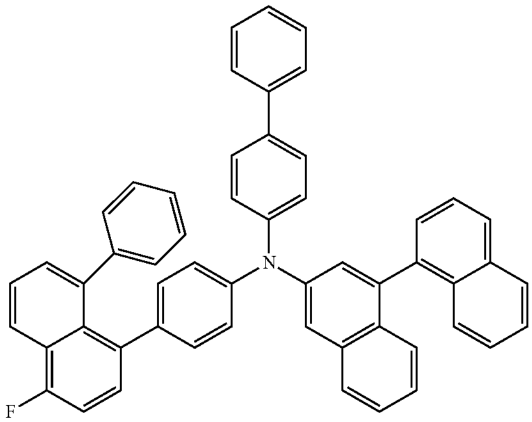
73
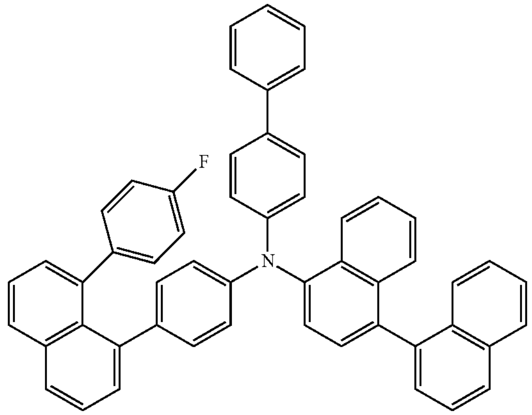
74
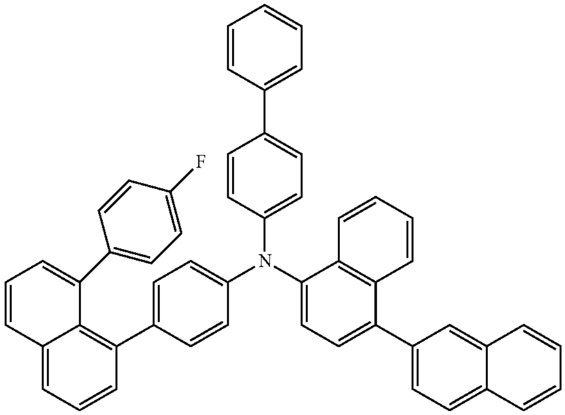
75
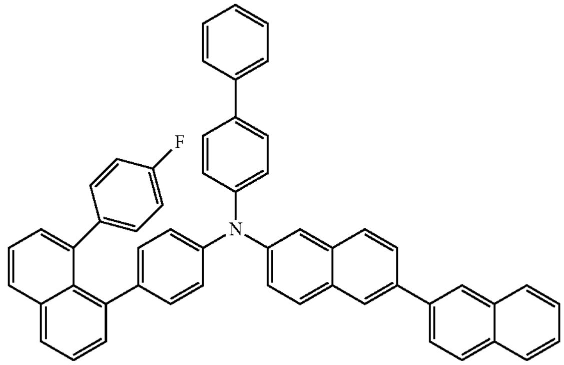
76
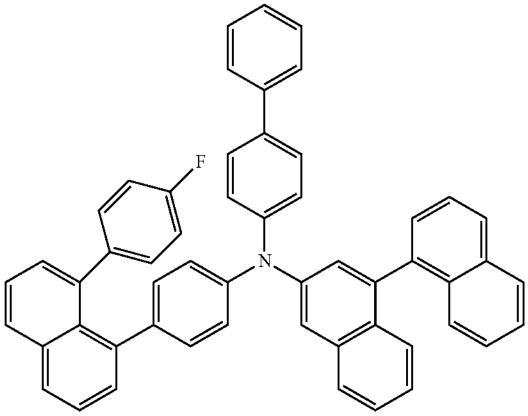

-continued
77
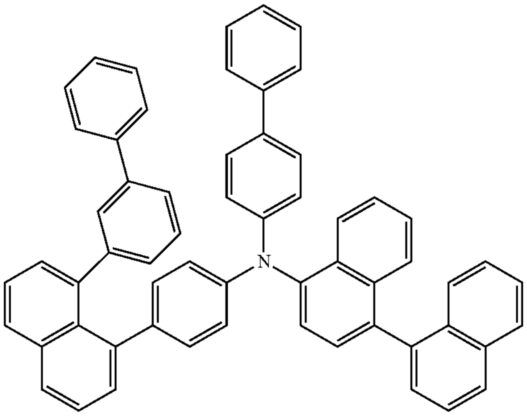
78
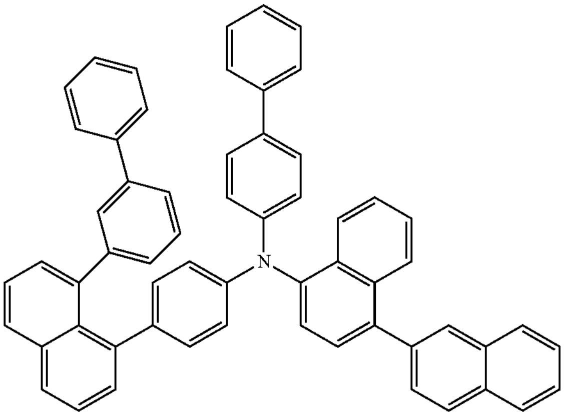
79
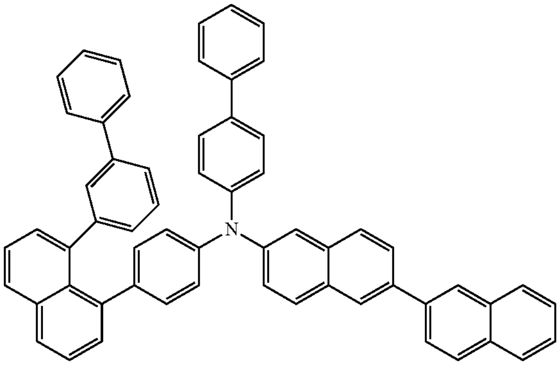
80
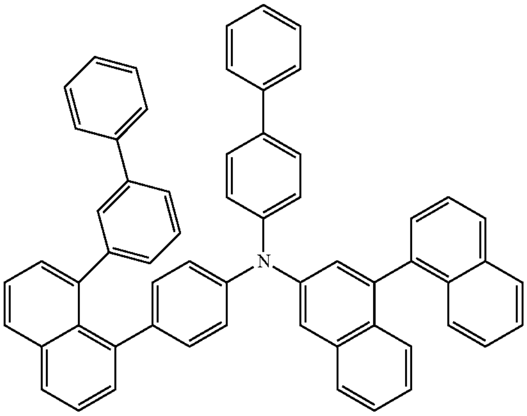
81
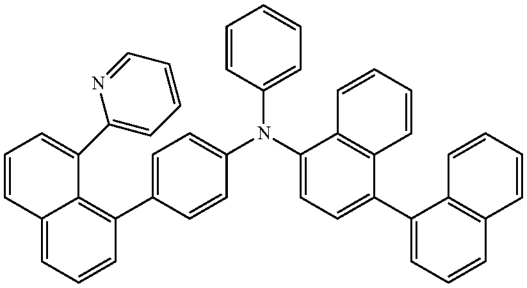
82
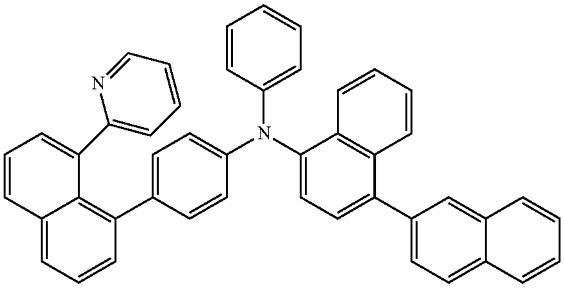
83
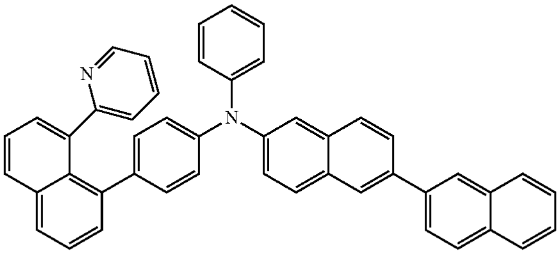
84
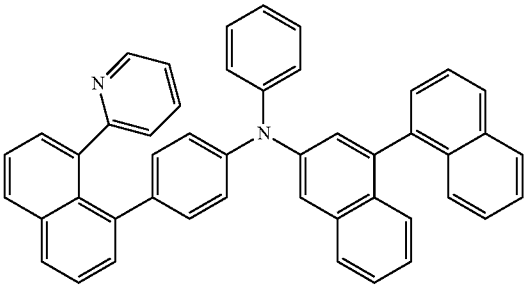

-continued
85
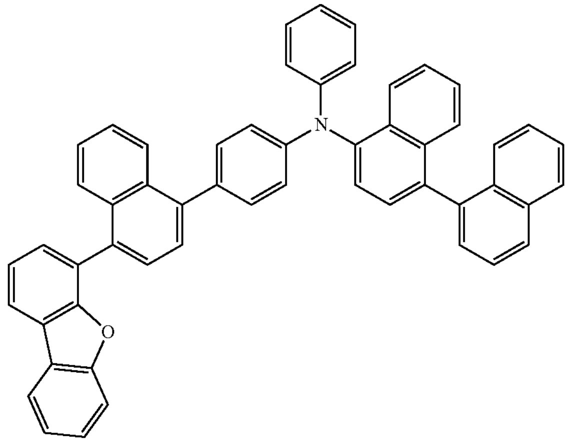
86
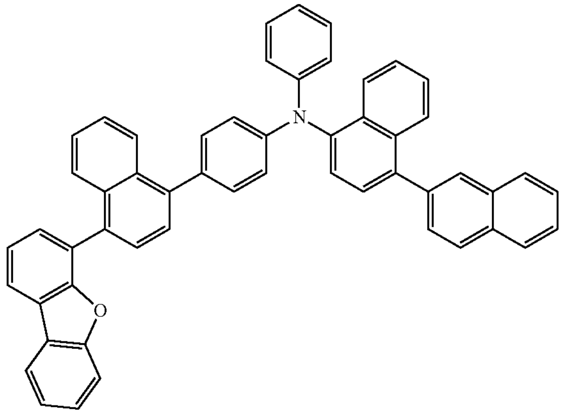
87
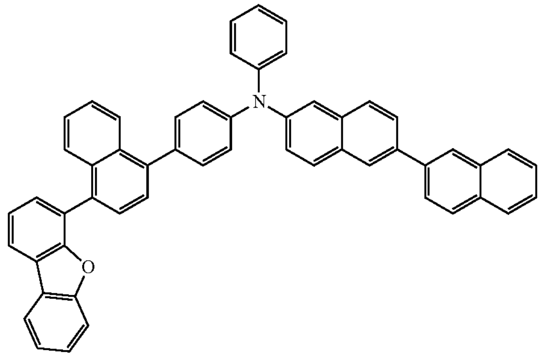
88
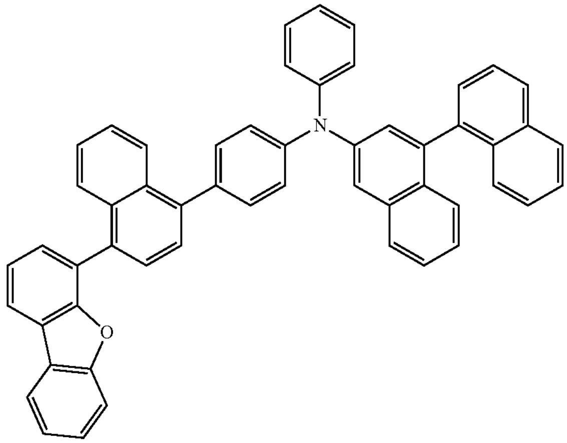
89
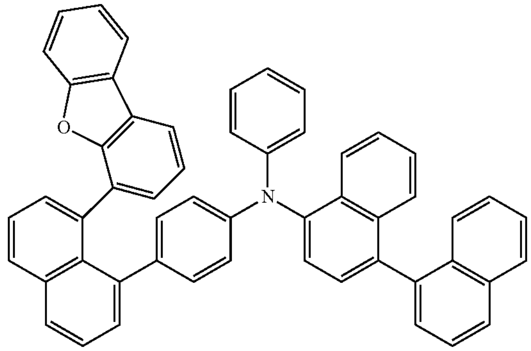
90
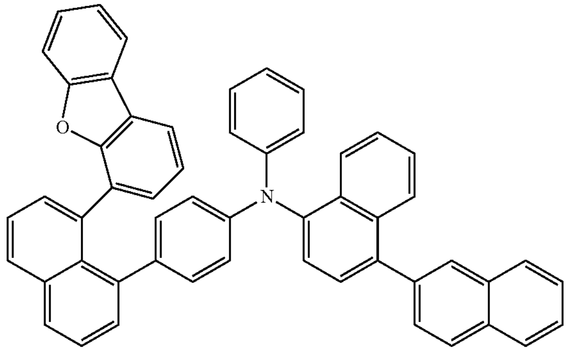

-continued
91
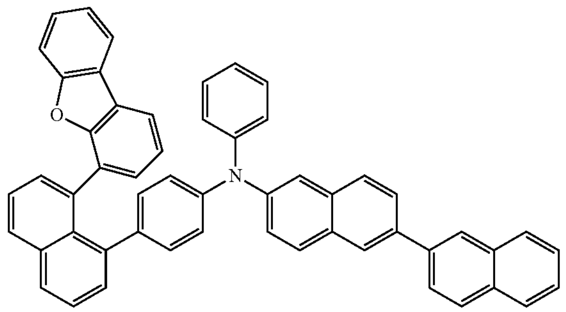
92
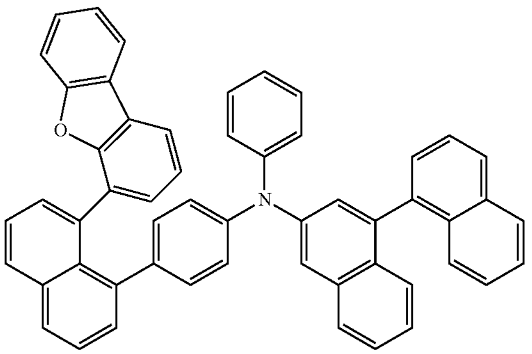
93
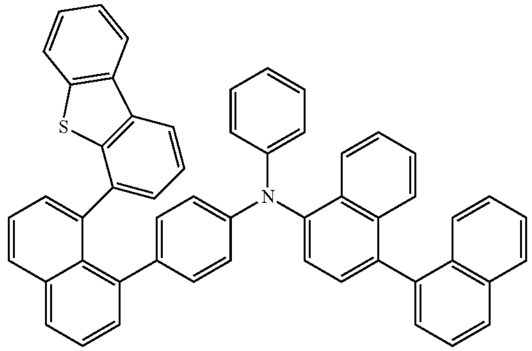
94
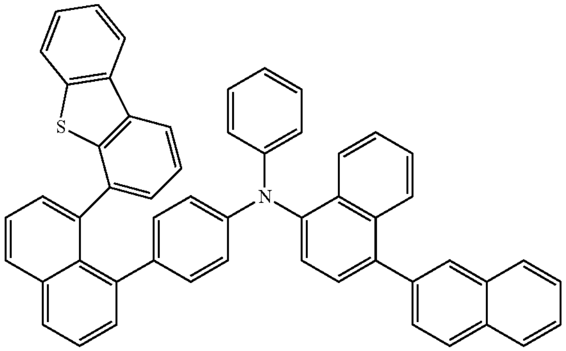
95
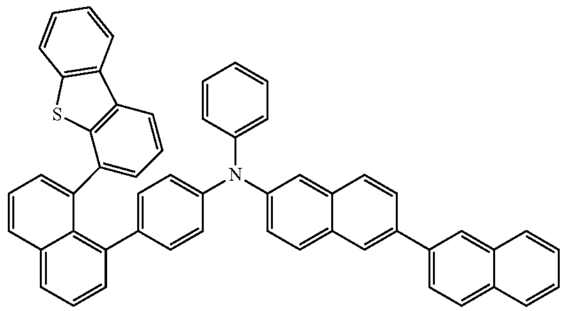
96
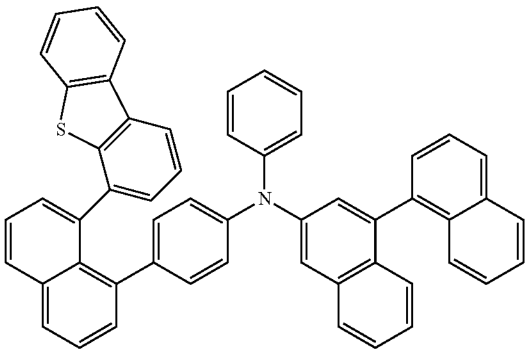
97
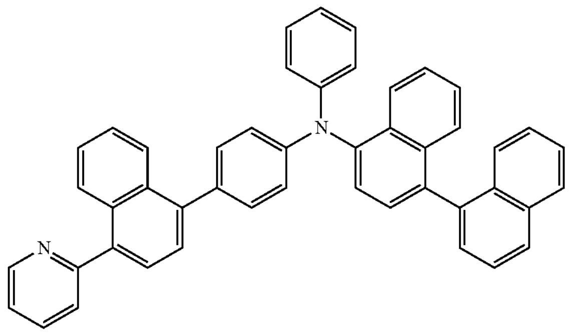
98
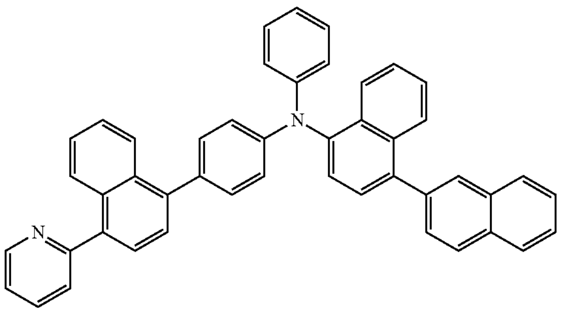

-continued
99
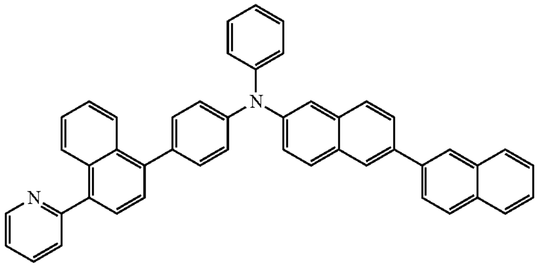
100
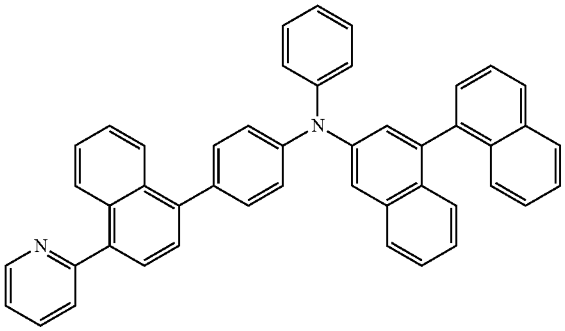
101
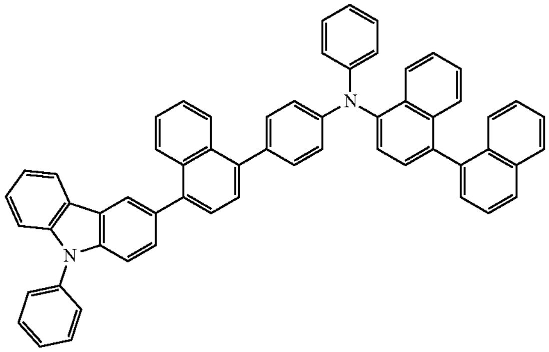
102
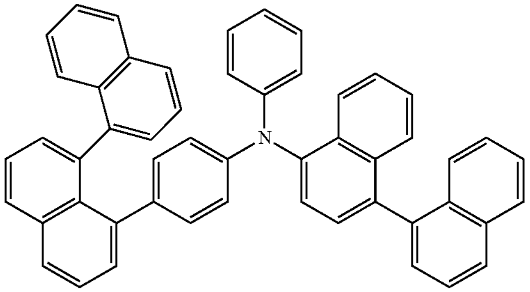
103
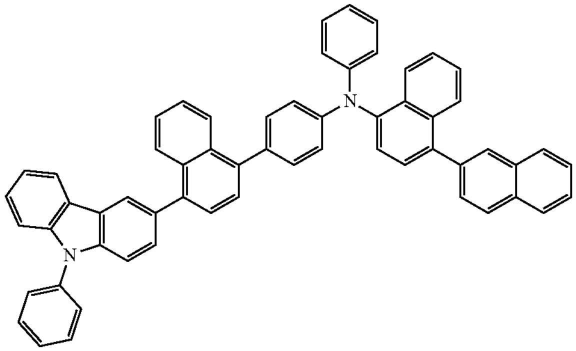
104
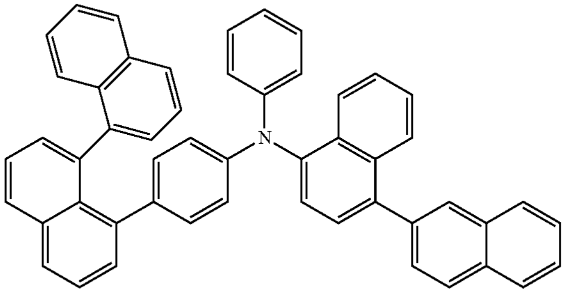
105
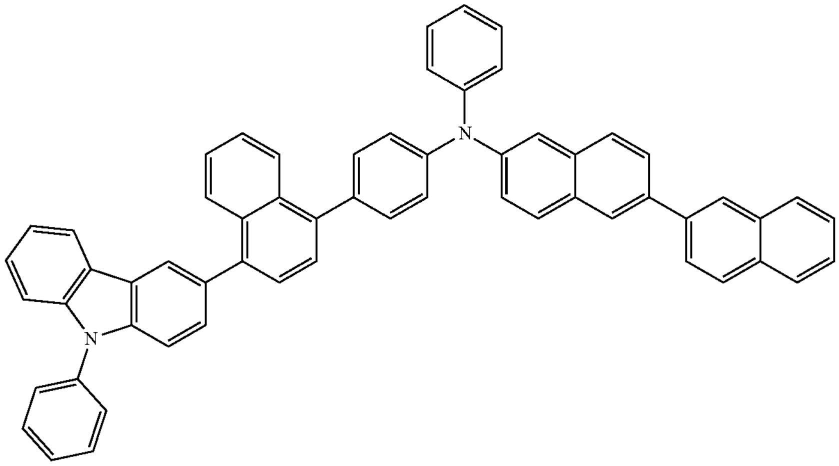

-continued
106
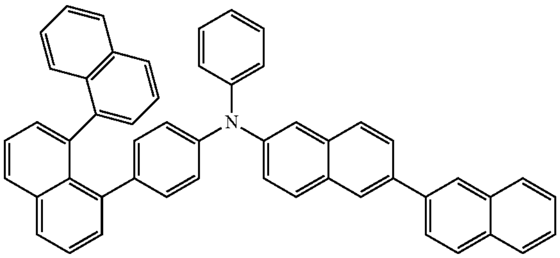
107
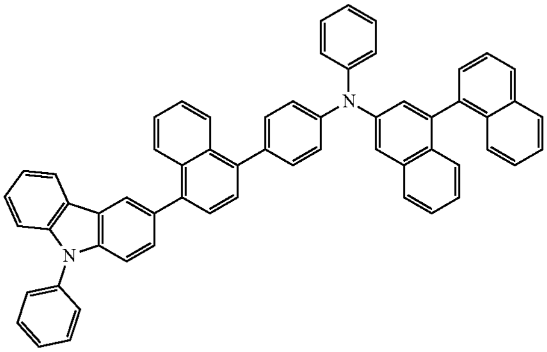
108
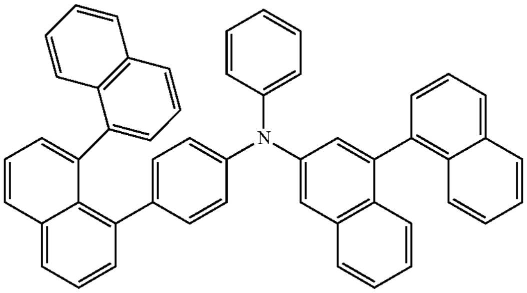
109
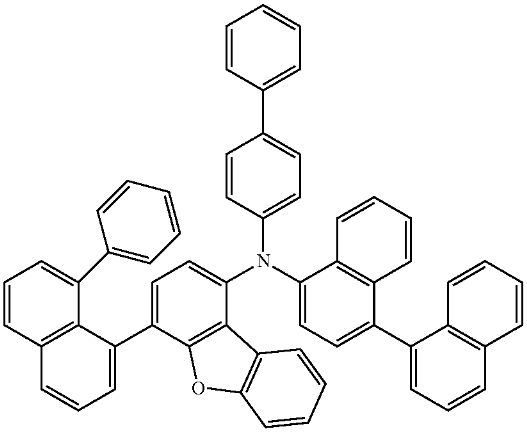
110
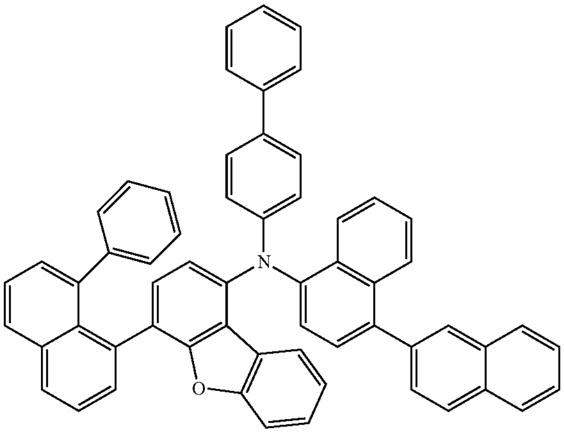
111
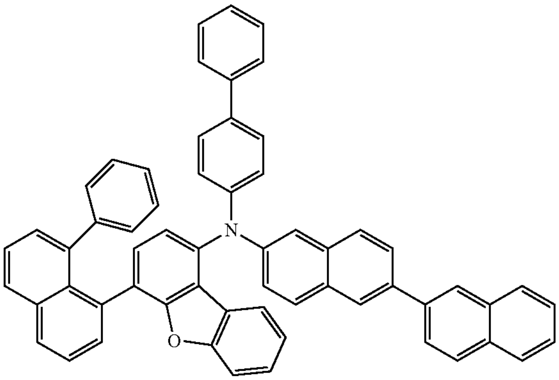

-continued
112
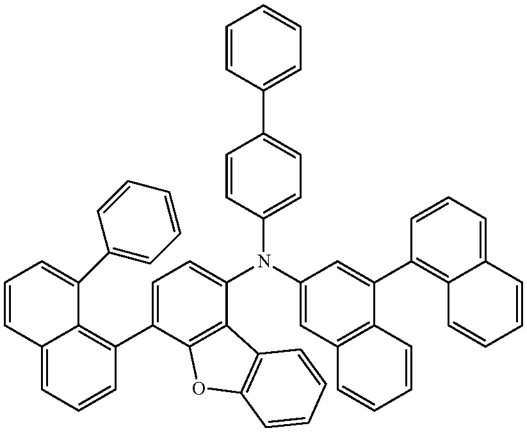
113
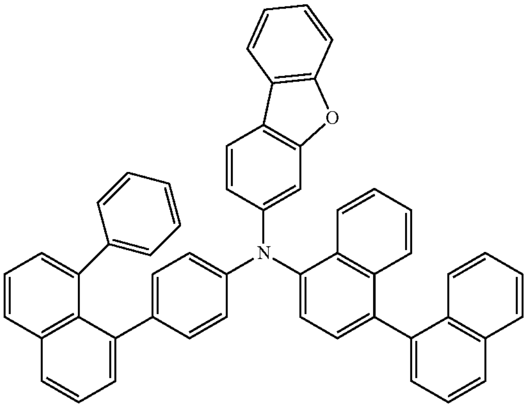
114
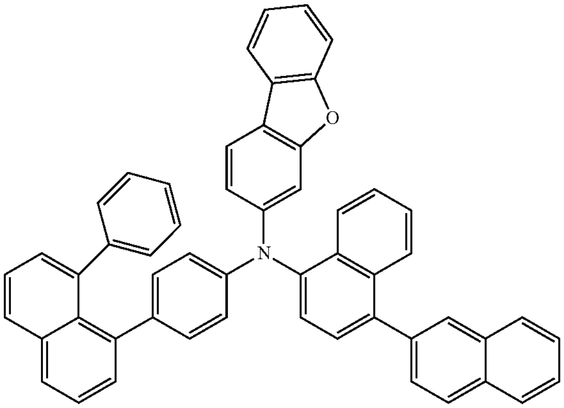
115
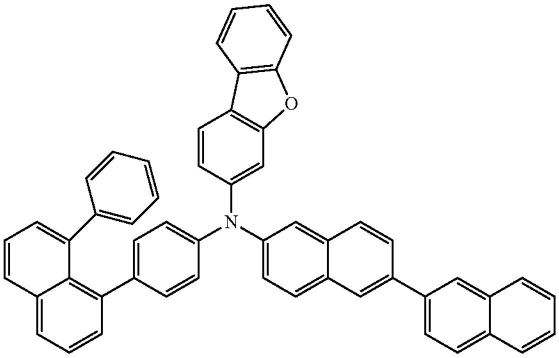
116
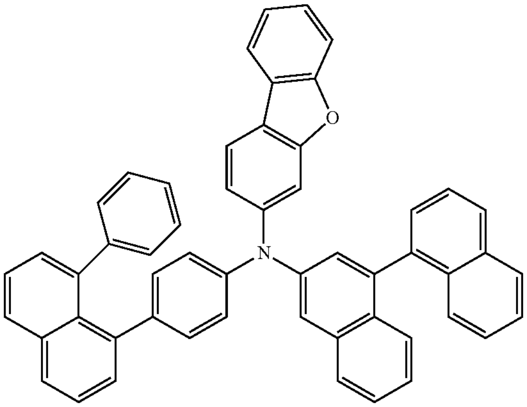
117
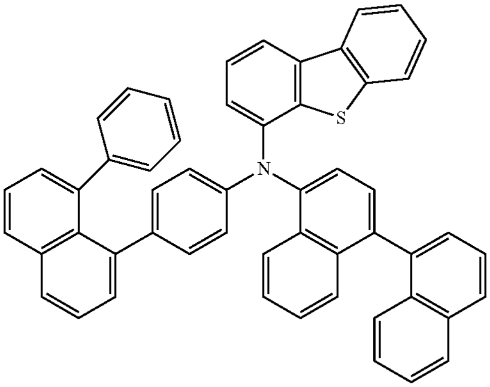

-continued
118
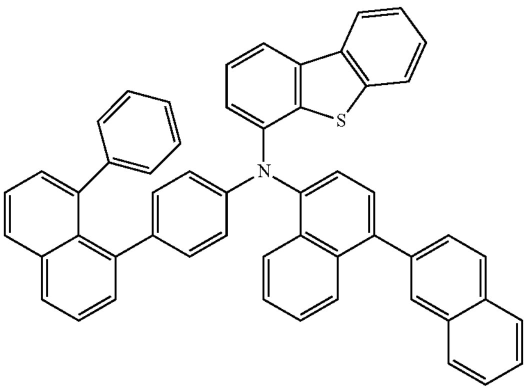
119
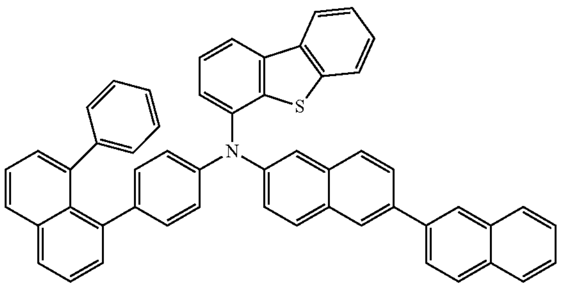
120
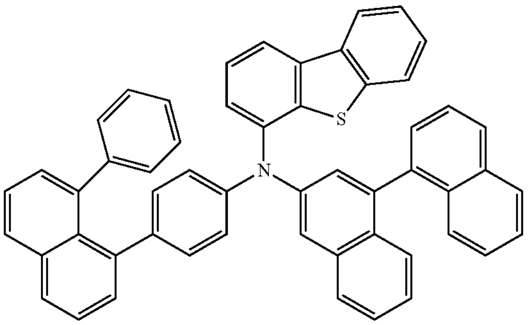
121
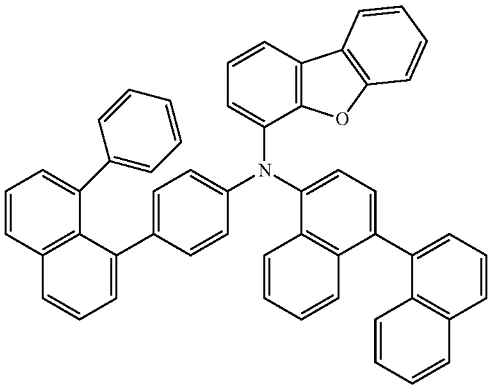
122
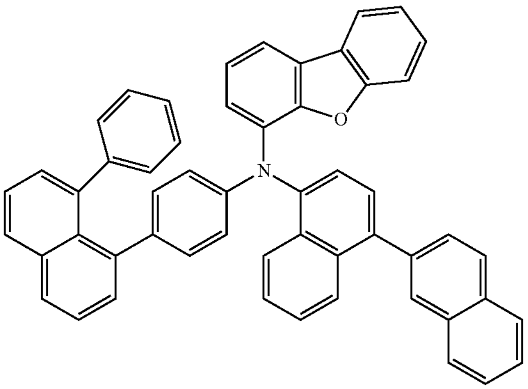
123
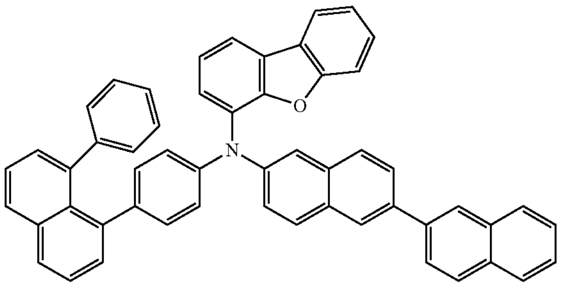
124
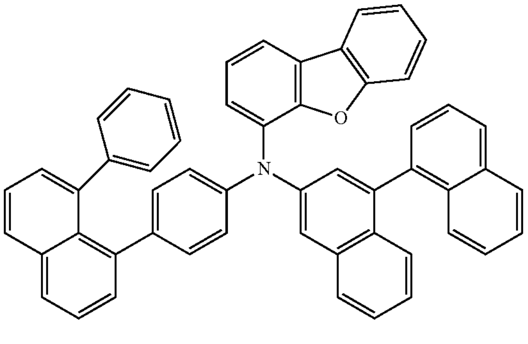
125
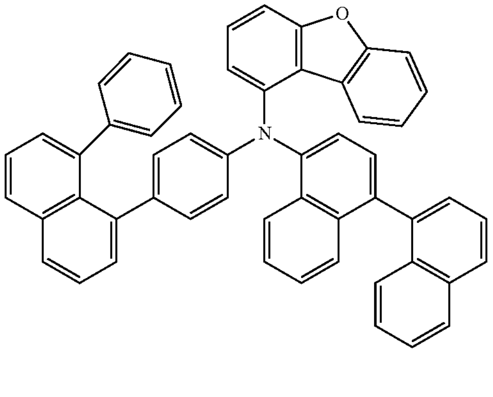

-continued
126
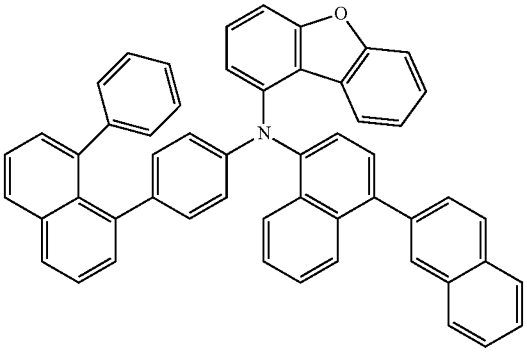
127
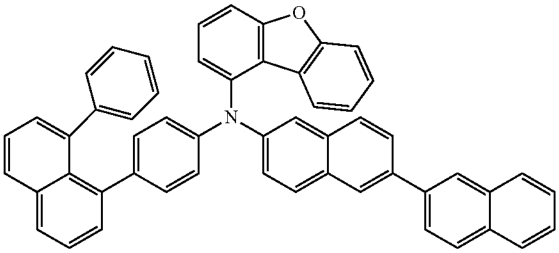
128
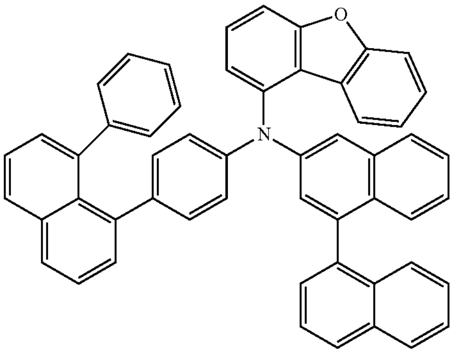
129
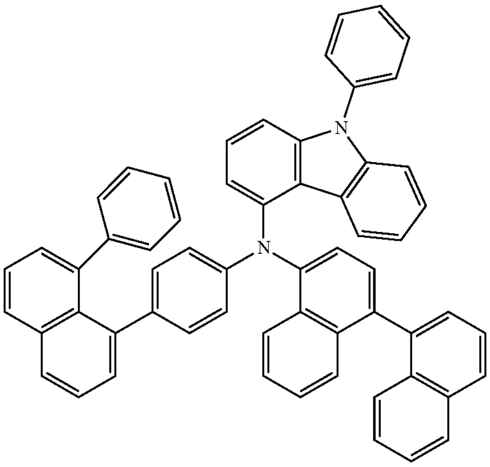
130
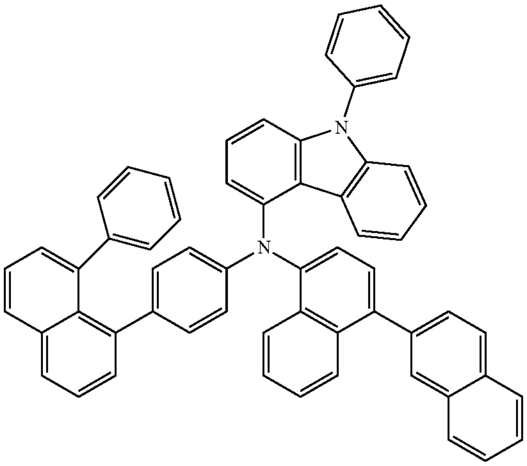
131
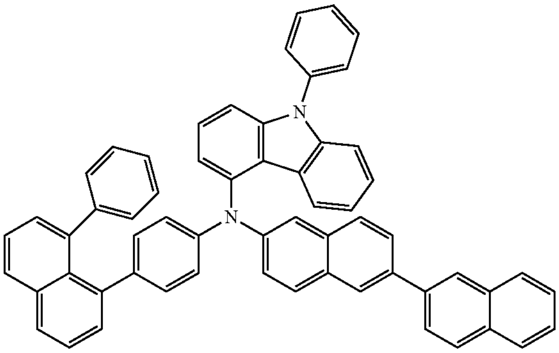

-continued
132
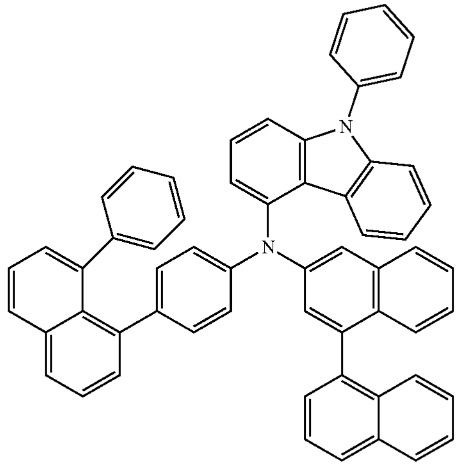
133
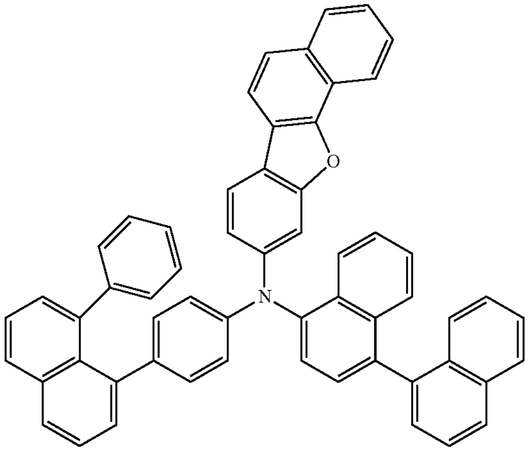
134
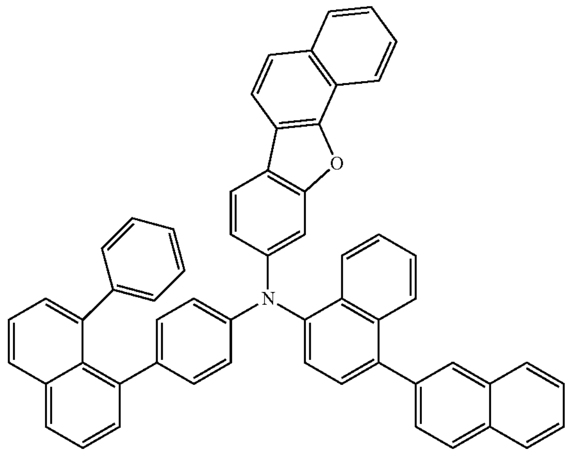
135
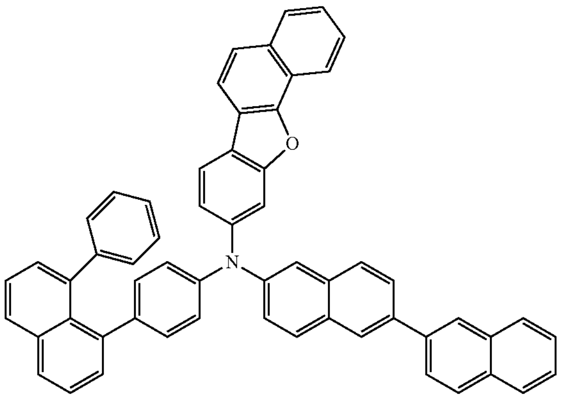
136
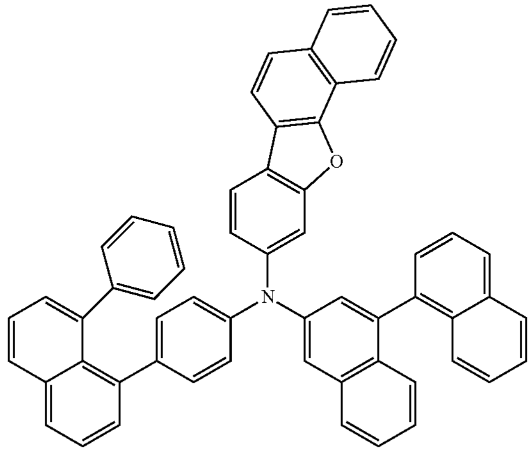
137
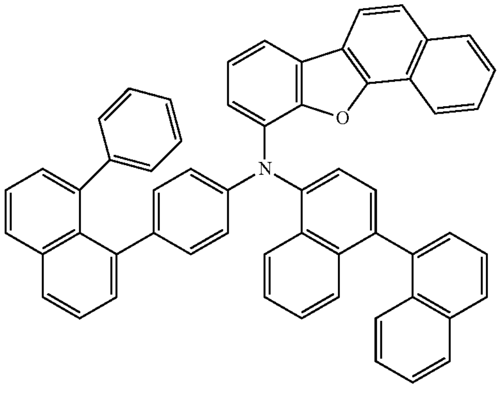

-continued
138
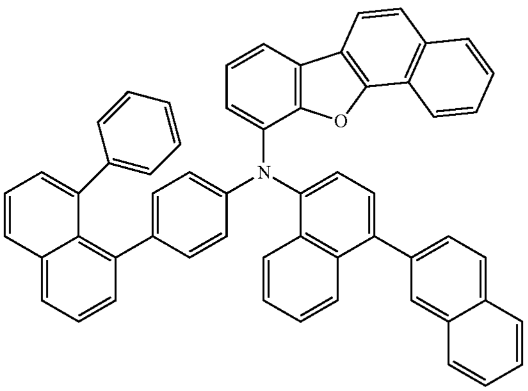
139
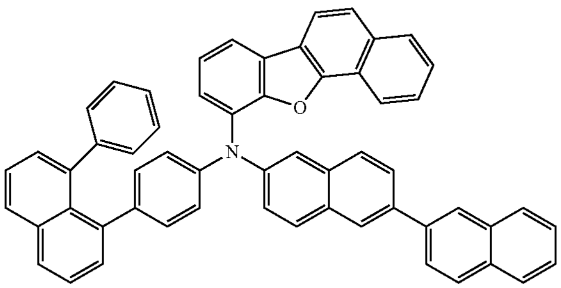
140
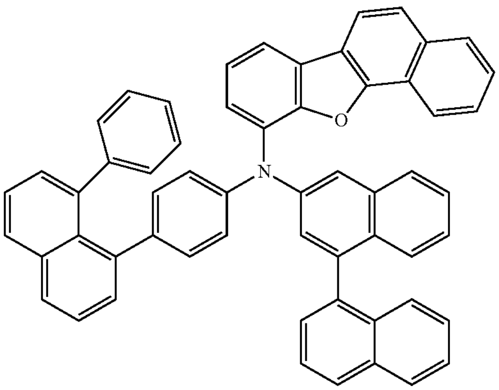
141
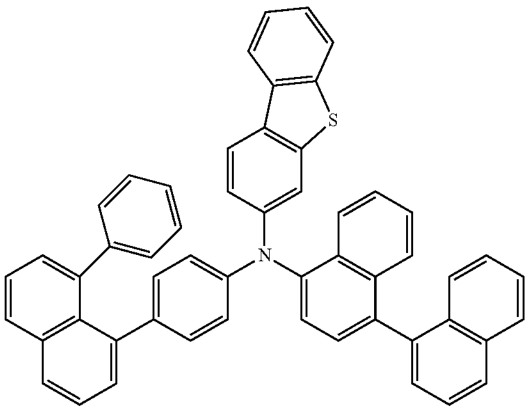
142
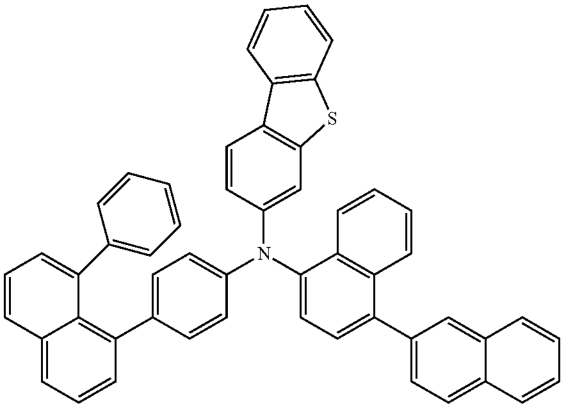
143
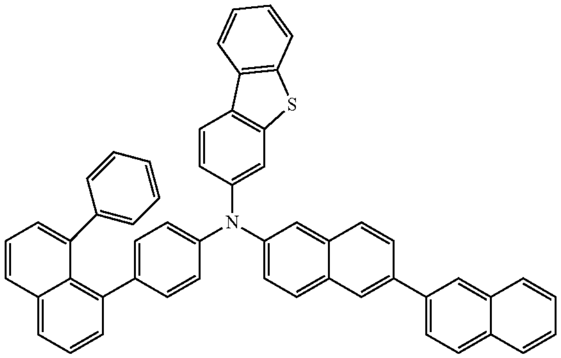
144
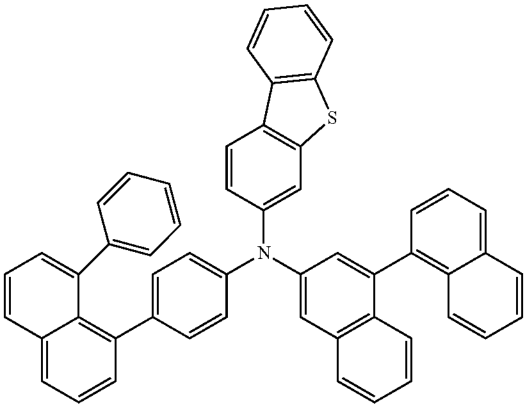
145
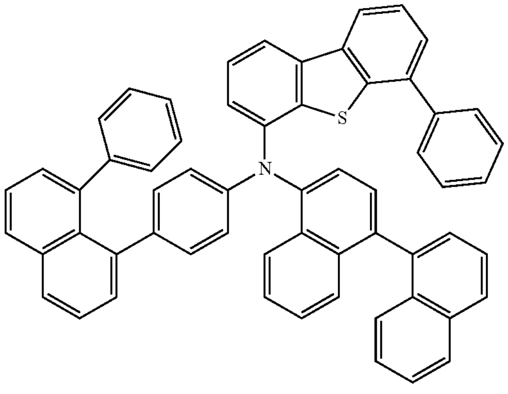

-continued
146
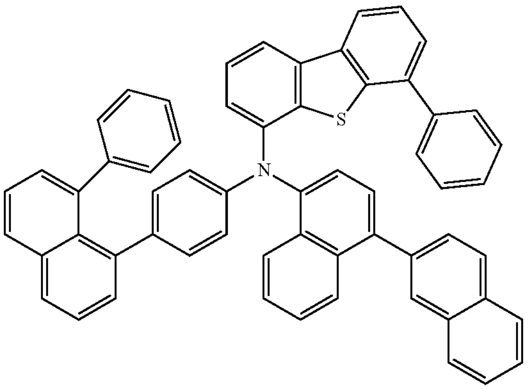
147
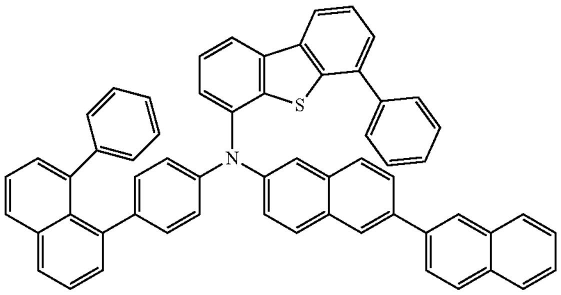
148
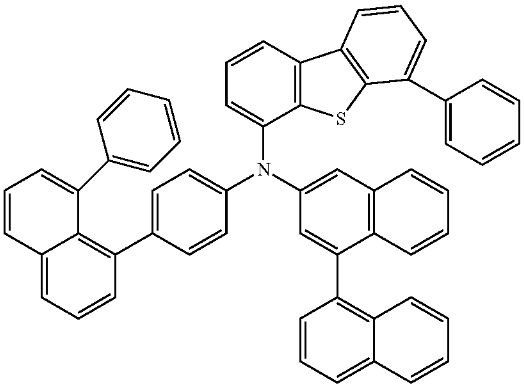
149
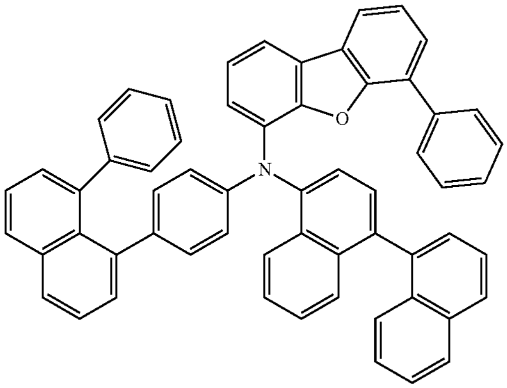
150
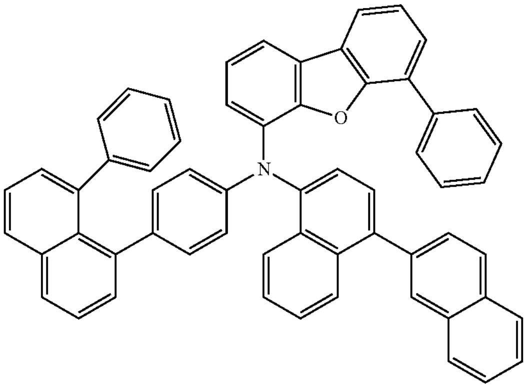
151
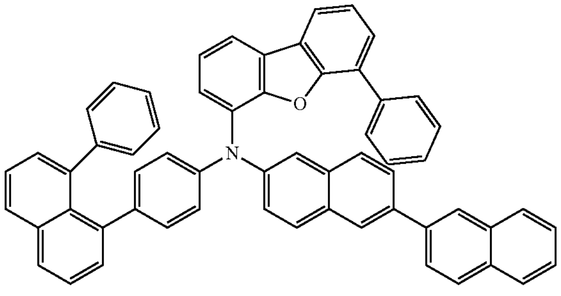

-continued
152
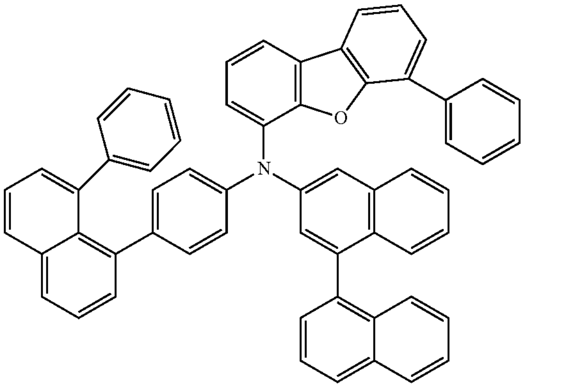
153
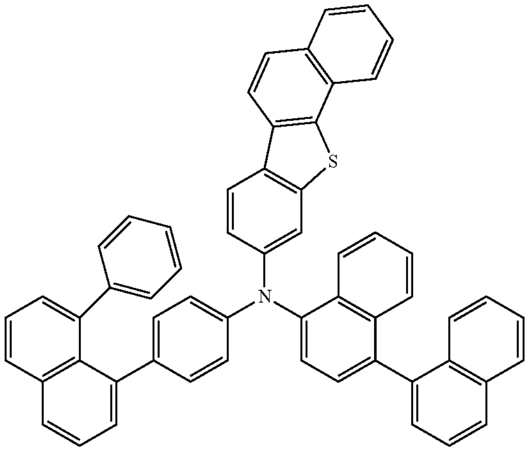
154
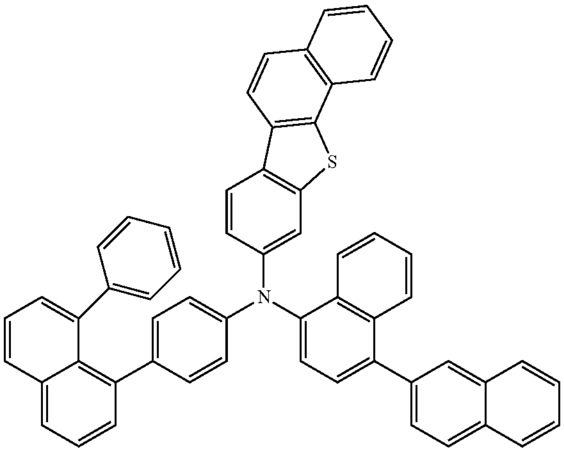
155
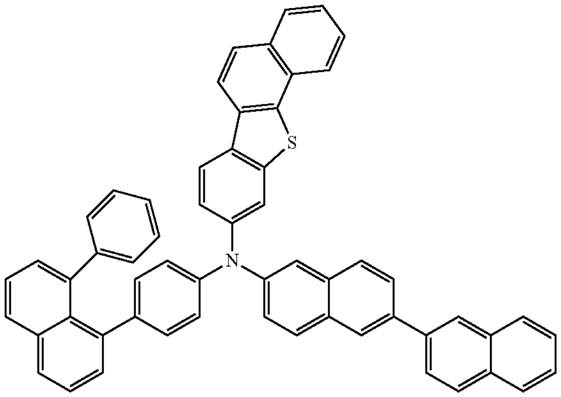
156
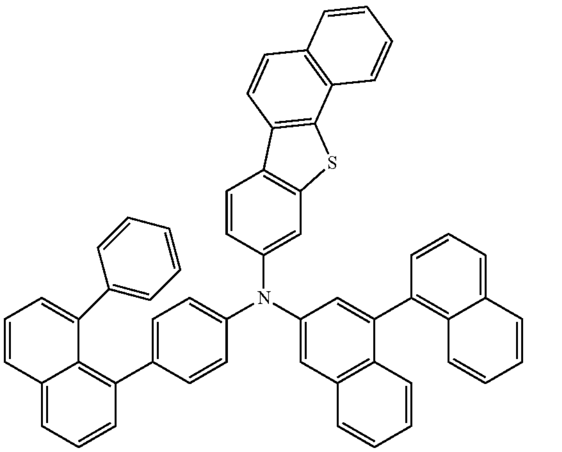
157
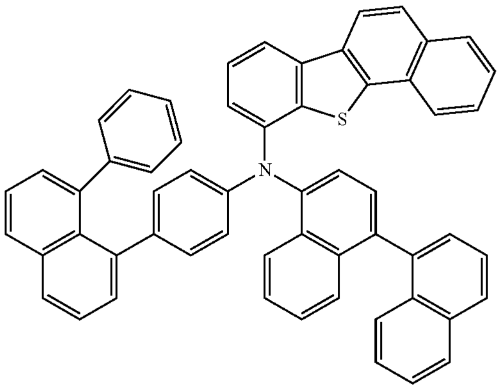

-continued
158
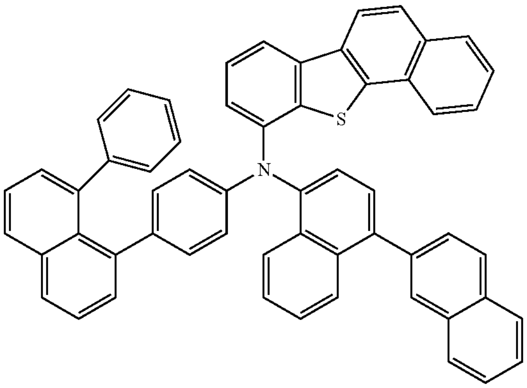
159
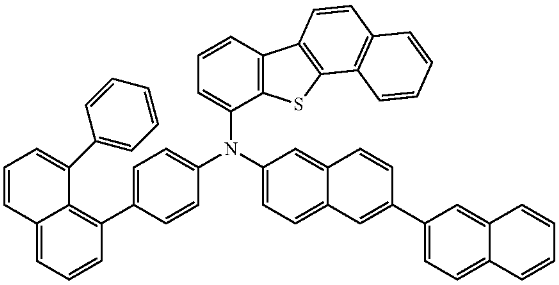
160
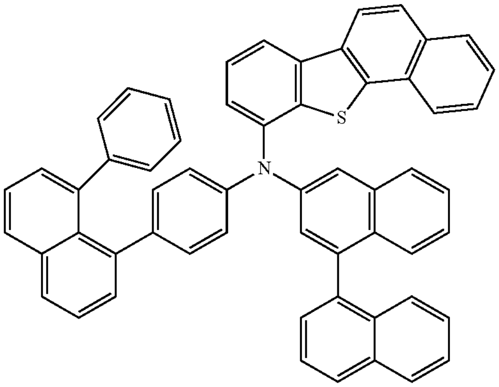
161
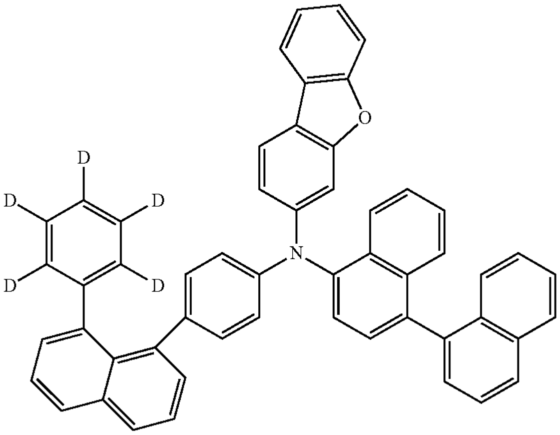
162
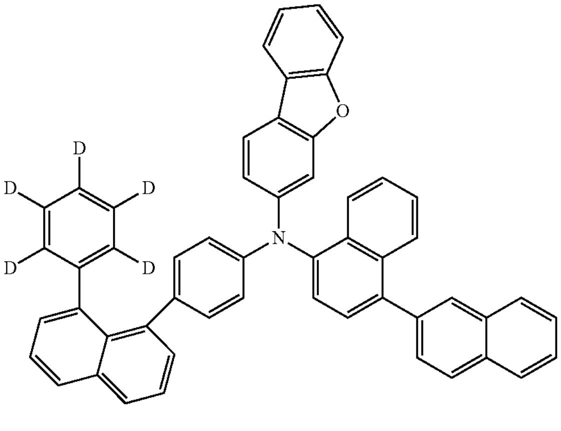
163
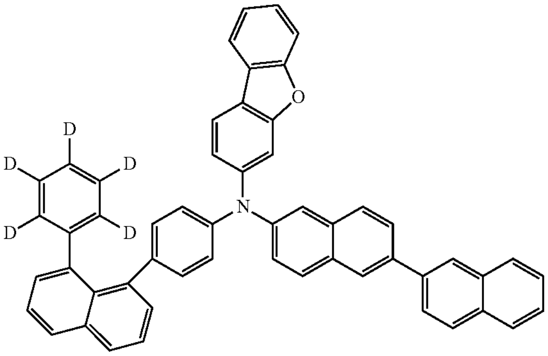

-continued
164
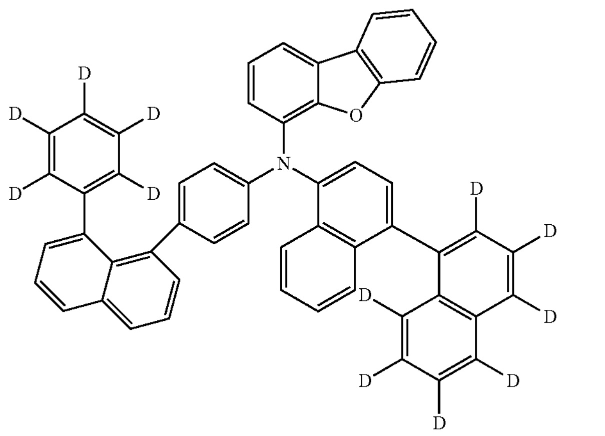
165
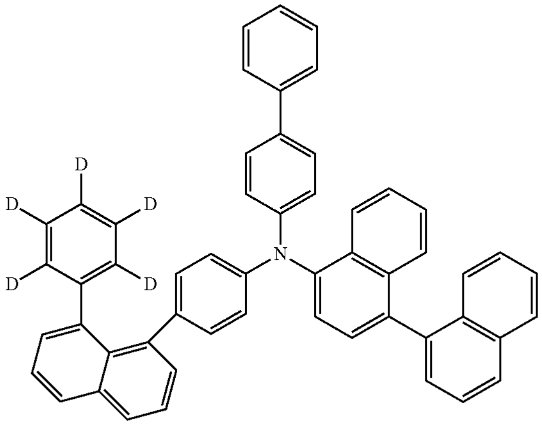
166
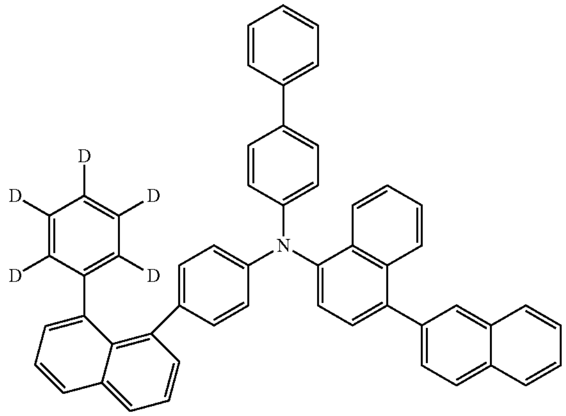
167
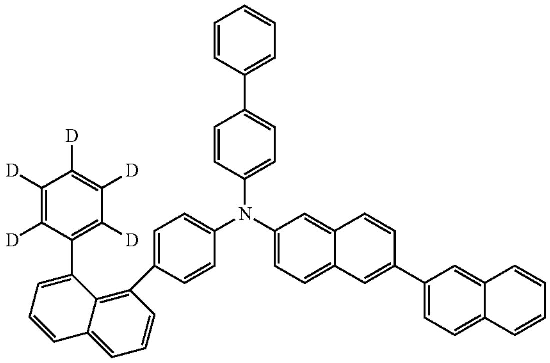
168
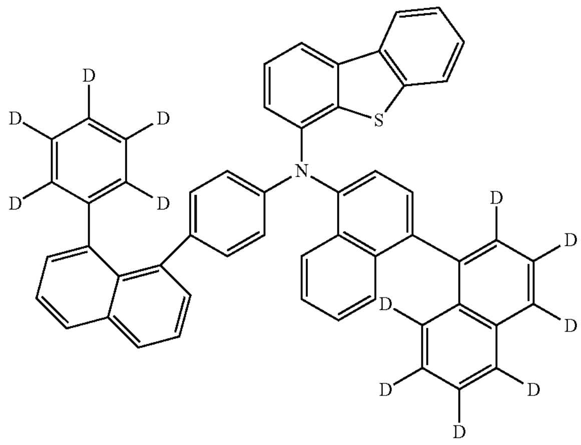
169
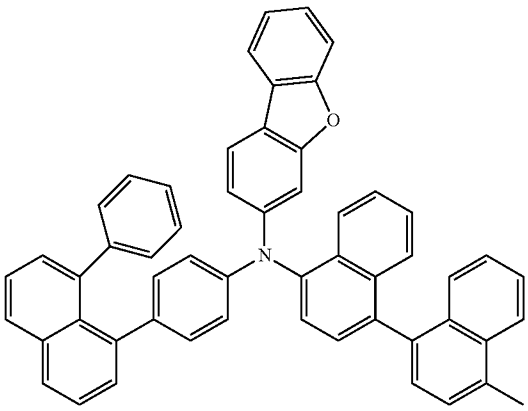

-continued
170
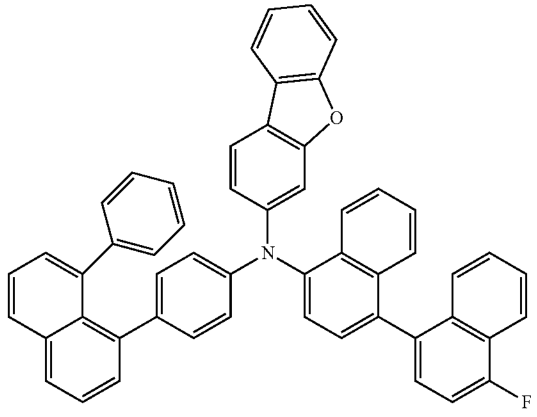
171
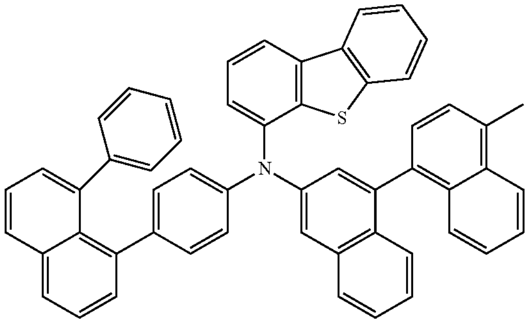
172
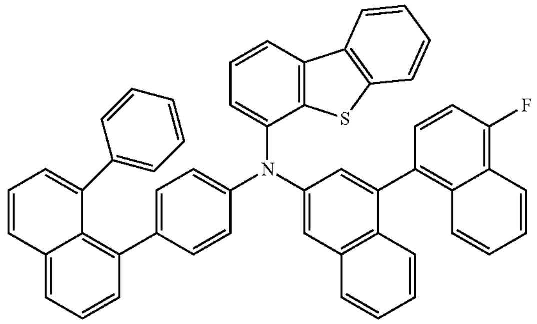
173
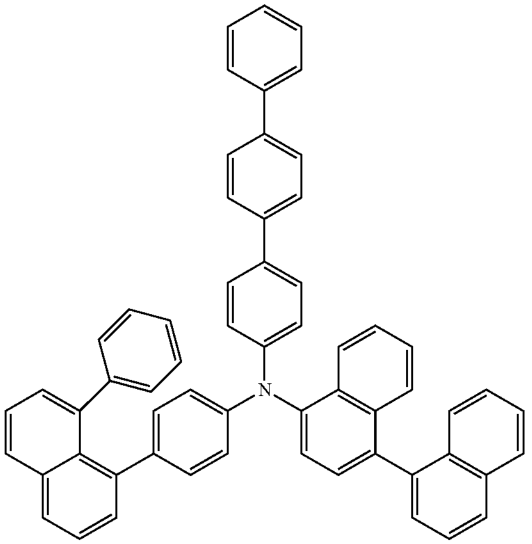
174
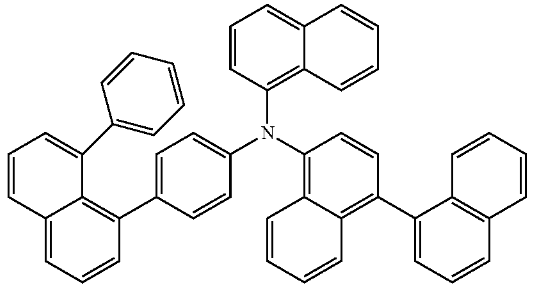
175
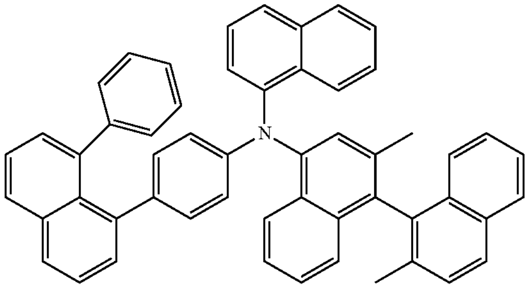

-continued
176
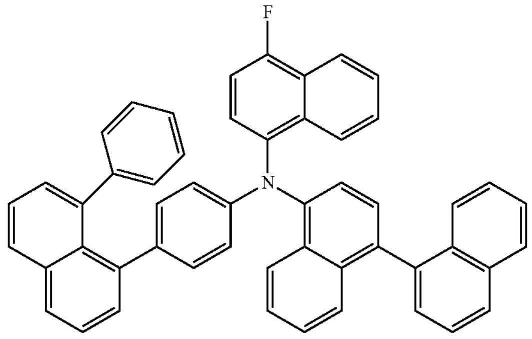
177
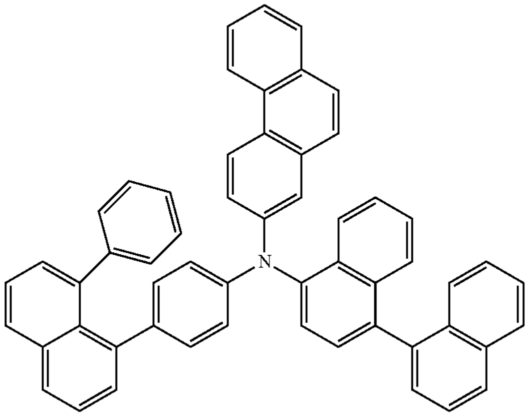
178
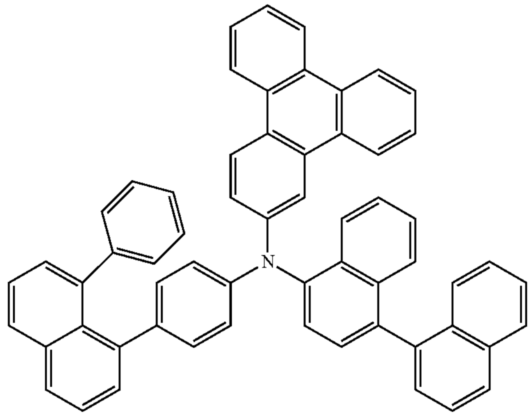
179
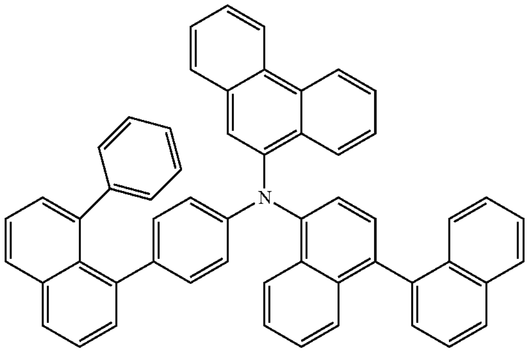
180
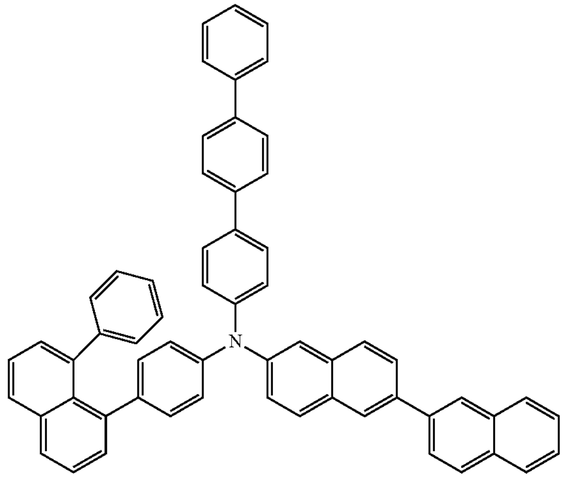
181
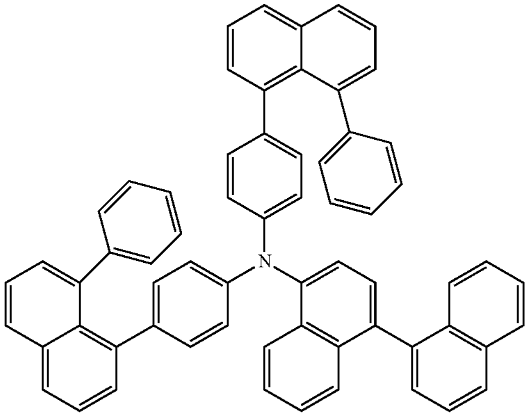

-continued
182
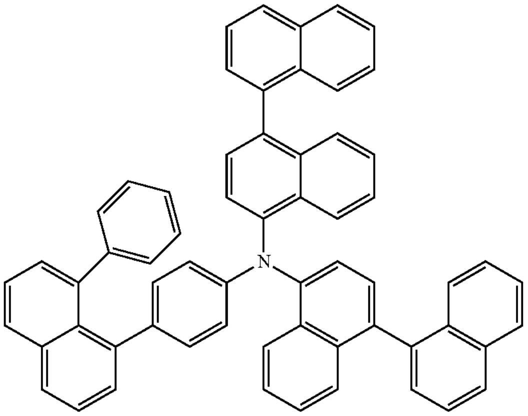
183
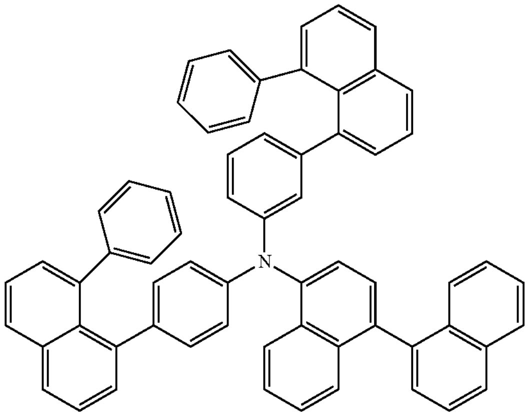
184
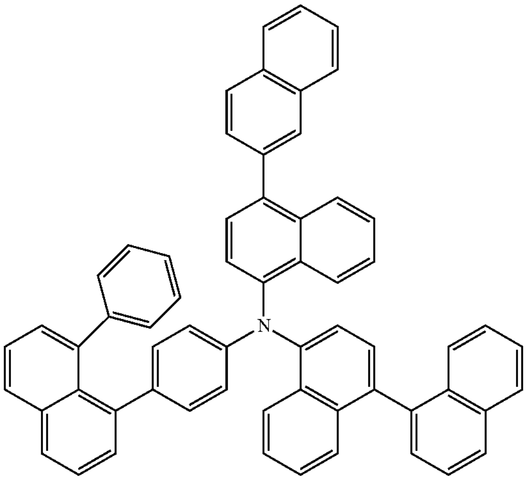
185
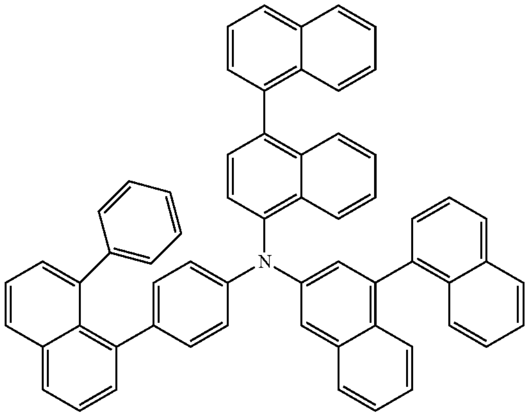
186
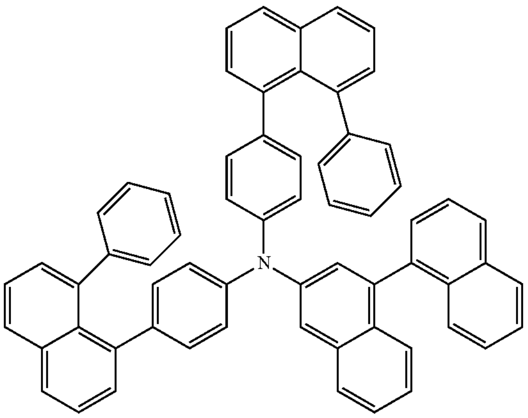
187
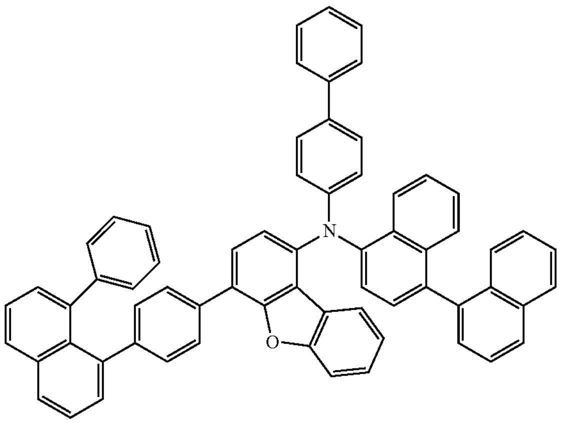

-continued
188
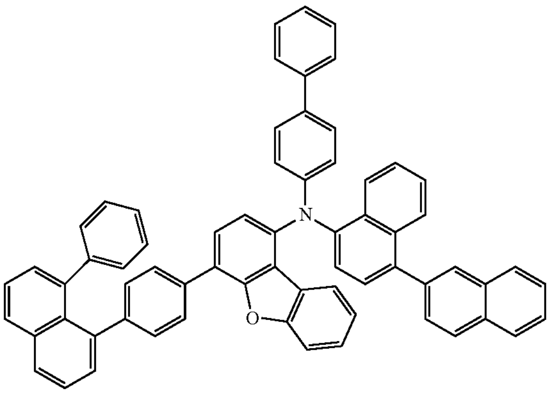
189
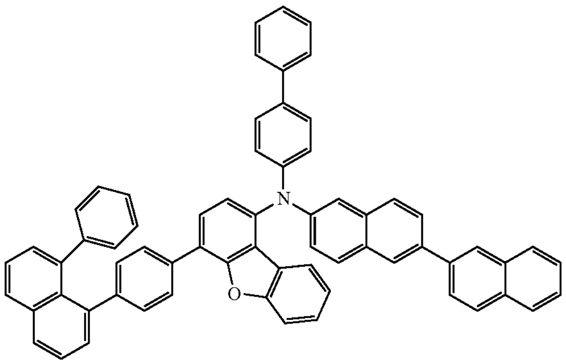
190
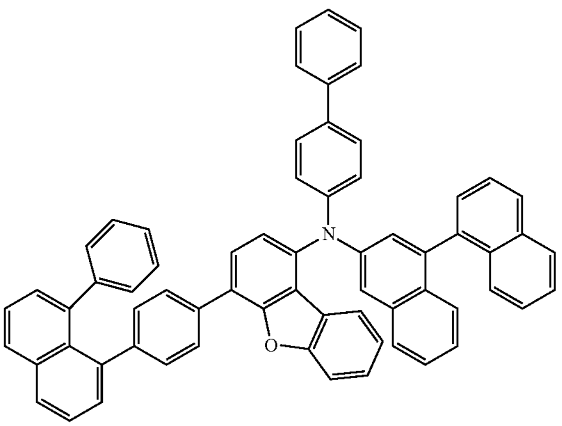
191
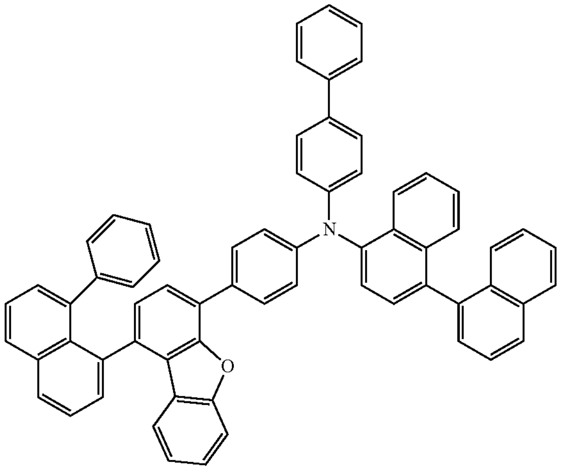
192
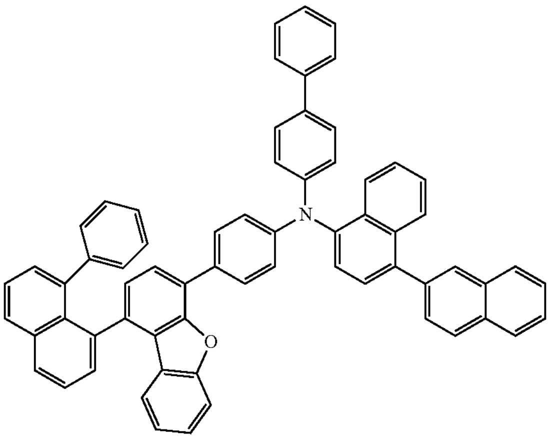
193
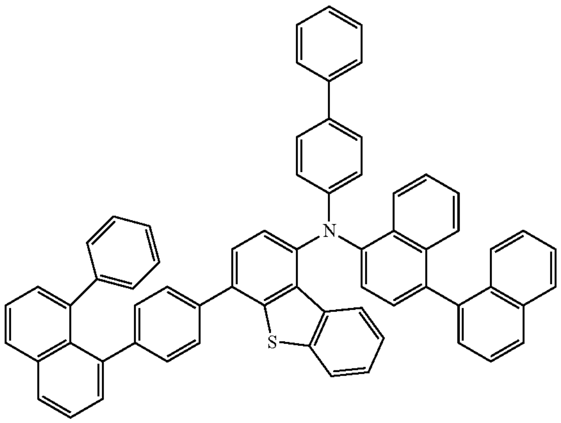

-continued
194
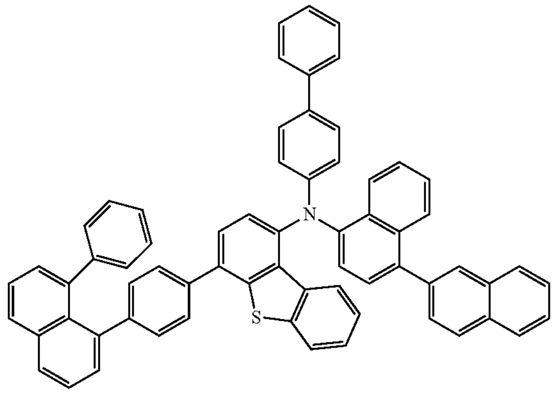
195
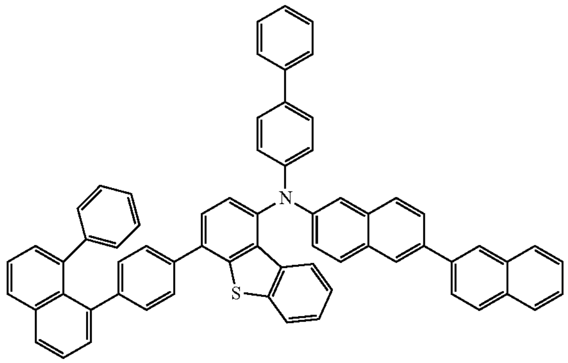
196
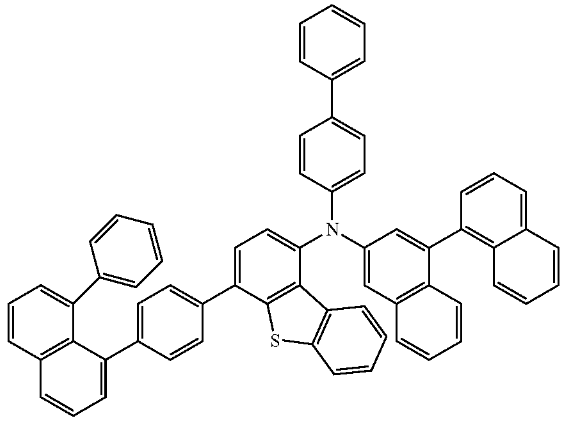
197
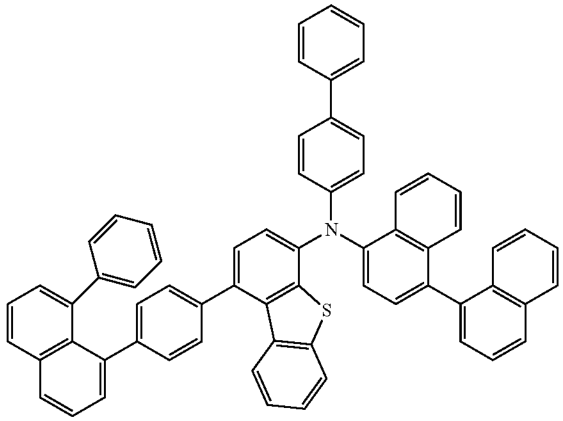
198
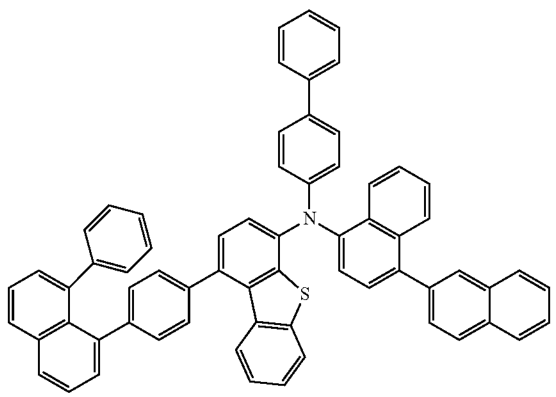
199
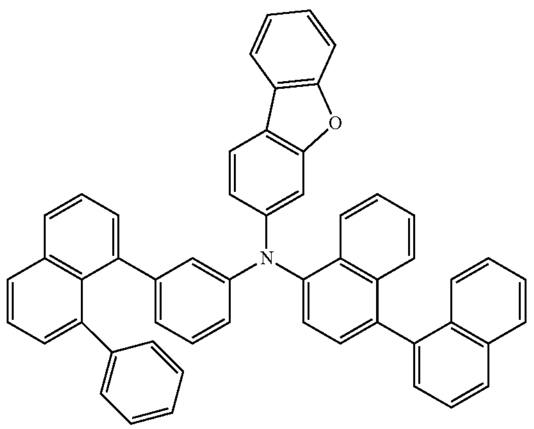

-continued
200
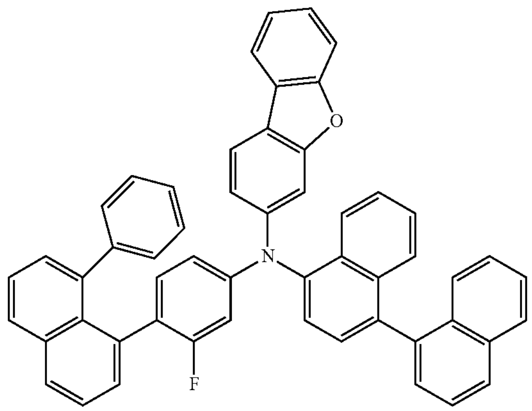
201
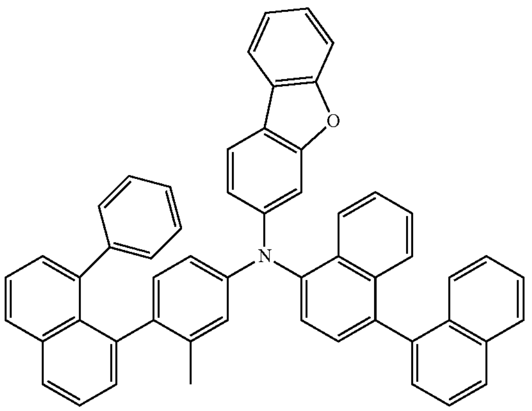
202
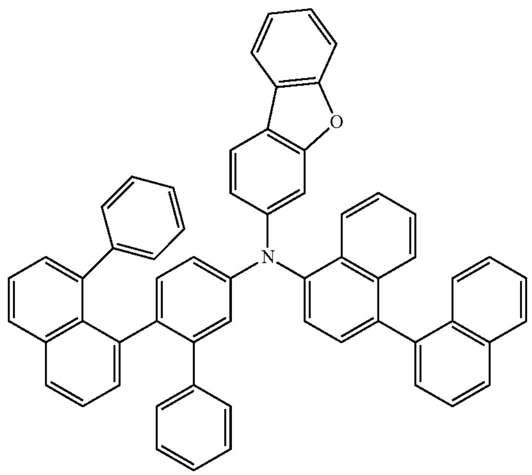
203
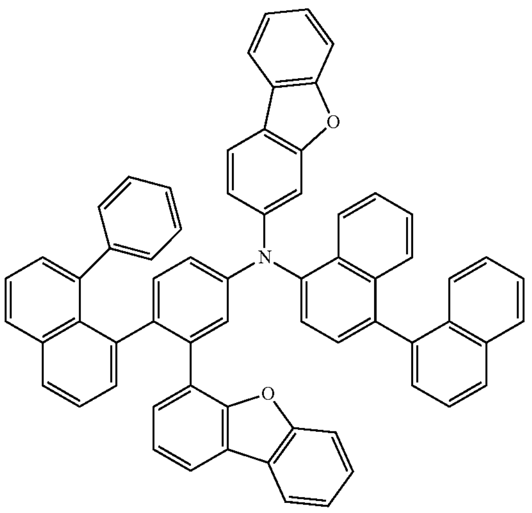
204
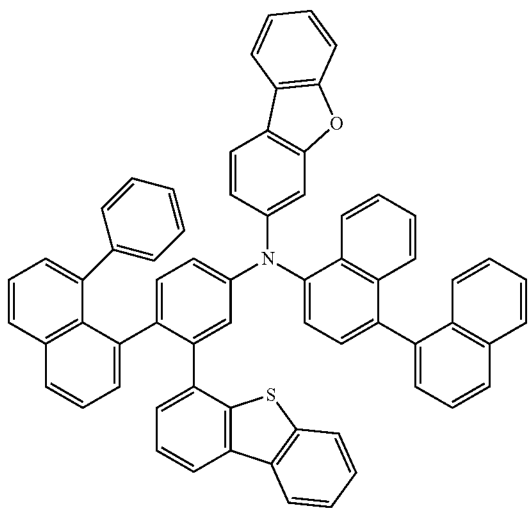
205
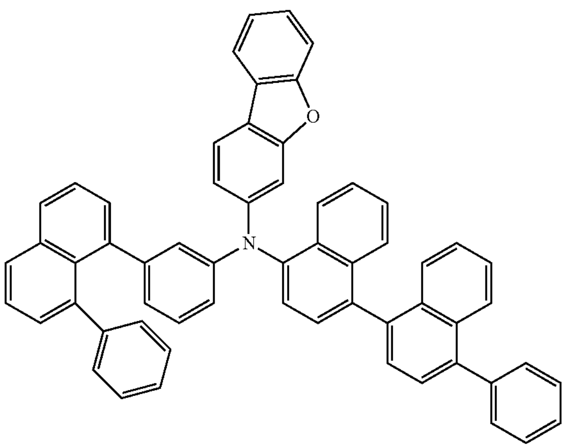

-continued
206
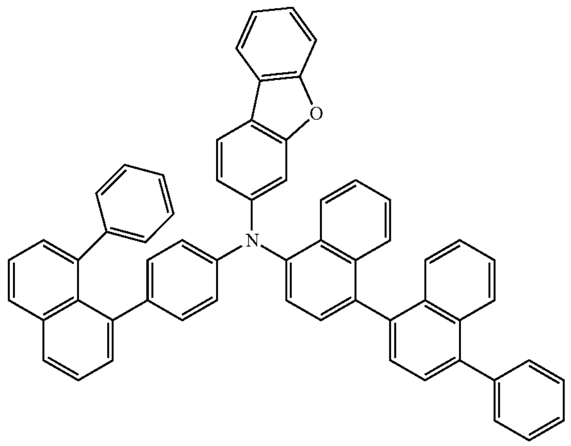
207
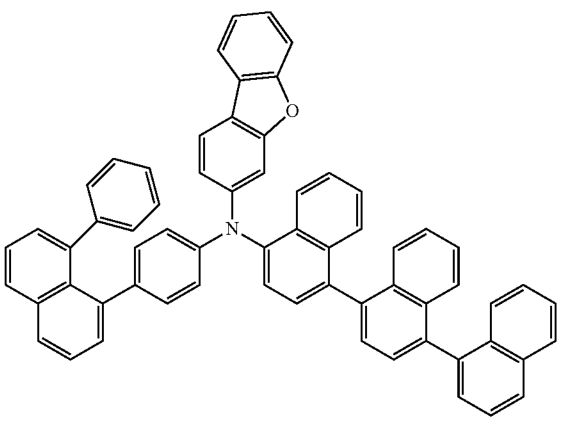
208
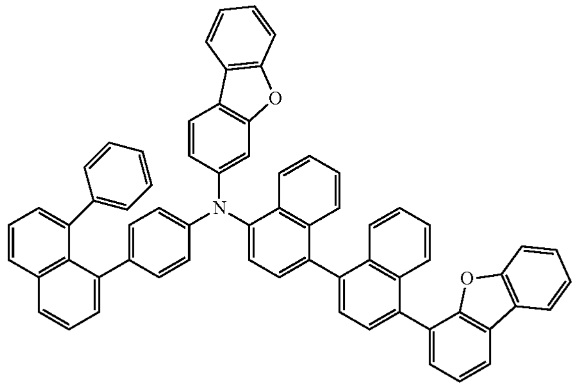
209
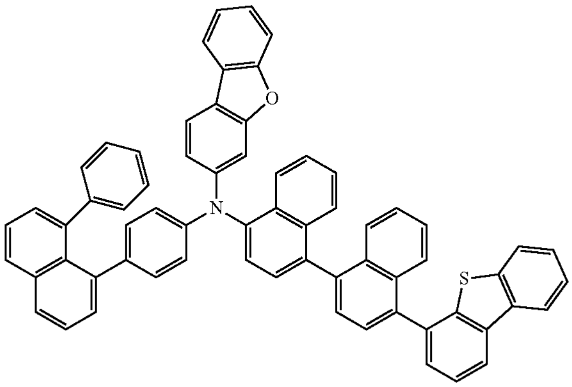
210
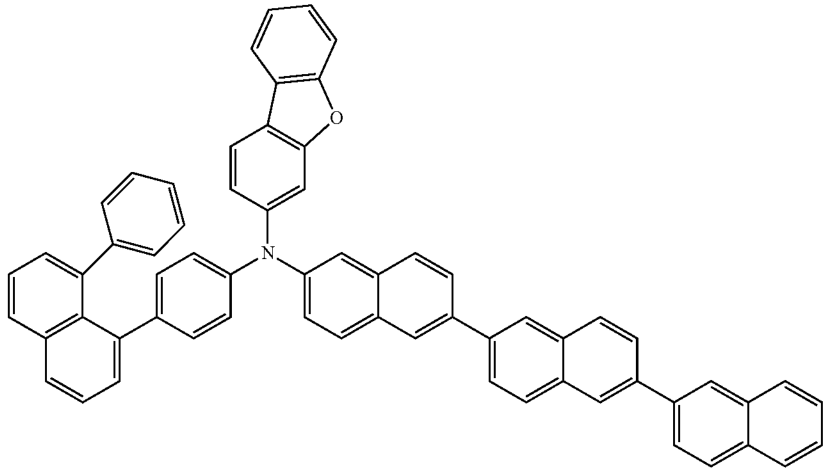

-continued
211
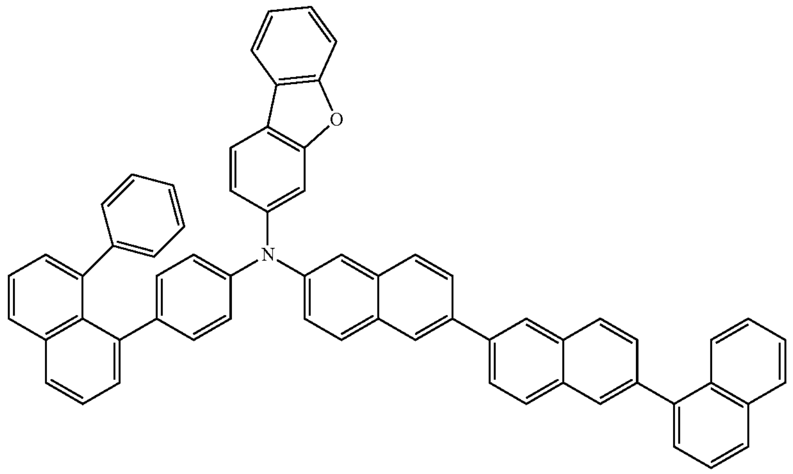
212
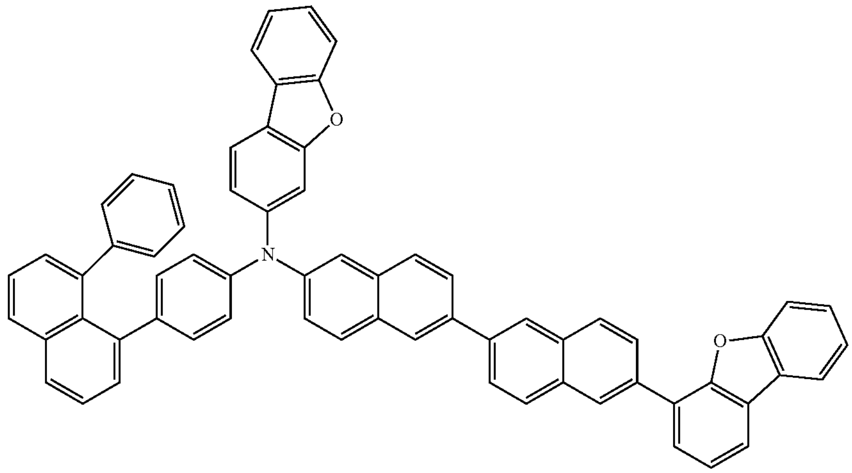
213
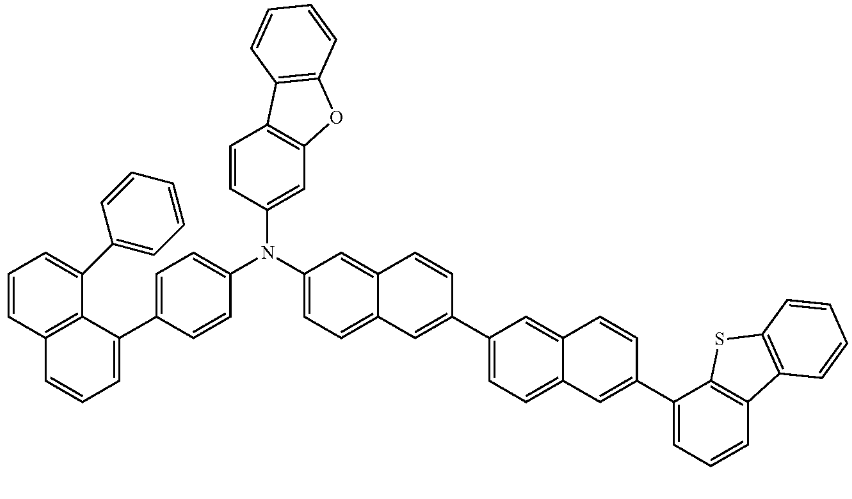

wherein in Compound Group 1,

D is a deuterium atom.

11. An amine compound represented by Formula 1:

[Formula 1]

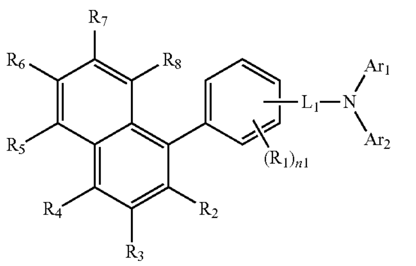

wherein in Formula 1, $L_1$ is direct linkage, a substituted or unsubstituted arylene group of 6 to 15 ring-forming carbon atoms, or a substituted or unsubstituted heteroarylene group of 2 to 15 ring-forming carbon atoms, $Ar_1$ is a phenyl group substituted with a substituted or unsubstituted alkyl group, a phenyl group substituted with a substituted or unsubstituted phenyl group, a phenyl group substituted with a substituted or unsubstituted naphthyl group, an unsubstituted phenyl group, a substituted or unsubstituted naphthyl group, a substituted or unsubstituted terphenyl group, a substituted or unsubstituted phenanthrene group, a substituted or unsubstituted triphenylene group, a substituted or unsubstituted carbazole group, a substituted or unsubstituted dibenzofuran group, a substituted or unsubstituted dibenzothiophene group, a substituted or unsubstituted naphthobenzofuran group, or a substituted or unsubstituted benzonaphthothiophene group, wherein $Ar_1$ does not include an adamantyl group, $Ar_2$ is a group represented by Formula 2, n1 is an integer from 0 to 4, $R_1$ is a hydrogen atom, a deuterium atom, a halogen atom, a substituted or unsubstituted oxy group, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms, or is combined with an adjacent group to form a ring, at least one of $R_2$ to $R_8$ is a substituted or unsubstituted aryl group of 6 to 30 ring-forming carbon atoms, or a substituted or unsubstituted heteroaryl group of 2 to 30 ring-forming carbon atoms, and the remainder of $R_2$ to $R_8$ are each independently a hydrogen atom, a deuterium atom, a halogen atom, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms:

[Formula 2]

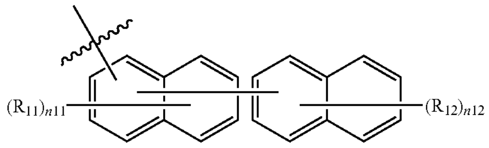

wherein in Formula 2, n11 is an integer from 0 to 6, n12 is an integer from 0 to 7, and $R_{11}$ and $R_{12}$ are each independently a hydrogen atom, a deuterium atom, a halogen atom, a substituted or unsubstituted alkyl group of 1 to 15 carbon atoms, a substituted or unsubstituted aryl group of 6 to 30 ring-forming carbon atoms, or a substituted or unsubstituted heteroaryl group of 2 to 30 ring-forming carbon atoms.

12. The amine compound of claim 11, wherein the amine compound represented by Formula 1 is represented by Formula 1-A1 or Formula 1-A2:

[Formula 1-A1]

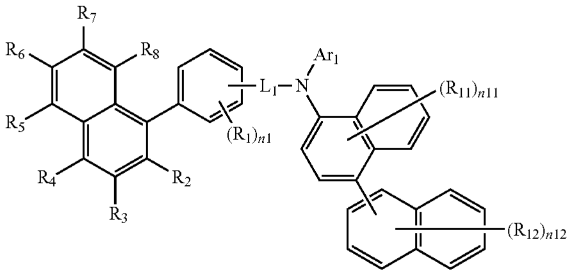

[Formula 1-A2]

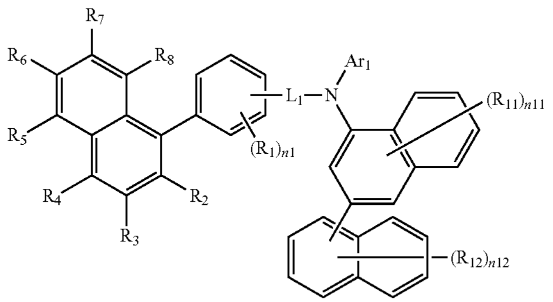

wherein in Formula 1-A1 and Formula 1-A2, $Ar_1$, $L_1$, n1, n11, n12, $R_1$ to $R_8$, $R_{11}$, and $R_{12}$ are the same as defined in Formula 1 and Formula 2.

13. The amine compound of claim 11, wherein the amine compound represented by Formula 1 is represented by Formula 1-B1 or Formula 1-B2:

[Formula 1-B1]

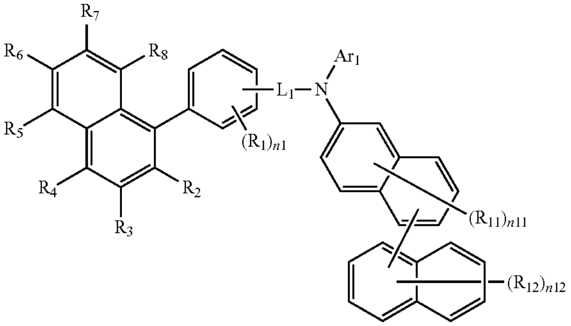

[Formula 1-B2]

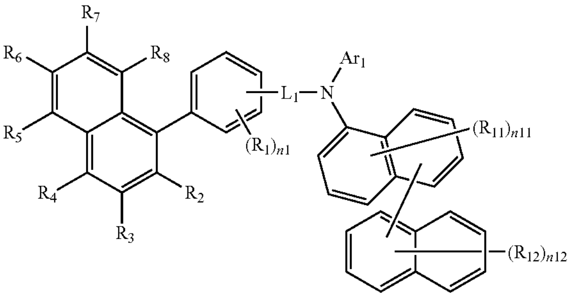

wherein in Formula 1-B1 and Formula 1-B2, $Ar_1$, $L_1$, n1, n11, n12, $R_1$ to $R_8$, $R_{11}$, and $R_{12}$ are the same as defined in Formula 1 and Formula 2.

14. The amine compound of claim 11, wherein the amine compound represented by Formula 1 is represented by Formula 1-C1 or Formula 1-C2:

[Formula 1-C1]

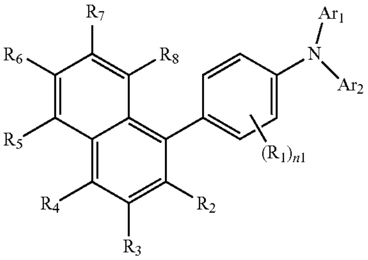

[Formula 1-C2]

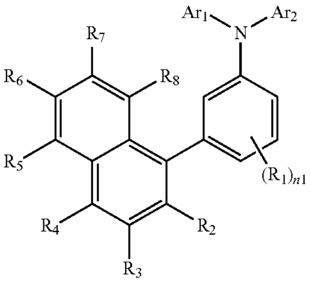

wherein in Formula 1-C1 and Formula 1-C2, $Ar_1$, $Ar_2$, n1, and $R_1$ to $R_8$ are the same as defined in Formula 1.

15. The amine compound of claim 11, wherein at least one of $R_4$ and $R_8$ is a substituted or unsubstituted phenyl group, a substituted or unsubstituted naphthyl group, a substituted or unsubstituted pyridine group, a substituted or unsubstituted carbazole group, a substituted or unsubstituted dibenzofuran group, or a substituted or unsubstituted dibenzothiophene group.

16. The amine compound of claim 11, wherein at least one of $R_1$ to $R_8$ comprises a deuterium atom as a substituent, or at least one of $R_{11}$ and $R_{12}$ is a deuterium atom.

17. The amine compound of claim 11, wherein the amine compound represented by Formula 1 is one selected from Compound Group 1:

[Compound Group 1]

1

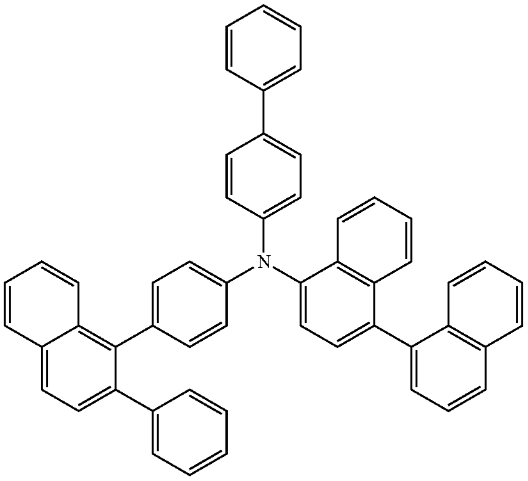

2

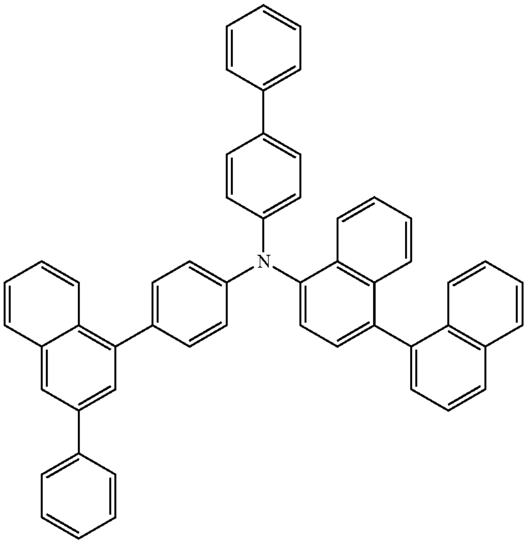

-continued
3
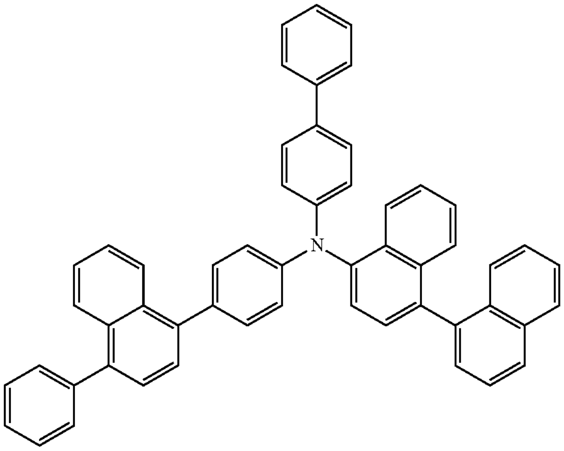
4
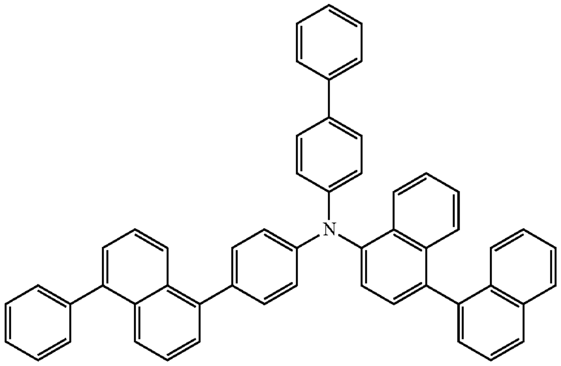
5
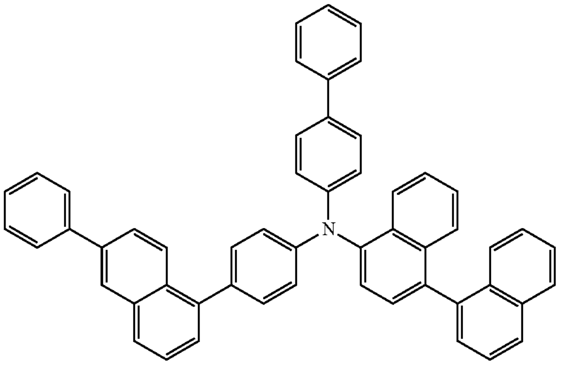
6
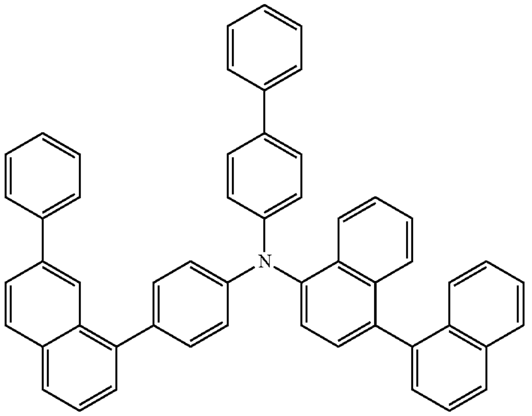
7
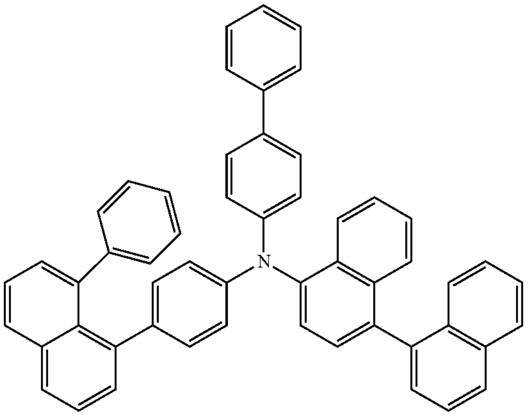
8
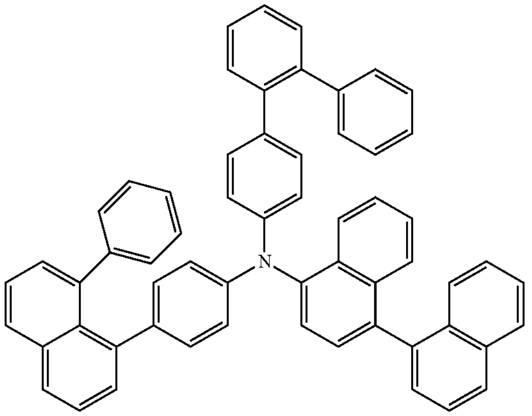

-continued
9
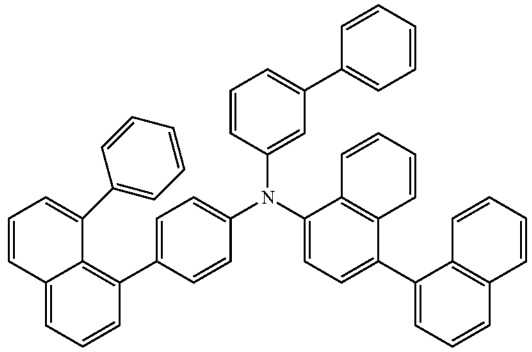
10
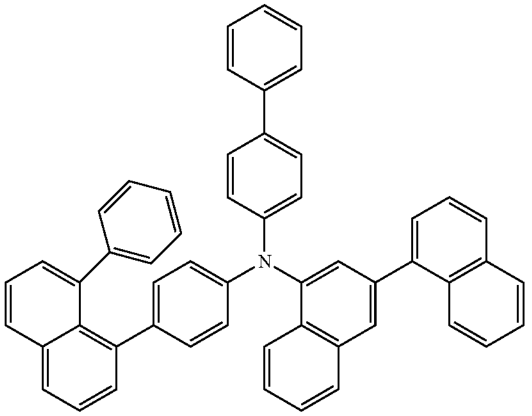
11
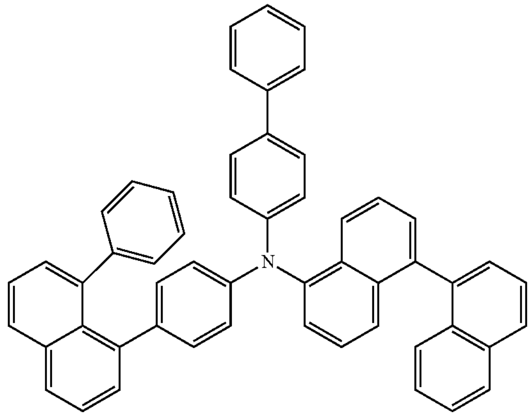
12
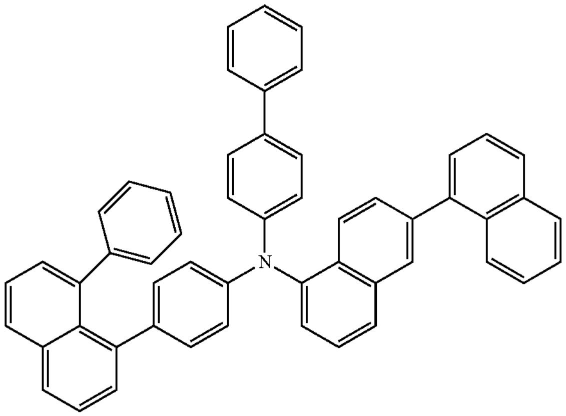
13
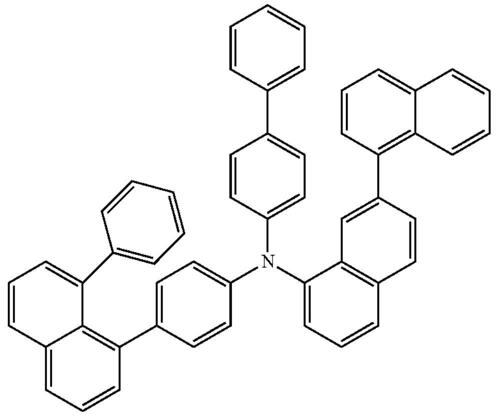
14
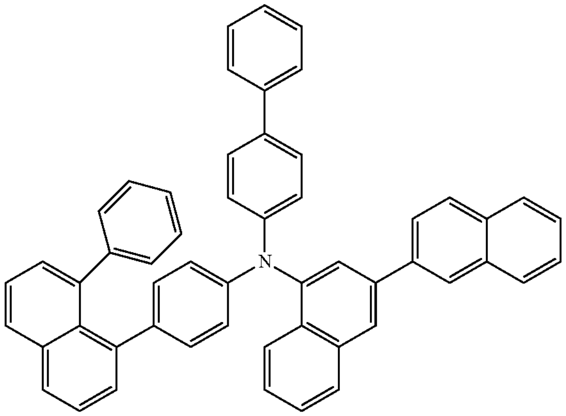

-continued
15
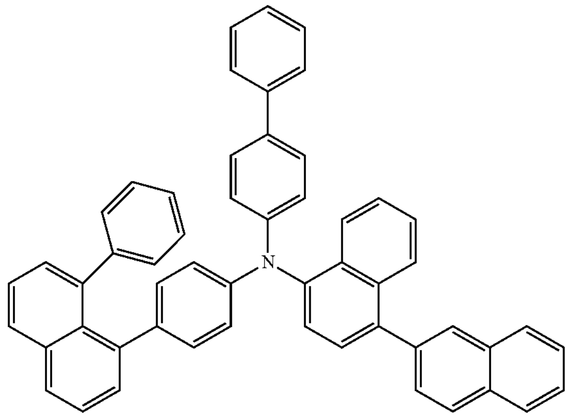
16
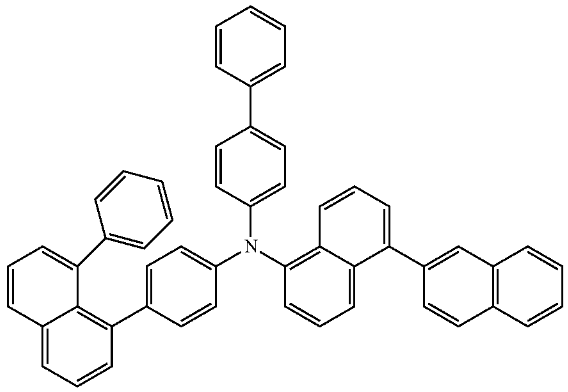
17
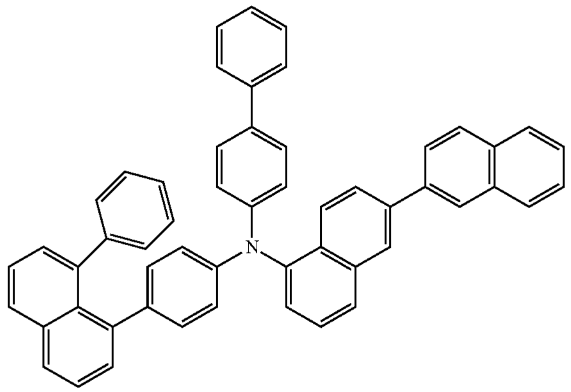
18
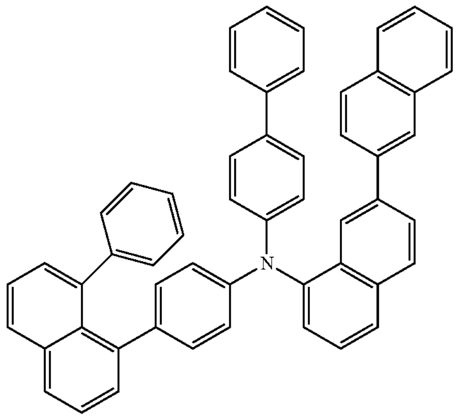
19
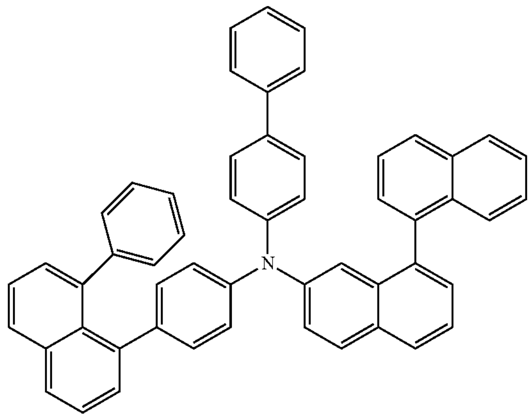
20
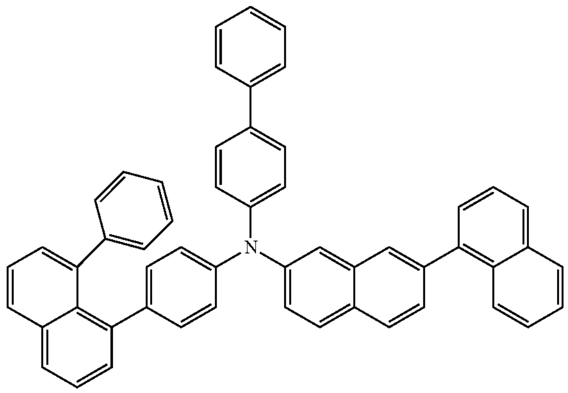

-continued
21
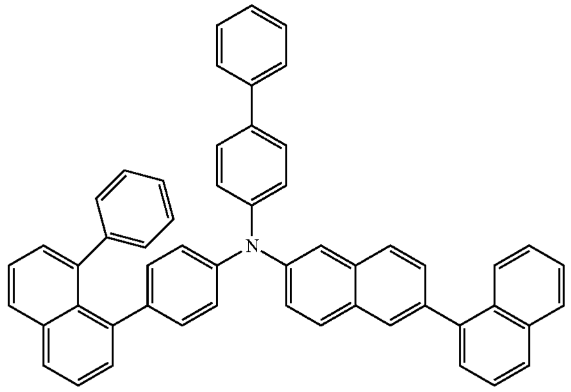
22
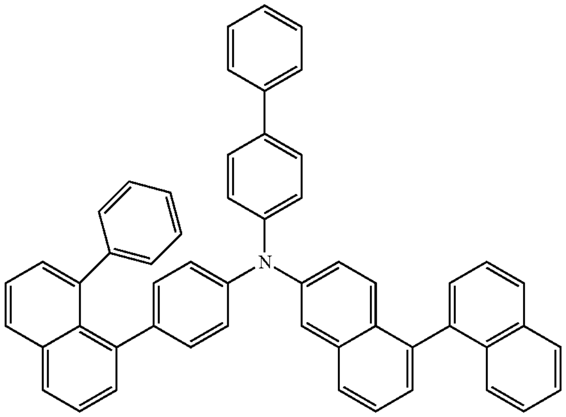
23
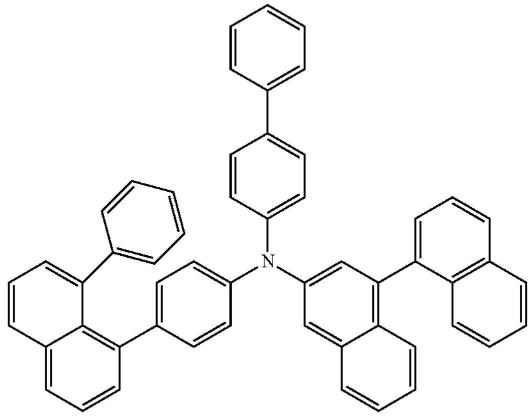
24
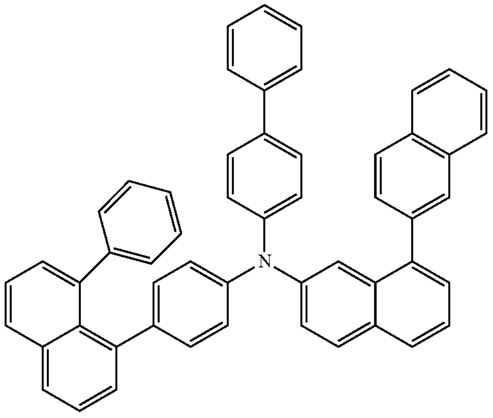
25
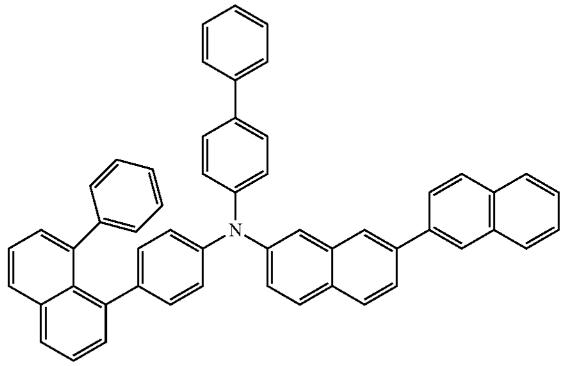
26
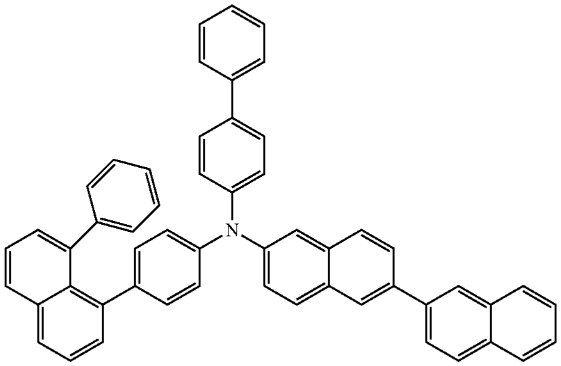

-continued
27
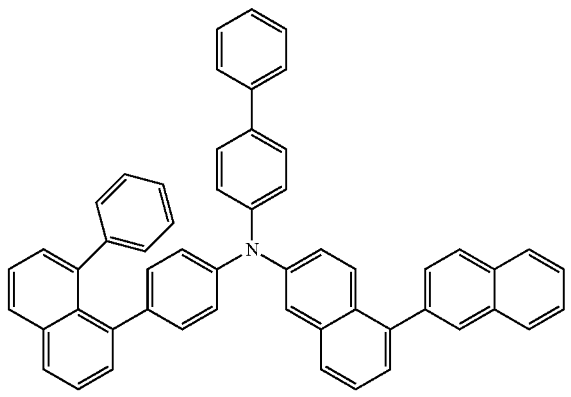
28
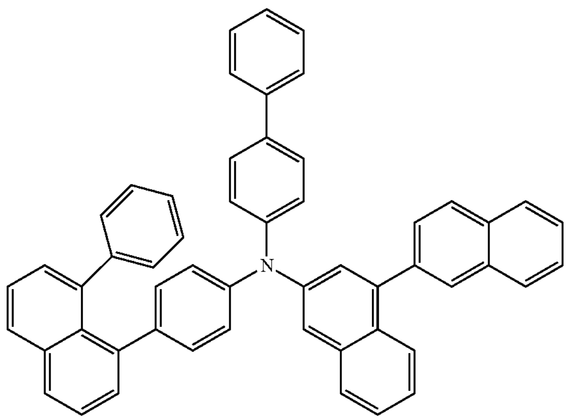
29
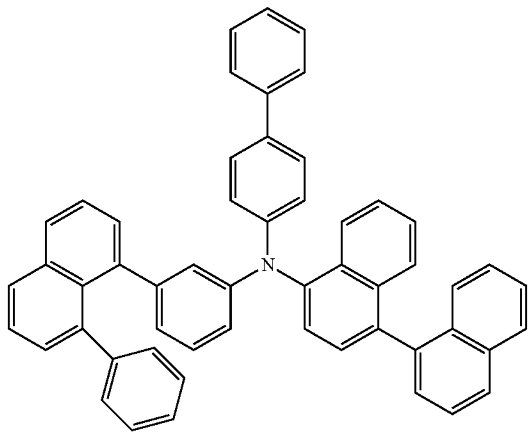
30
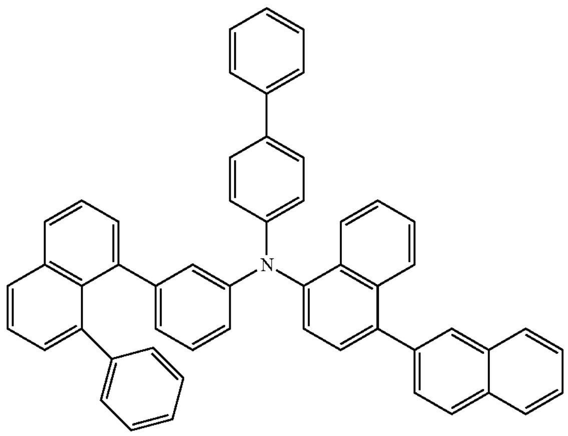
31
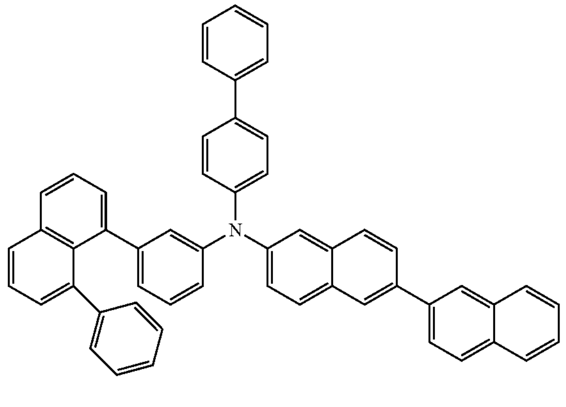
32
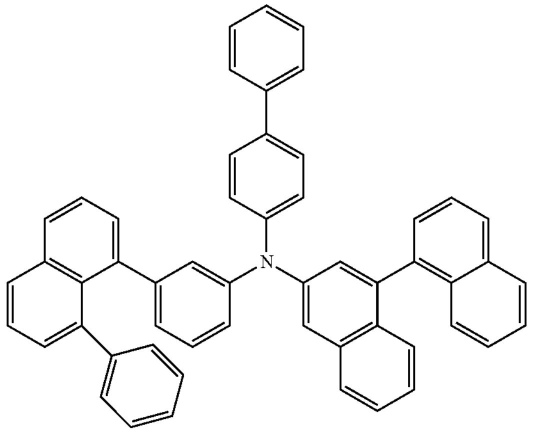

-continued
33
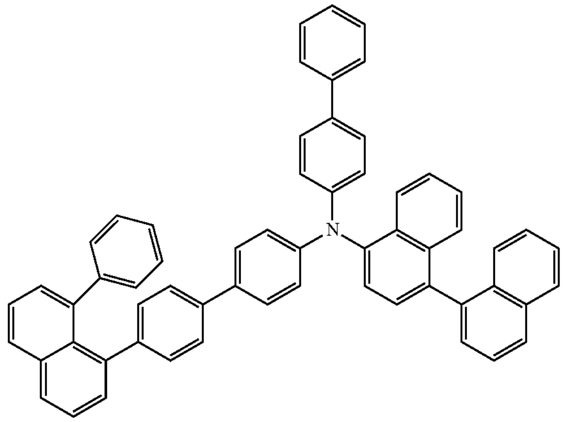
34
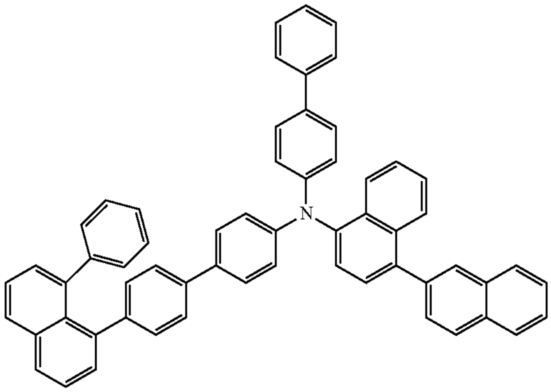
35
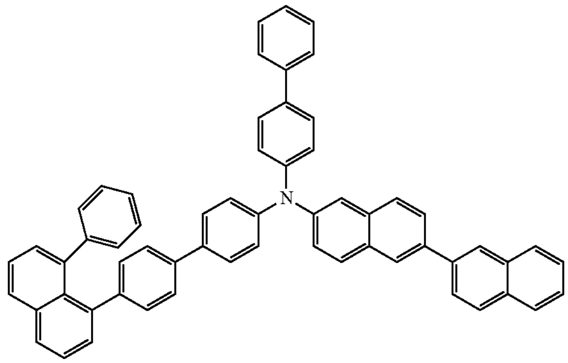
36
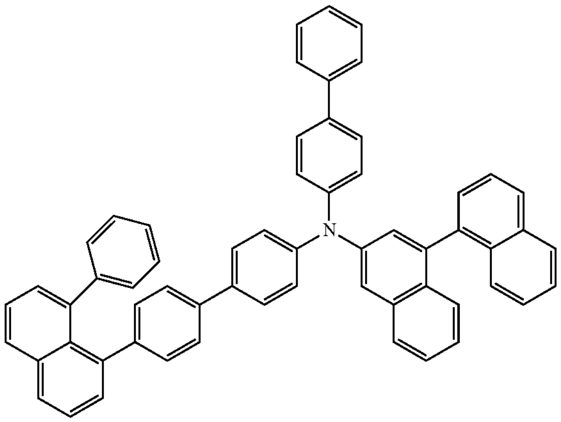
37
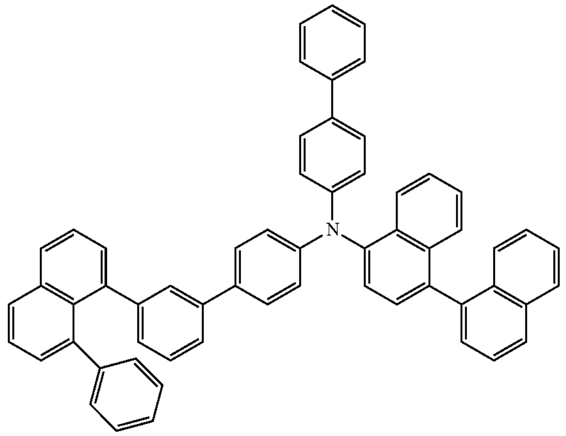
38
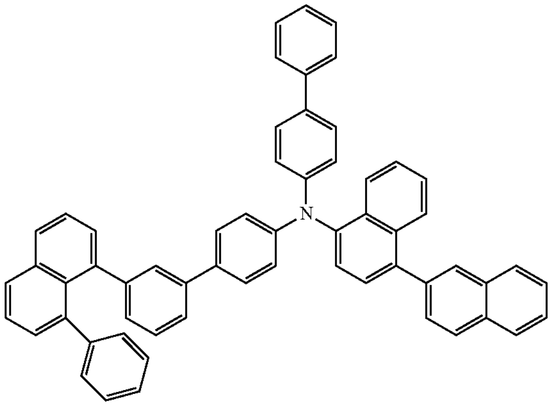

-continued
39
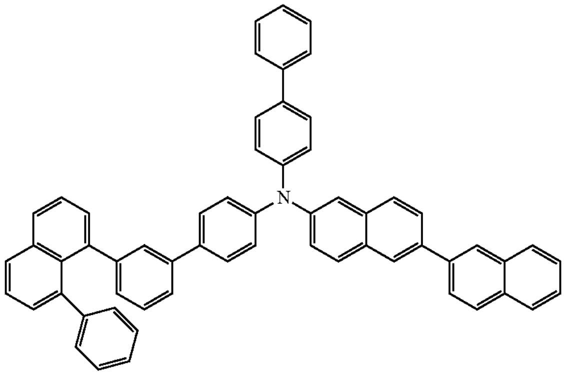
40
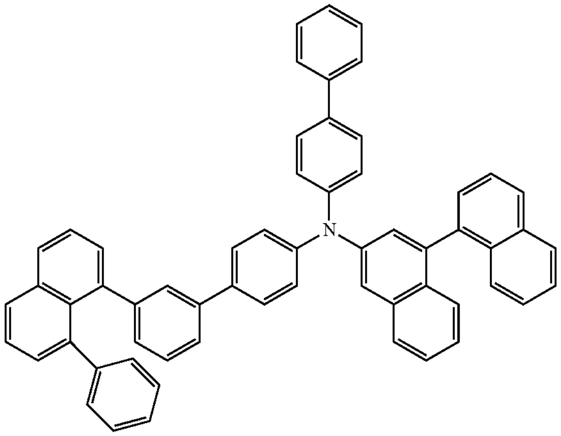
41
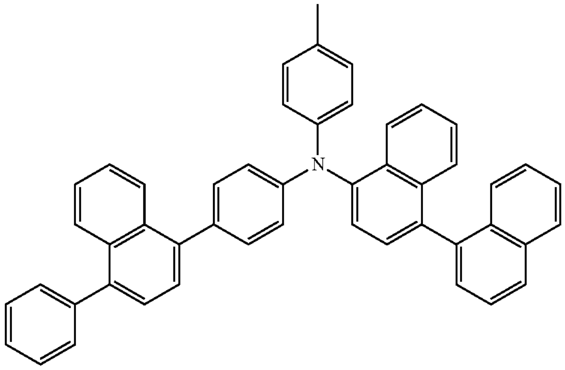
42
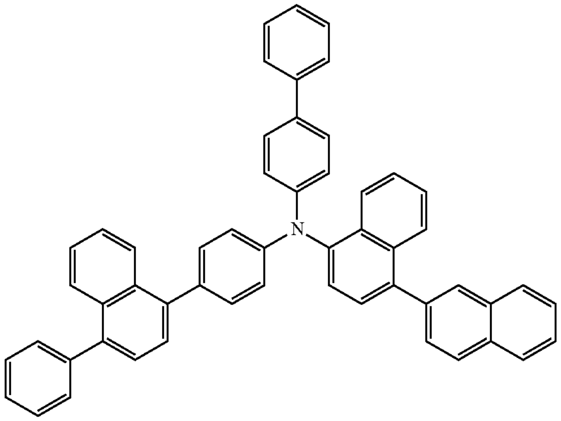
43
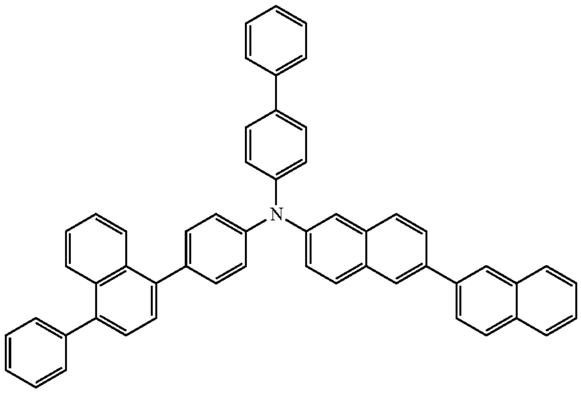
44
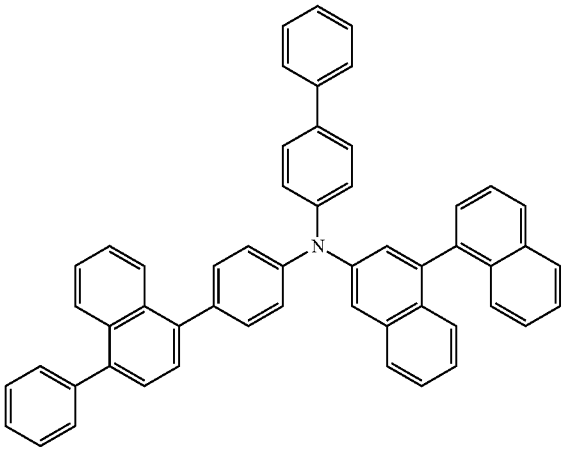

-continued
45
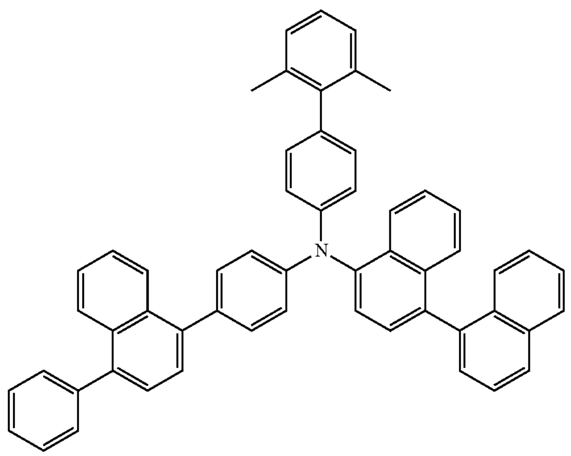
46
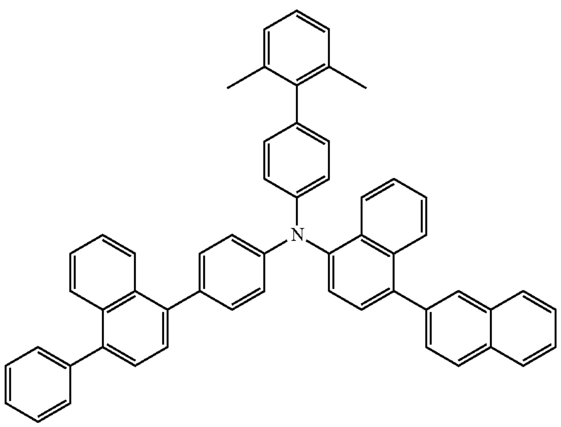
47
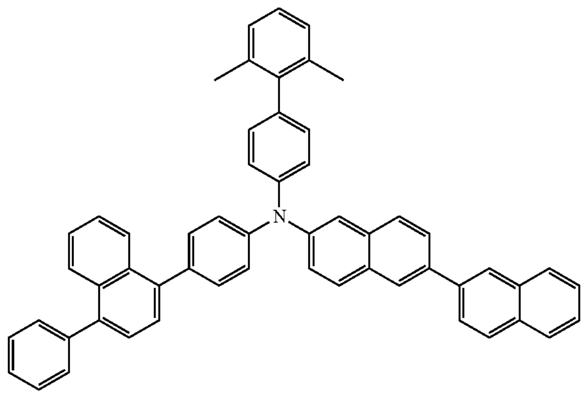
48
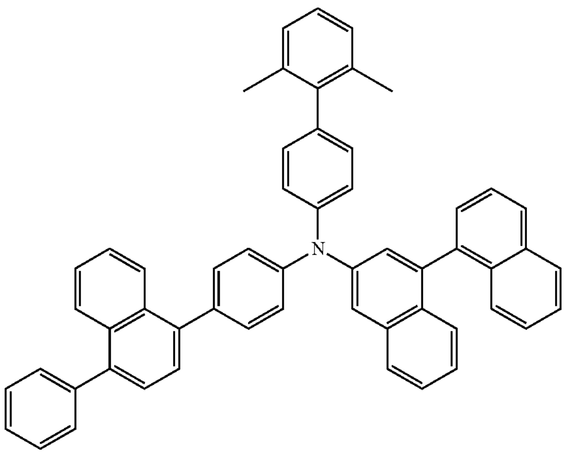
49
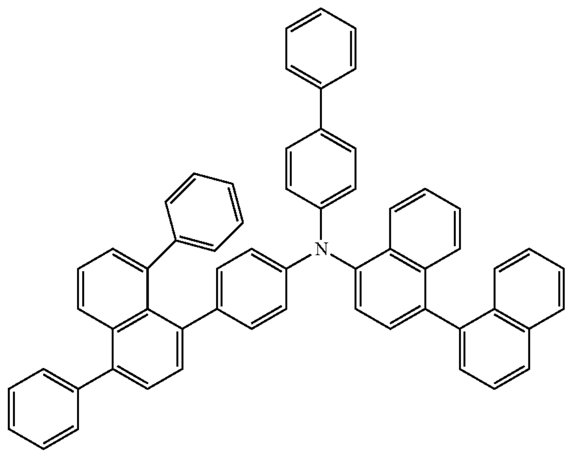
50
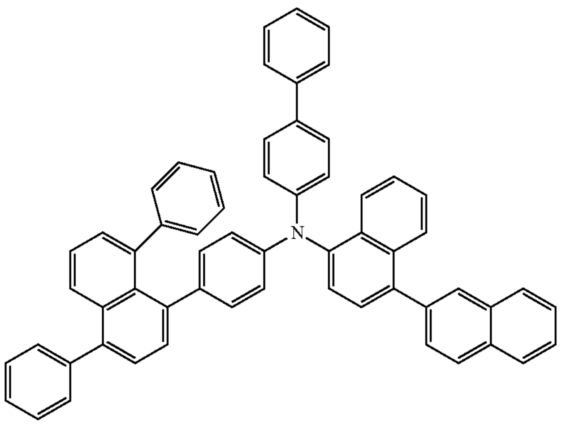

-continued
51
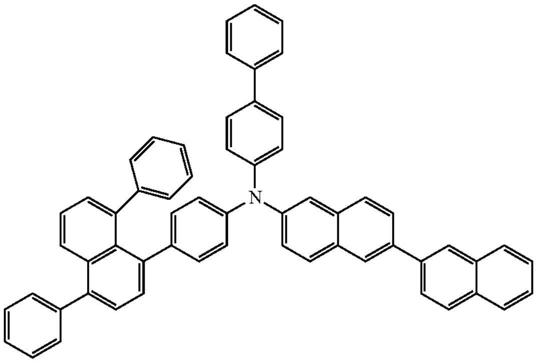
52
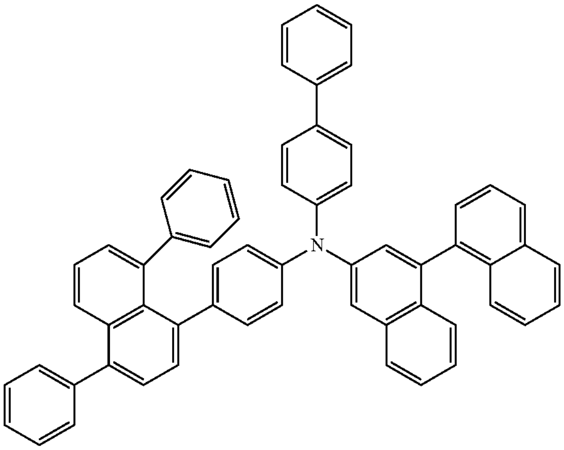
53
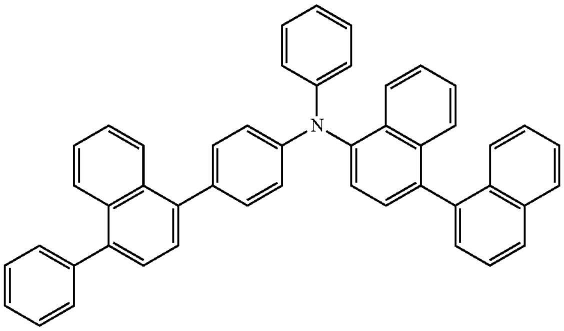
54
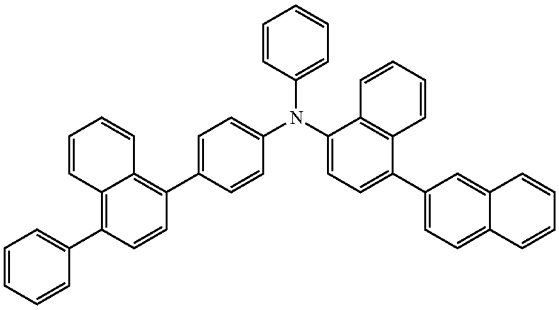
55
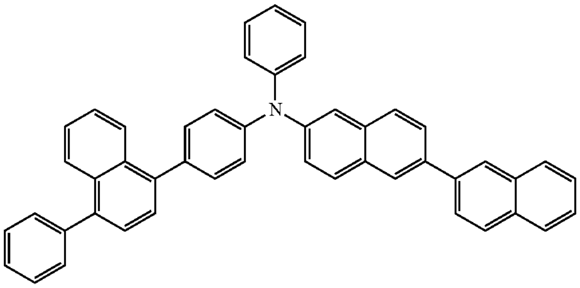
56
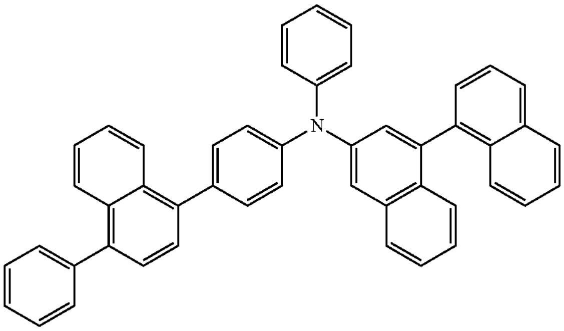
57
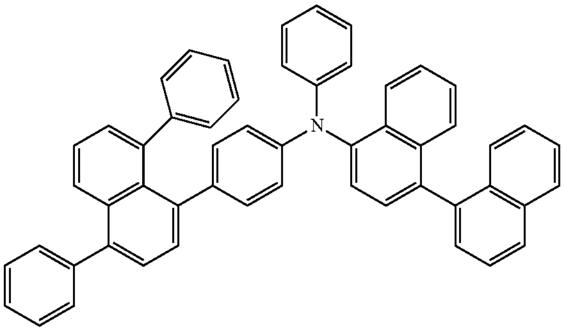
58
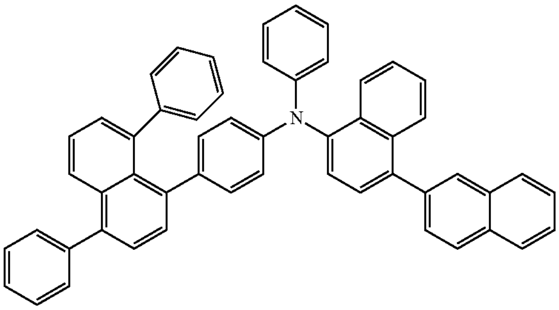

-continued
59
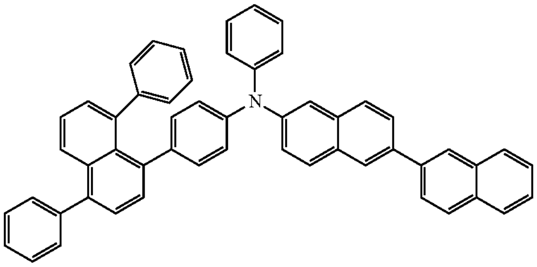
60
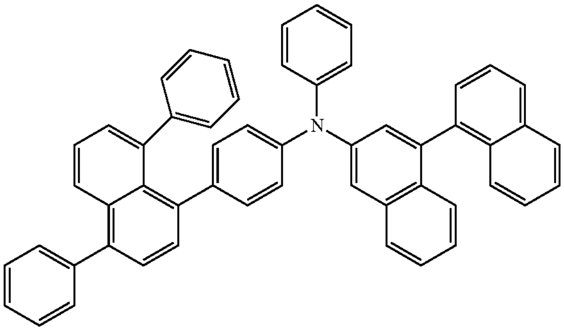
61
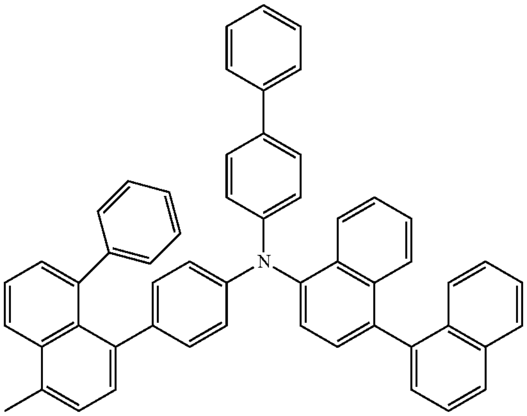
62
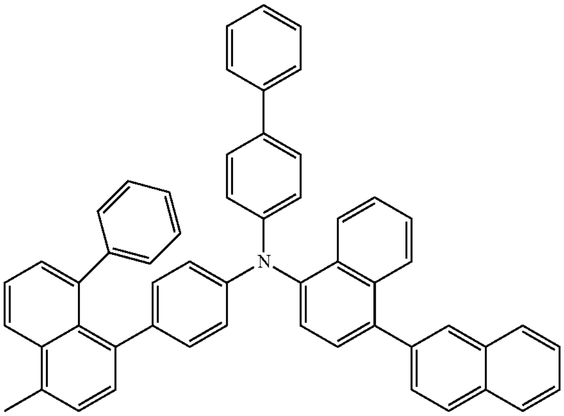
63
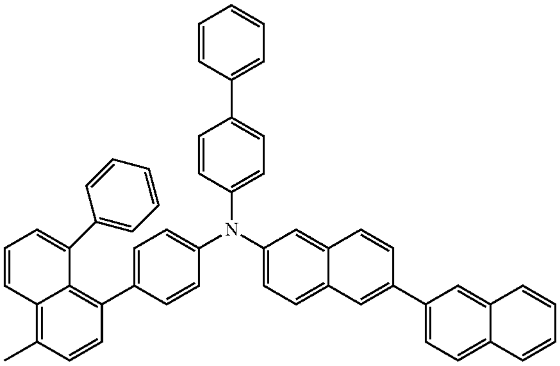
64
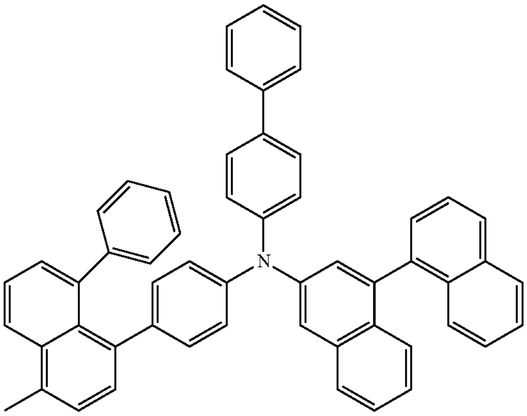

-continued
65
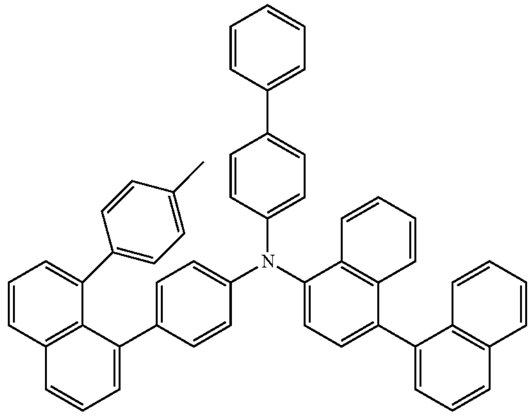
66
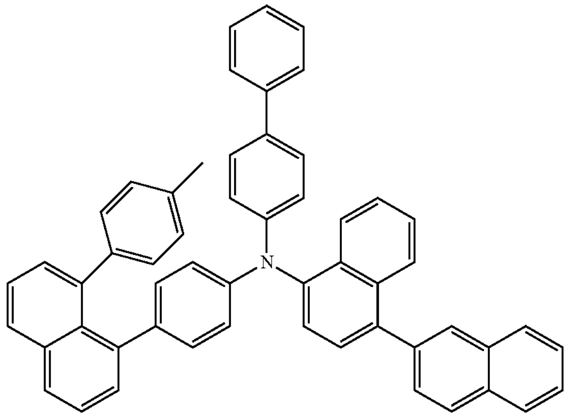
67
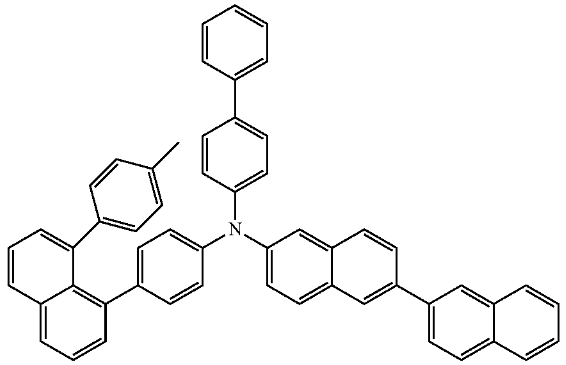
68
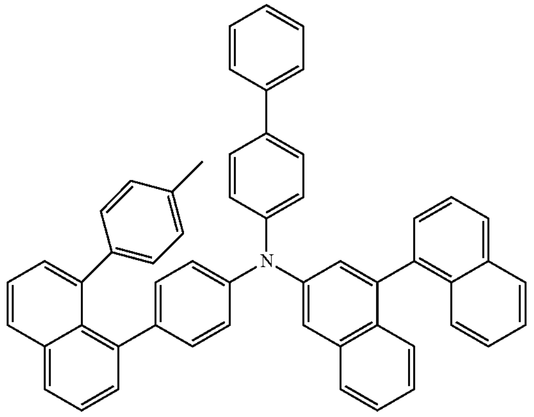
69
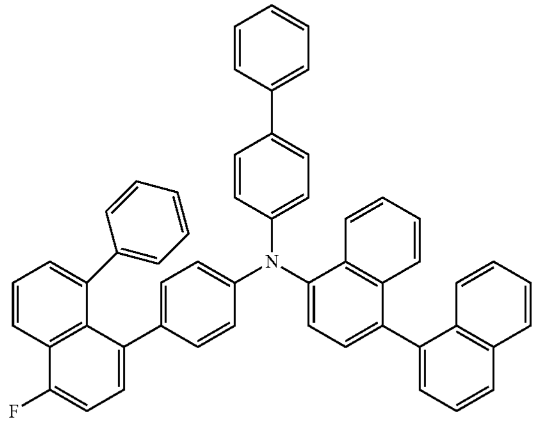
70
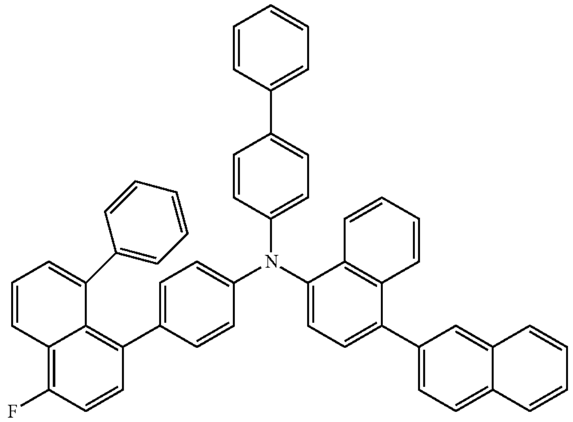

-continued
71
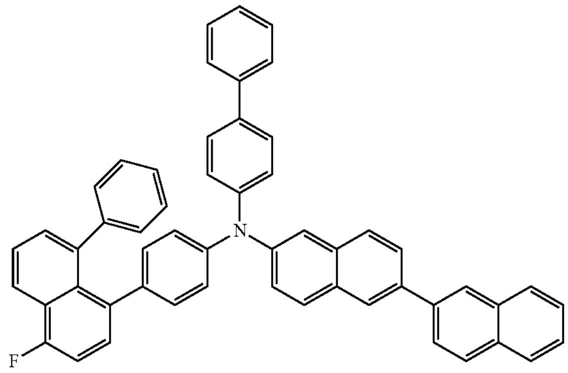
72
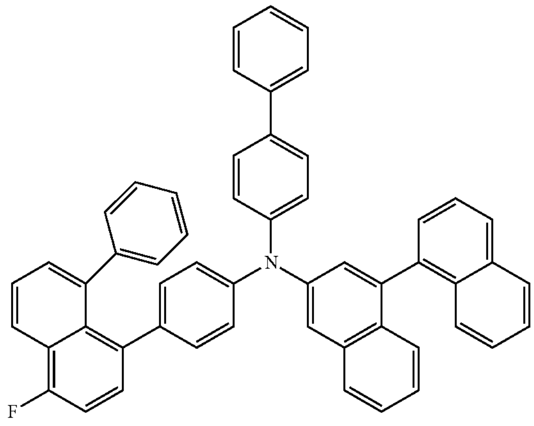
73
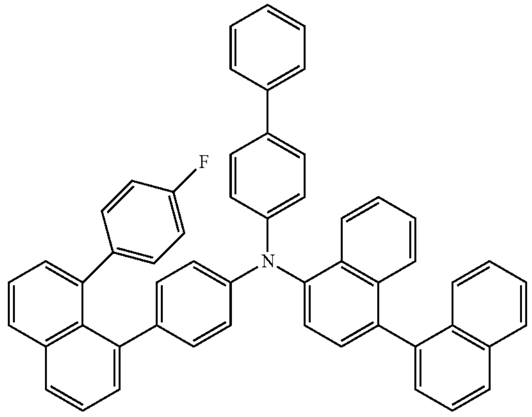
74
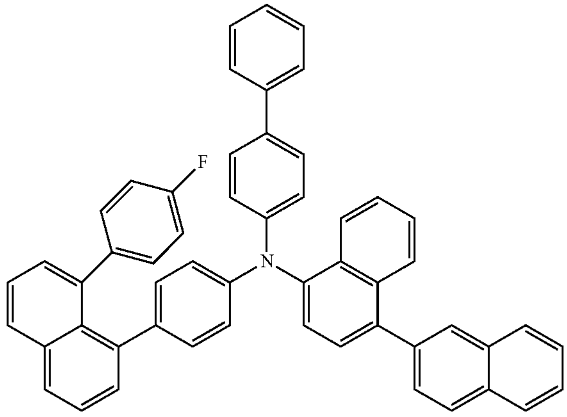
75
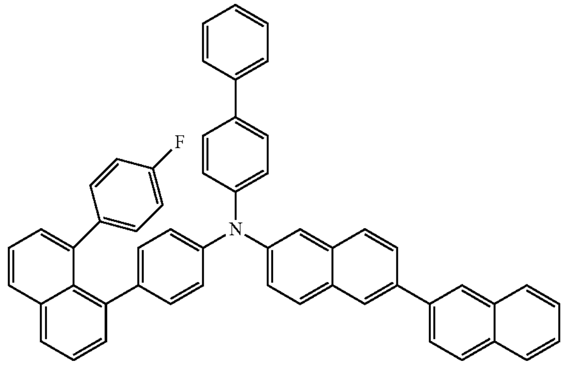
76
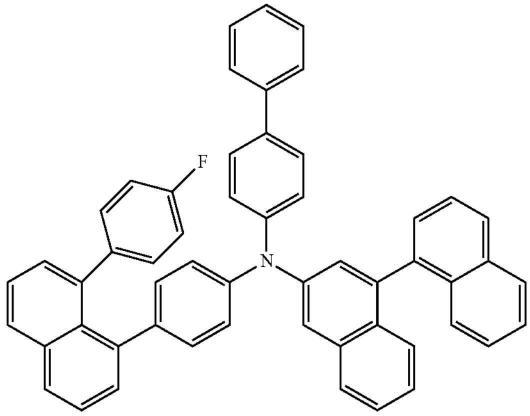

-continued
77
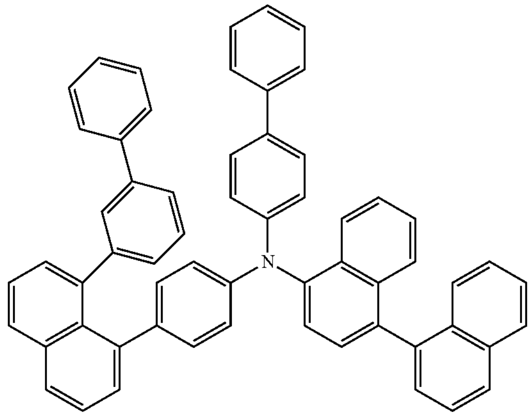
78
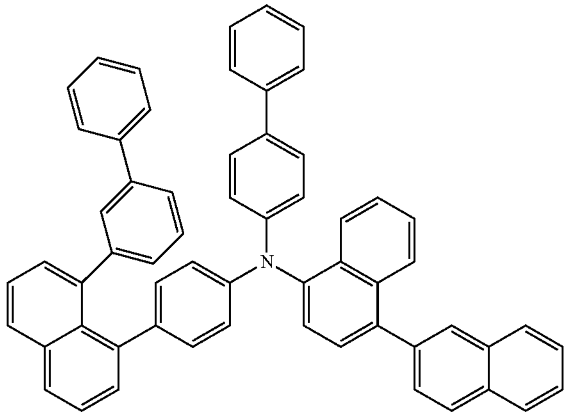
79
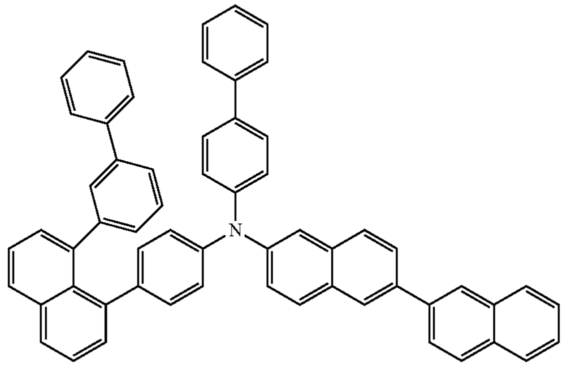
80
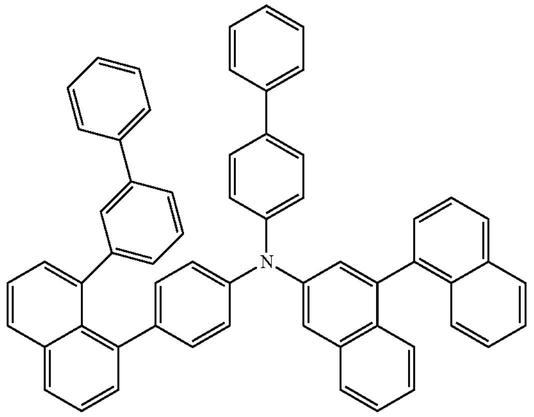
81
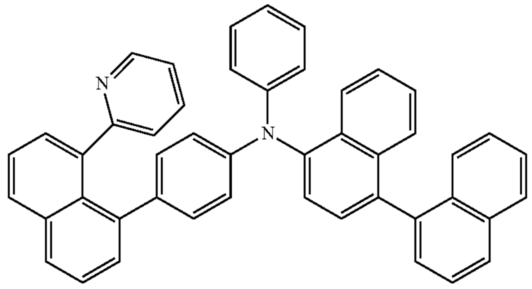
82
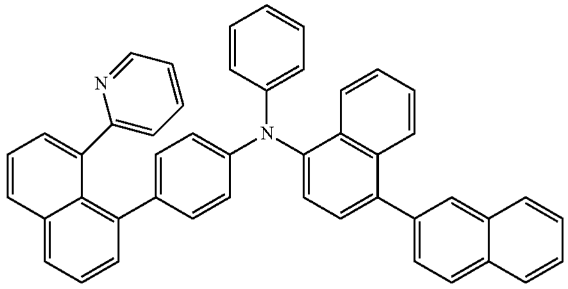
83
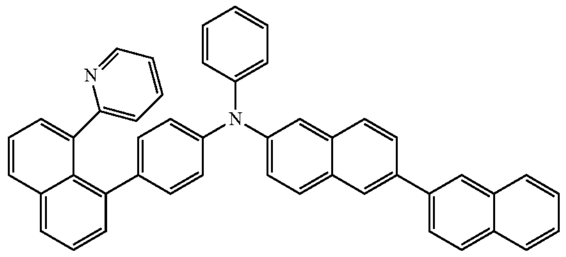
84
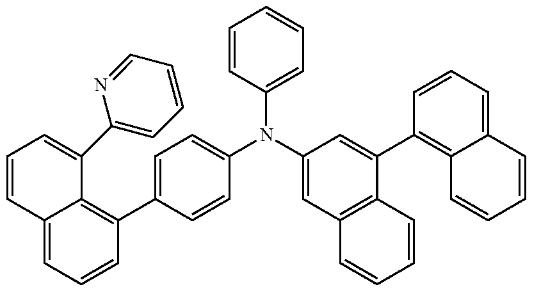

-continued
85
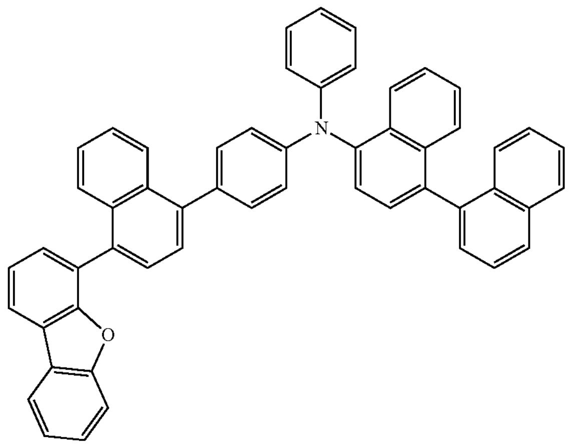
86
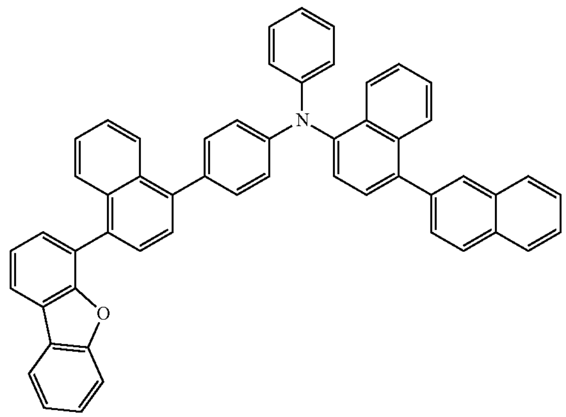
87
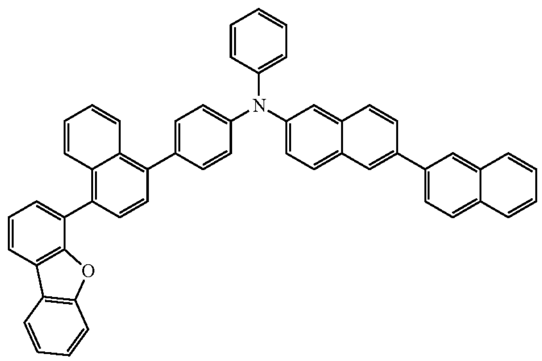
88
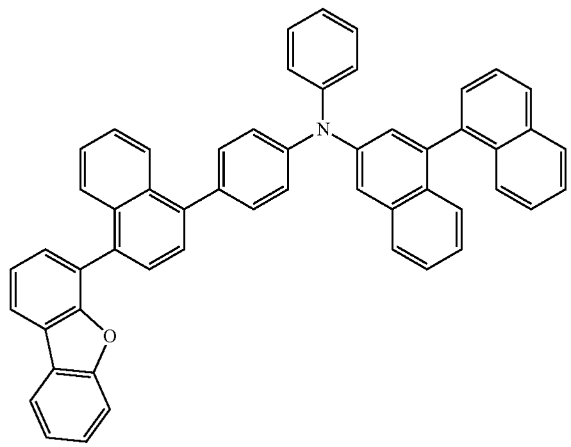
89
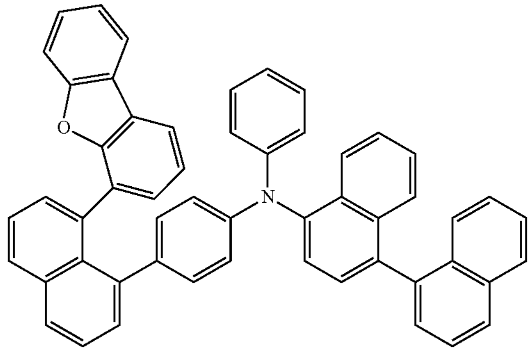
90
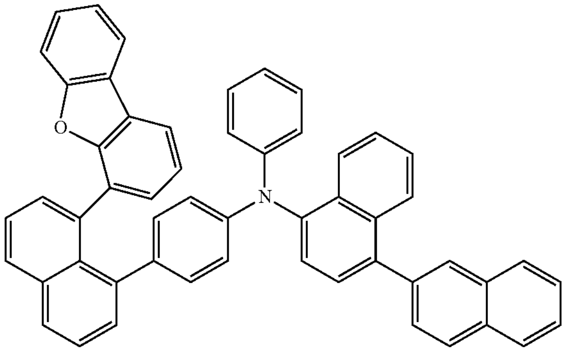

-continued
91
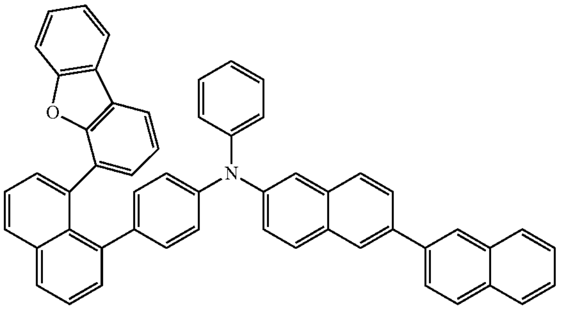
92
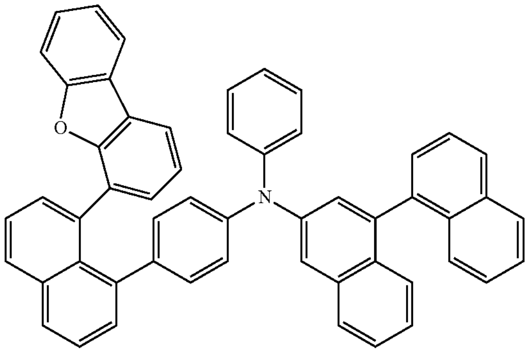
93
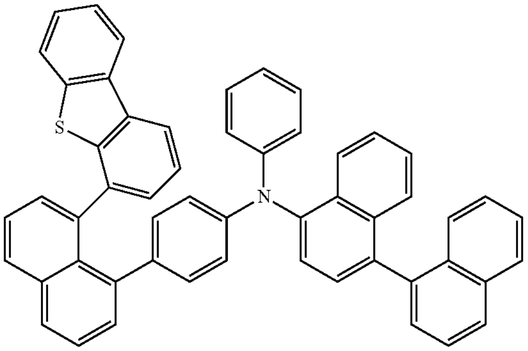
94
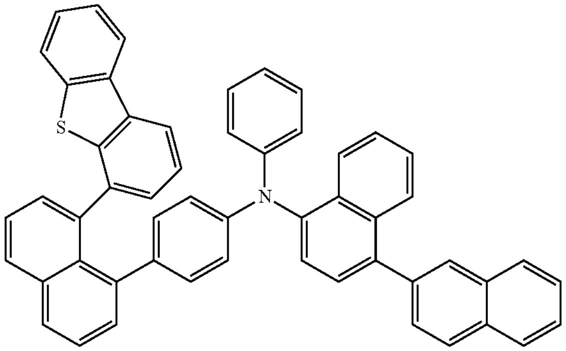
95
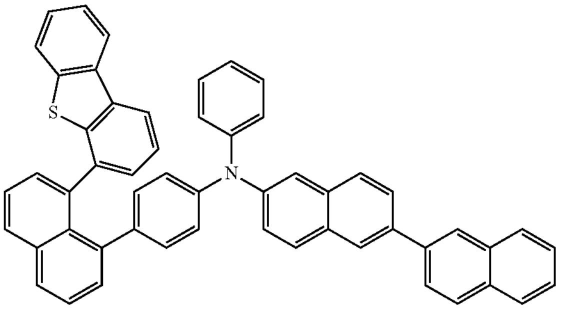
96
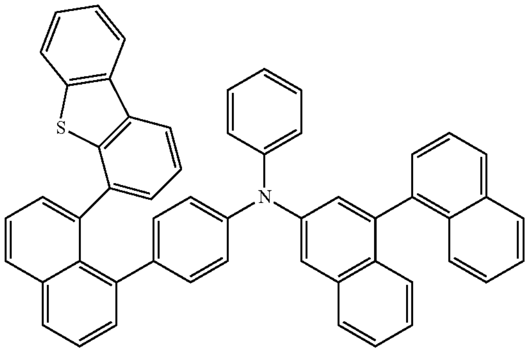
97
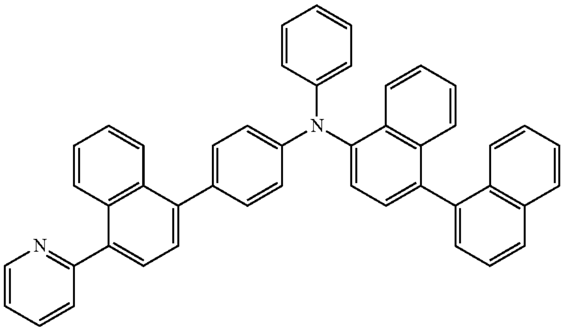
98
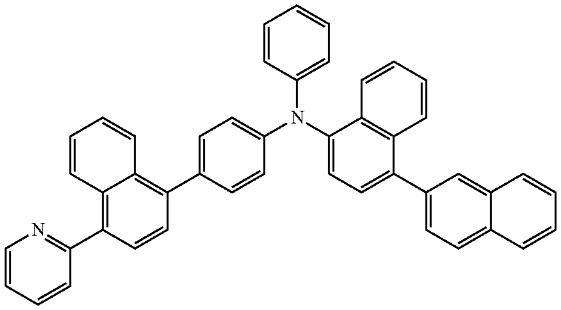

-continued
99
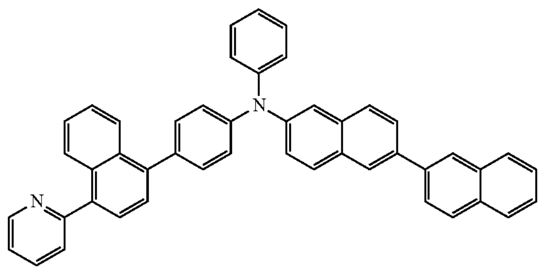
100
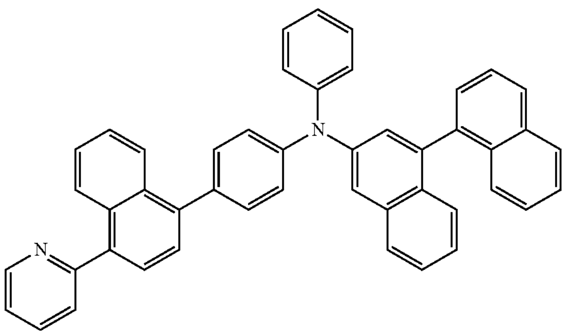
101
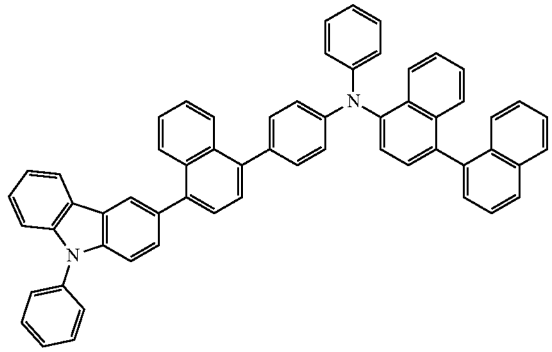
102
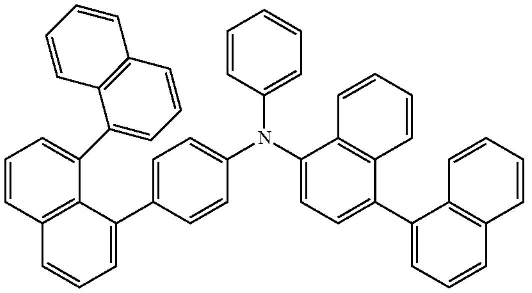
103
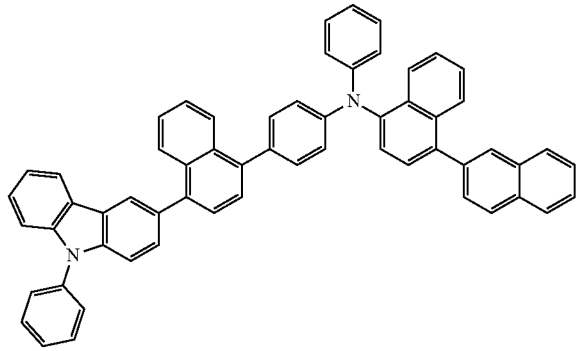
104
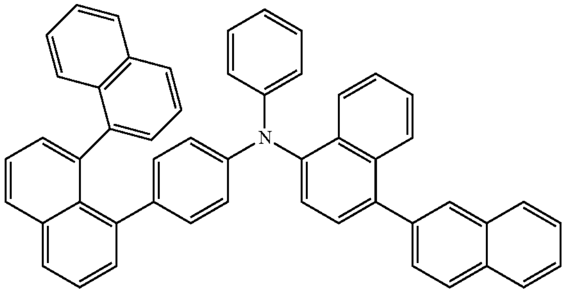
105
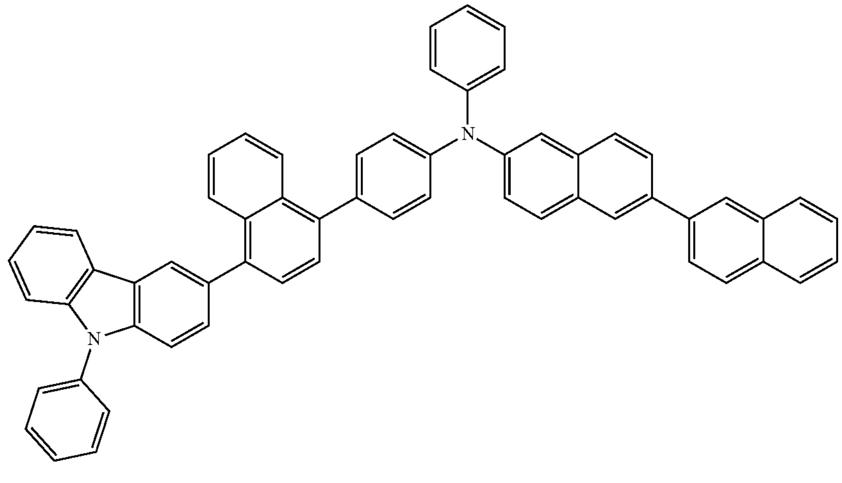

-continued
106
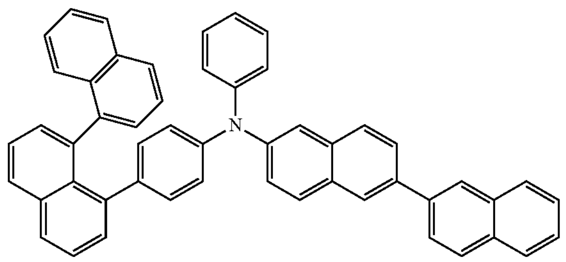
107
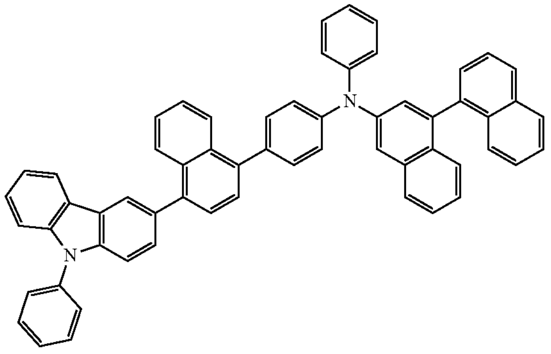
108
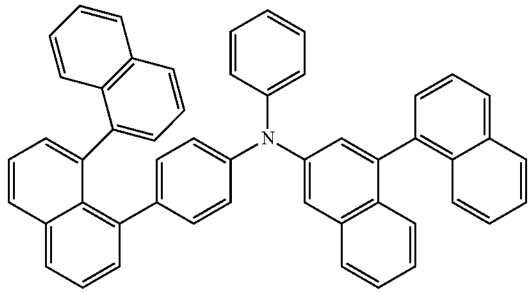
109
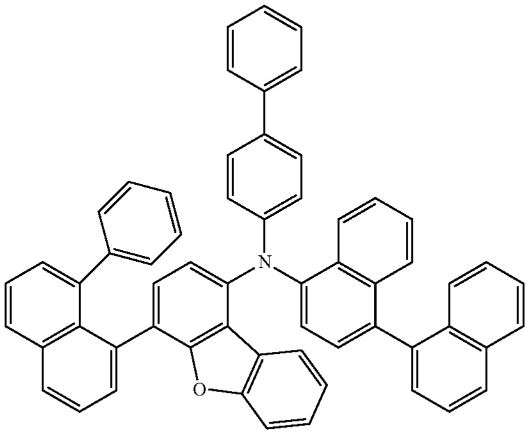
110
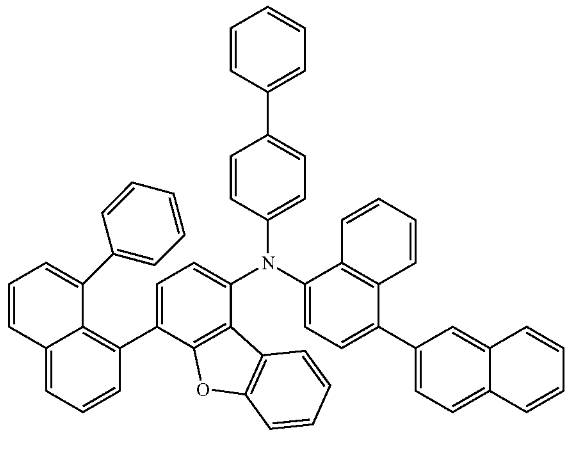
111
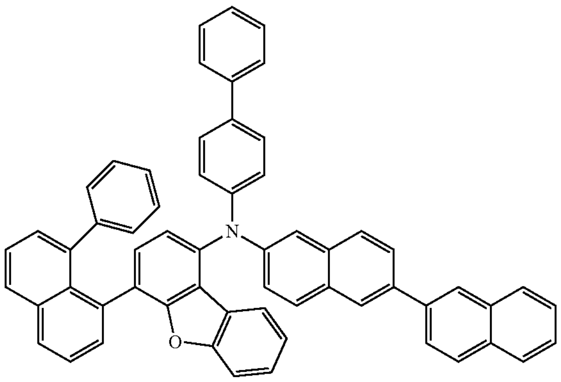

-continued
112
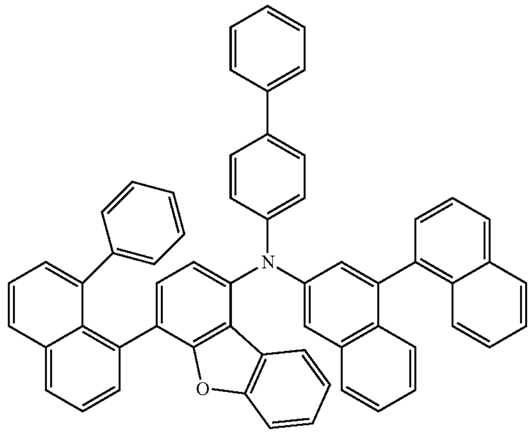
113
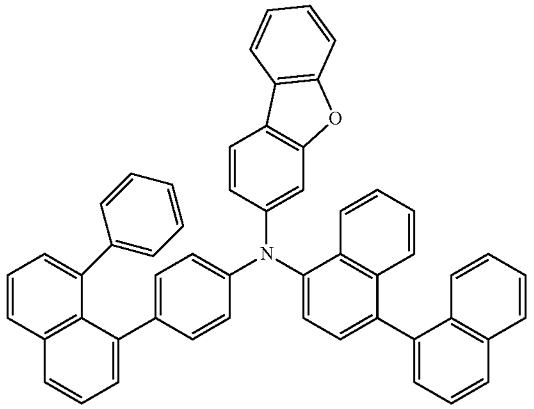
114
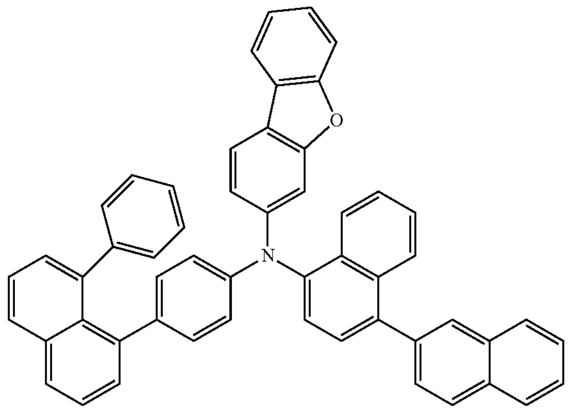
115
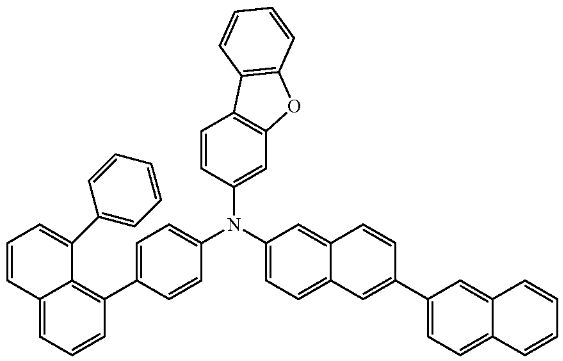
116
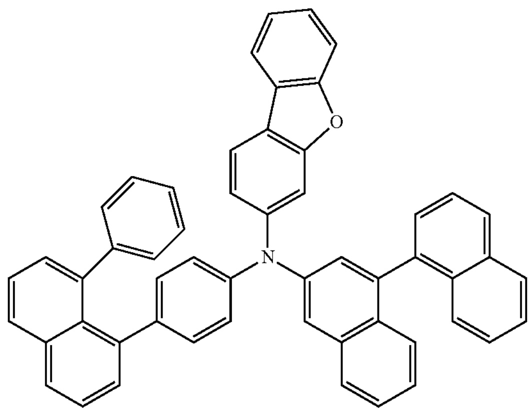
117
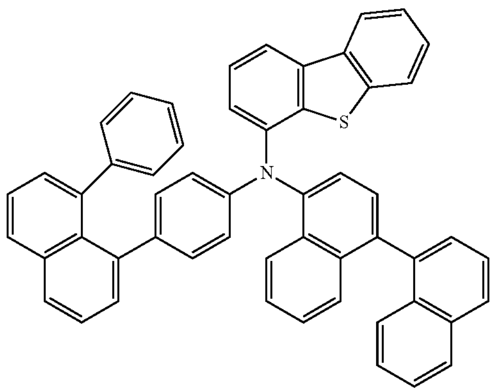

-continued
118
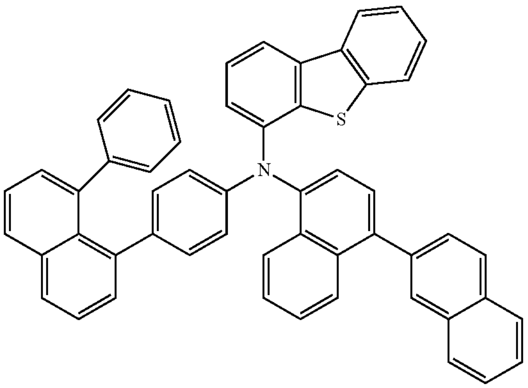
119
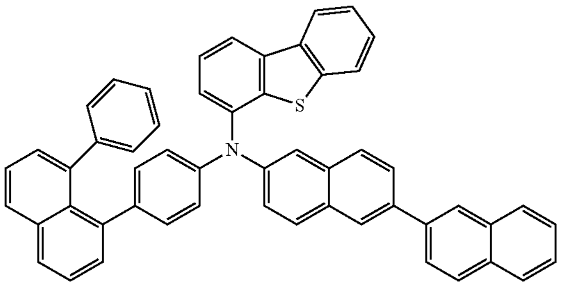
120
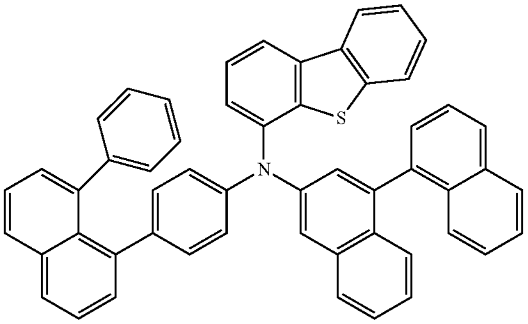
121
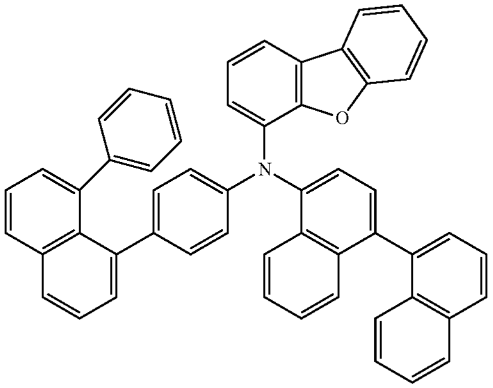
122
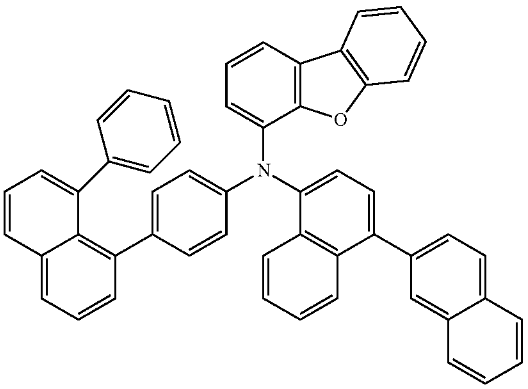
123
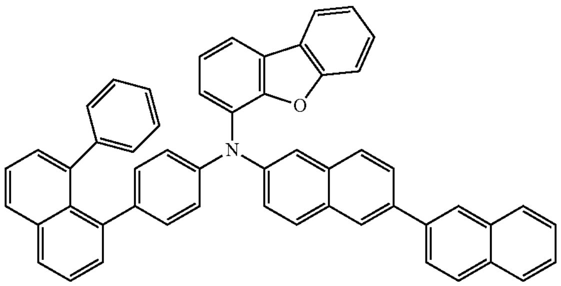
124
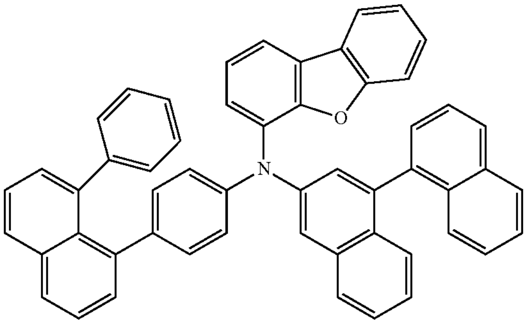
125
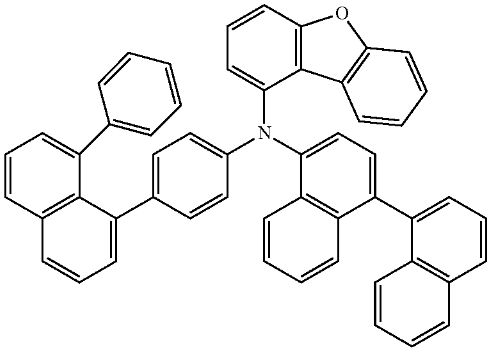

-continued
126
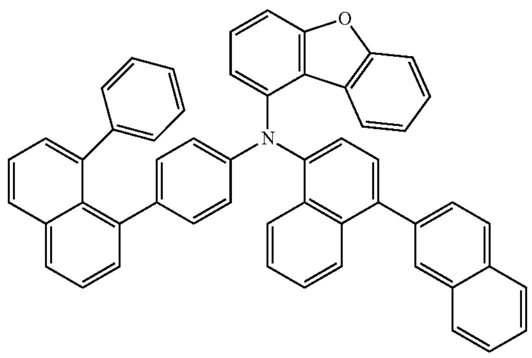
127
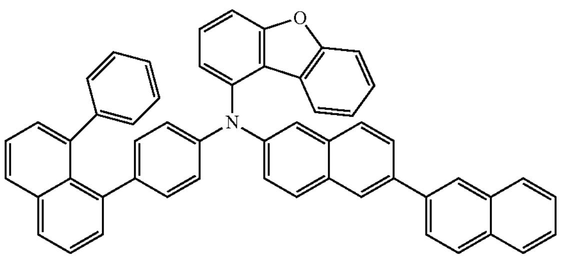
128
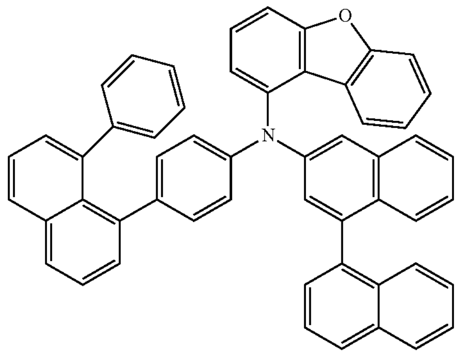
129
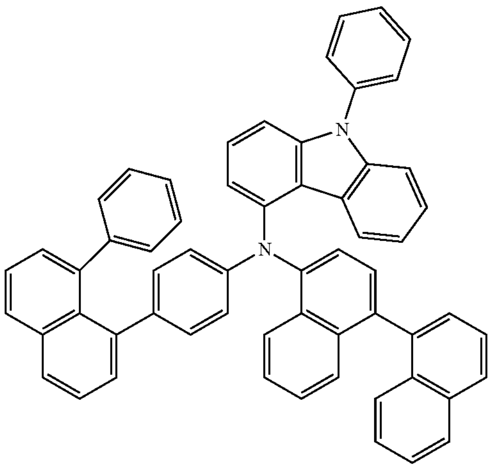
130
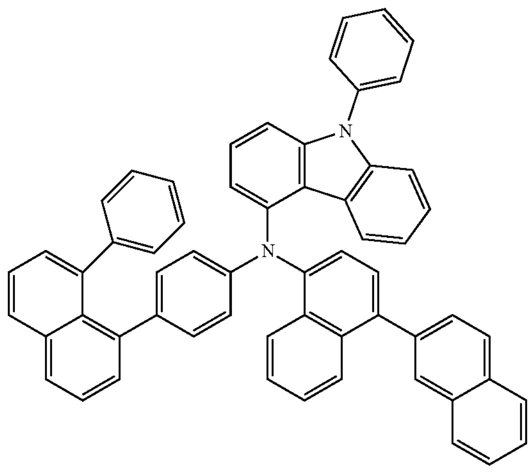
131
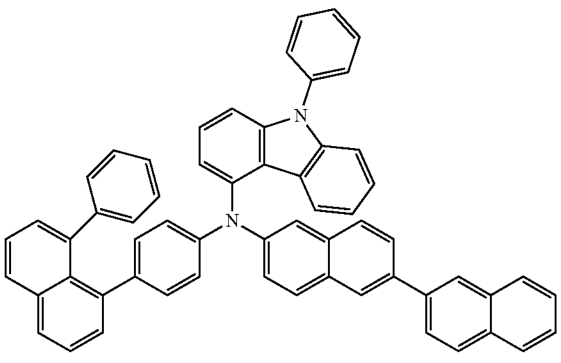

-continued
132
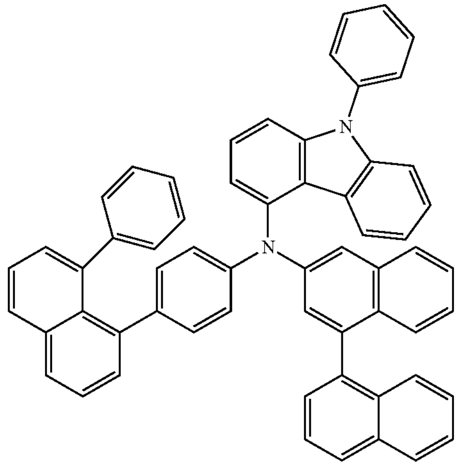
133
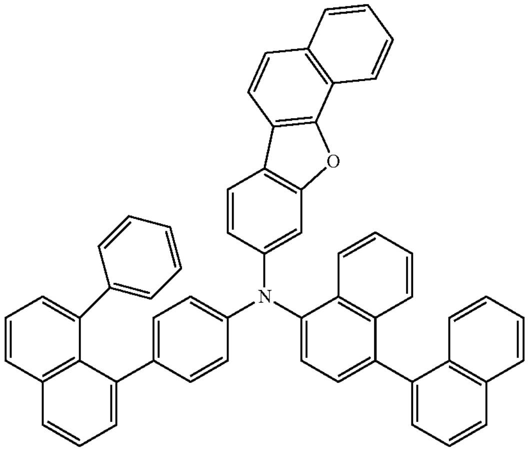
134
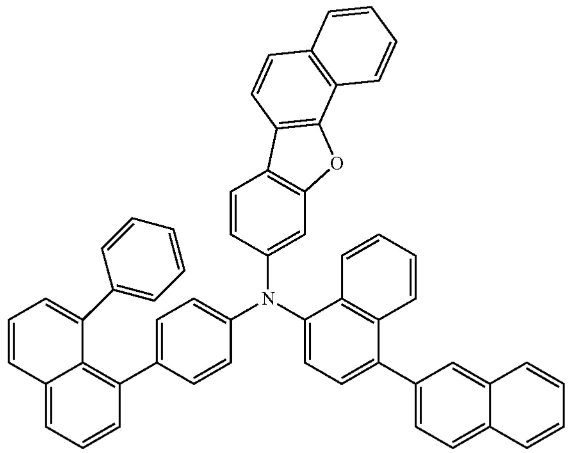
135
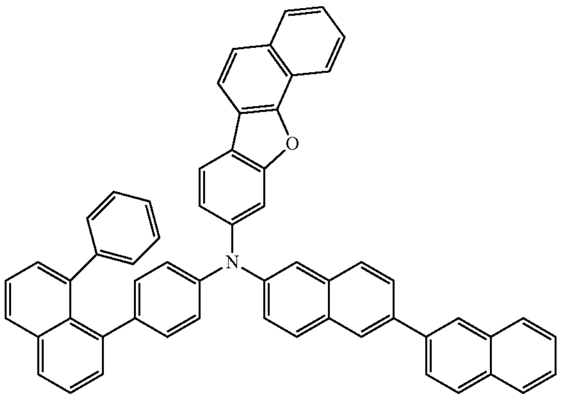
136
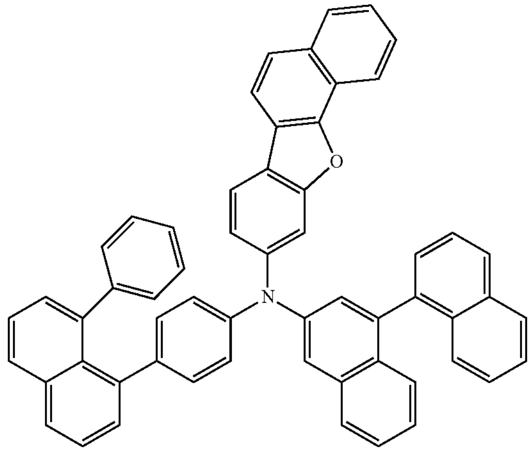
137
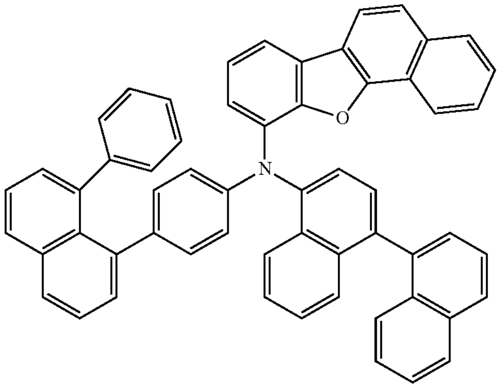

-continued
138
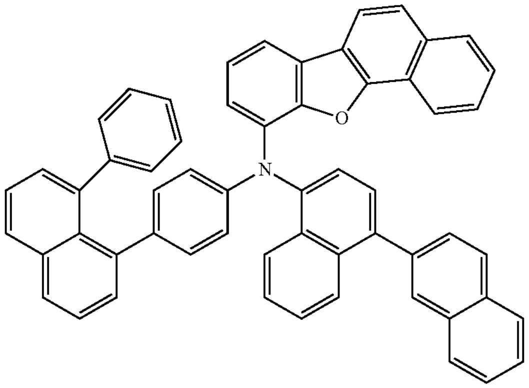
139
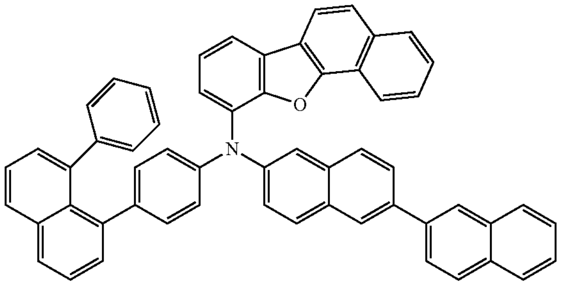
140
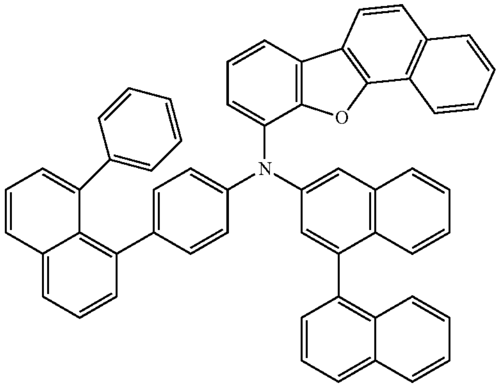
141
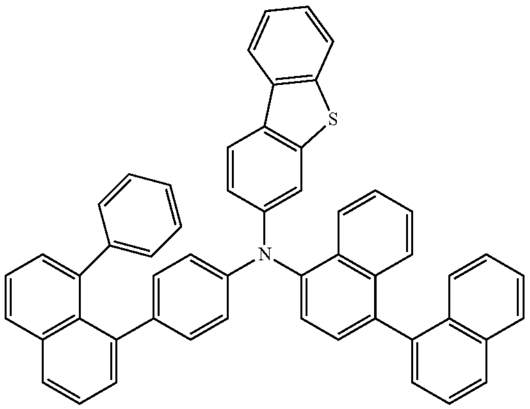
142
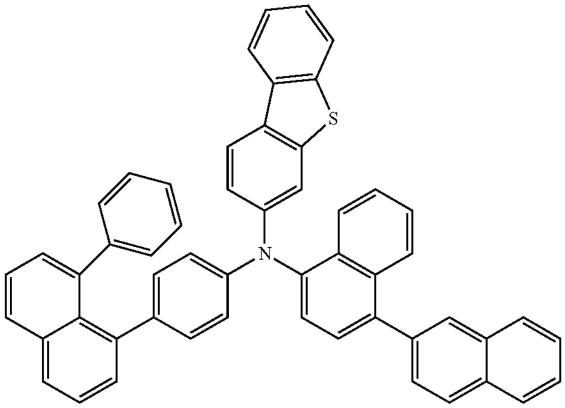
143
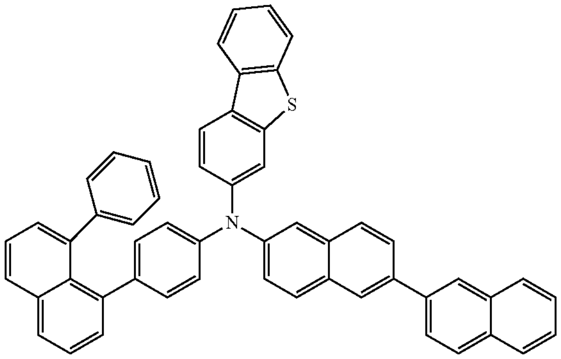
144
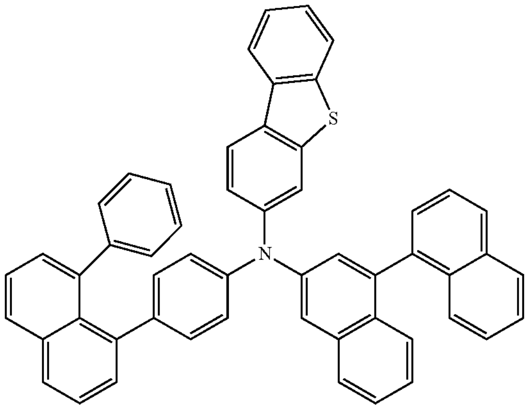
145
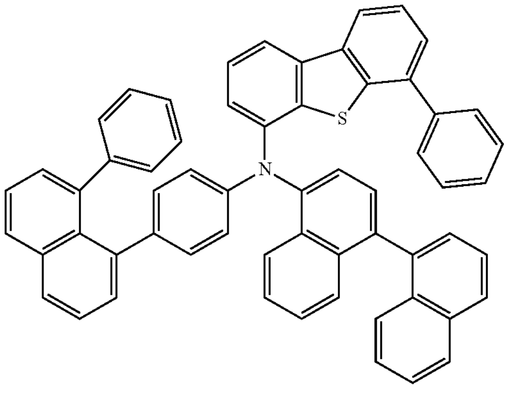

-continued
146
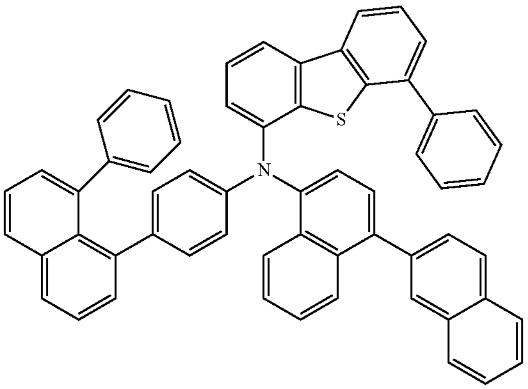
147
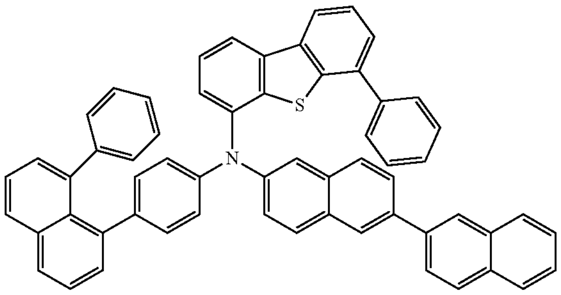
148
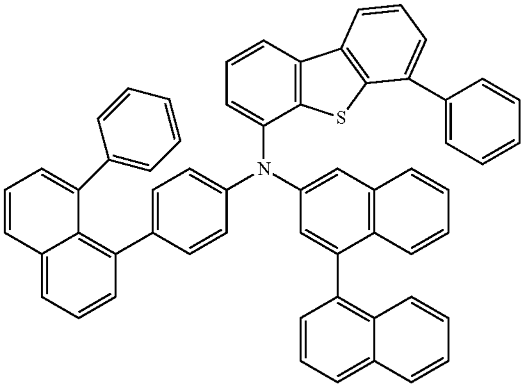
149
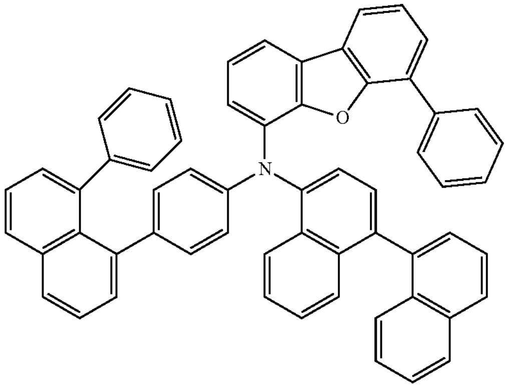
150
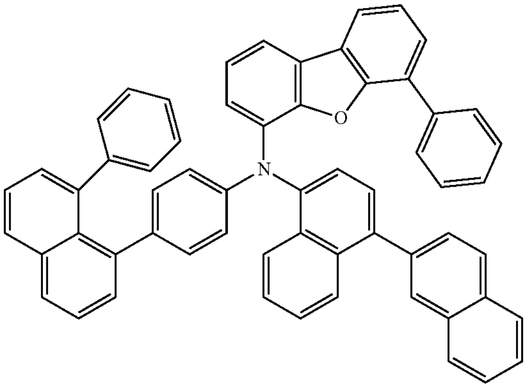
151
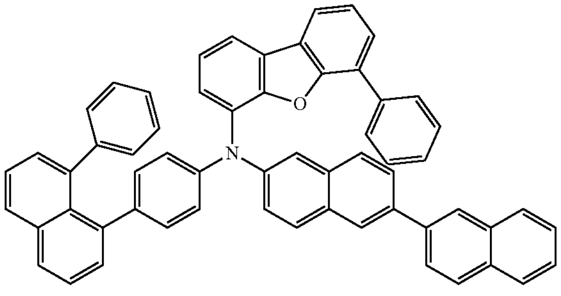

-continued
152
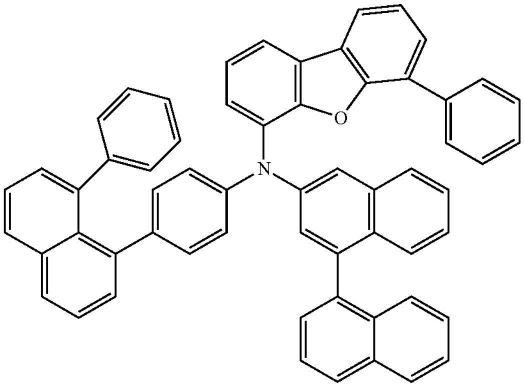
153
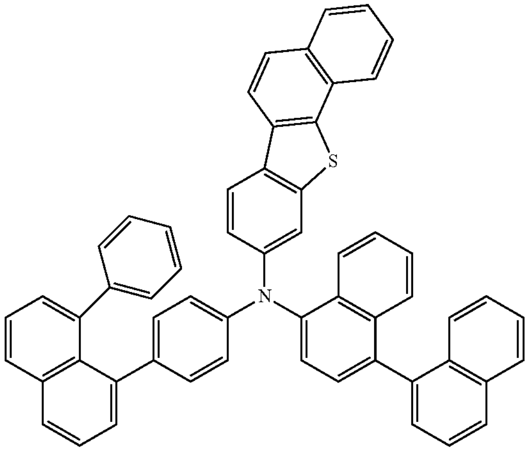
154
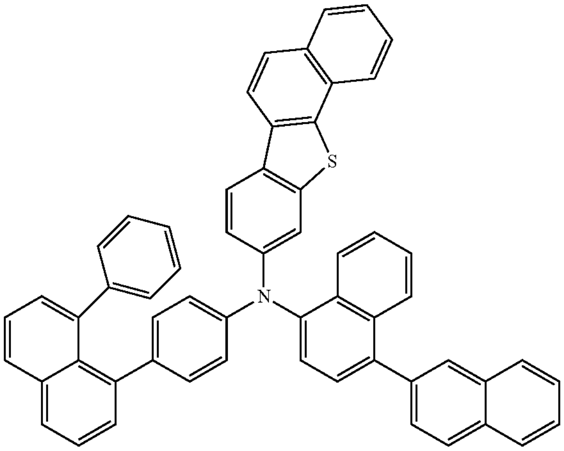
155
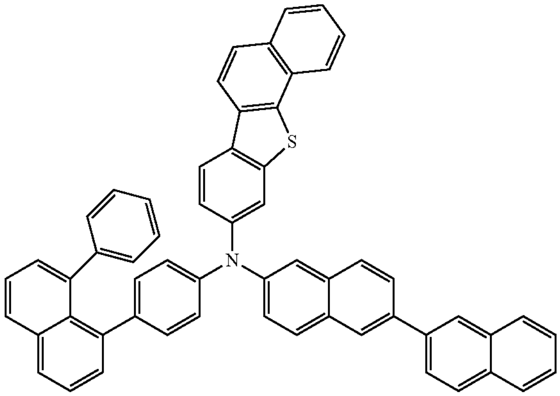
156
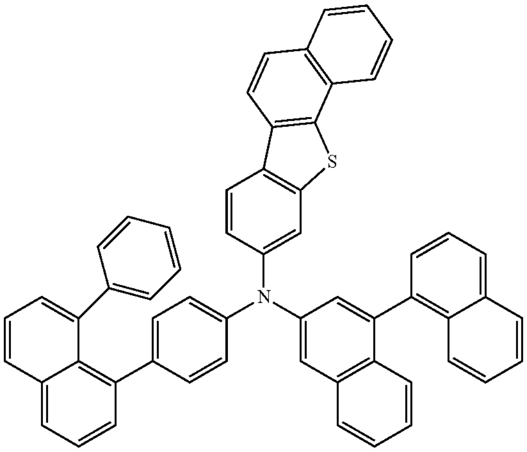
157
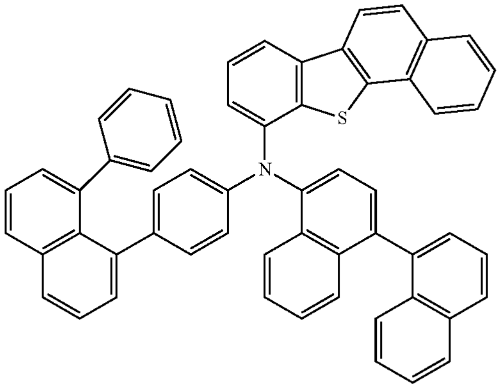

-continued
158
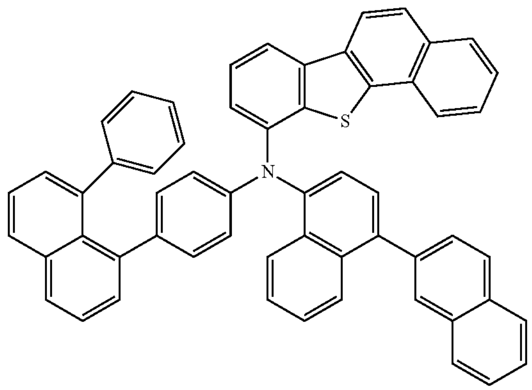
159
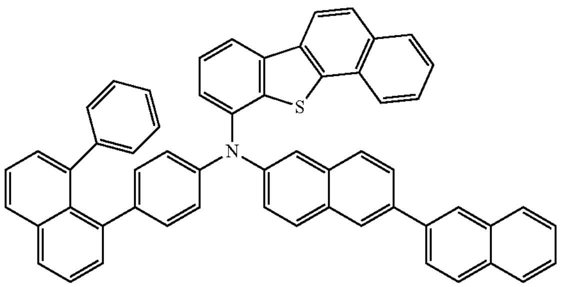
160
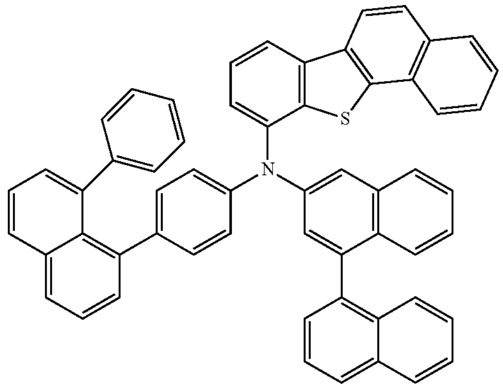
161
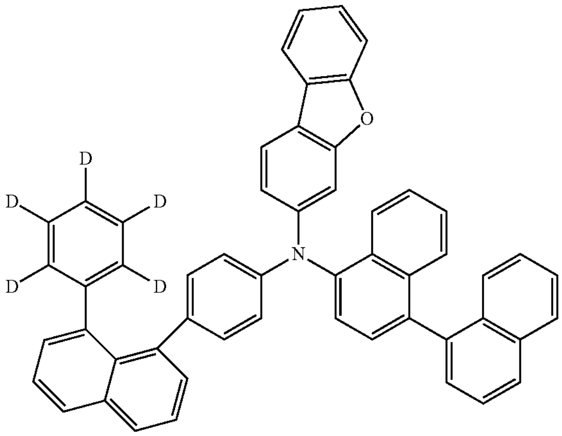
162
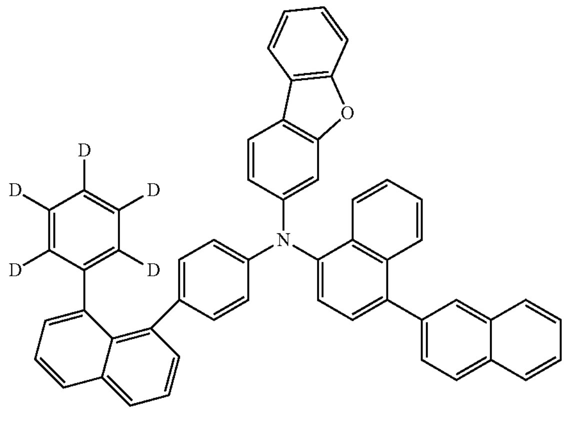
163
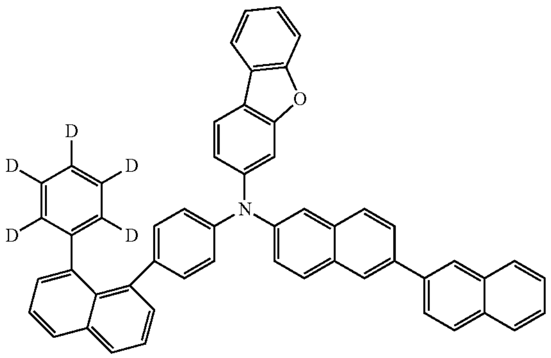

-continued
164
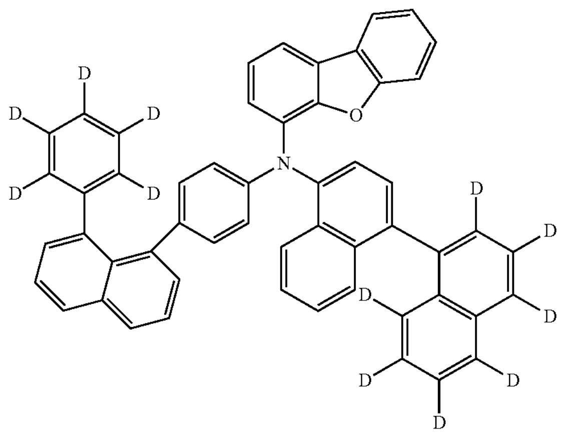
165
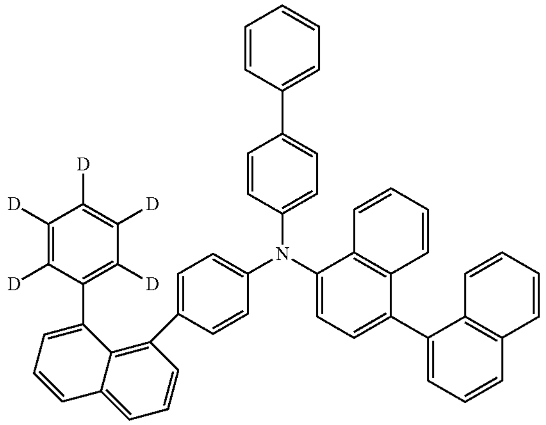
166
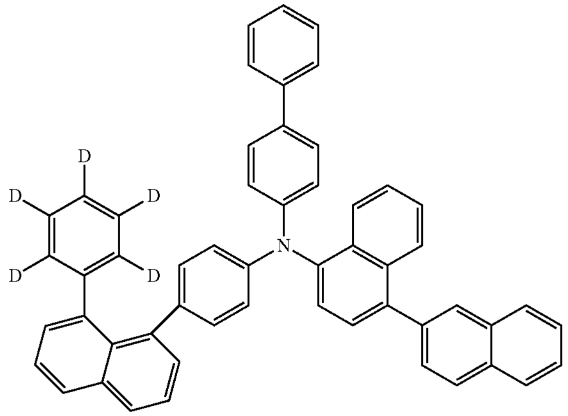
1667
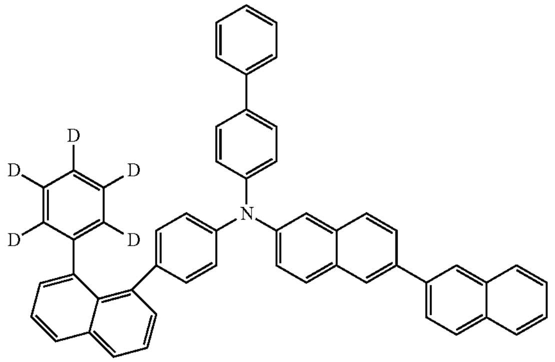
168
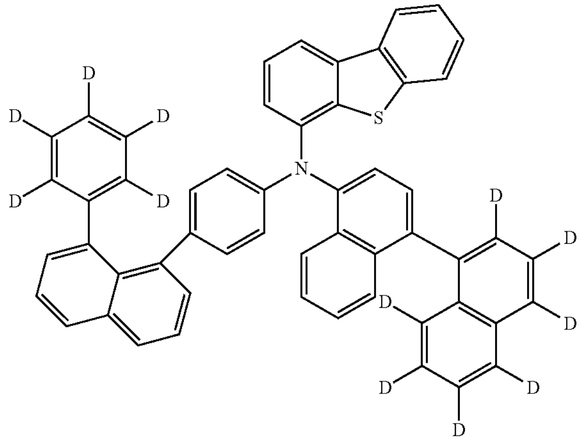
169
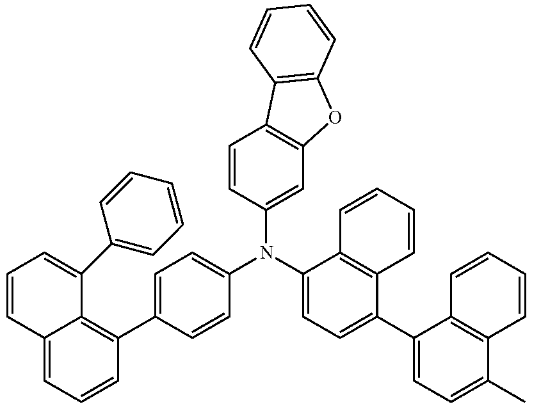

-continued
170
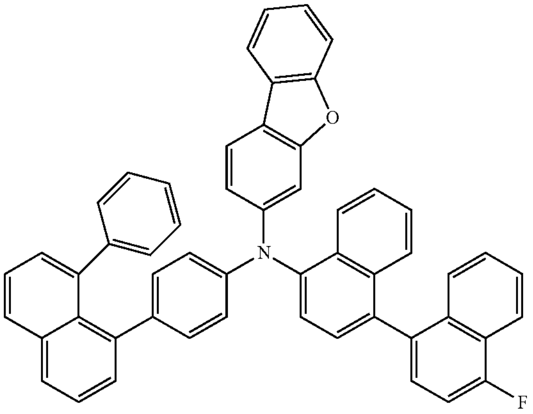
171
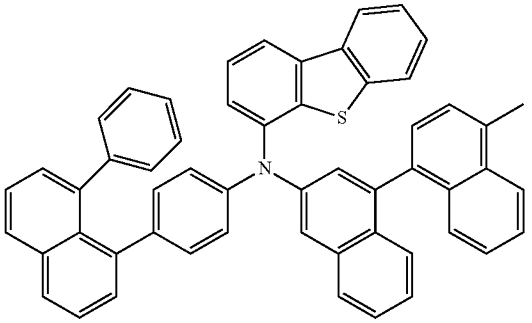
172
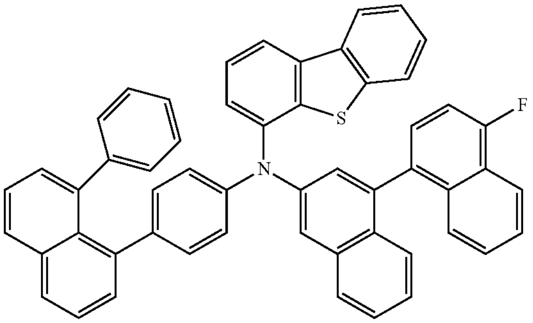
173
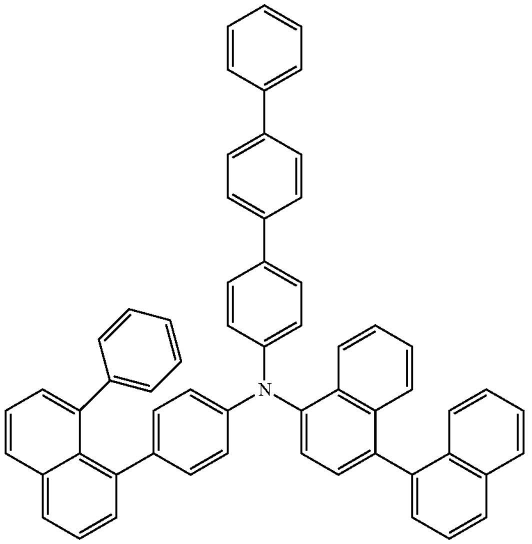
174
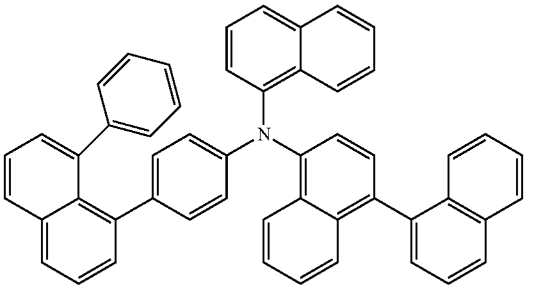
175
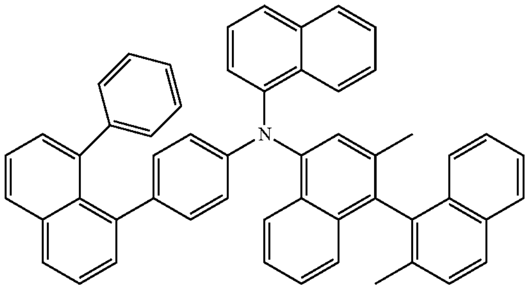

-continued
176
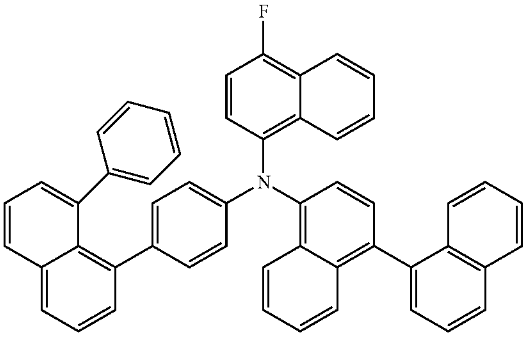
177
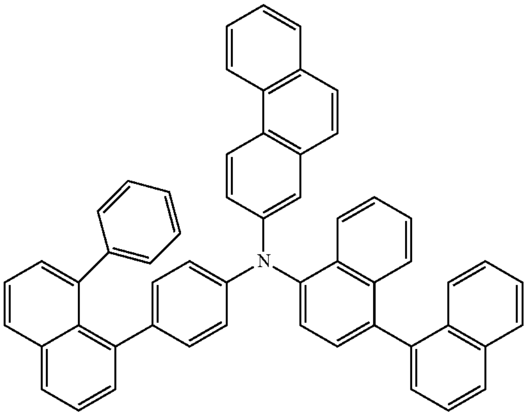
178
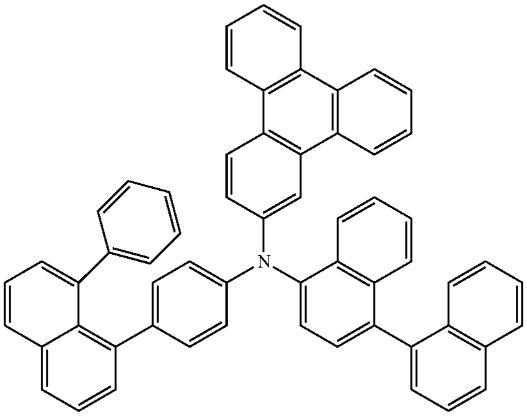
179
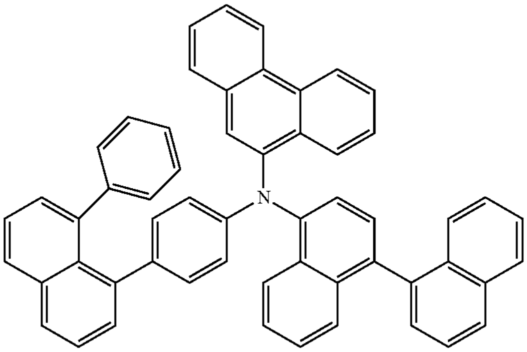
180
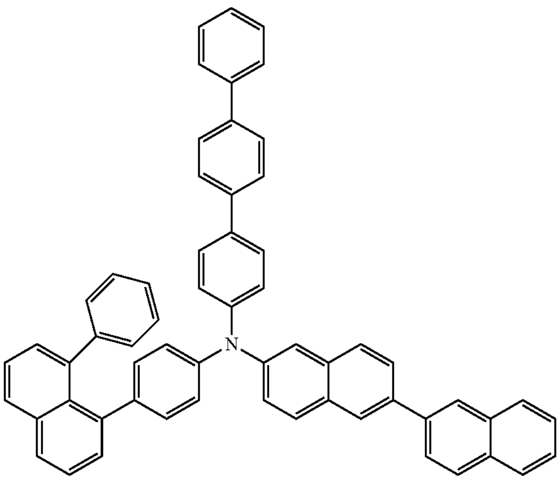
181
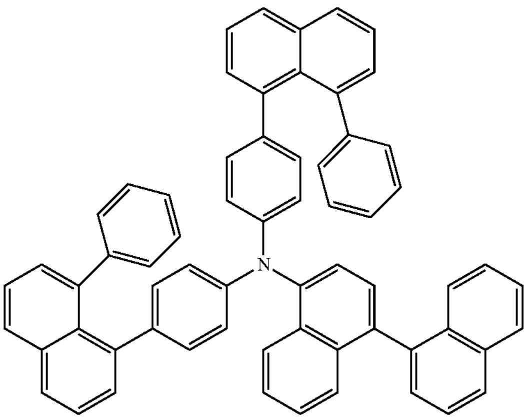

-continued
182
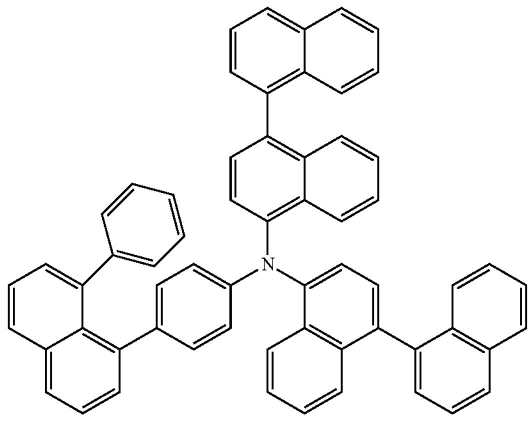
183
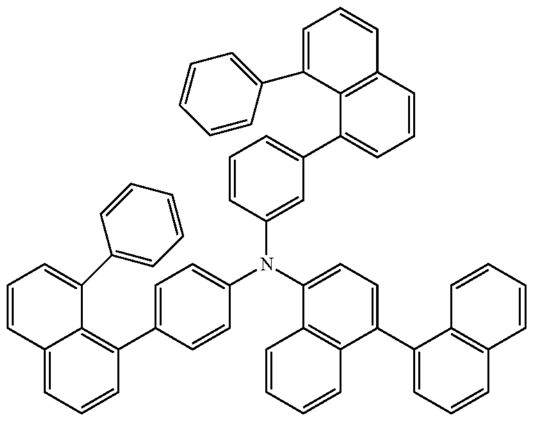
184
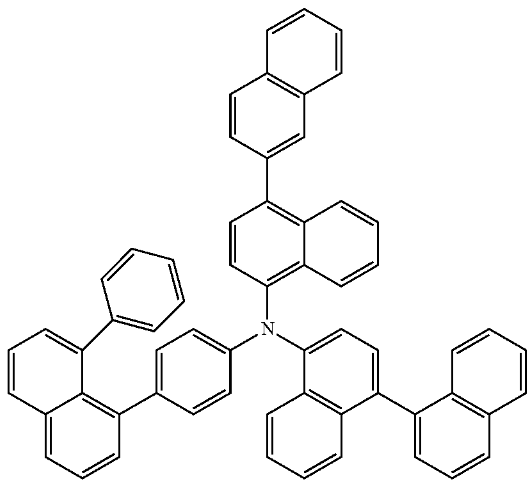
185
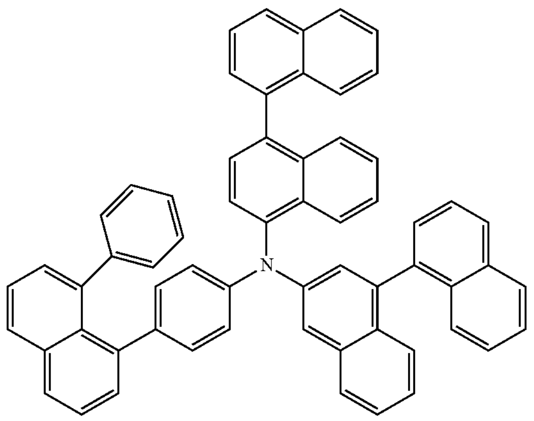
186
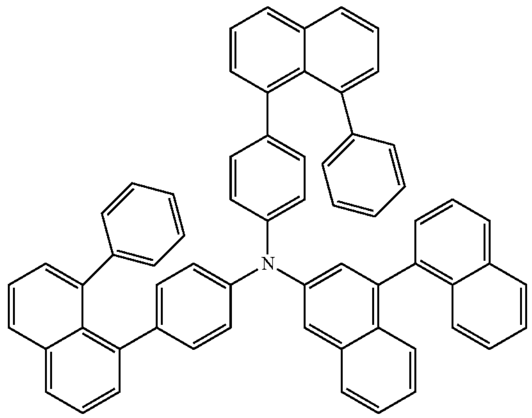
187
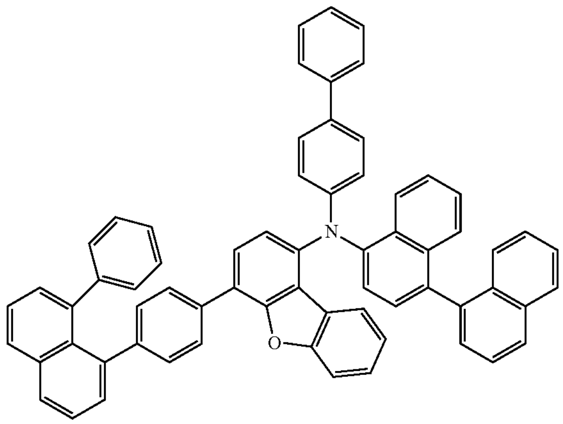

-continued
188
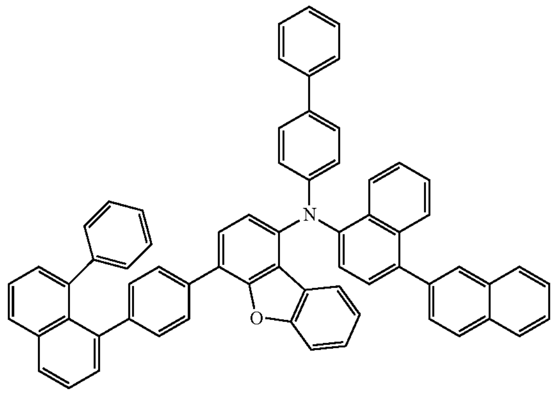
189
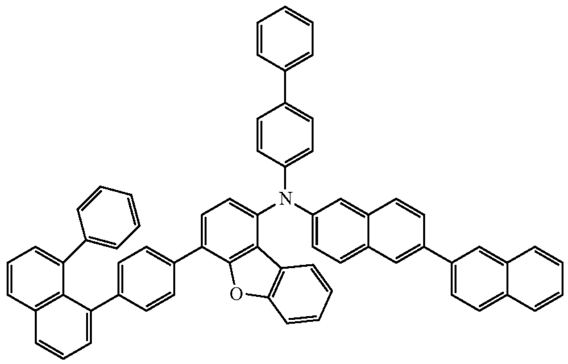
190
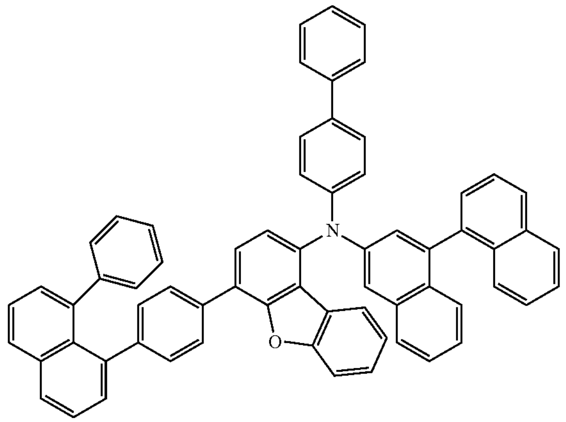
191
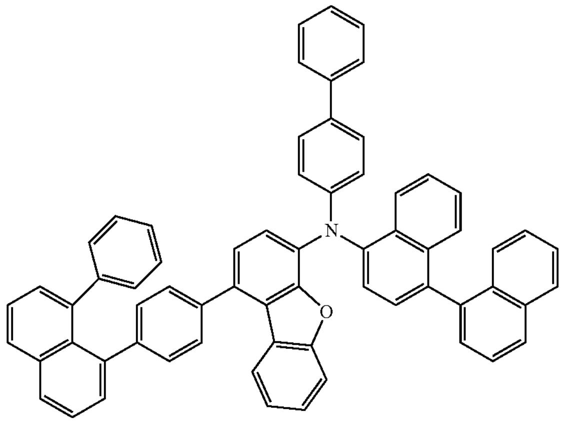
192
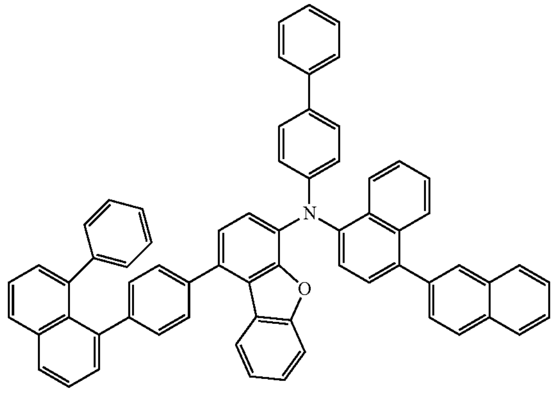
193
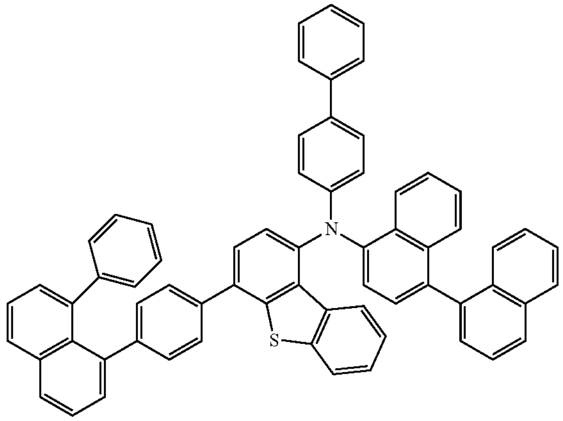

-continued
194
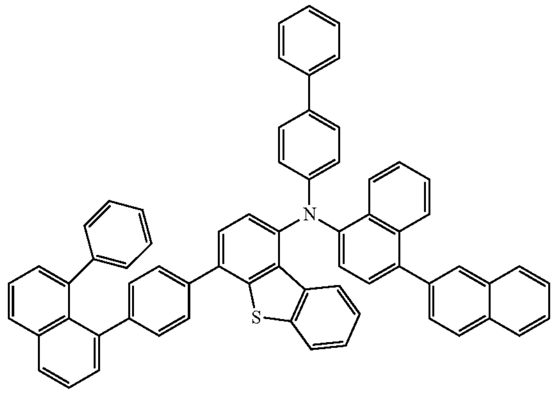
195
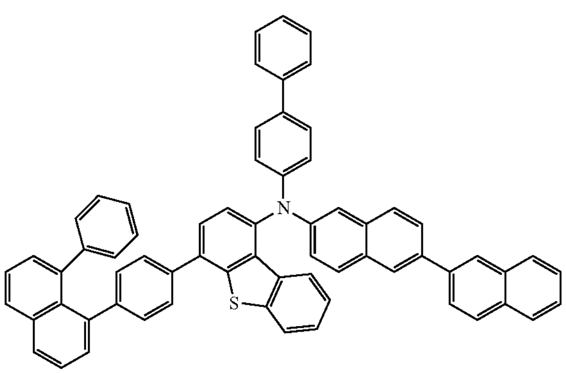
196
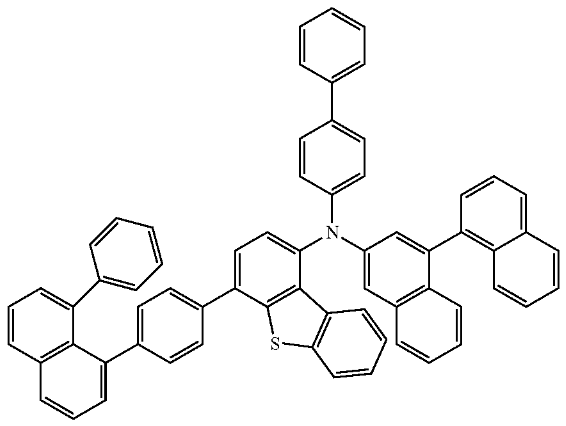
197
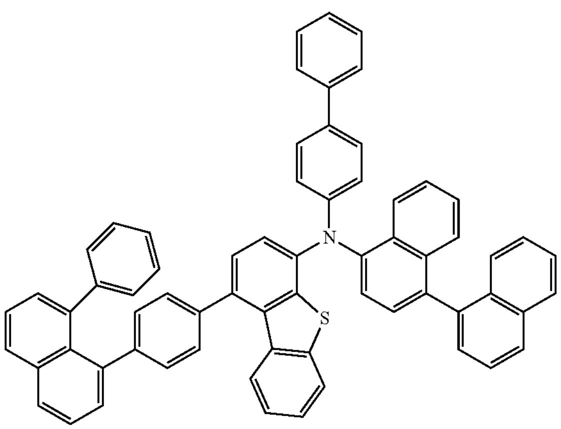
198
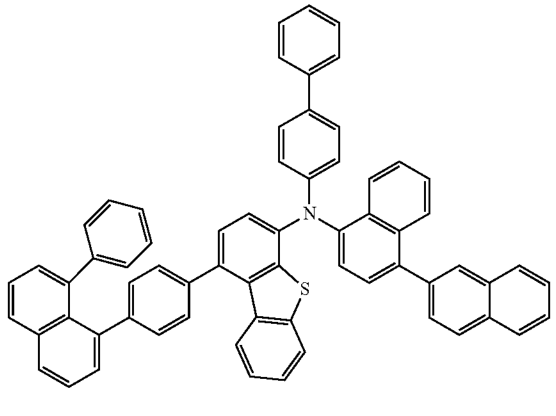
199
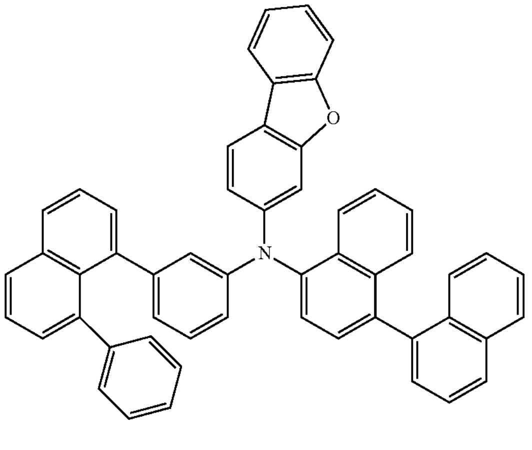

-continued
200
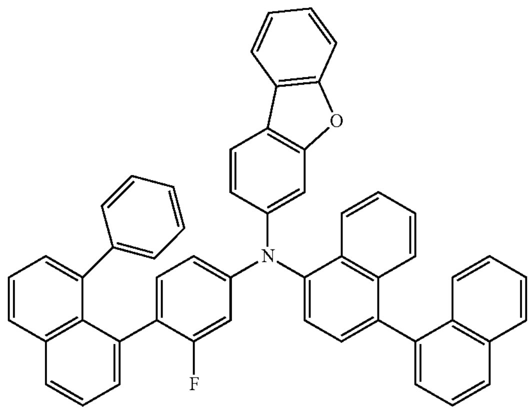
201
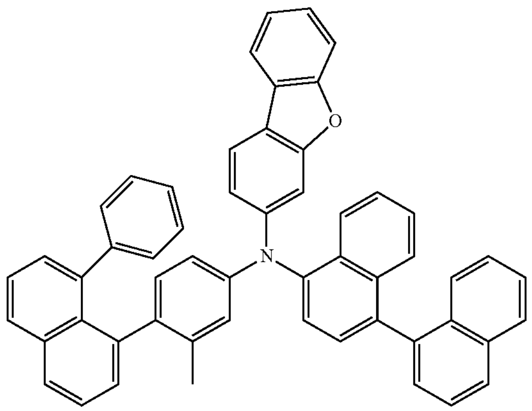
202
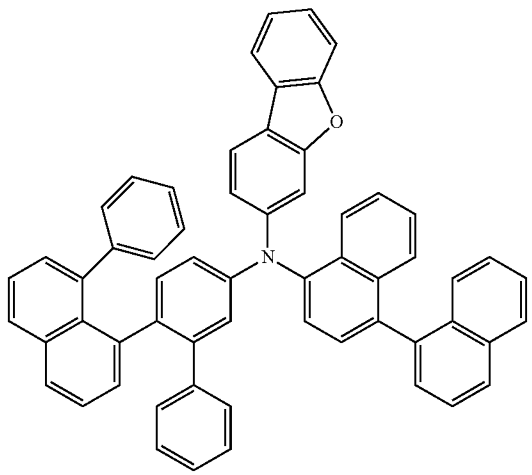
203
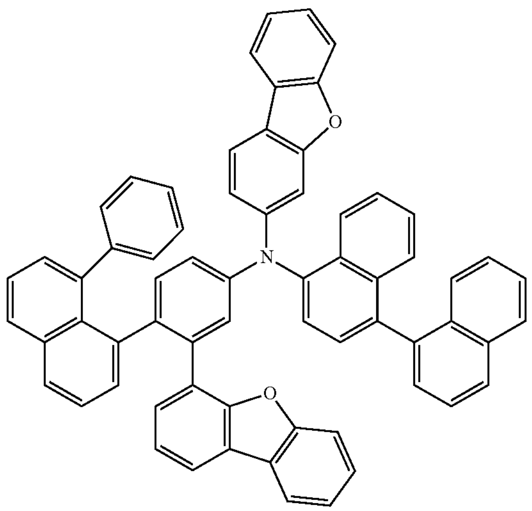
204
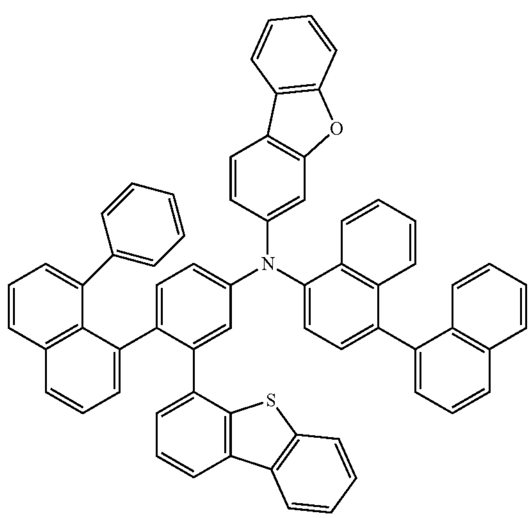
205
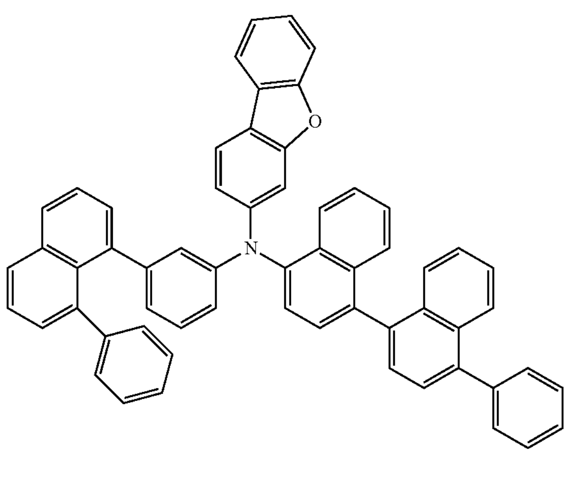

-continued
206
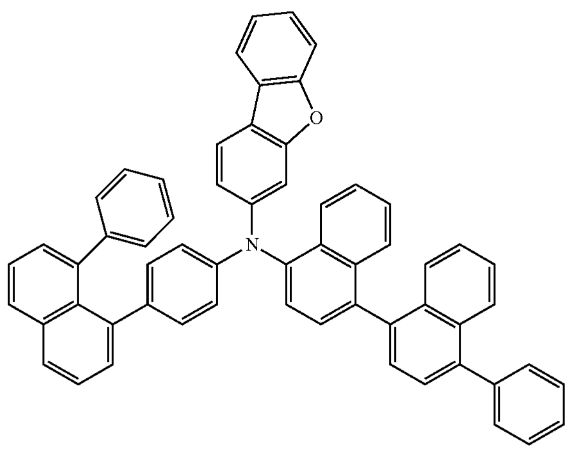
207
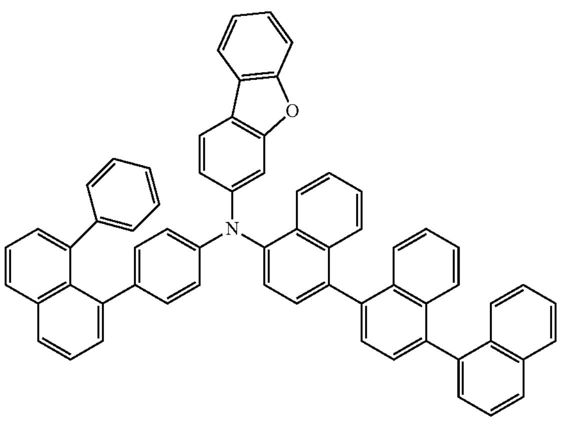
208
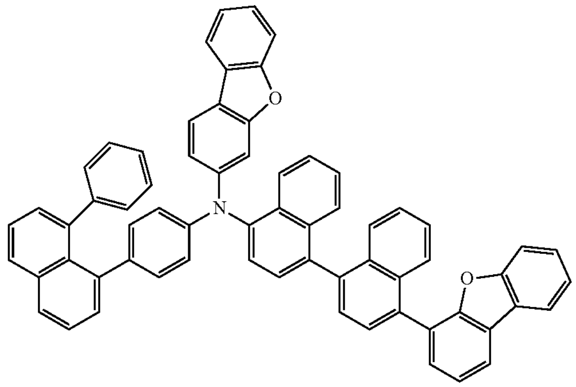
209
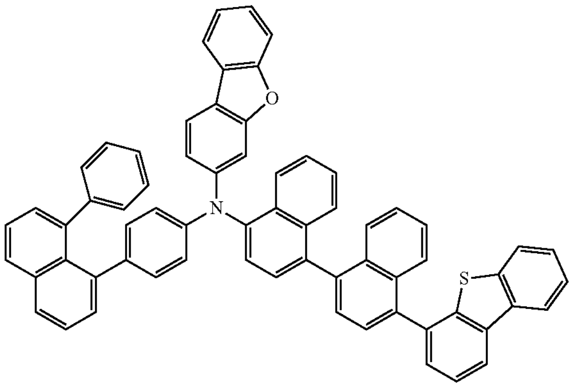
210
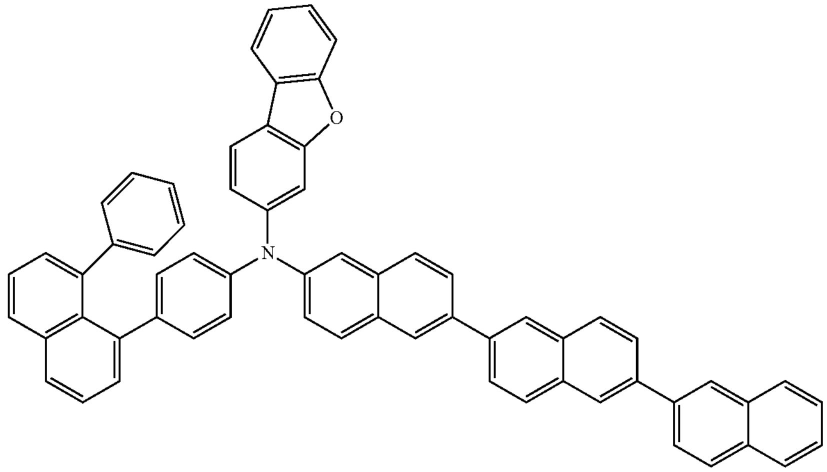

-continued
211
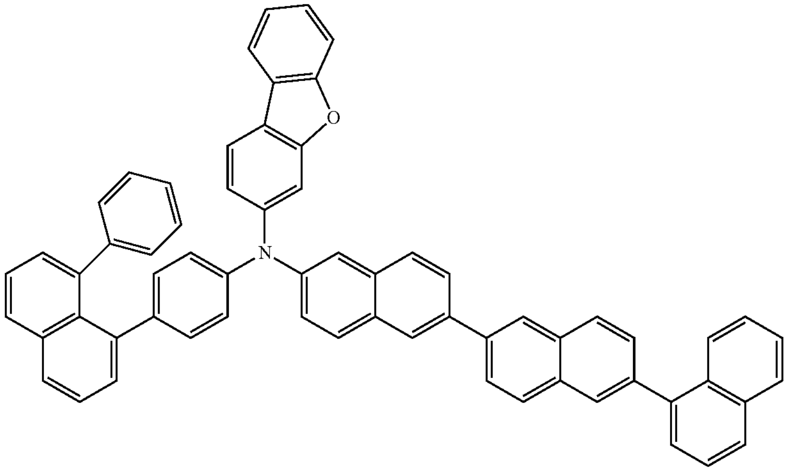
212
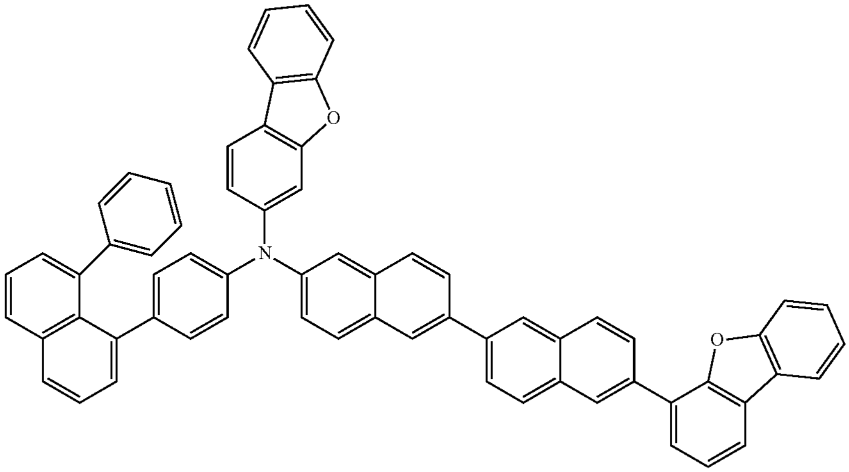
213
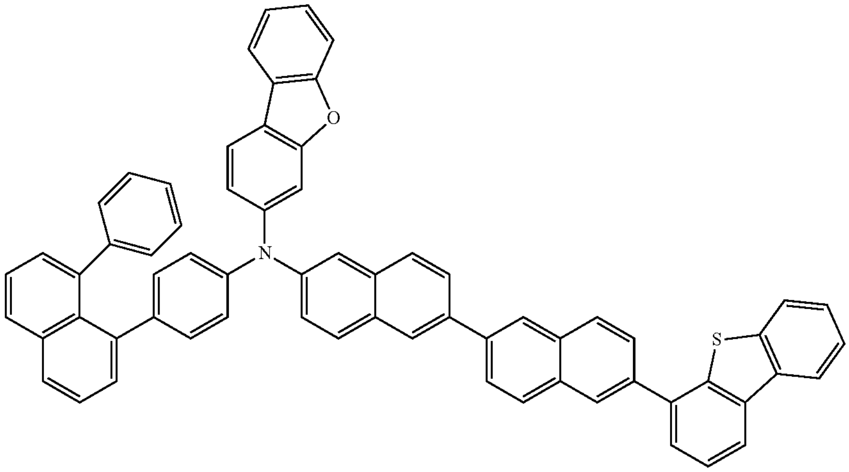
wherein in Compound Group 1,
D is a deuterium atom.
* * * * *